United States Patent
Goldberg et al.

(10) Patent No.: US 11,084,827 B2
(45) Date of Patent: Aug. 10, 2021

(54) TRIAZOLOPYRIMIDINE COMPOUNDS AND THEIR USE IN TREATING CANCER

(71) Applicant: Dizal (Jiangsu) Pharmaceutical Co., Ltd., Wuxi (CN)

(72) Inventors: Frederick Woolf Goldberg, Cambridge (GB); Attilla Kuan Tsuei Ting, Cambridge (GB); Gillian McGregor Lamont, Cambridge (GB); David Buttar, Cambridge (GB); Jason Grant Kettle, Cambridge (GB)

(73) Assignee: Dizal (Jiangsu) Pharmaceutical Co., Ltd., Wuxi (CN)

(*) Notice: Subject to any disclaimer, the term of this patent is extended or adjusted under 35 U.S.C. 154(b) by 0 days.

(21) Appl. No.: 17/095,729

(22) Filed: Nov. 11, 2020

(65) Prior Publication Data
US 2021/0087196 A1    Mar. 25, 2021

Related U.S. Application Data

(63) Continuation of application No. PCT/EP2019/062020, filed on May 10, 2019.

(60) Provisional application No. 62/670,075, filed on May 11, 2018.

(51) Int. Cl.
C07D 487/04    (2006.01)
A61P 35/00    (2006.01)

(52) U.S. Cl.
CPC ............ C07D 487/04 (2013.01); A61P 35/00 (2018.01); *C07B 2200/13* (2013.01)

(58) Field of Classification Search
CPC .... C07D 487/04; A61P 35/00; C07B 2200/13
See application file for complete search history.

(56) References Cited

FOREIGN PATENT DOCUMENTS

WO    WO 2004/065394    *    8/2004    ............ C07D 513/04

* cited by examiner

*Primary Examiner* — Erich A Leeser
(74) *Attorney, Agent, or Firm* — Jun He Law Offices P.C.; Zhaohui Wang

(57) ABSTRACT

The invention concerns compounds of Formula (I):

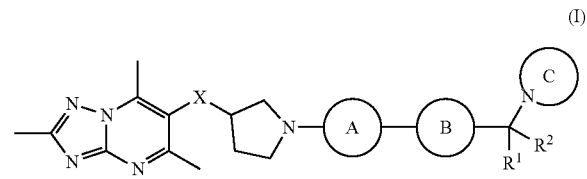

or pharmaceutically acceptable salts thereof, wherein $R^1$, $R^2$, X, Ring A, Ring B and Ring C have any of the meanings hereinbefore defined in the description; process for their preparation; pharmaceutical compositions containing them and their use in treating MCT4 mediated diseases.

18 Claims, 5 Drawing Sheets
Specification includes a Sequence Listing.

DSC Thermogram of Compound A, Form A

TRIAZOLOPYRIMIDINE COMPOUNDS AND THEIR USE IN TREATING CANCER

CROSS-REFERENCE TO RELATED APPLICATIONS

This application is a Continuation of PCT Patent Application No. PCT/EP2019/062020, filed on May 10, 2019, which claims foreign priority of U.S. provisional Application No. 62/670,075, filed on May 11, 2018. Each of these applications is hereby incorporated by reference herein in its entirety.

FIELD

The specification generally relates to triazolopyrimidine compounds and pharmaceutically acceptable salts thereof. These compounds and their pharmaceutically acceptable salts selectively inhibit MCT4, and the specification therefore also relates to the use of such compounds and salts thereof to treat or prevent MCT4 mediated disease, including cancer. The specification further relates to crystalline forms of triazolopyrimidine compounds and pharmaceutically acceptable salts thereof; pharmaceutical compositions comprising such compounds and salts; kits comprising such compounds and salts; methods of manufacture of such compounds and salts; and to methods of treating MCT4 mediated disease, including cancer, using such compounds and salts.

BACKGROUND

Monocarboxylate transporters are encoded by the SLC16 gene family. The family is also known as the monocarboxylate transporter (MCT) family since the first members to be identified were demonstrated to be responsible for the proton-linked transport of monocarboxylates such as L-lactate, pyruvate and ketone bodies across the plasma membrane. Direct demonstration of proton-linked lactate and pyruvate transport has been demonstrated for MCT1 (SLC16A1), MCT2 (SLC16A7), MCT3 (SLC16A8) and MCT4 (SLC16A3). The nomenclature for the MCT family is taken from Halestrap and Price, Biochemical Journal (1999) 343: 281-299.

MCTs possess 12 transmembrane helices and functional expression requires interaction with single transmembrane domain chaperones known as CD147 (also known as basigin and EMMPRIN) and embigin. CD147 acts as an essential chaperone to take MCT1 and MCT4 to the plasma membrane where the transporter and CD147 remain tightly associated (Kirk et al. (2000) EMBO J. 19: 3896-3904). Correct plasma membrane expression of MCT2 shows a strong preference for embigin over CD147 (Wilson et al (2005) J. Biol. Chem. 280: 27213-27221).

It is well established that tumours display altered metabolism (Vander Heiden (2011) Nat. Drug Dis. 10:671-684). Tumours are composed of well oxygenated (aerobic) and poorly oxygenated (hypoxic) regions. Compared to normal cells, tumour cells have an increased dependency on the glycolytic pathway for ATP generation either via aerobic glycolysis (the Warburg effect) or anaerobic glycolysis as a consequence of tumour hypoxia. Highly proliferating tumours and hypoxic tumours appear to be particularly dependent upon glycolysis to meet their energy and biosynthetic requirements. Widespread clinical use of FDG-PET (Fluorodeoxyglucose Positron Emission Tomography)—PET scanning with the tracer fluorine-18 (F-18) fluorodeoxyglucose (FDG), has demonstrated that this glycolytic phenotype is observed in a range of solid and haematological tumours. As a result, FDG-PET can be used for diagnosis, staging, and monitoring treatment of cancers. FDG-PET combined with computer tomography has a >90% sensitivity and specificity for the detection of metastases of most epithelial tumours (Mankoff et al. (2007) Clin. Cancer Res. 13:3460-3469).

A by-product of the increased glycolytic rates in tumours is the accumulation of lactate. Intracellular lactate can be transported out of tumour cells via the monocarboxylate transporters (MCTs 1, 2, 3 & 4) (Halestrap and Price, Biochem J. (1999) 343; 291-299). Lactate that is produced by tumour cells can be taken up by stromal and oxygenated tumour cells (via the monocarboxylate transporters MCT1 and MCT2) to regenerate pyruvate that can be used to fuel oxidative phosphorylation (OXPHOS) (Koukouris et al., Cancer Res. (2006) 66; 632-637; Sonveaux et al., J. Clin. Invest. (2008) 118; 3930-3942). One of the key factors in driving the glycolytic phenotype of tumours is the activation of hypoxia-inducible factor (HIF), a transcription factor that is activated by hypoxic stress. MCT4 is a HIF target gene and is up-regulated by hypoxia and is required to export lactate from glycolytic tumours (Ullah et al. (2006) J. Biol. Chem. 281:9030-9037). The kinetic properties of MCT4 are tuned to its role in exporting lactic acid derived from glycolysis because its very high Km for pyruvate (150 mM) ensures that pyruvate is not exported from the cell. This is essential because NADH derived from reduction of pyruvate to lactate is required to drive glycolytic flux (Halestrap and Wilson (2012) IUMBM Life 64: 109-119).

MCT4 is over-expressed in a range of solid tumours compared to normal epithelium including renal tumours (Fisel et al. (2013) Clin. Cancer Res. 19: 5170-5181; Gerlinger et al. J. Pathol. 227: 146-156), pancreatic tumours (Baek et al. (2014) Cell Rep. 9:2233-2249), colorectal tumours (Pinheiro et al., Virchows Arch. (2008) 452; 139-146), HNSCC (Zhu et al. (2014) PLoS One 9:e87904), breast cancer (Doyen et al. (2014) Biochem. Biophys. Res. Commun. 451:54-61), prostate cancer (Pertega-Gomes et al. BMC Cancer (2011) 11:312) and liver cancer (Gao et al. (2015) J Cancer Res. 141: 1151-1162).

Recent data has indicated that lactate plays an important role in regulating immune cell function. Lactate has been shown to inhibit the activity of immune effector cells such as T cells and NK cells. Lactic acid suppresses the proliferation and activation of human T cells ex vivo (Fisher et al. (2007) Blood 109:3812-3819; Haas et al. (2015) PLoS Biol 13). Husain et al. have demonstrated that NK cells from LDHA-depleted tumours showed improved cytolytic function and lactate treatment of NK cells reduced their cytotoxic activity (Husain et al. (2013) J. Immunol. 191:1486-1495). Furthermore, Brand et al. demonstrated that in immunocompetent mice, knock-down of LDHA reduced lactic acid production and an increased infiltration of IFN-γ-producing T and NK cells was observed in tumours (Brand et al. (2016) Cell Metab. 24:657-671). Lactate has also been shown to inhibit monocyte activation and dendritic cell differentiation (Gottfried et al. (2006) Blood 107:2013-2021; Dietl et al. (2010) J. Immunol. 184:1200-1209) and also induce M2 (immunosuppressive) tumour associated macrophage polarisation (Colegio et al. (2014) Nature 513: 559-563). Taken together, these data support the hypothesis that lactate produced as a by-product of the glycolytic phenotype of tumours drives an immunosuppressive effect in the tumour microenvironment.

Lactate accumulation in the tumour microenvironment is accompanied by acidosis (due to the co-transport with protons). A low pH in the tumour microenvironment has been associated with extracellular matrix degradation and migration of tumour cells (Gillies and Gatenby (2015) Cancer J. 21: 88-96).

Potent inhibitors of MCT1/2 have been described in WO2004/065394 which shows that in T-lymphocytes, lactate efflux occurs via MCT1, as small molecule inhibitors of MCT1 result in accumulation of intracellular lactate (Murray et al., Nat. Chem Biol. (2005) 1; 371-376).

However, there is also a need for inhibitors of MCT4 that inhibit the transport of lactate into MCT4-dependent cells, demonstrate good bioavailability and are suitable for dosing.

SUMMARY

Briefly, this specification describes, in part, a compound of Formula (I):

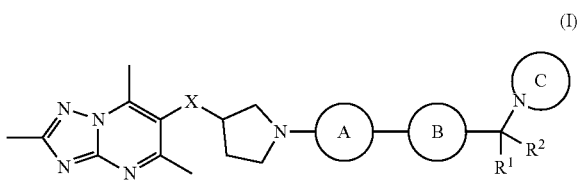

or a pharmaceutically acceptable salt thereof, wherein:

$R^1$ and $R^2$ each independently represent hydrogen or methyl;

X represents $CH_2$ or O;

Ring A and Ring B each independently represent a ring selected from phenyl, pyridinyl, pyrazinyl, pyrimidinyl and pyridazinyl, wherein each of Ring A and Ring B are independently optionally substituted with one or more substituents selected from $C_{1-3}$ alkyl and $C_{1-3}$ alkoxy;

Ring C represents a 5 to 9 membered monocyclic or bicyclic saturated heterocycloalkyl optionally containing one or more additional heteroatoms independently selected from O, N and S, wherein Ring C is optionally substituted with one or more substituents selected from $C_{1-3}$ alkyl, optionally substituted with methoxy or hydroxyl; dioxo, $C_{0-2}$ alkyl-$C(O)N(Me)_2$, $C(O)C_{1-2}$alkyl and $S(O)_2C_{1-2}$ alkyl.

This specification also describes, in part, a pharmaceutical composition which comprises a compound of Formula (I), or a pharmaceutically acceptable salt thereof, and at least one pharmaceutically acceptable excipient.

This specification also describes, in part, a compound of Formula (I), or a pharmaceutically acceptable salt thereof, for use in therapy.

This specification also describes, in part, a compound of Formula (I), or a pharmaceutically acceptable salt thereof, for use in the treatment of cancer.

This specification also describes, in part, a compound of Formula (I), or a pharmaceutically acceptable salt thereof, for the manufacture of a medicament for the treatment of cancer.

This specification also describes, in part, a method for treating cancer in a warm-blooded animal in need of such treatment, which comprises administering to the warm-blooded animal a therapeutically effective amount of a compound of Formula (I), or a pharmaceutically acceptable salt thereof.

DESCRIPTION OF ILLUSTRATIVE EMBODIMENTS

Figure 1:
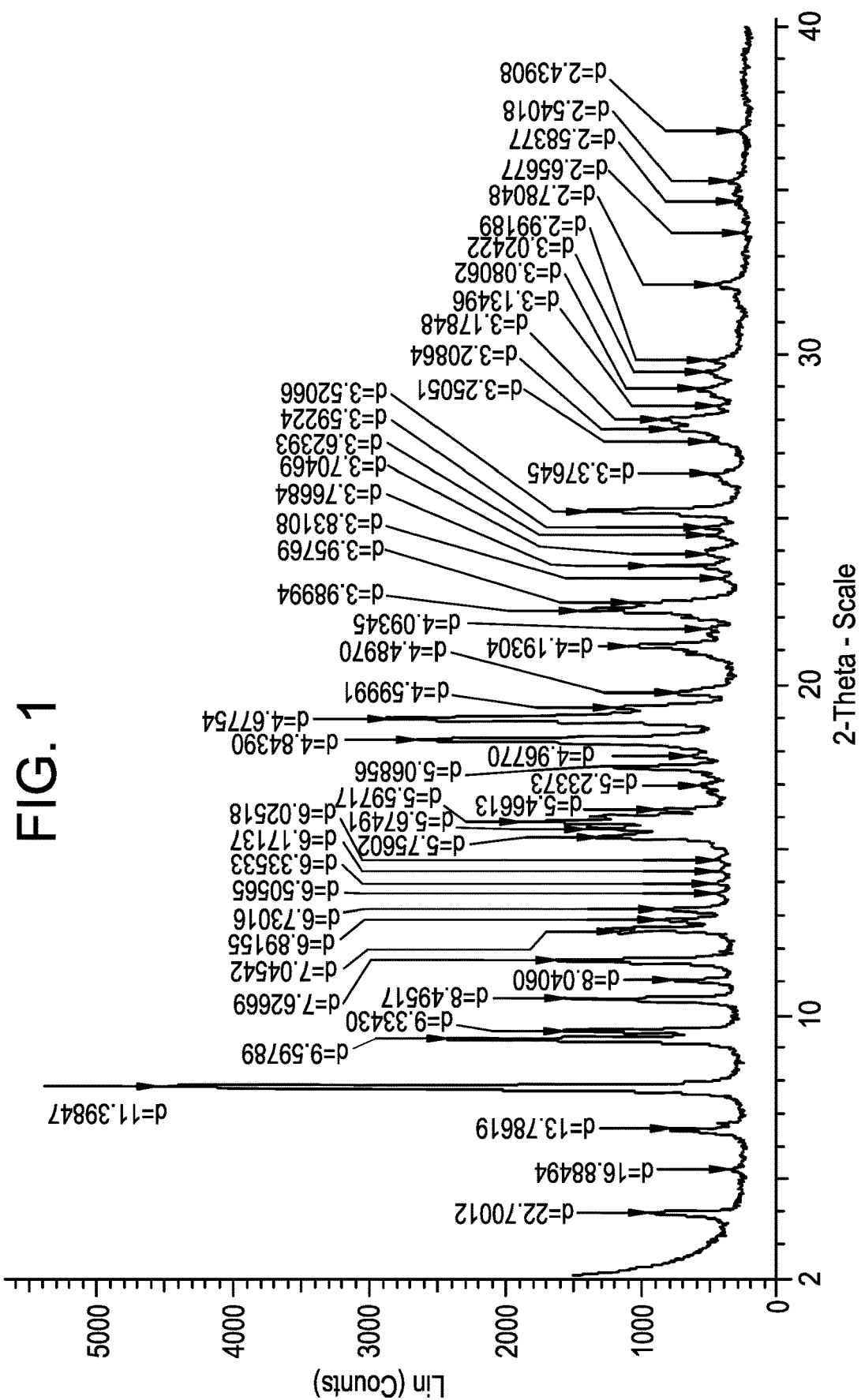
FIG. 1 shows the X-ray powder diffraction (XRPD) pattern for Form A of (R)-4-((6-(4-(3-((2,5,7-trimethyl-[1,2,4]triazolo[1,5-a]pyrimidin-6-yl)oxy)pyrrolidin-1-yl)phenyl)pyridazin-3-yl)methyl)morpholine (Compound A, Example 62).

Many embodiments of the invention are detailed throughout the specification and will be apparent to a reader skilled in the art. The invention is not to be interpreted as being limited to any particular embodiment(s) thereof.

In the first embodiment there is provided a compound of Formula (I):

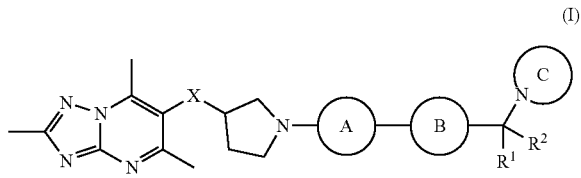

or a pharmaceutically acceptable salt thereof, wherein:

$R^1$ and $R^2$ each independently represent hydrogen or methyl;

X represents $CH_2$ or O;

Ring A and Ring B each independently represent a ring selected from phenyl, pyridinyl, pyrazinyl, pyrimidinyl and pyridazinyl, wherein each of Ring A and Ring B are independently optionally substituted with one or more substituents selected from $C_{1-3}$ alkyl and $C_{1-3}$ alkoxy;

Ring C represents a 5 to 9 membered monocyclic or bicyclic saturated heterocycloalkyl optionally containing one or more additional heteroatoms independently selected from O, N and S, wherein the heterocycloalkyl is optionally substituted with one or more substituents selected from $C_{1-3}$ alkyl, optionally substituted with methoxy or hydroxyl; dioxo, $C_{0-2}$ alkyl-$C(O)N(Me)_2$, $C(O)C_{1-2}$alkyl and $S(O)_2C_{1-2}$ alkyl.

The term "heterocycloalkyl" means a 5 to 9 membered saturated nitrogen-containing non-aromatic ring (Ring C in Formula (I)) comprising one or more additional heteroatoms independently selected from nitrogen, oxygen and sulphur. Examples of suitable heterocycloalkyl groups include morpholinyl, piperazinyl, piperidinyl, thiomorpholinyl, diazabicyclooctanyl, octahydropyrrolo[1,2-a]pyrazinyl, pyrrolidinyl, diazepanyl, oxazepanyl and azepanyl. For the avoidance of doubt, substituents on the heterocycloalkyl ring may be linked via either a carbon atom or a heteroatom.

The term "dioxo" means two oxo substituents which are attached to the same atom. Examples of dioxo substitution include instances where Ring C represents thiomorpholinyl, where the sulphur atom is substituted with two oxo groups, i.e. where Ring C is thiomorpholine-1,1-dioxide.

The prefix $C_{p-q}$ in $C_{p-q}$ alkyl and other terms (where p and q are integers) indicates the range of carbon atoms that are present in the group, for example $C_{1-3}$ alkyl includes $C_1$ alkyl (methyl), $C_2$ alkyl (ethyl) and $C_3$ alkyl (propyl as n-propyl and isopropyl). In one embodiment, the $C_{1-3}$ alkyl is methyl.

The term $C_{p-q}$ alkoxy comprises —O—$C_{p-q}$ alkyl groups. For example, $C_{1-3}$ alkoxy includes $C_1$ alkoxy (methoxy), $C_2$ alkoxy (ethoxy) and $C_3$ alkoxy (propoxy as n-propoxy and isopropoxy). In one embodiment, the $C_{1-3}$ alkoxy is methoxy.

Where the term "optionally" is used, it is intended that the subsequent feature may or may not occur. As such, use of the term "optionally" includes instances where the feature is present, and also instances where the feature is not present. For example, a group "optionally substituted by one methoxy group" includes groups with and without a methoxy substituent.

The term "substituted" means that one or more hydrogens (for example one or two hydrogens, or alternatively one hydrogen) on the designated group is replaced by the indicated substituent(s) (for example one or two substituents, or alternatively one substituent), provided that any atom(s) bearing a substituent maintains a permitted valency. Substituent combinations encompass only stable compounds and stable synthetic intermediates. "Stable" means that the relevant compound or intermediate is sufficiently robust to be isolated and have utility either as a synthetic intermediate or as an agent having potential therapeutic utility. If a group is not described as "substituted", or "optionally substituted", it is to be regarded as unsubstituted (i.e. that none of the hydrogens on the designated group have been replaced).

The term "pharmaceutically acceptable" is used to specify that an object (for example a salt, dosage form, excipient) is suitable for use in patients. An example list of pharmaceutically acceptable salts can be found in the *Handbook of Pharmaceutical Salts: Properties, Selection and Use*, P. H.

A further embodiment provides any of the embodiments defined herein (for example the embodiment of claim 1) with the proviso that one or more specific Examples (for instance, one, two or three specific Examples) selected from the group consisting of Examples 1, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86 and 87 is individually disclaimed.

In one embodiment, X represents $CH_2$. In another embodiment, X represents O.

In one embodiment, $R^1$ and $R^2$ both represent hydrogen. In another embodiment, $R^1$ and $R^2$ both represent methyl. In another embodiment, $R^1$ represents hydrogen and $R^2$ represents methyl. In one embodiment, $R^1$ and $R^2$ both represent hydrogen or $R^1$ represents hydrogen and $R^2$ represents methyl.

Ring A is selected from phenyl, pyridinyl, pyrazinyl, pyrimidinyl and pyridazinyl.

Ring B is selected from phenyl, pyridinyl, pyrazinyl, pyrimidinyl and pyridazinyl.

In Formula (I), Ring A is attached to the nitrogen of a pyrrolidine ring and to Ring B, and Ring B is attached to Ring A and to the group —$C(R^1R^2)$-Ring C. Ring A and Ring B may be optionally further substituted as defined herein. In one embodiment, the pyrrolidine ring and Ring B are in para (i.e. 1,4) orientation on Ring A. In another embodiment, Ring A and the group —$C(R^1R^2)$-Ring C are in para (i.e. 1,4) orientation on Ring B. In one embodiment, the pyrrolidine ring and Ring B are in para (i.e. 1,4) orientation on Ring A and Ring A and the group —$C(R^1R^2)$-Ring C are in para (i.e. 1,4) orientation on Ring B In yet another embodiment, the pyrrolidine ring and Ring B are in para (i.e. 1,4) orientation on Ring A and Ring A and the group —$C(R^1R^2)$-Ring C are in para (i.e. 1,4) orientation on Ring B and Ring A and Ring B are linked to each other via a ring carbon and are linked to the remainder of the molecule via a ring carbon.

In one embodiment, at least one of Ring A or Ring B is selected from pyridinyl, pyrazinyl, pyrimidinyl and pyridazinyl.

In one embodiment, Ring A and Ring B are each independently selected from phenyl, pyridazinyl and pyrazinyl. In another embodiment, Ring A and Ring B are each independently selected from phenyl and pyridazinyl. In another embodiment, Ring A is phenyl and Ring B is pyridazinyl. In another embodiment, Ring A is pyrazinyl and Ring B is phenyl.

In one embodiment, Ring A and Ring B are optionally substituted with one or two substituents selected from $C_{1-3}$ alkyl and $C_{1-3}$ alkoxy. In one embodiment, Ring A and Ring B are each independently optionally substituted by one substituent selected from $C_{1-3}$ alkyl and $C_{1-3}$ alkoxy. In one embodiment, Ring A and Ring B are each independently optionally substituted by one substituent selected from methyl and methoxy.

In one embodiment, Ring C represents a 5 to 7 membered monocyclic saturated heterocycloalkyl ring. In another embodiment, Ring C represents an 8 or 9 membered bicyclic saturated heterocycloalkyl ring. The bicyclic heterocycloalkyl ring may be a bridged or fused bicyclic ring.

In one embodiment, Ring C is selected from the group consisting of morpholinyl, piperazinyl, piperidinyl, thiomorpholinyl, diazabicyclooctanyl, octahydropyrrolo[1,2-a]pyrazinyl, pyrrolidinyl, diazepanyl, oxazepanyl and azepanyl.

In one embodiment, Ring C is selected from the group consisting of morpholin-4-yl, piperazin-4-yl, piperidin-1-yl, thiomorpholine-4-yl, 3,8-diazabicyclo[3.2.1]octan-8-yl, octahydropyrrolo[1,2-a]pyrazin-2-yl, pyrrolidine-1-yl, 1,4-diazepan-1-yl, 1,4-oxazepan-4-yl, azepanyl-1-yl.

In one embodiment, Ring C is morpholinyl or piperazinyl. In one embodiment, Ring C is morpholin-4-yl or piperazin-4-yl.

In one embodiment, Ring C is morpholinyl. In one embodiment, Ring C is morpholin-4-yl.

In one embodiment, Ring C is piperazinyl. In one embodiment, Ring C is piperazin-4-yl.

In one embodiment, Ring C is optionally substituted with one or more (e.g. one, two or three) substituents independently selected from hydroxyl; ethyl optionally substituted with methoxy or hydroxyl; dioxo, $C(O)N(Me)_2$, $CH_2C(O)N(Me)_2$, $C(O)Me$ and $S(O)_2Me$. In one embodiment, Ring C is substituted with $C(O)Me$ or methyl.

In one embodiment, Ring C is piperazin-4-yl-ethanone. In another embodiment, Ring C is 4-methyl-1-piperazinyl.

In one embodiment:
$R^1$ and $R^2$ are both hydrogen;
X represents $CH_2$ or O;
Ring A and Ring B each independently represent a ring selected from phenyl, pyridinyl, pyrazinyl, pyrimidinyl and pyridazinyl, wherein each of Ring A and Ring B are independently optionally substituted with one or more substituents selected from $C_{1-3}$ alkyl and $C_{1-3}$ alkoxy;
Ring C represents a 5 to 9 membered monocyclic or bicyclic saturated heterocycloalkyl optionally containing one or more additional heteroatoms independently selected from O, N and S, wherein the heterocycloalkyl is optionally substituted with one or more substituents selected from $C_{1-3}$ alkyl, optionally substituted with methoxy or hydroxyl; dioxo, $C_{0-2}$ alkyl-$C(O)N(Me)_2$, $C(O)C_{1-2}$alkyl and $S(O)_2$ $C_{1-2}$alkyl.

In one embodiment:
$R^1$ and $R^2$ are both hydrogen;
X represents O;
Ring A and Ring B are each independently selected from phenyl and pyridazinyl;
Ring C represents morpholinyl or piperazinyl wherein the piperazinyl is optionally substituted with $C_{1-3}$ alkyl, optionally substituted with methoxy or hydroxyl; $C_{0-2}$ alkyl-$C(O)N(Me)_2$, $C(O)C_{1-2}$ alkyl and $S(O)_2C_{1-2}$ alkyl.

In one embodiment:
$R^1$ and $R^2$ are both hydrogen;
X represents $CH_2$;
Ring A and Ring B are each independently selected from phenyl, pyridazinyl and pyrazinyl;
Ring C represents morpholinyl, piperazinyl or pyrazinyl wherein the pyrazinyl or piperazinyl is optionally substituted with $C_{1-3}$ alkyl, optionally substituted with methoxy or hydroxyl; $C_{0-2}$ alkyl-$C(O)N(Me)_2$, $C(O)C_{1-2}$ alkyl and $S(O)_2C_{1-2}$alkyl.

A further embodiment provides a compound of Formula (Ia):

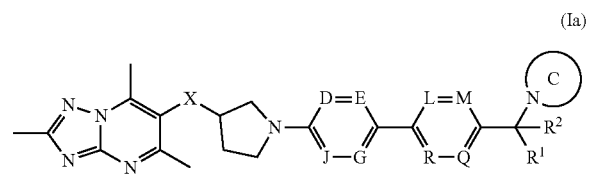

or a pharmaceutically acceptable salt thereof, wherein
$R^1$ and $R^2$ each independently represent hydrogen or methyl;
X represents $CH_2$ or O;
D, E, G, J, L, M, Q and R each independently represent N or $CR^3$, wherein no more than two of D, E, G and J represent N and wherein no more than two of L, M, Q and R represent N;
$R^3$ represents hydrogen, $C_{1-3}$ alkyl or $C_{1-3}$ alkoxy;
Ring C represents a 5 to 9 membered monocyclic or bicyclic saturated heterocycloalkyl optionally containing one or more additional heteroatoms independently selected from O, N and S, wherein the heterocycloalkyl is optionally substituted with one or more substituents selected from $C_{1-3}$ alkyl, optionally substituted with methoxy or hydroxyl; dioxo, $C_{0-2}$ alkyl-$C(O)N(Me)_2$, $C(O)C_{1-2}$alkyl and $S(O)_2C_{1-2}$ alkyl.

In one embodiment, $R^1$ and $R^2$ both represent hydrogen. In another embodiment, $R^1$ and $R^2$ both represent methyl. In another embodiment, $R^1$ represents hydrogen and $R^2$ represents methyl. In one embodiment, $R^1$ and $R^2$ both represent hydrogen or $R^1$ represents hydrogen and $R^2$ represents methyl.

D, E, G and J each independently represent N or $CR^3$, wherein no more than two of D, E, G and J represent N.

L, M, Q and R each independently represent N or $CR^3$, wherein no more than two of L, M, Q and R represent N.

In one embodiment, D, E, G and J each independently represent $CR^3$. In another embodiment, one of D, E, G and J represents N and the remainder each independently represent $CR^3$. In another embodiment, two of D, E, G and J represent N and the remainder both independently represent $CR^3$.

In one embodiment, L, M, Q and R each independently represent $CR^3$. In another embodiment, one of L, M, Q and R represents N and the remainder each independently represent $CR^3$. In another embodiment, two of L, M, Q and R represent N and the remainder both independently represent $CR^3$.

In one embodiment, D, E, G and J each independently represent $CR^3$ and L, M, Q and R each independently represent N or $CR^3$, wherein no more than two of L, M, Q and R represent N. In one embodiment, one of D, E, G and J represents N and the remainder each independently represent $CR^3$ and L, M, Q and R each independently represent N or $CR^3$, wherein no more than two of L, M, Q and R represent N. In one embodiment, two of D, E, G and J represent N and the remainder both independently represent $CR^3$ and L, M, Q and R each independently represent N or $CR^3$, wherein no more than two of L, M, Q and R represent N.

In one embodiment, D, E, G and J represent N or $CR^3$, wherein no more than two of D, E, G and J represent N and L, M, Q and R each independently represent $CR^3$. In one embodiment, D, E, G and J represent N or $CR^3$, wherein no more than two of D, E, G and J represent N and one of L, M, Q and R represents N and the remainder each independently represent $CR^3$. In one embodiment, D, E, G and J represent N or $CR^3$, wherein no more than two of D, E, G and J represent N and two of L, M, Q and R represent N and the remainder both independently represent $CR^3$.

In one embodiment, D, E, G and J each independently represent $CR^3$ and L, M, Q and R each independently represent $CR^3$.

In one embodiment, D, E, G and J each independently represent $CR^3$ and one of L, M, Q and R represents N and the remainder each independently represent $CR^3$.

In one embodiment, D, E, G and J each independently represent $CR^3$ and two of L, M, Q and R represent N and the remainder both independently represent $CR^3$.

In one embodiment, one of D, E, G and J represents N and the remainder each independently represent $CR^3$ and L, M, Q and R each independently represent $CR^3$.

In one embodiment, one of D, E, G and J represents N and the remainder each independently represent $CR^3$ and one of L, M, Q and R represents N and the remainder each independently represent $CR^3$.

In one embodiment, one of D, E, G and J represents N and the remainder each independently represent $CR^3$ and two of L, M, Q and R represent N and the remainder both independently represent $CR^3$.

In one embodiment, two of D, E, G and J represent N and the remainder both independently represent $CR^3$ and L, M, Q and R each independently represent $CR^3$.

In one embodiment, two of D, E, G and J represent N and the remainder both independently represent $CR^3$ and one of L, M, Q and R represents N and the remainder each independently represent $CR^3$.

In one embodiment, two of D, E, G and J represent N and the remainder both independently represent $CR^3$ and two of L, M, Q and R represent N and the remainder both independently represent $CR^3$.

In one embodiment, the ring containing D, E, G and J is a ring selected from phenyl, pyridinyl, pyrazinyl, pyrimidinyl and pyridazinyl. In one embodiment, the ring containing D, E, G and J is a ring selected from phenyl, pyridazinyl and pyrazinyl. In one embodiment, the ring is selected from phenyl and pyridazinyl.

In one embodiment, the ring containing L, M, Q and R is a ring selected from phenyl, pyridinyl, pyrazinyl, pyrimidinyl and pyridazinyl. In one embodiment, the ring containing L, M, Q and R is a ring selected from phenyl, pyridazinyl and pyrazinyl. In one embodiment, the ring is selected from phenyl and pyridazinyl.

In another embodiment, the ring containing D, E, G and J is phenyl and the ring containing L, M, Q and R is pyridazinyl. In another embodiment, the ring containing D, E, G and J is pyrazinyl and the ring containing L, M, Q and R is phenyl.

In one embodiment, the ring containing D, E, G and J and the ring containing L, M, Q and R are each independently optionally substituted with one or two substituents, i.e. where $R^3$ represents $C_{1-3}$ alkyl and $C_{1-3}$ alkoxy. In one embodiment, the ring containing D, E, G and J and the ring containing L, M, Q and R are each independently optionally substituted with one substituent, i.e. where $R^3$ represents $C_{1-3}$ alkyl and $C_{1-3}$ alkoxy. In one embodiment, the ring containing D, E, G and J and the ring containing L, M, Q and R are each independently optionally substituted with one substituent where $R^3$ is selected from methyl and methoxy.

In one embodiment, Ring C represents a 5 to 7 membered monocyclic saturated heterocycloalkyl ring. In another embodiment, Ring C represents an 8 or 9 membered bicyclic saturated heterocycloalkyl ring. The bicyclic heterocycloalkyl ring may be a bridged or fused bicyclic ring.

In one embodiment, Ring C is selected from the group consisting of morpholinyl, piperazinyl, piperidinyl, thiomorpholinyl, diazabicyclooctanyl, octahydropyrrolo[1,2-a]pyrazinyl, pyrrolidinyl, diazepanyl, oxazepanyl and azepanyl.

In one embodiment, Ring C is selected from the group consisting of morpholin-4-yl, piperazin-4-yl, piperidin-1-yl, thiomorpholine-4-yl, 3,8-diazabicyclo[3.2.1]octan-8-yl, octahydropyrrolo[1,2-a]pyrazin-2-yl, pyrrolidine-1-yl, 1,4-diazepan-1-yl, 1,4-oxazepan-4-yl, azepanyl-1-yl.

In one embodiment, Ring C is morpholinyl or piperazinyl. In one embodiment, Ring C is morpholin-4-yl or piperazin-4-yl.

In one embodiment, Ring C is morpholinyl. In one embodiment, Ring C is morpholin-4-yl.

In one embodiment, Ring C is piperazinyl. In one embodiment, Ring C is piperazin-4-yl.

In one embodiment, Ring C is optionally substituted with one or more (e.g. one, two or three) substituents independently selected from hydroxyl; ethyl optionally substituted with methoxy or hydroxyl; dioxo, $C(O)N(Me)_2$, $CH_2C(O)N(Me)_2$, $C(O)Me$ and $S(O)_2Me$. In one embodiment, Ring C is substituted with $C(O)Me$ or methyl.

In one embodiment, Ring C is piperazin-4-yl-ethanone. In another embodiment, Ring C is 4-methyl-1-piperazinyl.

In one embodiment:
$R^1$ and $R^2$ are both hydrogen;
X represents $CH_2$ or O;
D, E, G, J, L, M, Q and R each independently represent N or $CR^3$, wherein no more than two of D, E, G and J represent N and wherein no more than two of L, M, Q and R represent N;
$R^3$ represents hydrogen, $C_{1-3}$ alkyl or $C_{1-3}$ alkoxy;
Ring C represents a 5 to 9 membered monocyclic or bicyclic saturated heterocycloalkyl optionally containing one or more additional heteroatoms independently selected from O, N and S, wherein the heterocycloalkyl is optionally substituted with one or more substituents selected from $C_{1-3}$ alkyl, optionally substituted with methoxy or hydroxyl; dioxo, $C_{0-2}$ alkyl-$C(O)N(Me)_2$, $C(O)C_{1-2}$ alkyl and $S(O)_2C_{1-2}$ alkyl.

In one embodiment:
$R^1$ and $R^2$ are both hydrogen;
X represents O;
D, E, G, J, L, M, Q and R each independently represent N or $CR^3$, wherein no more than two of D, E, G and J represent N and wherein no more than two of L, M, Q and R represent N;
$R^3$ represents hydrogen, methyl or methoxy;
Ring C represents morpholinyl or piperazinyl wherein the piperazinyl is optionally substituted with $C_{1-3}$ alkyl, optionally substituted with methoxy or hydroxyl; $C_{0-2}$ alkyl-$C(O)N(Me)_2$, $C(O)C_{1-2}$ alkyl and $S(O)_2C_{1-2}$ alkyl.

In one embodiment:
$R^1$ and $R^2$ are both hydrogen;
X represents $CH_2$;
D, E, G, J, L, M, Q and R each independently represent N or $CR^3$, wherein no more than two of D, E, G and J represent N and wherein no more than two of L, M, Q and R represent N;
$R^3$ is selected from hydrogen, methyl or methoxy;
Ring C represents morpholinyl, piperazinyl or pyrazinyl wherein the pyrazinyl or piperazinyl is optionally substituted with $C_{1-3}$ alkyl, optionally substituted with methoxy or hydroxyl; $C_{0-2}$ alkyl-$C(O)N(Me)_2$, $C(O)C_{1-2}$ alkyl and $S(O)_2C_{1-2}$ alkyl.

A further embodiment provides a compound of Formula (Ib):

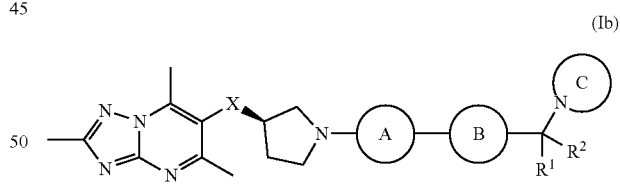

(Ib)

or a pharmaceutically acceptable salt thereof, wherein $R^1$, $R^2$, X, Ring A, Ring B and Ring C are as defined herein.

A further embodiment provides a compound of Formula (Ic):

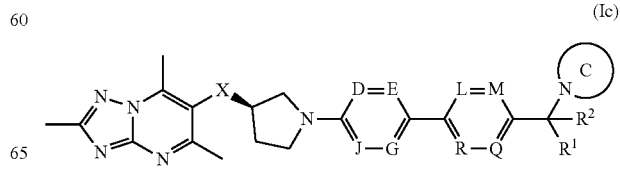

(Ic)

or a pharmaceutically acceptable salt thereof, wherein R¹, R², X, D, E, G, J, L, M, Q, R and Ring C are as defined herein.

In one embodiment there is provided a compound of Formula (I), or a pharmaceutically acceptable salt thereof, wherein the compound is selected from the group consisting of:

(R)-4-((6'-(3-((2,5,7-trimethyl-[1,2,4]triazolo[1,5-a]pyrimidin-6-yl)methyl)pyrrolidin-1-yl)-[3,3'-bipyridin]-6-yl)methyl)morpholine;

(R)-2,5,7-trimethyl-6-((1-(6'-((4-methylpiperazin-1-yl)methyl)-[3,3'-bipyridin]-6-yl)pyrrolidin-3-yl)methyl)-[1,2,4]triazolo[1,5-a]pyrimidine;

(R)-2,5,7-trimethyl-6-((1-(5-(4-((4-methylpiperazin-1-yl)methyl)phenyl)pyridin-2-yl)pyrrolidin-3-yl)methyl)-[1,2,4]triazolo[1,5-a]pyrimidine;

(R)-4-(4-(2-(3-((2,5,7-trimethyl-[1,2,4]triazolo[1,5-a]pyrimidin-6-yl)methyl)pyrrolidin-1-yl)pyrimidin-5-yl)benzyl)morpholine;

(R)-4-((5-(5-(3-((2,5,7-trimethyl-[1,2,4]triazolo[1,5-a]pyrimidin-6-yl)methyl)pyrrolidin-1-yl)pyridin-2-yl)pyrazin-2-yl)methyl)morpholine;

(R)-2,5,7-trimethyl-6-((1-(6-(4-((4-methylpiperazin-1-yl)methyl)phenyl)pyridin-3-yl)pyrrolidin-3-yl)methyl)-[1,2,4]triazolo[1,5-a]pyrimidine;

(R)-4-((6-(5-(3-((2,5,7-trimethyl-[1,2,4]triazolo[1,5-a]pyrimidin-6-yl)methyl)pyrrolidin-1-yl)pyridin-2-yl)pyridazin-3-yl)methyl)morpholine;

6-(((R)-1-(2-(4-(((S)-2,4-dimethylpiperazin-1-yl)methyl)phenyl)pyrimidin-5-yl)pyrrolidin-3-yl)methyl)-2,5,7-trimethyl-[1,2,4]triazolo[1,5-a]pyrimidine;

(R)-4-((5-(5-(3-((2,5,7-trimethyl-[1,2,4]triazolo[1,5-a]pyrimidin-6-yl)methyl)pyrrolidin-1-yl)pyrimidin-2-yl)pyridin-2-yl)methyl)morpholine;

(R)-6-((1-(2-(2-methoxy-4-((4-methylpiperazin-1-yl)methyl)phenyl)pyrimidin-5-yl)pyrrolidin-3-yl)methyl)-2,5,7-trimethyl-[1,2,4]triazolo[1,5-a]pyrimidine;

(R)-2,5,7-trimethyl-6-((1-(2-(2-methyl-4-((4-methylpiperazin-1-yl)methyl)phenyl)pyrimidin-5-yl)pyrrolidin-3-yl)methyl)-[1,2,4]triazolo[1,5-a]pyrimidine;

6-(((R)-1-(2-(4-(((3R,5S)-3,5-dimethylpiperazin-1-yl)methyl)phenyl)pyrimidin-5-yl)pyrrolidin-3-yl)methyl)-2,5,7-trimethyl-[1,2,4]triazolo[1,5-a]pyrimidine;

(R)-N,N-dimethyl-2-(4-(4-(5-(3-((2,5,7-trimethyl-[1,2,4]triazolo[1,5-a]pyrimidin-6-yl)methyl)pyrrolidin-1-yl)pyrimidin-2-yl)benzyl)piperazin-1-yl)acetamide;

(R)-2-(4-(4-(5-(3-((2,5,7-trimethyl-[1,2,4]triazolo[1,5-a]pyrimidin-6-yl)methyl)pyrrolidin-1-yl)pyrimidin-2-yl)benzyl)piperazin-1-yl)ethanol;

(R)-1-(4-(4-(5-(3-((2,5,7-trimethyl-[1,2,4]triazolo[1,5-a]pyrimidin-6-yl)methyl)pyrrolidin-1-yl)pyrimidin-2-yl)benzyl)piperazin-1-yl)ethenone;

(R)-6-((1-(2-(4-((4-(2-methoxyethyl)piperazin-1-yl)methyl)phenyl)pyrimidin-5-yl)pyrrolidin-3-yl)methyl)-2,5,7-trimethyl-[1,2,4]triazolo[1,5-a]pyrimidine;

(R)-4-(4-(5-(3-((2,5,7-trimethyl-[1,2,4]triazolo[1,5-a]pyrimidin-6-yl)methyl)pyrrolidin-1-yl)pyrimidin-2-yl)benzyl)morpholine;

(R)-2,5,7-trimethyl-6-((1-(2-(4-((4-methylpiperazin-1-yl)methyl)phenyl)pyrimidin-5-yl)pyrrolidin-3-yl)methyl)-[1,2,4]triazolo[1,5-a]pyrimidine;

(R)-2,5,7-trimethyl-6-((1-(4-(5-((4-methylpiperazin-1-yl)methyl)pyrazin-2-yl)phenyl)pyrrolidin-3-yl)methyl)-[1,2,4]triazolo[1,5-a]pyrimidine;

(R)-2,5,7-trimethyl-6-((1-(4-(2-((4-methylpiperazin-1-yl)methyl)pyrimidin-5-yl)phenyl)pyrrolidin-3-yl)methyl)-[1,2,4]triazolo[1,5-a]pyrimidine;

(R)-4-((6-(4-(3-((2,5,7-trimethyl-[1,2,4]triazolo[1,5-a]pyrimidin-6-yl)methyl)pyrrolidin-1-yl)phenyl)pyridin-3-yl)methyl)morpholine;

(R)-2,5,7-trimethyl-6-((1-(4-(6-((4-methylpiperazin-1-yl)methyl)pyridazin-3-yl)phenyl)pyrrolidin-3-yl)methyl)-[1,2,4]triazolo[1,5-a]pyrimidine;

(R)-2,5,7-trimethyl-6-((1-(4-(5-((4-methylpiperazin-1-yl)methyl)pyrimidin-2-yl)phenyl)pyrrolidin-3-yl)methyl)-[1,2,4]triazolo[1,5-a]pyrimidine;

(R)-4-((6-(4-(3-((2,5,7-trimethyl-[1,2,4]triazolo[1,5-a]pyrimidin-6-yl)methyl)pyrrolidin-1-yl)phenyl)pyrazin-2-yl)methyl)morpholine;

(R)-2,5,7-trimethyl-6-((1-(4-(5-((4-methylpiperazin-1-yl)methyl)pyridin-2-yl)phenyl)pyrrolidin-3-yl)methyl)-[1,2,4]triazolo[1,5-a]pyrimidine;

(R)-4-(4-((3-((2,5,7-trimethyl-[1,2,4]triazolo[1,5-a]pyrimidin-6-yl)methyl)pyrrolidin-1-yl)phenyl)pyrimidin-2-yl)methyl)morpholine;

(R)-4-((6-(4-(3-((2,5,7-trimethyl-[1,2,4]triazolo[1,5-a]pyrimidin-6-yl)methyl)pyrrolidin-1-yl)phenyl)pyridazin-3-yl)methyl)morpholine;

(S)-4-((6-(4-(3-((2,5,7-trimethyl-[1,2,4]triazolo[1,5-a]pyrimidin-6-yl)methyl)pyrrolidin-1-yl)phenyl)pyridazin-3-yl)methyl)morpholine;

(R)-6-((1-(5-(2-methoxy-4-((4-methylpiperazin-1-yl)methyl)phenyl)-6-methylpyrazin-2-yl)pyrrolidin-3-yl)methyl)-2,5,7-trimethyl-[1,2,4]triazolo[1,5-a]pyrimidine;

2,5,7-trimethyl-6-(((R)-1-(5-(4-(((3R,5S)-3,4,5-trimethylpiperazin-1-yl)methyl)phenyl)pyrazin-2-yl)pyrrolidin-3-yl)methyl)-[1,2,4]triazolo[1,5-a]pyrimidine;

6-(((R)-1-(5-(4-(((R)-3,4-dimethylpiperazin-1-yl)methyl)phenyl)pyrazin-2-yl)pyrrolidin-3-yl)methyl)-2,5,7-trimethyl-[1,2,4]triazolo[1,5-a]pyrimidine;

6-(((R)-1-(5-(4-(((R)-2,4-dimethylpiperazin-1-yl)methyl)phenyl)pyrazin-2-yl)pyrrolidin-3-yl)methyl)-2,5,7-trimethyl-[1,2,4]triazolo[1,5-a]pyrimidine;

2,5,7-trimethyl-6-(((R)-1-(5-(4-(((2R,5R)-2,4,5-trimethylpiperazin-1-yl)methyl)phenyl)pyrazin-2-yl)pyrrolidin-3-yl)methyl)-[1,2,4]triazolo[1,5-a]pyrimidine;

2,5,7-trimethyl-6-(((R)-1-(5-(4-(((2S,5R)-2,4,5-trimethylpiperazin-1-yl)methyl)phenyl)pyrazin-2-yl)pyrrolidin-3-yl)methyl)-[1,2,4]triazolo[1,5-a]pyrimidine;

2,5,7-trimethyl-6-[[(3R)-1-[5-[4-(1-piperidylmethyl)phenyl]pyrazin-2-yl]pyrrolidin-3-yl]methyl]-[1,2,4]triazolo[1,5-a]pyrimidine;

(R)-6-((1-(5-(4-((4-ethylpiperazin-1-yl)methyl)phenyl)pyrazin-2-yl)pyrrolidin-3-yl)methyl)-2,5,7-trimethyl-[1,2,4]triazolo[1,5-a]pyrimidine;

(R)-2,5,7-trimethyl-6-((1-(5-(5-((4-methylpiperazin-1-yl)methyl)pyridin-2-yl)pyrazin-2-yl)pyrrolidin-3-yl)methyl)-[1,2,4]triazolo[1,5-a]pyrimidine;

6-(((R)-1-(5-(4-(((3R,5S)-3,5-dimethylpiperazin-1-yl)methyl)phenyl)pyrazin-2-yl)pyrrolidin-3-yl)methyl)-2,5,7-trimethyl-[1,2,4]triazolo[1,5-a]pyrimidine;

2-{4-[4-(5-{(3R)-3-[(2,5,7-trimethyl[1,2,4]triazolo[1,5-a]pyrimidin-6-yl)methyl]pyrrolidin-1-yl}pyrazin-2-yl)benzyl]piperazin-1-yl}ethanol;

(R)-6-((1-(5-(4-((4-(2-methoxyethyl)piperazin-1-yl)methyl)phenyl)pyrazin-2-yl)pyrrolidin-3-yl)methyl)-2,5,7-trimethyl-[1,2,4]triazolo[1,5-a]pyrimidine;

(R)-6-((1-(5-(2-methoxy-4-((4-methylpiperazin-1-yl)methyl)phenyl)pyrazin-2-yl)pyrrolidin-3-yl)methyl)-2,5,7-trimethyl-[1,2,4]triazolo[1,5-a]pyrimidine;

{1-[4-(5-{(3R)-3-[(2,5,7-trimethyl[1,2,4]triazolo[1,5-a]pyrimidin-6-yl)methyl]pyrrolidin-1-yl}pyrazin-2-yl)benzyl]piperidin-4-yl}methanol;

6-{[(3R)-1-(5-{4-[(1,1-dioxidothiomorpholin-4-yl)methyl] phenyl}pyrazin-2-yl)pyrrolidin-3-yl]methyl}-2,5,7-trimethyl[1,2,4]triazolo[1,5-a]pyrimidine;

2,5,7-trimethyl-6-({(3R)-1-[5-(4-{[4-(methylsulfonyl)piperidin-1-yl]methyl}phenyl)pyrazin-2-yl]pyrrolidin-3-yl}methyl) [1,2,4]triazolo[1,5-a]pyrimidine;

(R)-4-((6-(3-methyl-5-(3-((2,5,7-trimethyl-[1,2,4]triazolo[1,5-a]pyrimidin-6-yl)methyl)pyrrolidin-1-yl)pyrazin-2-yl)pyridin-3-yl)methyl)morpholine;

6-(((R)-1-(5-(4-(((S)-3,4-dimethylpiperazin-1-yl)methyl) phenyl)pyrazin-2-yl)pyrrolidin-3-yl)methyl)-2,5,7-trimethyl-[1,2,4]triazolo[1,5-a]pyrimidine;

(R)-4-((5-(5-(3-((2,5,7-trimethyl-[1,2,4]triazolo[1,5-a]pyrimidin-6-yl)methyl)pyrrolidin-1-yl)pyrazin-2-yl)pyridin-2-yl)methyl)morpholine;

6-(((R)-1-(5-(4-(((S)-2,4-dimethylpiperazin-1-yl)methyl) phenyl)pyrazin-2-yl)pyrrolidin-3-yl)methyl)-2,5,7-trimethyl-[1,2,4]triazolo[1,5-a]pyrimidine;

(R)-4-(4-3-methyl-5-(3-((2,5,7-trimethyl[1,2,4]triazolo[1, 5-a]pyrimidin-6-yl)methyl)pyrrolidin-1-yl)pyrazin-2-yl) benzyl)morpholine;

2,5,7-trimethyl-6-({(3R)-1-[5-(4-{[4-(methylsulfonyl)piperazin-1-yl]methyl}phenyl)pyrazin-2-yl]pyrrolidin-3-yl}methyl) [1,2,4]triazolo[1,5-a]pyrimidine;

(R)-N,N-dimethyl-2-(4-(4-(5-(3-((2,5,7-trimethyl-[1,2,4]triazolo[1,5-a]pyrimidin-6-yl)methyl)pyrrolidin-1-yl) pyrazin-2-yl)benzyl)piperazin-1-yl)acetamide;

(R)-2,5,7-trimethyl-6-((1-(6-methyl-5-(4-((4-methylpiperazin-1-yl)methyl)phenyl)pyrazin-2-yl)pyrrolidin-3-yl) methyl)-[1,2,4]triazolo[1,5-a]pyrimidine;

N,N-dimethyl-4-[4-(5-{(3R)-3-[(2,5,7-trimethyl[1,2,4]triazolo[1,5-a]pyrimidin-6-yl)methyl]pyrrolidin-1-yl}pyrazin-2-yl)benzyl]piperazine-1-carboxamide;

(R)-2,5,7-trimethyl-6-((1-(5-(3-methyl-4-((4-methylpiperazin-1-yl)methyl)phenyl)pyrazin-2-yl)pyrrolidin-3-yl) methyl)-[1,2,4]triazolo[1,5-a]pyrimidine;

(R)-2,5,7-trimethyl-6-((1-(5-(6-((4-methylpiperazin-1-yl) methyl)pyridin-3-yl)pyrazin-2-yl)pyrrolidin-3-yl) methyl)-[1,2,4]triazolo[1,5-a]pyrimidine;

(R)-1-(4-(4-(5-(3-((2,5,7-trimethyl-[1,2,4]triazolo[1,5-a]pyrimidin-6-yl)methyl)pyrrolidin-1-yl)pyrazin-2-yl)benzyl) piperazin-1-yl)ethenone;

(R)-2,5,7-trimethyl-6-((1-(5-(4-((4-methylpiperazin-1-yl) methyl)phenyl)pyrazin-2-yl)pyrrolidin-3-yl)methyl)-[1,2, 4]triazolo[1,5-a]pyrimidine;

(R)-4-(4-(5-(3-((2,5,7-trimethyl-[1,2,4]triazolo[1,5-a]pyrimidin-6-yl)methyl)pyrrolidin-1-yl)pyrazin-2-yl)benzyl) morpholine;

(R)-4-(4-(6-(3-((2,5,7-trimethyl-[1,2,4]triazolo[1,5-a]pyrimidin-6-yl)methyl)pyrrolidin-1-yl)pyridazin-3-yl)benzyl)morpholine;

(R)-4-((6-(4-(3-((2,5,7-trimethyl-[1,2,4]triazolo[1,5-a]pyrimidin-6-yl)oxy)pyrrolidin-1-yl)phenyl)pyridazin-3-yl) methyl)morpholine;

(S)-4-((6-(4-(3-((2,5,7-trimethyl-[1,2,4]triazolo[1,5-a]pyrimidin-6-yl)oxy)pyrrolidin-1-yl)phenyl)pyridazin-3-yl) methyl)morpholine;

(R)-2,5,7-trimethyl-6-((1-(4-(6-(piperidin-1-ylmethyl) pyridazin-3-yl)phenyl)pyrrolidin-3-yl)oxy)-[1,2,4]triazolo[1,5-a]pyrimidine;

(R)-2,5,7-trimethyl-6-((1-(4-(6-((4-methylpiperazin-1-yl) methyl)pyridazin-3-yl)phenyl)pyrrolidin-3-yl)oxy)-[1,2, 4]triazolo[1,5-a]pyrimidine;

2,5,7-trimethyl-6-(((3R)-1-(4-(6-((3-methyl-3,8-diazabicyclo[3.2.1]octan-8-yl)methyl)pyridazin-3-yl)phenyl)pyrrolidin-3-yl)oxy)-[1,2,4]triazolo[1,5-a]pyrimidine;

6-(((R)-1-(4-(6-(((R)-hexahydropyrrolo[1,2-a]pyrazin-2 (1H)-yl)methyl)pyridazin-3-yl)phenyl)pyrrolidin-3-yl) oxy)-2,5,7-trimethyl-[1,2,4]triazolo[1,5-a]pyrimidine;

6-(((R)-1-(4-(6-(((S)-hexahydropyrrolo[1,2-a]pyrazin-2 (1H)-yl)methyl)pyridazin-3-yl)phenyl)pyrrolidin-3-yl) oxy)-2,5,7-trimethyl-[1,2,4]triazolo[1,5-a]pyrimidine;

(R)-4-((5-(4-(3-((2,5,7-trimethyl-[1,2,4]triazolo[1,5-a]pyrimidin-6-yl)oxy)pyrrolidin-1-yl)phenyl)pyrimidin-2-yl) methyl)morpholine;

(R)-4-((5-(4-(3-((2,5,7-trimethyl-[1,2,4]triazolo[1,5-a]pyrimidin-6-yl)oxy)pyrrolidin-1-yl)phenyl)pyrazin-2-yl) methyl)morpholine;

(R)-1-(4-((6-(4-(3-((2,5,7-trimethyl-[1,2,4]triazolo[1,5-a] pyrimidin-6-yl)oxy)pyrrolidin-1-yl)phenyl)pyridazin-3-yl)methyl)piperazin-1-yl)ethan-1-one;

(R)-6-((1-(4-(6-((4-ethylpiperazin-1-yl)methyl)pyridazin-3-yl)phenyl)pyrrolidin-3-yl)oxy)-2,5,7-trimethyl-[1,2,4]triazolo[1,5-a]pyrimidine;

(R)-6-((1-(4-(6-((4-(2-methoxyethyl)piperazin-1-yl)methyl) pyridazin-3-yl)phenyl)pyrrolidin-3-yl)oxy)-2,5,7-trimethyl-[1,2,4]triazolo[1,5-a]pyrimidine;

(R)-4-((6'-(3-((2,5,7-trimethyl-[1,2,4]triazolo[1,5-a]pyrimidin-6-yl)oxy)pyrrolidin-1-yl)-[2,3-bipyridin]-5-yl) methyl)morpholine;

(R)-4-((6'-(3-((2,5,7-trimethyl-[1,2,4]triazolo[1,5-a]pyrimidin-6-yl)oxy)pyrrolidin-1-yl)-[3,3-bipyridin]-6-yl) methyl)morpholine;

(R)-2,5,7-trimethyl-6-((1-(2-(4-((4-methylpiperazin-1-yl) methyl)phenyl)pyrimidin-5-yl)pyrrolidin-3-yl)oxy)-[1,2, 4]triazolo[1,5-a]pyrimidine;

(R)-2,5,7-trimethyl-6-((1-(5-(4-((4-methylpiperazin-1-yl) methyl)phenyl)pyrazin-2-yl)pyrrolidin-3-yl)oxy)-[1,2,4] triazolo[1,5-a]pyrimidine;

(R)-4-(4-(5-(3-((2,5,7-trimethyl-[1,2,4]triazolo[1,5-a]pyrimidin-6-yl)oxy)pyrrolidin-1-yl)pyrazin-2-yl)benzyl) morpholine;

1-[4-[[4-[5-[(3R)-3-[(2,5,7-trimethyl-[1,2,4]triazolo[1,5-a] pyrimidin-6-yl)methyl]pyrrolidin-1-yl]pyrazin-2-yl]phenyl]methyl]-1,4-diazepan-1-yl]ethenone; (R)-2,5,7-trimethyl-6-((1-(5-(4-(pyrrolidin-1-ylmethyl)phenyl)pyrazin-2-yl)pyrrolidin-3-yl)methyl)-[1,2,4]triazolo[1,5-a] pyrimidine;

(R)-2,5,7-trimethyl-6-((1-(5-(5-(pyrrolidin-1-ylmethyl)pyridin-2-yl)pyrazin-2-yl)pyrrolidin-3-yl)methyl)-[1,2,4]triazolo[1,5-a]pyrimidine;

(R)-2,5,7-trimethyl-6-((1-(5-(6-(pyrrolidin-1-ylmethyl)pyridin-3-yl)pyrazin-2-yl)pyrrolidin-3-yl)methyl)-[1,2,4]triazolo[1,5-a]pyrimidine;

(R)-2,5,7-trimethyl-6-((1-(5-(4-((4-methyl-1,4-diazepan-1-yl)methyl)phenyl)pyrazin-2-yl)pyrrolidin-3-yl)methyl)-[1,2,4]triazolo[1,5-a]pyrimidine;

(R)-4-((6-(4-(3-((2,5,7-trimethyl-[1,2,4]triazolo[1,5-a]pyrimidin-6-yl)oxy)pyrrolidin-1-yl)phenyl)pyridazin-3-yl) methyl)-1,4-oxazepane;

(R)-6-((1-(4-(6-(azepan-1-ylmethyl)pyridazin-3-yl)phenyl) pyrrolidin-3-yl)oxy)-2,5,7-trimethyl-[1,2,4]triazolo[1,5-a]pyrimidine;

4-[(1R)-1-[4-[5-[(3R)-3-[(2,5,7-trimethyl-[1,2,4]triazolo[1, 5-a]pyrimidin-6-yl)oxy]pyrrolidin-1-yl]pyrazin-2-yl]phenyl]ethyl]morpholine; and 4-[(1S)-1-[4-[5-[(3R)-3-[(2,5,7-trimethyl-[1,2,4]triazolo[1, 5-a]pyrimidin-6-yl)oxy]pyrrolidin-1-yl]pyrazin-2-yl]phenyl]ethyl]morpholine.

In one embodiment there is provided a compound of Formula (I), or a pharmaceutically acceptable salt thereof, wherein the compound is selected from the group consisting of:

(R)-4-((6-(4-(3-((2,5,7-trimethyl-[1,2,4]triazolo[1,5-a]pyrimidin-6-yl)oxy)pyrrolidin-1-yl)phenyl)pyridazin-3-yl)methyl)morpholine;

(R)-1-(4-((6-(4-(3-((2,5,7-trimethyl-[1,2,4]triazolo[1,5-a]pyrimidin-6-yl)oxy)pyrrolidin-1-yl)phenyl)pyridazin-3-yl)methyl)piperazin-1-yl)ethan-1-one;

(R)-2,5,7-trimethyl-6-((1-(5-(4-((4-methylpiperazin-1-yl)methyl)phenyl)pyrazin-2-yl)pyrrolidin-3-yl)methyl)-[1,2,4]triazolo[1,5-a]pyrimidine; and (R)-4-((6-(4-(3-((2,5,7-trimethyl-[1,2,4]triazolo[1,5-a]pyrimidin-6-yl)methyl)pyrrolidin-1-yl)phenyl)pyridazin-3-yl)methyl)morpholine.

In one embodiment there is provided a compound of Formula (I), or a pharmaceutically acceptable salt thereof, wherein the compound is (R)-4-((6-(4-(3-((2,5,7-trimethyl-[1,2,4]triazolo[1,5-a]pyrimidin-6-yl)oxy)pyrrolidin-1-yl)phenyl)pyridazin-3-yl)methyl)morpholine (also referred to as Compound A).

In one embodiment there is provided a compound of Formula (I), or a pharmaceutically acceptable salt thereof, wherein the compound is (R)-1-(4-((6-(4-(3-((2,5,7-trimethyl-[1,2,4]triazolo[1,5-a]pyrimidin-6-yl)oxy)pyrrolidin-1-yl)phenyl)pyridazin-3-yl)methyl)piperazin-1-yl)ethan-1-one.

In one embodiment there is provided a compound of Formula (I), or a pharmaceutically acceptable salt thereof, wherein the compound is (R)-2,5,7-trimethyl-6-((1-(5-(4-((4-methylpiperazin-1-yl)methyl)phenyl)pyrazin-2-yl)pyrrolidin-3-yl)methyl)-[1,2,4]triazolo[1,5-a]pyrimidine.

In one embodiment there is provided a compound of Formula (I), or a pharmaceutically acceptable salt thereof, wherein the compound is (R)-4-((6-(4-(3-((2,5,7-trimethyl-[1,2,4]triazolo[1,5-a]pyrimidin-6-yl)methyl)pyrrolidin-1-yl)phenyl)pyridazin-3-yl)methyl)morpholine.

In one embodiment, the compound of Formula (I) is in the free base form.

Compounds and salts described in this specification may exist in solvated forms and unsolvated forms. For example, a solvated form may be a hydrated form, such as a hemi-hydrate, a mono-hydrate, a di-hydrate, a tri-hydrate or an alternative quantity thereof. The invention encompasses all such solvated and unsolvated forms of compounds of Formula (I), particularly to the extent that such forms possess MCT4 inhibitory activity, as for example measured using the tests described herein.

Atoms of the compounds and salts described in this specification may exist as their isotopes. The invention encompasses all compounds of Formula (I) where an atom is replaced by one or more of its isotopes (for example a compound of Formula (I) where one or more carbon atom is an or $^{13}$C carbon isotope, or where one or more hydrogen atoms is a $^{2}$H or $^{3}$H isotope, or where one or more nitrogen atoms is a $^{15}$N isotope or where one of more oxygen atoms is an $^{17}$O or $^{18}$O isotope).

Compounds and salts described in this specification may exist in optically active or racemic forms by virtue of one or more asymmetric carbon atoms. The invention includes any optically active or racemic form of a compound of Formula (I) which possesses MCT4 inhibitory activity, as for example measured using the tests described herein. The synthesis of optically active forms may be carried out by standard techniques of organic chemistry well known in the art, for example by synthesis using optically active materials or by resolution of a racemic form.

Therefore, in one embodiment there is provided a compound of Formula (I), or a pharmaceutically acceptable salt thereof, which is a single optical isomer being in an enantiomeric excess (% e.e.) of ≥95%, ≥98% or ≥99%. In one embodiment, the single optical isomer is present in an enantiomeric excess (% e.e.) of ≥99%.

Some of the compounds of Formula (I) may be crystalline and may have more than one crystalline form. It is to be understood that the invention encompasses any crystalline or amorphous form, or mixtures thereof, which possess properties useful in MCT4 inhibitory activity. It is well known how to determine the efficacy of a crystalline or amorphous form by the standard tests described hereinafter.

It is generally known that crystalline materials may be analysed using conventional techniques such as, for example, X-ray powder diffraction (hereinafter XRPD) analysis and Differential Scanning calorimetry (hereinafter DSC).

As an example, the compound of Example 62 exhibits crystallinity and a crystalline form, Form A, has been identified.

Accordingly, a further aspect of the disclosure is Form A of Compound A (Example 62).

According to the disclosure there is provided a crystalline form, Form A, of Compound A which has an XRPD pattern with at least one specific peak at about 2-theta=7.8°, measured using CuKα radiation.

According to the disclosure there is provided a crystalline form, Form A, of Compound A which has an XRPD pattern with at least one specific peak at about 2-theta=19.0°, measured using CuKα radiation.

According to the disclosure there is provided a crystalline form, Form A, of Compound A which has an XRPD pattern with at least two specific peaks at about 2-theta=7.8° and 19.0°, measured by CuKα radiation.

According to the disclosure there is provided a crystalline form, Form A, of Compound A which has an XRPD pattern with specific peaks at about 2-theta=7.8, 9.2, 9.5, 10.4, 11.6, 15.8, 18.3 19.0, 22.3 and 25.3°, measured by CuKα radiation.

According to the disclosure there is provided crystalline form, Form A, of Compound A which has an XRPD pattern substantially the same as the XRPD pattern shown in FIG. 1, measured by CuKα radiation.

According to the disclosure there is provided a crystalline form, Form A, of Compound A which has an XRPD pattern with at least one specific peak at 2-theta=7.8° plus or minus 0.2° 2-theta, measured by CuKα radiation.

According to the disclosure there is provided a crystalline form, Form A, of Compound A which has an XRPD pattern with at least one specific peak at 2-theta=19.0° plus or minus 0.2° 2-theta, measured by CuKα radiation.

According to the disclosure there is provided a crystalline form, Form A, of Compound A which has an XRPD pattern with at least two specific peaks at 2-theta=7.8° and 19.0° wherein said values may be plus or minus 0.2° 2-theta, measured by CuKα radiation.

According to the disclosure there is provided a crystalline form, Form A, of Compound A which has an XRPD pattern with specific peaks at 2-theta=7.8, 9.2, 9.5, 10.4, 11.6, 15.8, 18.3 19.0, 22.3 and 25.3° wherein said values may be plus or minus 0.2° 2-theta, measured by CuKα radiation.

Figure 2:
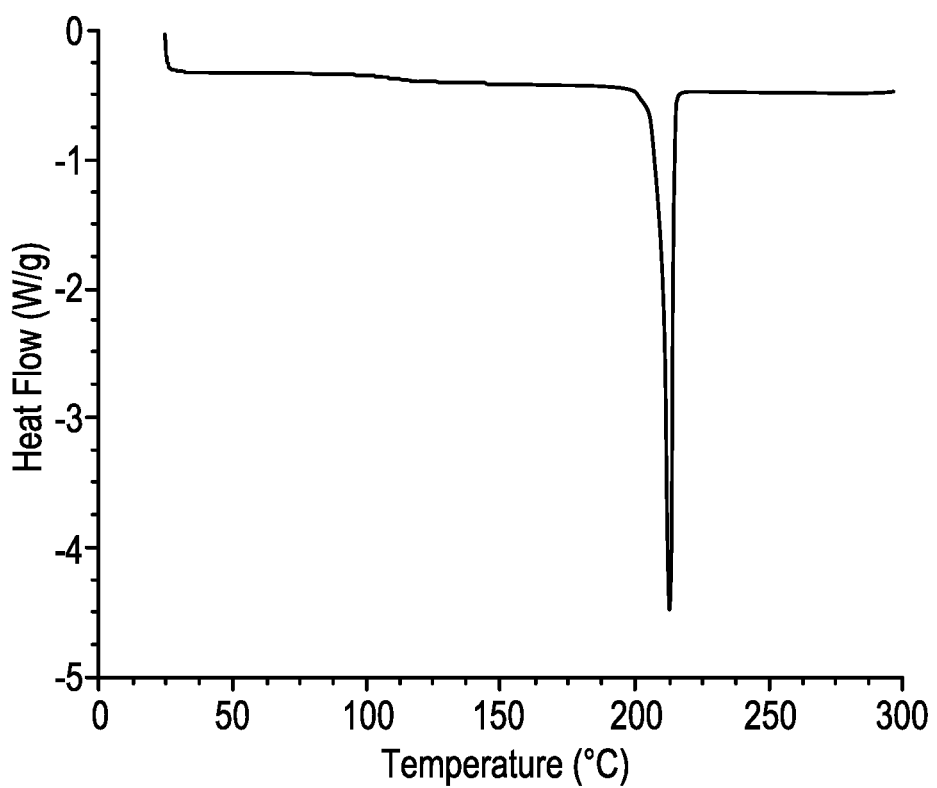
FIG. 2 shows the DSC for Form A of (R)-4-((6-(4-(3-((2,5,7-trimethyl-[1,2,4]triazolo[1,5-a]pyrimidin-6-yl)oxy)pyrrolidin-1-yl)phenyl)pyridazin-3-yl)methyl)morpholine (Compound A, Example 62).

DSC analysis of Compound A, Form A shows a melting endotherm with an onset of about 210.2° C. and a peak at about 213.2° C. (FIG. 2).

Thus DSC analysis shows Compound A, Form A is a high melting solid with an onset of melting at about 210.2° C. and a peak at about 213.2° C.

When it is stated that the present disclosure relates to a crystalline form of Form A of Compound A, the degree of crystallinity is conveniently greater than about 60%, more conveniently greater than about 80%, preferably greater than about 90% and more preferably greater than about 95%. Most preferably the degree of crystallinity is greater than about 98%.

It will be understood that the 2-theta values of the XRPD pattern may vary slightly from one machine to another or from one sample to another, and so the values quoted are not to be construed as absolute.

It is known that an XRPD pattern may be obtained which has one or more measurement errors depending on measurement conditions (such as equipment or machine used). In particular, it is generally known that intensities in an XRPD pattern may fluctuate depending on measurement conditions. Therefore it should be understood that Compound A, Form A of the present disclosure is not limited to the crystals that provide XRPD patterns identical to the XRPD pattern shown in FIG. 1, and any crystals providing XRPD patterns substantially the same as that shown in FIG. 1 fall within the scope of the present disclosure. A person skilled in the art of XRPD is able to judge the substantial identity of XRPD patterns.

Persons skilled in the art of XRPD will understand that the relative intensity of peaks can be affected by, for example, grains above 30 microns in size and non-unitary aspect ratios, which may affect analysis of samples. The skilled person will also understand that the position of reflections can be affected by the precise height at which the sample sits in the diffractometer and the zero calibration of the diffractometer. The surface planarity of the sample may also have a small effect. Hence the diffraction pattern data presented are not to be taken as absolute values. (Jenkins, R & Snyder, R. L. 'Introduction to X-Ray Powder Diffractometry' John Wiley & Sons 1996; Bunn, C. W. (1948), Chemical Crystallography, Clarendon Press, London; Klug, H. P. & Alexander, L. E. (1974), X-Ray Diffraction Procedures).

Generally, a measurement error of a diffraction angle in an X-ray powder diffractogram is approximately plus or minus 0.2° 2-theta, and such degree of a measurement error should be taken into account when considering the XRPD pattern in FIG. 1 and when reading Table A. Furthermore, it should be understood that intensities might fluctuate depending on experimental conditions and sample preparation (preferred orientation).

The compounds of Formula (I) include one or more chiral centres. To the extent a structure or chemical name in this specification does not indicate chirality, the structure or name is intended to encompass any single stereoisomer (i.e. any single chiral isomer) corresponding to that structure or name, as well as any mixture of stereoisomers (e.g. a racemate). It is well-known in the art how such optically-active forms can be prepared. For example, a single stereoisomer can be obtained by isolating it from a mixtures of isomers (e.g. a racemate) using, for example, chiral chromatographic separation. In other embodiments, a single stereoisomer is obtained through direct synthesis from, for example, a chiral starting material.

Compounds of Formula (I), where X represents O, may for example be prepared by the reaction of a compound of Formula (II):

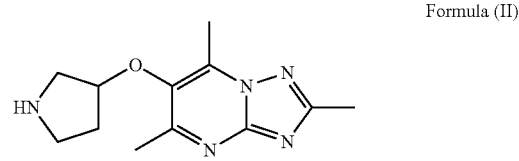

Formula (II)

or a salt thereof, with a compound of Formula (III):

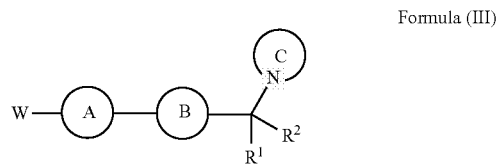

Formula (III)

or a salt thereof, where W is a suitable leaving group, for example Cl, Br, I or OTf, and $R^1$, $R^2$, Ring A, Ring B and Ring C are as defined in any of the embodiments herein. The reaction is conveniently performed in a suitable solvent (for example 2-methyltetrahydrofuran) in the presence of a base (for example cesium carbonate) and in the presence of a suitable catalyst (for example Ruphos Pd $3^{rd}$ Generation) and ligand (for example Ruphos) at a suitable temperature (for example in the range 60° C. to 80° C.).

Alternatively, depending on the nature of Ring A, the compounds of Formula (I), or pharmaceutically acceptable salt thereof, may also be prepared by reaction of a compound of Formula (II), or salt thereof, and a compound of Formula (III), or salt thereof, using standard aromatic substitution conditions, well known to those skilled in the art, for example with a suitable base (for example diisopropylethylamine) in a suitable solvent (for example 1-butanol) at a suitable temperature (for example in the range of 60° C. to 120° C.).

Compounds of Formula (II) and (III), and salts thereof, are therefore useful as intermediates in the preparation of the compounds of Formula (I) and provide a further embodiment.

The compounds of Formula (II) may for example be prepared by the following scheme, Scheme 1:

Scheme 1

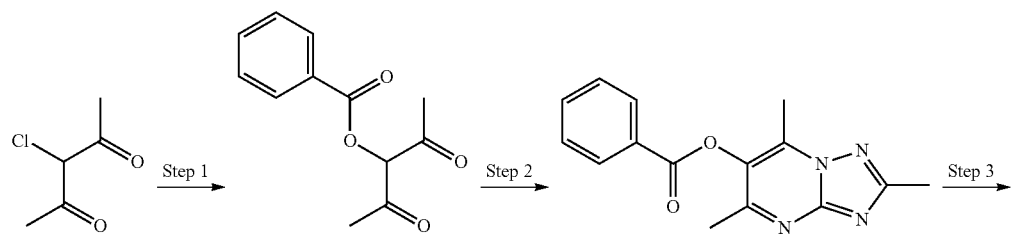

-continued

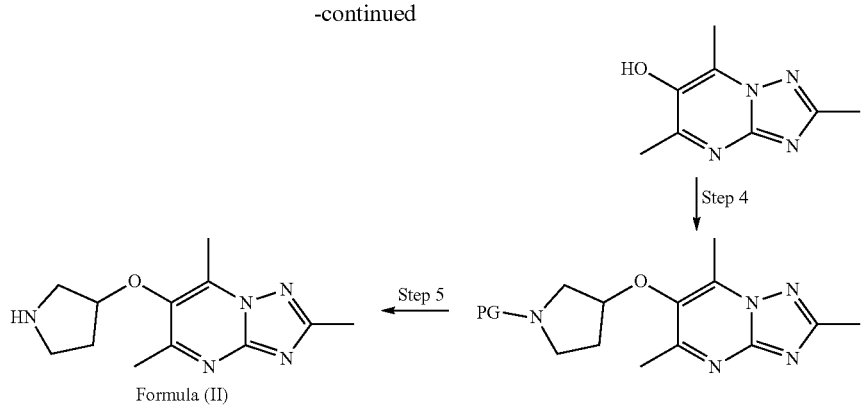

Formula (II)

wherein PG is a suitable nitrogen protecting group, for example Boc.

Step 1: Performed using a suitable nucleophile (for example benzoic acid) in the presence of a suitable base (for example KOH) in a suitable solvent (for example DMF) at a suitable temperature (for example in the range of 20° C. to 50° C.).

Step 2: Performed using a suitable cyclisation substrate (for example 3-methyl-1H-1,2,4-triazol-5-amine) in a suitable solvent (for example AcOH) at a suitable temperature (for example in the range of 70° C. to 90° C.).

Step 3: Performed under standard hydrolysis conditions, well known to those skilled in the art, for example 1M NaOH (aq) in EtOH at RT.

Step 4: Performed using standard conditions well known to those skilled in the art. The reaction may be performed using standard Mitsunobu conditions with a suitable alcohol substrate (for example tert-butyl-3-hydroxypyrrolidine-1-carboxylate) with triphenylphosphine and DIAD in THF at RT.

Step 5: Performed using standard deprotection conditions well known to those skilled in the art. For example, when PG is Boc the reaction may be performed using 4M HCl in 1,4-dioxane in MeOH at RT.

Compounds of Formula (III), where $R^1$ and $R^2$ are hydrogen, may for example be prepared by reacting a compound of Formula (IV)

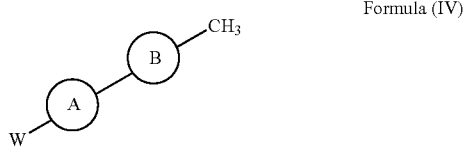

Formula (IV)

or a salt thereof with a suitable chlorinating reagent (for example trichloroisocyanuric acid) in a suitable solvent (for example dichloroethane) followed by reacting with a suitable Ring C based amine (for example morpholine) at a suitable temperature (for example at RT), wherein W is a suitable leaving group, for example Cl, Br, I or OTf, and Ring A, Ring B and Ring C are as defined in any of the embodiments herein. In one embodiment Ring A is phenyl and Ring B is pyradazinyl.

Compounds of Formula (I), where X represents $CH_2$, may for example be prepared by the reaction of compounds of Formula (III), or a salt thereof, where $R^1$, $R^2$, Ring A, Ring B and Ring C are as defined in any of the embodiments herein, with a compound of Formula (V)

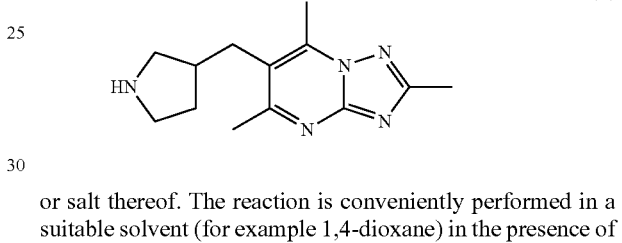

Formula (V)

or salt thereof. The reaction is conveniently performed in a suitable solvent (for example 1,4-dioxane) in the presence of a base (for example cesium carbonate) and in the presence of a suitable catalyst (for example Ruphos Pd $3^{rd}$ Generation) and ligand (for example Ruphos) at a suitable temperature (for example 60° C. to 90° C.).

Compounds of Formula (V) are therefore also useful as intermediates in the preparation of the compounds of Formula (I) and provide a further embodiment.

The compounds of Formula (V) may for example be prepared by the following scheme, Scheme 2:

Scheme 2

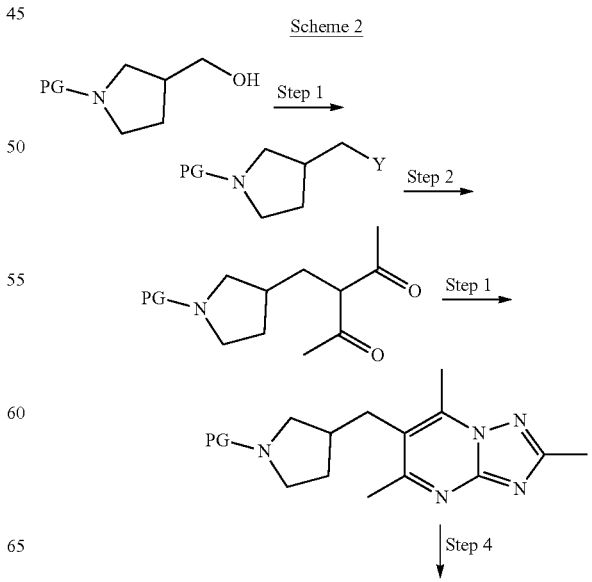

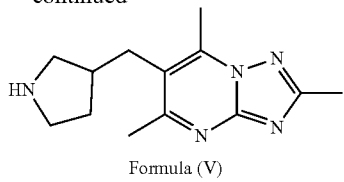

Formula (V)

wherein PG is a suitable nitrogen protecting group, for example Boc and Y is a suitable leaving group, for example Cl, Br, I or OMs.

Step 1: Performed using conditions that convert OH into a suitable leaving group, for example if Br is chosen as leaving group then the reaction may be performed using conditions well known to those skilled in the art for example with triphenylphosphine, tetrabromomethane, in DCM in a temperature range of 0° C. to RT.

Step 2: Performed using a suitable nucleophile (for example pentane-2,4-dione) in the presence of a suitable base (for example potassium carbonate) in a suitable solvent (for example DMF) at a suitable temperature (for example in the range of 60° C. to 80° C.).

Step 3: Performed using a suitable cyclisation substrate (for example 3-methyl-1H-1,2,4-triazol-5-amine) in a suitable solvent (for example AcOH) at a suitable temperature (for example in the range of (70° C. to 90° C.).

Step 4: Performed using standard deprotection conditions well known to those skilled in the art. For example, when PG is Boc the reaction may be performed using 4M HCl in 1,4-dioxane in MeOH at RT.

Alternatively, compounds of Formula (I), where X represents $CH_2$, may be prepared by reacting a compound of Formula (VI)

Formula (VI)

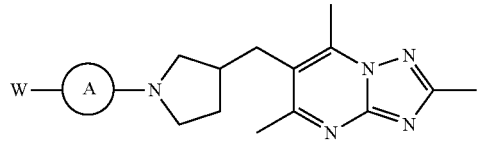

or salt thereof, where W is a suitable leaving group, for example Cl, Br, I or OTf and Ring A is as defined in any of the embodiments herein, with a compound of Formula (VII)

Formula (VII)

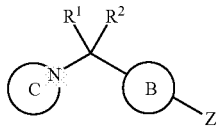

or salt thereof, where Z is a suitable leaving group, for example, pinacol boronate ester, boronic acid or organotin and $R^1$, $R^2$, Ring B and Ring C are as defined in any of the embodiments herein. When Z is pinacol boronate ester then the reaction is conveniently performed in a suitable solvent (for example a mixture of 1,4-dioxane and water) in the presence of a base (for example cesium carbonate) and in the presence of a suitable catalyst (for example Xphos Pd $2^{nd}$ Generation) at a suitable temperature (for example 60° C. to 90° C.). In one embodiment, $R^1$ and $R^2$ represent hydrogen, Ring A is pyrazinyl, Ring B is phenyl and Ring C is 4-methyl-1-piperazinyl.

The compounds of Formula (VI), or salt thereof, may be prepared by reacting a compound of Formula (V), or salt thereof, with Ring A using standard aromatic substitution chemistry. Ring A will have a suitable leaving group (for example chlorine or bromine) and the reaction is conveniently performed in a suitable solvent (for example 1-butanol) in the presence of a suitable base (for example diisopropylethylamine) at a suitable temperature (for example 60° C. to 120° C.). Alternatively, the compounds of Formula (VI), or salt thereof, may be prepared by reacting a compound of Formula (V), or salt thereof, with Ring A using standard cross coupling conditions. Ring A will have a suitable leaving group (for example chlorine, bromine or iodine) in a suitable solvent (for example 1,4-dioxane) in the presence of a base (for example cesium carbonate) and in the presence of a suitable catalyst (for example Ruphos Pd $3^{rd}$ Generation) at a suitable temperature (for example 60° C. to 90° C.).

Alternatively, compounds of Formula (I), where X represents $CH_2$, may be prepared by reaction of a compound with Formula (VIII)

Formula (VIII)

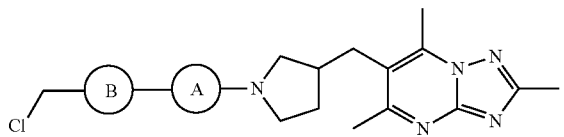

or salt thereof, with a suitable Ring C based amine, where Ring A, Ring B and Ring C are as defined in any of the embodiments herein. The reaction may be performed under standard conditions, well known to those skilled in the art, for example with triethylamine in THF at 60° C.

Alternatively, compounds of Formula (I), where X represents $CH_2$, may be prepared by reaction of a compound with Formula (IX)

Formula (IX)

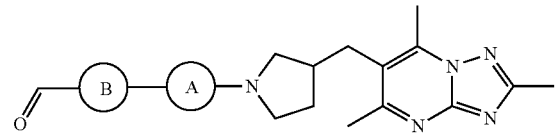

or salt thereof, with a suitable Ring C based amine, where Ring A, Ring B and Ring C are as defined in any of the embodiments herein. The reaction may be performed under standard conditions, well known to those skilled in the art, for example with sodium triacetoxyborohydride, AcOH in DCM at RT.

It will be appreciated that certain of the various ring substituents in the compounds of the present disclosure may be introduced by standard aromatic substitution reactions or generated by conventional functional group modifications either prior to or immediately following the processes mentioned above, and as such are included in the process aspect of the disclosure. For example compounds of Formula (I) may be converted into further compounds of Formula (I) by standard aromatic substitution reactions or by conventional functional group modifications. Such reactions and modifications include, for example, introduction of a substituent by means of an aromatic substitution reaction, reduction of substituents, alkylation of substituents and oxidation of substituents. The reagents and reaction conditions for such procedures are well known in the chemical art.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

In any of the embodiments where a compound of Formula (II) to (IX) or a salt thereof is mentioned it is to be understood that such salts do not need to be pharmaceutically acceptable salts.

Compounds of Formula (I), and any intermediates used to make these, can be prepared by methods similar to those shown in the Examples section.

Biological Assays

The following in vitro assays were used to measure the effects of the compounds described herein.

Throughout the description of the assays the following abbreviations have been used: BCECF AM=2',7'-Bis-(2-Carboxyethyl)-5-(and-6)-Carboxyfluorescein, Acetoxymethyl Ester; DMSO=Dimethyl Sulphoxide; FBS=Foetal Bovine Serum; HBSS=Hanks Balanced Salt Solution; HEPES=4-(2-hydroxyethyl)-1-piperazineethanesulfonic acid; OD=Optical Density; RPMI=Roswell Park Memorial Institute 1640 Medium.

Compound efficacy within the assays was determined via measurement of an $IC_{50}$ value (the concentration of test compound that inhibited 50% of biological activity). $IC_{50}$ values were calculated using a smart fitting model within the Screener (Genedata AG) analysis package.

Rationale:

MCT4 is predominantly expressed in normal skeletal muscle and is upregulated in a range of solid tumours where it has a role in facilitating the efflux of lactate from the cell thereby preventing intracellular acidification. Thus inhibition of MCT4 activity represents a potential therapeutic opportunity in an oncology setting. MCT1 is a closely related monocarboxylate transporter and as such a key selectivity target for MCT4 inhibitors. Even though MCT4 is primarily involved in cellular efflux of lactate it is possible to drive influx of lactate in an in vitro system as described for assay systems (b) and (d) below.

The purpose of these tests is to identify compounds which affect lactate efflux in a natively glycolytic cell-line predominantly expressing MCT4, and the transport of lactate into cells within the following in vitro assay systems:

a) SK-Br-3 cells (ATCC HTB-30)—a natively glycolytic human breast adenocarcinoma line predominantly expressing MCT4 (confirmed by Western blotting)
b) NCI-H358 cells (ATCC CRL-5807)—a human lung adenocarcinoma line predominantly expressing MCT4, a small amount of MCT2 and no MCT1 (confirmed by Western blotting)
c) K562 cells (ATCC CCL-243)—a human erythroleukemia line predominantly expressing MCT1, a small amount of MCT2 and no MCT4 (confirmed by Western blot)
d) INS-1 MCT4 cells (parental INS-1 line gifted to AstraZeneca from the University of Geneva, Switzerland)—a rat pancreatic beta-cell line natively null for all MCT isoforms and engineered in-house to stably express human MCT4 (confirmed by Western blot).

Assay System (a):

Compounds of Formula I in 100% DMSO were added to empty 384 well assay plates (Costar #3712) via acoustic dispensing (120 nl/well over a concentration range). SK-Br-3 cells (ATCC HTB-30) were seeded into the assay plates—directly onto the test compound—at a density of 4000 cells/well, in 40 µl RPMI (Sigma #R0883) medium containing 1% L glutamine (Sigma #G7513) and 20% FBS (Sigma #F7524). Assay plates were lidded and incubated for 4 hours at 37° C. and 5% $CO_2$.

Following incubation with test compound, 5 µl of media was transferred to a secondary 384 well assay plate (Costar #3712) using an automated tip-based pipetting platform (CyBio Felix). The amount of lactic acid present in the media was quantified via a commercial lactate detection kit (Trinity Biotech #735-10) employing the following coupled-enzymatic principle: Lactic acid is converted to pyruvate and $H_2O_2$ by lactate oxidase; in the presence of the $H_2O_2$ formed, peroxidase catalyzes the oxidative condensation of a chromogen precursor to produce a coloured dye with an absorption maximum at 540 nm (increasing absorbance being directly proportional to increasing lactate within the sample). The absorbance was then measured on an automated microplate reader (PerkinElmer EnVision) using a 535 nm filter and OD values normalised to control wells—treated with either DMSO (maximum assay signal) or chemistry related to that described in this patent (minimum assay signal)—before fitting concentration response curves to determine an $IC_{50}$ value.

Assay Systems (b), (c):

Compounds of Formula I in 100% DMSO were added to empty 384 well assay plates (Costar #3683) via acoustic dispensing (90 nl/well over a concentration range).

NCI-H358 cells (ATCC CRL-5807) or K562 cells (ATCC CCL-243) were defrosted directly from cryopreservation, washed and re-suspended in HBSS (Gibco #14170) with 1 mM [final] HEPES (Gibco #15630).

Cells were loaded with the pH sensitive dye BCECF AM (Invitrogen #B1150) before being washed to remove excess dye and seeded into the assay plates—directly onto the test compound—at a density of 15,000 cells/well (NCI-H358) or 30,000 cells/well (K562), in 30 µl HBSS with 1 mM [final] HEPES. Assay plates were lidded and spun in a plate centrifuge at 170 g for 1 minute. Plates were then wrapped in foil and incubated in the dark for 1 hour at room temperature.

Following incubation with test compound, 10 µl of 25 mM Sodium-L-Lactate (Sigma #L7022) made up in HBSS with 1 mM [final] HEPES was directly added into 30 µl media within the test wells—resulting in 6.25 mM [final]. This addition was performed directly on the FLIPR Tetra platform (Molecular Devices) as part of a real-time kinetic read protocol. The cellular fluorescence using the filter set Ex470-495_Em515-575 was measured over time and the change from base-line (pre-lactate addition) to 'lactate addition+80 seconds' was recorded. A percentage change from base-line was calculated for each test well and values normalised to control wells treated with either DMSO (maximum assay signal) or chemistry related to that described in this patent (minimum assay signal) before fitting concentration response curves to determine an $IC_{50}$ value.

Assay System (d):

Compounds of Formula I in 100% DMSO were added to empty 384 well assay plates (Costar #3683) via acoustic dispensing (90 nl/well over a concentration range).

INS-1 MCT4 cells were generated through transfection of the parental cell background with the following DNA sequence, inserted into a pcDNA3.1 (ThermoFisher #V79020) mammalian expression vector:

(SEQ ID NO: 1)
atgggaggggccgtggtggacgagggcccacaggcgtcaag gcccctgacggcggctggggctgggccgtgctcttcggctgt ttcgtcatcactggcttctcctacgccttccccaaggccgtc agtgtcttcttcaaggagctcatacaggagtttgggatcggc tacagcgacacagcctggatctcctccatcctgctggccatg ctctacgggacaggtccgctctgcagtgtgtgcgtgaaccgc tttggctgccggcccgtcatgcttgtggggggtctctttgcg tcgctgggcatggtggctgcgtccttttgccggagcatcatc caggtctacctcaccactggggtcatcacggggttgggtttg gcactcaacttccagccctcgctcatcatgctgaaccgctac ttcagcaagcggcgcccccatggccaacgggctggcggcagca ggtagccctgtcttcctgtgtgccctgagcccgctggggcag ctgctgcaggaccgctacggctggcggggcggcttcctcatc ctgggcggcctgctgctcaactgctgcgtgtgtgccgcactc atgaggcccctggtggtcacggcccagccgggctcggggccg ccgcgacccctcccggcgcctgctagacctgagcgtcttccgg gaccgcggctttgtgctttacgccgtggccgcctcggtcatg gtgctggggctcttcgtcccgcccgtgttcgtggtgagctac gccaaggacctgggcgtgcccgacaccaaggccgccttcctg ctcaccatcctgggcttcattgacatcttcgcgcggccggcc gcgggcttcgtggcggggcttgggaaggtgcggccctactcc gtctacctcttcagcttctccatgttcttcaacggcctcgcg gacctggcgggctctacgcgggcgactacgcggcctcgtg gtcttctgcatcttctttggcatctcctacggcatggtgggg gccctgcagttcgaggtgctcatggccatcgtgggcacccac aagttctccagtgccattggcctggtgctgctgatggaggcg gtggccgtgctcgtcgggcccccttcggggaggcaaactcctg gatgcgacccacgtctacatgtacgtgttcatcctggcgggg gccgaggtgctcacctcctccctgattttgctgctgggcaac ttcttctgcattaggaagaagcccaaagagccacagcctgag gtggcggccgcggaggaggagaagctccacaagcctcctgca gactcggggtggacttgcgggaggtggagcatttcctgaag -continued
gctgagcctgagaaaaacggggaggtggttcacaccccggaa acaagtgtctga The resultant cell pool was continually cultured at 37° C. and 5% $CO_2$ under antibiotic selection in RPMI (Sigma #R0883) medium containing 1% L glutamine (Sigma #G7513), 10% FBS (Sigma #F7524), 10 mM [final] HEPES (Gibco #15630), 0.004% β-Mercaptoethanol (Sigma #M6250) and 100 µg/ml Geneticin (ThermoFisher #10131027). An individual clone was selected and expanded before being cryopreserved in a number of individual vials for continued use. Prior to testing in the biological assay, an individual INS-1 MCT4 cryovial was defrosted and continually passaged over a number of weeks—in the Geneticin selection media described previously—to obtain the requesite cell number. At the point of test, cells were detetched from the surface of the culture flasks, pooled, washed and re-suspended in HBSS (Gibco #14170) with 1 mM [final] HEPES (Gibco #15630).

Cells were loaded with the pH sensitive dye BCECF AM (Invitrogen #B1150) before being washed to remove excess dye and seeded into the assay plates—directly onto the test compound—at a density of 15,000 cells/well, in 30 µl HBSS with 1 mM [final] HEPES. Assay plates were lidded and spun in a plate centrifuge at 170 g for 1 minute. Plates were then wrapped in foil and incubated in the dark for 1 hour at room temperature.

Following incubation with test compound, 10 µl of 25 mM Sodium-L-Lactate (Sigma #L7022) made up in HBSS with 1 mM [final] HEPES was directly added into 30 µl media within the test wells—resulting in 6.25 mM [final]. This addition was performed directly on the FLIPR Tetra platform (Molecular Devices) as part of a real-time kinetic read protocol. The cellular fluorescence using the filter set Ex470-495_Em515-575 was measured over time and the change from base-line (pre-lactate addition) to 'lactate addition+80 seconds' was recorded. A percentage change from base-line was calculated for each test well and values normalised to control wells treated with either DMSO (maximum assay signal) or chemistry related to that described in this patent (minimum assay signal) before fitting concentration response curves to determine an $IC_{50}$ value.

The following in vivo assays were used to measure the effects of the compounds described herein in combination with other agents.

Human Lung Cancer Xenograft Model VEGFR TKI Combination

The in vivo efficacy of MCT4 inhibitors has been tested in human xenograft models. The NSCLC cell line NCI H358 can be grown as a subcutaneous xenograft in female nude mice and tumour volume calculated from bilateral caliper measurements. For efficacy studies three million NCI H358 cells were inoculated sub-cutaneously onto the left flank of the animal in a volume of 0.1 ml serum free media (RPMI) and matrigel. Animals were assigned into treatment groups 14 days after cell implantation and received either AZD2171 (3 mg/kg QD) (Wedge et al., (2005) Cancer Res. 65:4389-4400), a compound of Formula (I) (100 mg/kg BID) or the combination of both by oral gavage. A vehicle control of 0.5% hydroxy propyl methyl cellulose/0.1% Tween 80 was dosed twice daily given orally. Dosing was continued for 17 days and tumour volume, body weight and tumour condition were recorded twice weekly for the duration of the study.

Figure 3:
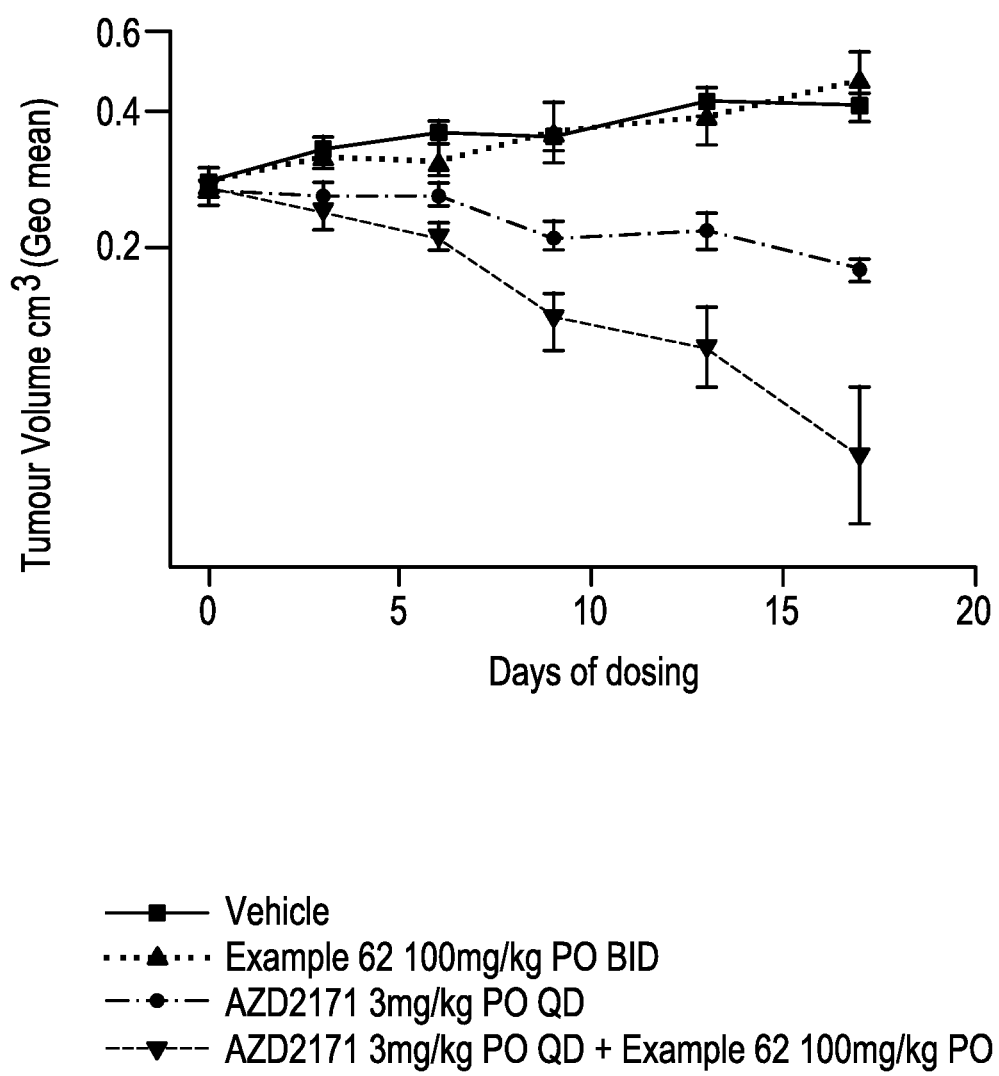
FIG. 3 shows the in vivo activity of an MCT4 inhibitor (Example 62) in combination with VEGFR TKI (AZD2171, also known as cediranib) in a lung cancer xenograft model.

The results of testing Example 62 are shown in FIG. 3. VEGF inhibitor AZD2171 was effective demonstrating a 33% (p≤0.001) tumour regression compared to the vehicle group. The combination of AZD2171 with the MCT4 inhibitor Example 62 demonstrated a more dramatic response equaling 72% tumour regression (p≤0.001 compared to the control) which was also significantly different (p=0.013) from the AZD2171 given alone. Group sizes at study termination: Vehicle n=11; Example 62 n=4; AZD2171 n=10; AZD2171 plus Example 62 n=9.

Mouse Syngeneic Model—α-CTLA4 Antibody Combination and αPD-1 Antibody Combinations The in vivo efficacy of MCT4 inhibitors has been tested in murine syngeneic models. To test the selective impact of MCT4 inhibitors of Formula (I), MCT1 was knocked-out (KO) of the MC38 syngeneic cell line model using CRISPR precise genome editing. The MC38 MCT1 KO murine colorectal cell line can be grown sub-cutaneously in female C57.Bl6 mice and tumour volume calculated from bilateral caliper measurements. For efficacy studies, ten million cells were inoculated subcutaneously onto the left flank of the animal in a volume of 0.1 ml serum free DMEM media. Animals were randomised by bodyweight at the time of cell implantation and treatment started the following day. In the first of these studies shown in FIG. 4, monotherapy treatment arms received either a compound of Formula (I) (100 mg/kg BID) by oral gavage or αCTLA4 antibody (anti-CTLA-4 9D9 mIgG1 antibody, described in WO200712373) (10 mg/kg twice weekly) intraperitoneally. Combination groups consisted of a compound of Formula (I) (100 or 10 mg/kg PO BID) with αCTLA4 antibody (10 mg/kg IP twice weekly). In the second of these studies shown in FIG. 5, monotherapy treatment arms received either a compound of Formula (I) (30 mg/kg PO BID) with αPD-1 antibody (from Bio X Cell, Catalogue #BE0146, Lot 665417s1, 6.78 mg/mL) (10 mg/kg IP twice weekly). In both studies dosing was continued for up to 6 weeks and tumour volume, body weight and tumour condition were recorded three times weekly. Vehicle was 0.5% hydroxy propyl methyl cellulose/0.1% Tween 80 given twice daily by oral gavage with PBS/a given twice weekly intraperitoneally in both studies.

Figure 4:
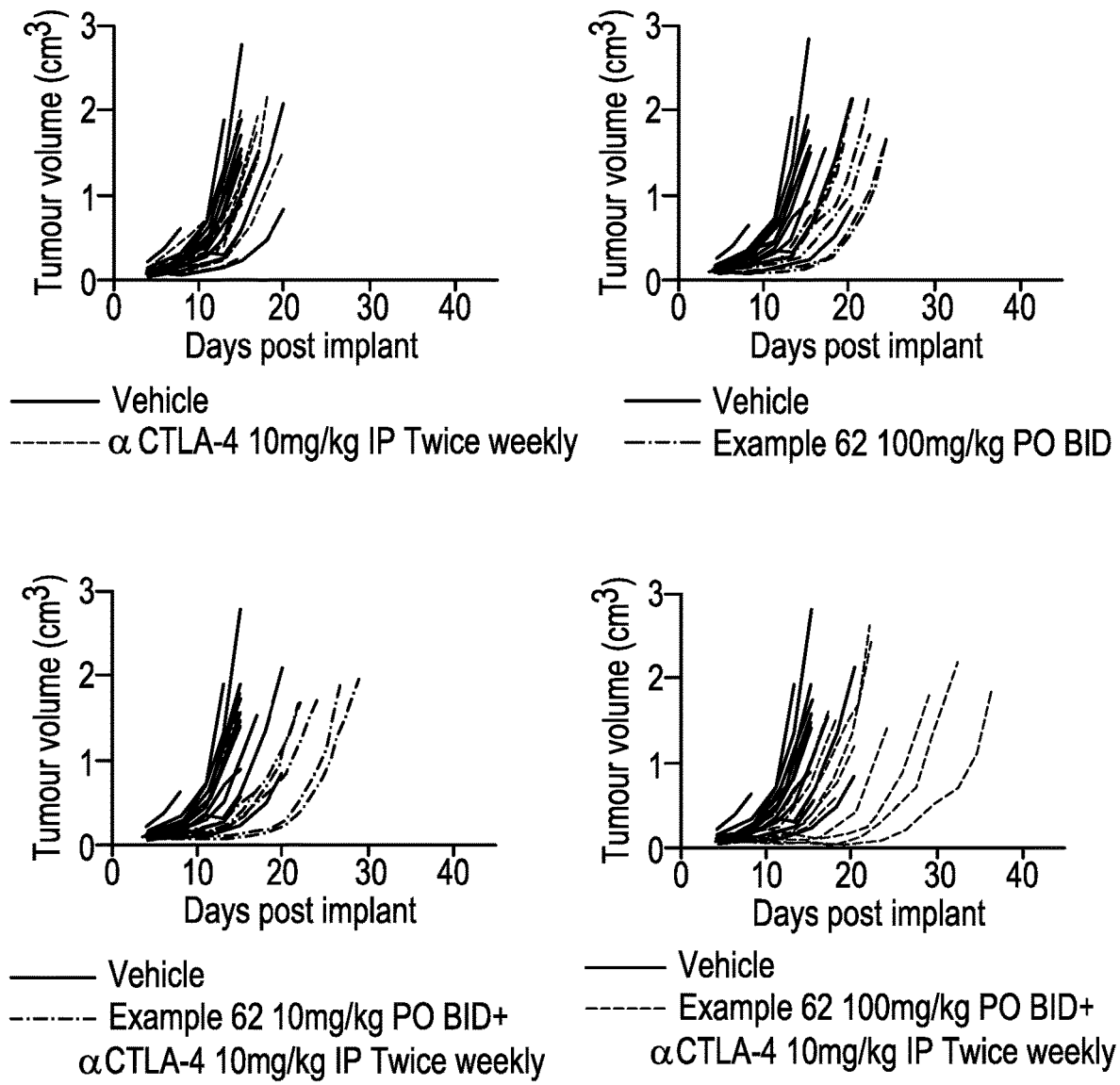
FIG. 4 shows the in vivo activity of an MCT4 inhibitor (Example 62) in combination with an α-CTLA4 antibody in a mouse syngeneic model.

The results of testing Example 62 in the first syngeneic study are shown in FIG. 4. Individual tumour growth profiles are shown with animals taken off study using time to event criteria based on a maximum tumour volume of 1.5 cm³, tumour condition or animal welfare limits. Due to animals coming off study during the later stages of the experiment, GeoMean percentage inhibition values were calculated on Day 15. Compared to vehicle control, Example 62 monotherapy (100 mg/kg) delivered 60.0%$^{p≤0.05}$ growth inhibition on that day. Monotherapy αCTLA4 (10 mg/kg) was ineffective with 6.1%$^{NS}$. The combination of Example 62 (10 and 100 mg/kg) with αCTLA4 antibody showed 67.4%$^{p≤0.01}$ and 82.2%$^{p≤0.001}$ inhibition respectively, with the Example 62 (100 mg/kg BID) plus αCTLA4 antibody combination reaching statistical significance (p=0.0311) from Example 62 (100 mg/kg BID) given alone. Group sizes on Day 15: Vehicle n=12; Example 62 (100 mg/kg) n=11; αCTLA4 Antibody (10 mg/kg) n=11; Example 62 (100 mg/kg) plus αCTLA4 antibody n=12; Example 62 (10 mg/kg) plus αCTLA4 antibody n=9.

Figure 5:
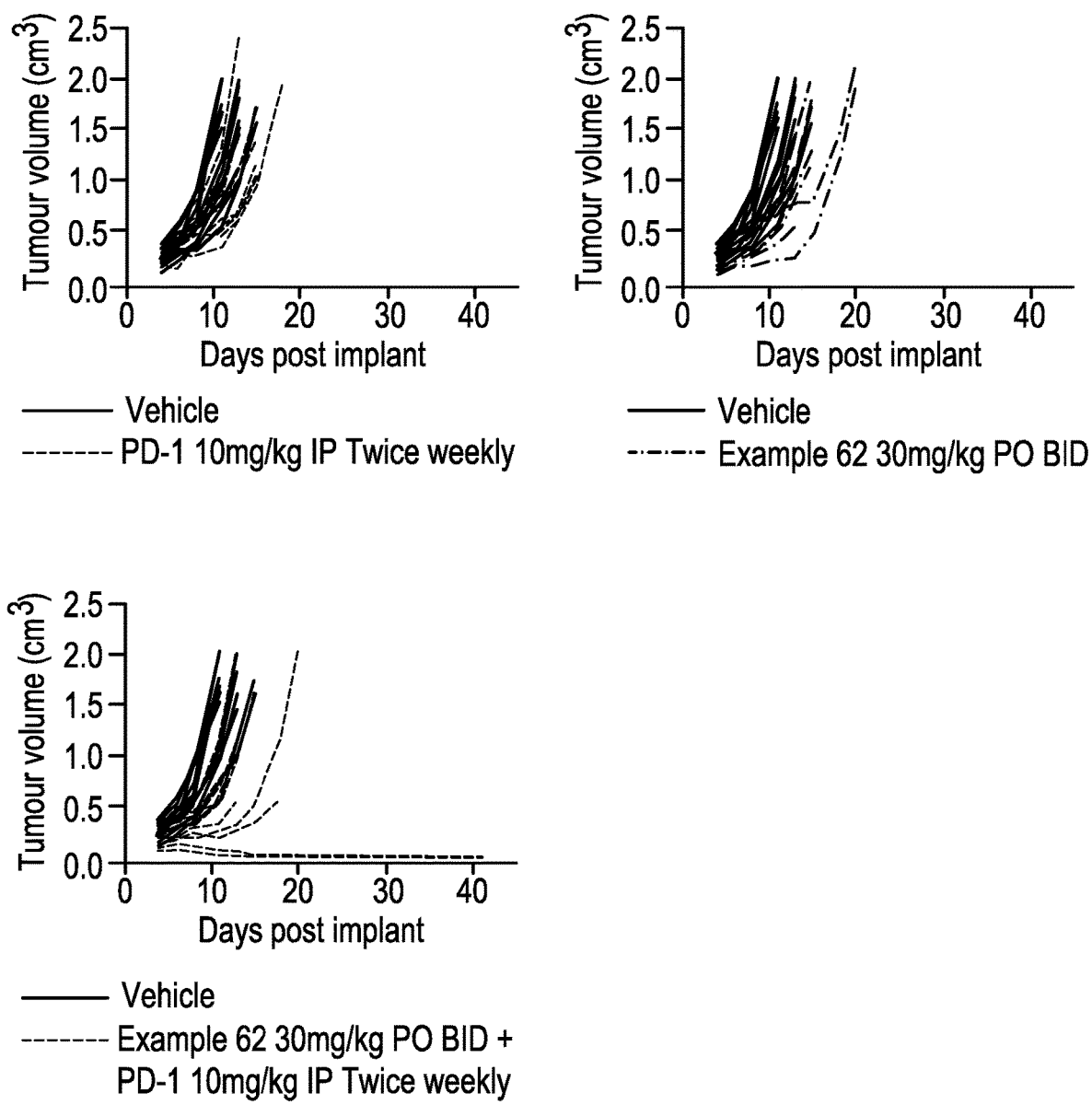
FIG. 5 shows the in vivo activity of MCT4 inhibitor (Example 62) in combination with an αPD-1 antibody in a mouse syngeneic model.

For the second syngeneic study testing Example 62 the results are shown in FIG. 5. Again, individual tumour growth profiles are shown with animals taken off study using time to event criteria based on a maximum tumour volume of 1.5 cm³, tumour condition or animal welfare limits. Due to animals reaching the time to event endpoint at different times during the later stages of the experiment GeoMean percentage inhibition values were calculated on Day 13. Compared to vehicle control, Example 62 monotherapy (30 mg/kg) delivered 30.1%$^{(NS)}$ growth inhibition on that day. Monotherapy αPD-1 (10 mg/kg) efficacy was similar, delivering 33.4%$^{NS}$ inhibition. The combination of Example 62 (30 mg/kg) with αPD-1 antibody was more effective than the monotherapies showing 82.3%$^{p≤0.001}$ growth inhibition. Group sizes on Day 13: Vehicle n=8; Example 62 (30 mg/kg) n=10; αPD-1 antibody (10 mg/kg) n=11; Example 62 (30 mg/kg) plus αPD-1 antibody n=10.

It should be noted that the spider plots shown in FIGS. 4 and 5 represent individual animal tumour growth data, comparing vehicle control growth with treatment groups.

The following data, from assays a) to d), was generated for the Examples (the pIC50 values reported are the calculated mean result of at least three repeat experiments, except for Example 32, marked *, where the pIC50 value is the calculated mean result of two repeat experiments):

| Example No. | MCT4 lactate efflux pIC50 (SKBR3) | MCT4 FLIPR pIC50 (H358) | MCT1 FLIPR pIC50 (K562) | MCT4 FLIPR pIC50 (INS-1) |
| --- | --- | --- | --- | --- |
| 1 | 9.5 | — | — | — |
| 4 | 9.2 | 7.4 | — | — |
| 5 | 9.3 | 7.9 | — | — |
| 6 | 9.2 | 8.1 | — | — |
| 7 | 9.5 | — | — | — |
| 8 | 9.2 | 7.6 | — | — |
| 9 | 9.3 | 7.8 | <4.7 | — |
| 10 | 9.3 | 7.5 | — | — |
| 11 | 9.5 | 8.1 | — | — |
| 12 | 8.4 | — | — | — |
| 13 | 8.6 | — | — | — |
| 14 | 8.7 | — | — | — |
| 15 | 9.0 | — | — | — |
| 16 | 9.3 | 7.5 | — | — |
| 17 | 9.6 | — | — | — |
| 18 | 9.2 | — | — | — |
| 19 | 9.7 | 8.1 | — | — |
| 20 | 9.3 | 7.4 | — | — |
| 21 | 8.9 | 7.7 | — | — |
| 22 | 9.0 | — | — | — |
| 23 | 9.4 | 8.2 | — | — |
| 24 | 9.0 | — | — | — |
| 25 | 9.1 | — | — | — |
| 26 | 9.6 | — | — | — |
| 27 | 9.2 | 7.7 | — | — |
| 28 | 9.6 | — | — | — |
| 29 | 9.5 | 7.9 | <4.8 | 8.6 |
| 30 | 7.6 | — | — | — |
| 31 | 8.5 | 7.3 | — | — |
| 32 | 8.9* | — | — | — |
| 33 | 8.6 | — | — | — |
| 34 | 8.8 | 7.2 | <4.6 | — |
| 35 | 9.2 | 7.8 | <4.6 | — |
| 36 | 9.3 | — | <4.6 | — |
| 37 | 9.4 | 8.2 | — | — |
| 38 | 8.4 | 7.5 | — | — |
| 39 | 8.6 | — | — | — |
| 40 | 8.9 | 7.2 | — | — |
| 41 | 9.1 | — | <4.6 | — |
| 42 | 9.1 | 8.0 | <4.6 | 8.2 |
| 43 | 9.2 | 7.7 | — | — |
| 44 | 9.2 | — | — | — |
| 45 | 9.7 | — | — | — |
| 46 | 9.7 | — | — | — |
| 47 | 8.7 | 8.0 | — | — |
| 48 | 8.8 | 8.0 | — | — |
| 49 | 9.2 | 8.1 | — | — |
| 50 | 9.3 | 7.8 | <4.6 | — |
| 51 | 9.3 | 8.1 | — | — |
| 52 | 9.7 | 8.0 | — | — |

-continued

| Example No. | MCT4 lactate efflux pIC50 (SKBR3) | MCT4 FLIPR pIC50 (H358) | MCT1 FLIPR pIC50 (K562) | MCT4 FLIPR pIC50 (INS-1) |
|---|---|---|---|---|
| 53 | 9.2 | 7.6 | — | — |
| 54 | 9.4 | 8.1 | — | — |
| 55 | 9.6 | 8.0 | — | — |
| 56 | 9.2 | 7.7 | — | — |
| 57 | 8.4 | 6.9 | — | — |
| 58 | 9.2 | 7.9 | <4.6 | — |
| 59 | 8.8 | 7.7 | <4.6 | 7.8 |
| 60 | 9.4 | 8.1 | 4.9 | 8.3 |
| 61 | 9.0 | 8.2 | — | — |
| 62 | 8.9 | 8.2 | <4.6 | 8.7 |
| 63 | 6.6 | — | — | — |
| 64 | 8.8 | 7.3 | <4.6 | 7.8 |
| 65 | 8.5 | 7.0 | <4.6 | 7.3 |
| 66 | 8.7 | 7.3 | <4.6 | 7.6 |
| 67 | 8.7 | 7.2 | <4.6 | 7.3 |
| 68 | 8.5 | 7.0 | <4.6 | 7.3 |
| 69 | 8.7 | 7.9 | <4.6 | 8.5 |
| 70 | 9.2 | 8.3 | <4.6 | 8.8 |
| 71 | 8.6 | 7.3 | <4.6 | 7.7 |
| 72 | 8.6 | 7.1 | <4.6 | 7.3 |
| 73 | 8.5 | 7.3 | <4.6 | 7.5 |
| 74 | 8.7 | 8.0 | <4.6 | 8.7 |
| 75 | 8.5 | 7.9 | <4.6 | 8.5 |
| 76 | 8.7 | — | <4.6 | — |
| 77 | 8.4 | 7.8 | — | — |
| 78 | 8.6 | 8.2 | — | — |
| 79 | 9.5 | — | — | — |
| 80 | 8.5 | 7.7 | — | — |
| 81 | 8.5 | 7.8 | 5.3 | 8.5 |
| 82 | 8.6 | 7.9 | — | — |
| 83 | 9.1 | — | — | — |
| 84 | 9.0 | 8.1 | <4.6 | 8.4 |
| 85 | 8.9 | 7.7 | <4.6 | 8.2 |
| 86 | 8.6 | 7.9 | <4.6 | 8.5 |
| 87 | 8.9 | 7.9 | <4.6 | 8.4 | dash "—" = not tested

The data shows that the compounds described herein affect both lactate efflux from a tumour cell line predominantly expressing MCT4 and in the appropriate conditions, inhibit transport of lactate into MCT4-dependent cells, and are therefore useful as MCT4 inhibitors.

Compounds may be further selected on the basis of further biological or physical properties which may be measured by techniques known in the art and which may be used in the assessment or selection of compounds for therapeutic or prophylactic application.

As a result of their MCT4 inhibitory activity, the compounds of Formula (I), and pharmaceutically acceptable salts thereof are expected to be useful in therapy.

The term "therapy" is intended to have its normal meaning of dealing with a disease in order to entirely or partially relieve one, some or all of its symptoms, or to correct or compensate for the underlying pathology. The term "therapy" also includes "prophylaxis" unless there are specific indications to the contrary. The terms "therapeutic" and "therapeutically" should be interpreted in a corresponding manner.

The term "prophylaxis" is intended to have its normal meaning and includes primary prophylaxis to prevent the development of the disease and secondary prophylaxis whereby the disease has already developed and the patient is temporarily or permanently protected against exacerbation or worsening of the disease or the development of new symptoms associated with the disease.

The term "treatment" is used synonymously with "therapy". Similarly the term "treat" can be regarded as "applying therapy" where "therapy" is as defined herein.

Where "cancer" is mentioned, this includes both non-metastatic cancer and also metastatic cancer, such that treating cancer involves treatment of both primary tumours and also tumour metastases.

In one embodiment there is provided a compound of Formula (I), or a pharmaceutically acceptable salt thereof, for use in therapy.

In one embodiment there is provided the use of a compound of Formula (I), or a pharmaceutically acceptable salt thereof, for the manufacture of a medicament.

In one embodiment there is provided a compound of Formula (I), or a pharmaceutically acceptable salt thereof, for use in the treatment of a disease mediated by MCT4. In one embodiment, the disease mediated by MCT4 is cancer. In one embodiment the cancer is selected from the group consisting of colorectal cancer, glioblastoma, gastric cancer, ovarian cancer, diffuse large B-cell lymphoma, chronic lymphocytic leukaemia, acute myeloid leukaemia, head and neck squamous cell carcinoma, breast cancer, prostate cancer, bladder cancer, hepatocellular carcinoma, renal cancer, thyroid cancer, pancreatic cancer, small cell lung cancer and non-small cell lung cancer.

In one embodiment the cancer is non-small cell lung cancer.

In one embodiment the cancer is lung adenocarcinoma.

In one embodiment there is provided a compound of Formula (I), or a pharmaceutically acceptable salt thereof, for use in the treatment of cancer.

In one embodiment there is provided the use of the compound of Formula (I), or a pharmaceutically acceptable salt thereof, for the manufacture of a medicament for the treatment of a disease mediated by MCT4. In one embodiment, the disease mediated by MCT4 is cancer. In one embodiment, the cancer is selected from the group consisting of colorectal cancer, glioblastoma, gastric cancer, ovarian cancer, diffuse large B-cell lymphoma, chronic lymphocytic leukaemia, acute myeloid leukaemia, head and neck squamous cell carcinoma, breast cancer, prostate cancer, bladder cancer, hepatocellular carcinoma, renal cancer, thyroid cancer, pancreatic cancer, small cell lung cancer and non-small cell lung cancer.

In one embodiment the cancer is non-small cell lung cancer.

In one embodiment the cancer is lung adenocarcinoma.

In one embodiment there is provided the use of the compound of Formula (I), or a pharmaceutically acceptable salt thereof, for the manufacture of a medicament for the treatment of cancer.

In one embodiment there is provided a method for treating a disease in which inhibition of MCT4 is beneficial in a warm-blooded animal in need of such treatment, which comprises administering to said warm-blooded animal a therapeutically effective amount of a compound of Formula (I), or a pharmaceutically acceptable salt thereof. In one embodiment, the disease is cancer. In one embodiment, the cancer is selected from the group consisting of colorectal cancer, glioblastoma, gastric cancer, ovarian cancer, diffuse large B-cell lymphoma, chronic lymphocytic leukaemia, acute myeloid leukaemia, head and neck squamous cell carcinoma, breast cancer, prostate cancer, bladder cancer, hepatocellular carcinoma, renal cancer, thyroid cancer, pancreatic cancer, small cell lung cancer and non-small cell lung cancer.

In one embodiment the cancer is non-small cell lung cancer.

In one embodiment the cancer is lung adenocarcinoma.

In one embodiment there is provided a method for treating cancer in a warm-blooded animal in need of such treatment, which comprises administering to said warm-blooded animal a therapeutically effective amount of a compound of Formula (I), or a pharmaceutically acceptable salt thereof.

Tumours that selectively express MCT4 over MCT1 have an increased likelihood of responding to treatment with a MCT4 inhibitor. Therefore, patients whose tumours express MCT1 at a low level are likely to respond better to an MCT4 inhibitor than those patients whose tumours express MCT1 at a higher level. Generally, patients whose tumours have a high MCT4:MCT1 expression ratio (due to the low level of MCT1 expression), are likely to show a better response, so evaluating the relative expression levels of both MCT1 and MCT4 provides a means for selecting patients for treatment with a MCT4 inhibitor. Methods for determining the relative expression levels of MCT1 and MCT4 are known in the art and are described in WO2010/089580, herein incorporated by reference.

In one embodiment, there is provided a method of treating cancer comprising (i) testing a tumour sample obtained from a patient suffering from or likely to suffer from cancer for selective expression of MCT4 over MCT1 and (ii) administering to the patient having the tumour which selectively expresses MCT4 over MCT1, a compound of Formula (I), or a pharmaceutically acceptable salt thereof.

In one embodiment, there is provided a compound of Formula (I), or a pharmaceutically acceptable salt thereof, for use in the treatment of cancer in a patient wherein the cancer tumour selectively expresses MCT4 over MCT1.

In one embodiment, there is provided use of a compound of Formula (I), or a pharmaceutically acceptable salt thereof, for the manufacture of a medicament for the treatment of cancer in a patient wherein the cancer tumour selectively expresses MCT4 over MCT1.

In one embodiment, there is provided a method for treating cancer in a warm-blooded animal in need of such treatment, which comprises administering to said warm-blooded animal a therapeutically effective amount of a compound of Formula (I), or a pharmaceutically acceptable salt thereof, wherein the cancer tumour selectively expresses MCT4 over MCT1.

The term "therapeutically effective amount" refers to an amount of a compound of Formula (I) as described in any of the embodiments herein which is effective to provide "therapy" in a subject, or to "treat" a disease or disorder in a subject. In the case of cancer, the therapeutically effective amount may cause any of the changes observable or measurable in a subject as described in the definition of "therapy", "treatment" and "prophylaxis" above. For example, the effective amount can reduce the number of cancer or tumour cells; reduce the overall tumour size; inhibit or stop tumour cell infiltration into peripheral organs including, for example, the soft tissue and bone; inhibit and stop tumour metastasis; inhibit and stop tumour growth; relieve to some extent one or more of the symptoms associated with the cancer; reduce morbidity and mortality; improve quality of life; or a combination of such effects. An effective amount may be an amount sufficient to decrease the symptoms of a disease responsive to inhibition of MCT4 activity. For cancer therapy, efficacy in vivo can, for example, be measured by assessing the duration of survival, time to disease progression (TTP), the response rates (RR), duration of response, and/or quality of life. As recognized by those skilled in the art, effective amounts may vary depending on route of administration, excipient usage, and co-usage with other agents. For example, where a combination therapy is used, the amount of the compound of Formula (I) or pharmaceutically acceptable salt described in this specification and the amount of the other pharmaceutically active agent(s) are, when combined, jointly effective to treat a targeted disorder in the animal patient. In this context, the combined amounts are in a "therapeutically effective amount" if they are, when combined, sufficient to decrease the symptoms of a disease responsive to inhibition of MCT4 activity as described above. Typically, such amounts may be determined by one skilled in the art by, for example, starting with the dosage range described in this specification for the compound of Formula (I) or pharmaceutically acceptable salt thereof and an approved or otherwise published dosage range(s) of the other pharmaceutically active compound(s).

"Warm-blooded animals" include, for example, humans.

The anti-cancer treatment described in this specification may be useful as a sole therapy, or may involve, in addition to administration of the compound of Formula (I), or a pharmaceutically acceptable salt thereof, conventional surgery, radiotherapy or chemotherapy; or a combination of such additional therapies. Such conventional surgery, radiotherapy or chemotherapy may be administered simultaneously, sequentially or separately to treatment with the compound of Formula (I) or a pharmaceutically acceptable salt thereof.

Where a combination therapy is administered "simultaneously", this includes treatment of a patient with a single dosage form (e.g. a tablet) comprising both a compound of Formula (I), or a pharmaceutically acceptable salt thereof and an additional anti-cancer substance; and also simultaneous dosing of separate dosage forms each separately comprising one of the respective combination partners.

Where a combination therapy is administered "sequentially" or "separately", this includes treatment of a patient with a first dosage form (e.g. a tablet) comprising a compound of Formula (I), or a pharmaceutically acceptable salt thereof, followed by treatment of the same patient with a second dosage form comprising an additional anti-cancer substance; or treatment of a patient with a single dosage form (e.g. a tablet) comprising a particular anti-cancer substance, followed by treatment of the same patient with a second dosage form comprising a compound of Formula (I), or a pharmaceutically acceptable salt thereof. The interval between the sequential or separate doses may be judged by a skilled practitioner with reference to the information in this specification.

In one embodiment there is provided a compound of Formula (I), or a pharmaceutically acceptable salt thereof, for use in the treatment of cancer, where the compound of Formula (I), or a pharmaceutically acceptable salt thereof is administered before surgery.

Administration of a compound of Formula (I), or a pharmaceutically acceptable salt thereof, before surgery to entirely or partially remove a cancer may be referred to as "neo-adjuvant therapy". In such a scenario, the goal of administering the compound of Formula (I), or a pharmaceutically acceptable salt thereof is generally to reduce the size of the target tumour in order to increase the chances of a successful resection. As such, the length of time the compound of Formula (I), or a pharmaceutically acceptable salt thereof is dosed before surgery may be judged by a skilled practitioner with reference to the information within this specification.

In one embodiment there is provided a compound of Formula (I), or a pharmaceutically acceptable salt thereof, for use in the treatment of cancer, where the compound of Formula (I), or a pharmaceutically acceptable salt thereof is administered after surgery.

In one embodiment there is provided a compound of Formula (I), or a pharmaceutically acceptable salt thereof, for use in the treatment of cancer, where the compound of Formula (I), or a pharmaceutically acceptable salt thereof is administered in combination with at least one additional anti-cancer substance.

In one embodiment there is provided a compound of Formula (I), or a pharmaceutically acceptable salt thereof, for use in the treatment of cancer, where the compound of Formula (I), or a pharmaceutically acceptable salt thereof is administered simultaneously, sequentially or separately with at least one additional anti-cancer substance.

The anti-cancer treatment defined herein may be applied as a sole therapy or may involve, in addition to the compounds of the specification, conventional surgery or radiotherapy or chemotherapy. Such chemotherapy may include one or more of the following categories of anti-tumour agents:
(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, pemetrexed, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example *vinca* alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);
(ii) antiangiogenic agents such as those which inhibit the effects of vascular endothelial growth factor, for example the anti-vascular endothelial cell growth factor antibody bevacizumab (Avastin™) and for example, a VEGF receptor tyrosine kinase inhibitor such as sorafenib, axitinib, pazopanib, sunitinib and cediranib;
(iii) immunotherapy approaches, including for example ex vivo and in vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies. Specific examples include monoclonal antibodies targeting PD-1 (e.g. nivolumab and pembrolizumab), PD-L1 (e.g. durvalumab and atezolizumab), CTLA4 (e.g. tremelimumab and ipilimumab) or CD73 (e.g. oleclumab), as well as CD40 ligand fusion proteins and GITR ligand fusion proteins;
(iv) inhibitors of lactate transporters, including for example MCT1 inhibitors such as AZD3965;
(v) agents that target tumour metabolism including those that inhibit GLS1, Complex I, mitochondrial pyruvate carrier inhibitors.

Therefore, in one embodiment there is provided a compound of Formula (I), or a pharmaceutically acceptable salt thereof, and at least one additional anti-tumour substance, for use in the treatment of cancer. In one embodiment there is provided a compound of Formula (I), or a pharmaceutically acceptable salt thereof, for use in the treatment of cancer, where the compound of Formula (I), or a pharmaceutically acceptable salt thereof is administered in combination with an additional anti-tumour substance. In one embodiment there is one additional anti-tumour substance. In one embodiment there are two additional anti-tumour substances. In one embodiment there are three or more additional anti-tumour substances.

In one embodiment there is provided a compound of Formula (I), or a pharmaceutically acceptable salt thereof, and at least one additional anti-tumour substance for use in the simultaneous, separate or sequential treatment of cancer. In one embodiment there is provided a compound of Formula (I), or a pharmaceutically acceptable salt thereof, for use in the treatment of cancer, where the compound of Formula (I), or a pharmaceutically acceptable salt thereof, is administered simultaneously, separately or sequentially with an additional anti-tumour substance.

In one embodiment there is provided a method of treating cancer in a warm-blooded animal who is in need of such treatment, which comprises administering to said warm-blooded animal a compound of Formula (I), or a pharmaceutically acceptable salt thereof and at least one additional anti-tumour substance, wherein the amounts of the compound of Formula (I), or a pharmaceutically acceptable salt thereof, and the additional anti-tumour substance are jointly effective in producing an anti-cancer effect.

In one embodiment there is provided a method of treating cancer in a warm-blooded animal who is in need of such treatment, which comprises administering to said warm-blooded animal a compound of Formula (I), or a pharmaceutically acceptable salt thereof, and simultaneously, separately or sequentially administering at least one additional anti-tumour substance to said warm-blooded animal, wherein the amounts of the compound of Formula (I), or pharmaceutically acceptable salt thereof, and the additional anti-tumour substance are jointly effective in producing an anti-cancer effect.

In any embodiment the additional anti-tumour substance is selected from the group consisting of one or more of the anti-tumour substances listed under points (i) (v) above.

In one embodiment there is provided a compound of Formula (I), or a pharmaceutically acceptable salt thereof, and at least one additional anti-tumour substance selected from the group consisting of PD-1 antibodies (e.g. nivolumab and pembrolizumab), PD-L1 antibodies (e.g. durvalumab and atezolizumab), CTLA4 antibodies (e.g. tremelimumab and ipilimumab), CD73 antibodies (e.g. oleclumab), CD40 ligand fusion proteins and GITR ligand fusion proteins, for use in the treatment of cancer.

In one embodiment there is provided a compound of Formula (I), or a pharmaceutically acceptable salt thereof, and at least one additional anti-tumour substance selected from the group consisting of PD-L1 antibodies (e.g. durvalumab and atezolizumab), for use in the treatment of cancer.

In one embodiment there is provided a compound of Formula (I), or a pharmaceutically acceptable salt thereof, and durvalumab for use in the treatment of cancer.

In one embodiment, the cancer is non-small cell lung cancer. In one embodiment, the cancer is lung adenocarcinoma.

In one embodiment there is provided a compound of Formula (I), or a pharmaceutically acceptable salt thereof, for use in the treatment of cancer, where the compound of Formula (I), or a pharmaceutically acceptable salt thereof, is administered simultaneously, separately or sequentially with at least one additional anti-tumour substance selected from the group consisting of PD-1 antibodies (e.g. nivolumab and pembrolizumab), PD-L1 antibodies (e.g. durvalumab and atezolizumab), CTLA4 antibodies (e.g. tremelimumab and ipilimumab), CD73 antibodies (e.g. oleclumab), CD40 ligand fusion proteins and GITR ligand fusion proteins.

In one embodiment there is provided a compound of Formula (I), or a pharmaceutically acceptable salt thereof, for use in the treatment of cancer, where the compound of Formula (I), or a pharmaceutically acceptable salt thereof, is administered simultaneously, separately or sequentially with at least one additional anti-tumour substance selected from the group consisting of PD-L1 antibodies (e.g. durvalumab and atezolizumab).

In one embodiment there is provided a compound of Formula (I), or a pharmaceutically acceptable salt thereof, for use in the treatment of cancer, where the compound of Formula (I), or a pharmaceutically acceptable salt thereof, is administered simultaneously, separately or sequentially with durvalumab.

In one embodiment, the cancer is non-small cell lung cancer. In one embodiment, the cancer is lung adenocarcinoma.

In one embodiment there is provided use of a compound of Formula (I), or a pharmaceutically acceptable salt thereof, for the manufacture of a medicament for the treatment of cancer, where the compound of Formula (I), or a pharmaceutically acceptable salt thereof is administered simultaneously, separately or sequentially with at least one additional anti-tumour substance selected from the group consisting of PD-1 antibodies (e.g. nivolumab and pembrolizumab), PD-L1 antibodies (e.g. durvalumab and atezolizumab), CTLA4 antibodies (e.g. tremelimumab and ipilimumab), CD73 antibodies (e.g. oleclumab), CD40 ligand fusion proteins and GITR ligand fusion proteins. In one embodiment there is provided use of a compound of Formula (I), or a pharmaceutically acceptable salt thereof, for the manufacture of a medicament for the treatment of cancer, where the compound of Formula (I), or a pharmaceutically acceptable salt thereof is administered simultaneously, separately or sequentially with at least one additional anti-tumour substance selected from the group consisting of PD-L1 antibodies (e.g. durvalumab and atezolizumab).

In one embodiment, there is provided use of a compound of Formula (I), or a pharmaceutically acceptable salt thereof, for the manufacture of a medicament for the treatment of cancer, where the compound of Formula (I), or a pharmaceutically acceptable salt thereof, is administered simultaneously, separately or sequentially with durvalumab.

In one embodiment the cancer is non-small cell lung cancer. In one embodiment the cancer is lung adenocarcinoma.

In one embodiment, there is provided a method for treating cancer in a warm-blooded animal in need of such treatment, which comprises administering to said warm-blooded animal a therapeutically effective amount of a compound of Formula (I), or a pharmaceutically acceptable salt thereof, simultaneously, separately or sequentially with at least one additional anti-tumour substance selected from the group consisting of PD-1 antibodies (e.g. nivolumab and pembrolizumab), PD-L1 antibodies (e.g. durvalumab and atezolizumab), CTLA4 antibodies (e.g. tremelimumab and ipilimumab), CD73 antibodies (e.g. oleclumab), CD40 ligand fusion proteins and GITR ligand fusion proteins.

In one embodiment, there is provided a method for treating cancer in a warm-blooded animal in need of such treatment, which comprises administering to said warm-blooded animal a therapeutically effective amount of a compound of Formula (I), or a pharmaceutically acceptable salt thereof, simultaneously, separately or sequentially with at least one additional anti-tumour substance selected from the group consisting of PD-L1 antibodies (e.g. durvalumab and atezolizumab).

In one embodiment, there is provided a method for treating cancer in a warm-blooded animal in need of such treatment, which comprises administering to said warm-blooded animal a therapeutically effective amount of a compound of Formula (I), or a pharmaceutically acceptable salt thereof, simultaneously, separately or sequentially with durvalumab.

In one embodiment the cancer is non-small cell lung cancer. In one embodiment the cancer is lung adenocarcinoma.

In one embodiment there is provided a pharmaceutical composition comprising a compound of Formula (I) and at least one additional anti-tumour substance, for use in the treatment of cancer. In one embodiment the pharmaceutical composition also comprises at least one pharmaceutically acceptable excipient. In one embodiment the anti-tumour substance is an anti-neoplastic agent. According to a further embodiment there is provided a kit comprising:

a) A compound of Formula (I), or a pharmaceutically acceptable salt thereof, in a first unit dosage form;

b) A further additional anti-tumour substance in a further unit dosage form;

c) Container means for containing said first and further unit dosage forms; and optionally d) Instructions for use.

The compounds of Formula (I), and pharmaceutically acceptable salts thereof, may be administered as pharmaceutical compositions, comprising one or more pharmaceutically acceptable excipients.

Therefore, in one embodiment there is provided a pharmaceutical composition comprising a compound of Formula (I), or a pharmaceutically acceptable salt thereof, and at least one pharmaceutically acceptable excipient. The compositions may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous or intramuscular dosing), or as a suppository for rectal dosing. The compositions may be obtained by conventional procedures using conventional pharmaceutical excipients, well known in the art. Thus, compositions intended for oral use may contain, for example, one or more colouring, sweetening, flavouring and/or preservative agents.

In one embodiment there is provided a pharmaceutical composition comprising a compound of Formula (I), or a pharmaceutically acceptable salt thereof, and at least one pharmaceutically acceptable excipient, for use in therapy.

In one embodiment there is provided a pharmaceutical composition comprising a compound of Formula (I), or a pharmaceutically acceptable salt thereof, and at least one pharmaceutically acceptable excipient, for use in the treatment of cancer. In one embodiment, said cancer is selected from the group consisting of colorectal cancer, glioblastoma, gastric cancer, ovarian cancer, diffuse large B-cell lymphoma, chronic lymphocytic leukaemia, acute myeloid leukaemia, head and neck squamous cell carcinoma, breast cancer, prostate cancer, bladder cancer, hepatocellular carcinoma, renal cancer, thyroid cancer, pancreatic cancer, small cell lung cancer and non-small cell lung cancer.

In one embodiment the cancer is non-small cell lung cancer.

In one embodiment the cancer is lung adenocarcinoma.

The compound of Formula (I) will normally be administered to a warm-blooded animal at a unit dose within the range 2.5-5000 mg/m$^2$ body area of the animal, or approximately 0.05-100 mg/kg, and this normally provides a therapeutically-effective dose. A unit dose form such as a tablet or capsule will usually contain, for example 0.1-500 mg of active ingredient. The daily dose will necessarily be varied depending upon the host treated, the particular route of administration, any therapies being co-administered, and the severity of the illness being treated.

EXAMPLES

Aspects of the present disclosure can be further defined by reference to the following non-limiting examples, which describe in detail preparation of certain compounds and intermediates of the present disclosure and methods for using compounds of the present disclosure. It will be apparent to those skilled in the art that many modifications, both to materials and methods, can be practiced without departing from the scope of the present disclosure.

Unless stated otherwise, starting materials were commercially available. All solvents and commercial reagents were of laboratory grade and were used as received.

General Experimental

The invention will now be illustrated in the following Examples in which, generally:
(i) operations were carried out at room temperature (rt), i.e. in the range 17 to 25° C. and under an atmosphere of an inert gas such as N$_2$ or Ar unless otherwise stated;
(ii) in general, the course of reactions was followed by thin layer chromatography (TLC) and/or analytical high performance liquid chromatography (HPLC or UPLC) which was usually coupled to a mass spectrometer (LCMS). The reaction times that are given are not necessarily the minimum attainable;
(iii) when necessary, organic solutions were dried over anhydrous MgSO$_4$ or Na$_2$SO$_4$, work-up procedures were carried out using traditional phase separating techniques or by using SCX as described in (xiii), evaporations were carried out either by rotary evaporation in vacuo or in a Genevac HT-4/EZ-2 or Biotage V10;
(iv) yields, where present, are not necessarily the maximum attainable, and when necessary, reactions were repeated if a larger amount of the reaction product was required;
(v) in general, the structures of the end-products of the Formula (I) were confirmed by nuclear magnetic resonance (NMR) and/or mass spectral techniques; electrospray mass spectral data were obtained using a Waters Acquity UPLC coupled to a Waters single quadrupole mass spectrometer acquiring both positive and negative ion data, and generally, only ions relating to the parent structure are reported; proton NMR chemical shift values were measured on the delta scale using either a Bruker AV500 spectrometer operating at a field strength of 500 MHz, a Bruker AV400 operating at 400 MHz or a Bruker AV300 operating at 300 MHz. Unless otherwise stated, NMR spectra were obtained at 500 MHz in d6-dimethylsulfoxide. The following abbreviations have been used (and derivatives thereof, e.g. dd, doublet of doublets, etc.): s, singlet; d, doublet; t, triplet; q, quartet; m, multiplet; br, broad; qn, quintet; p, pentet
(vi) unless stated otherwise compounds containing an asymmetric carbon and/or sulfur atom were not resolved;
(vii) intermediates were not necessarily fully purified but their structures and purity were assessed by TLC, analytical HPLC/UPLC, and/or NMR analysis and/or mass spectrometry;
(viii) unless otherwise stated, flash column chromatography (fcc) was performed on Merck Kieselgel silica (Art. 9385) or on reversed phase silica (Fluka silica gel 90 C18) or on Silicycle cartridges (40-63 μm silica, 4 to 330 g weight) or on Puriflash cartridges (50 μm silica, 4 to 330 g weight) or on Grace resolv cartridges (4 to 120 g) or on RediSep Rf 1.5 Flash columns or on RediSep Rf high performance Gold Flash columns (150 to 415 g weight) or on RediSep Rf Gold C18 Reversed-phase columns (20-40 μm silica) either manually or automated using an Isco CombiFlash Companion system or similar system;
(ix) preparative reverse phase HPLC (RP HPLC) was performed on C18 reversed-phase silica typically using a Waters XSelect CSH C18 or Phenomenex Gemini-NX axia Prep C18 OBD column (5 μm silica, 30 mm diameter, 100 mm length) using decreasingly polar mixtures as eluent, for example [containing 0.1% formic acid or 0.3-0.5% aqueous ammonium hydroxide (d=0.91)] as solvent A and acetonitrile as solvent B; a typical procedure would be as follows: a solvent gradient over 10-20 minutes, at 40-50 mL per minute, from a 95:5 mixture of solvents A and B respectively to a 5:95 mixture of solvents A and B (or alternative ratio as appropriate).
(x) the following analytical UPLC methods were used; in general, reverse-phase C18 silica was used with a flow rate of 1 mL/minute and detection was by Electrospray Mass Spectrometry and by UV absorbance recording a wavelength range of 220-320 nm. Analytical UPLC was performed on CSH C18 reverse-phase silica, using a Waters XSelect CSH C18 column with dimensions 2.1×50 mm and particle size 1.7 micron). Gradient analysis was employed using decreasingly polar mixtures as eluent, for example decreasingly polar mixtures of water (containing 0.1% formic acid or 0.1% ammonia) as solvent A and acetonitrile as solvent B. A typical 2 minute analytical UPLC method would employ a solvent gradient over 1.3 minutes, at approximately 1 mL per minute, from a 97:3 mixture of solvents A and B respectively to a 3:97 mixture of solvents A and B.
(xi) where certain compounds were obtained as an acid-addition salt, for example a mono-hydrochloride salt or a di-hydrochloride salt, the stoichiometry of the salt was based on the number and nature of the basic groups in the compound, the exact stoichiometry of the salt was generally not determined, for example by means of elemental analysis data;
(xii) where reactions refer to the use of a microwave, one of the following microwave reactors were used: Biotage Initiator, Personal Chemistry Emrys Optimizer, Personal Chemistry Smithcreator or CEM Explorer;
(xiii) compounds were purified by strong cation exchange (SCX) chromatography using Isolute SPE flash SCX-2 or SCX-3 columns (International Sorbent Technology Limited, Mid Glamorgan, UK);

(xiv) chiral preparative chromatography was carried out using HPLC or SFC using a Waters SFC 100 or equivalent. A chiral stationary phase such as a cellulose or amylose chiral Daicel column or equivalent was chosen to optimise separation of isomers within the sample. Semi preparative separations typically used a chiral column with dimensions 30×250 mm, 5 micron with SFC flow rates of 100 ml/min or HPLC flow rate of 40 ml/min. Detection was by UV absorbance or mass spectrometric detection. For UV detection a generic wavelength, typically 220 nm or 254 nm, was used or a wavelength was chosen to maximise the product response. For mass detection, a soft ionization technique such as electrospray ionization was employed allowing the product to be detected by targeting MH+ response. Samples were dissolved in a compatible solvent for injection into the chromatographic system. For SFC separations, column temperature was held constant at approximately 40° C. and back pressure regulated to a constant pressure of approximately 100-150 bar.

(xv) chiral analysis was carried out using SFC or HPLC using a Waters UPC2 SFC, Agilent 1200 HPLC or equivalent. A chiral stationary phase such as a cellulose or amylose chiral Daicel columns or equivalent was chosen to optimise separation of isomers within the sample. Analytical separations typically used a chiral column with dimensions 3.0× 150 mm, 3 micron with SFC flow rates of 2 ml/min or HPLC flow rates 0.5 ml/min. Detection was by UV absorbance (DAD) and/or mass spectrometry (full scan). The sample was dissolved in a compatible solvent at a concentration of approximately 0.5 mg/ml and injected directly into the chromatographic system. For SFC separations, column temperature was held constant at approximately 40° C. and back pressure regulated to a constant pressure of approximately 100-150 bar.

(xvi) in general Examples and intermediate compounds were named using ACD Name, "Structure to Name" part of ChemDraw Ultra (CambridgeSoft) or Biovia Draw 2016;

(xvii) where reactions refer to being degassed this can be performed for example by purging the reaction solvent with a constant flow of nitrogen for a suitable period of time (for example 5 to 10 minutes)

(xviii) in addition to the ones mentioned above, the following abbreviations have been used:

| | | | |
|---|---|---|---|
| DMF | N,N-dimethylformamide | DMA | N,N-dimethylacetamide |
| DCM | dichloromethane | THF | tetrahydrofuran |
| conc. | Concentrated | m/z | mass spectrometry peak(s) |
| TBAF | tetra n-butylammonium fluoride | NMP | 1-methylpyrrolidin-2-one |
| | | DIPEA | N,N-diisopropylethylamine |
| EtOAc | ethyl acetate | | |
| DME | 1,2-dimethoxyethane | MeOH | methanol |
| MeCN | acetonitrile | MeOD | d₄-methanol |
| Et₂O | diethyl ether | DBU | 1,8-diazabicyclo[5.4.0]undec-7-ene |
| AcOH | acetic acid | | |
| Ac₂O | acetic anhydride | | |
| h | hour(s) | DCE | 1,2-dichloroethane |
| MTBE | methyl tert-butyl ether | DMAP | 4-dimethylaminopyridine |
| rt | room temperature | EtOH | ethanol |
| NBS | N-Bromosuccinimide | Sat. | saturated |
| HATU | 1-[Bis(dimethylamino) methylene]-1H-1,2,3-triazolo[4,5-b]pyridinium 3-oxide hexafluorophosphate | fcc | flash column chromatography |
| | | FA | Formic acid |
| | | SCX | Strong cation exchange |
| SFC | Supercritical fluid chromatography | RuPhos | dicyclohexyl(2',6'-diisopropoxy-[1,1'-biphenyl]-2-yl)phosphine |
| DEA | Diethylamine | | |

(xix) For XRPD analysis the instrument used was a Bruker D4. The X-ray powder diffractogram was determined by mounting a sample of the crystalline material on a Bruker single silicon crystal (SSC) wafer mount and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5418 angstroms. The collimated X-ray source was passed through an automatic variable divergence slit set at V20 and the reflected radiation directed through a 5.89 mm anti scatter slit and a 9.55 mm detector slit. Samples were measured in reflection geometry in θ-2θ configuration over the scan range 2° to 40° 2θ with a nominal 0.12 second exposure per 0.02° increment. The instrument was equipped with a Position sensitive detector (Lynxeye). Persons skilled in the art of X-ray powder diffraction will understand that the relative intensity of peaks can be affected by, for example, grains above 30 microns in size and non-unitary aspect ratios that may affect analysis of samples. The skilled person will also understand that the position of reflections can be affected by the precise height at which the sample sits in the diffractometer and the zero calibration of the diffractometer. The surface planarity of the sample may also have a small effect. Hence the diffraction pattern data presented are not to be taken as absolute values;

(xx) For the Differential Scanning calorimetry the instrument used was TA Instruments Q2000 DSC. Typically less than 3 mg of material contained in a standard aluminium pan fitted with a lid was heated over the temperature range 25° C. to 300° C. at a constant heating rate of 10° C. per minute. A purge gas using nitrogen was used—flow rate 50 mL per minute. Thermal data was analysed using standard software, e.g., Universal v. 4.5A from TA INSTRUMENTS®.

Intermediate 1: (R)-tert-butyl 3-(bromomethyl)pyrrolidine-1-carboxylate

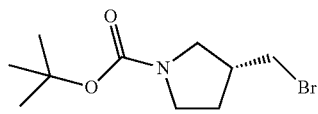

Triphenylphosphine (78 g, 298.1 mmol) was added portionwise to (R)-tert-butyl 3-(hydroxymethyl)pyrrolidine-1-carboxylate (50 g, 248.4 mmol) and CBr₄ (115 g, 347.8 mmol) in DCM (1 L) at 0° C. over a period of 5 min. The reaction mixture was allowed to warm to rt, and was stirred at rt for 16 h, then was concentrated in vacuo and purified by fcc, eluting with 0-16% EtOAc in petroleum ether, to afford the title compound (61.6 g, 94%) as a colourless oil; ¹H NMR (300 MHz, CDCl₃) 1.47 (9H, s), 1.72 (1H, dq), 1.99-2.16 (1H, m), 2.52-2.68 (1H, m), 3.10 (1H, dd), 3.26-3.44 (3H, m), 3.49 (1H, ddd), 3.59 (1H, dd).

Intermediate 2: (R)-tert-butyl 3-(2-acetyl-3-oxobutyl)pyrrolidine-1-carboxylate

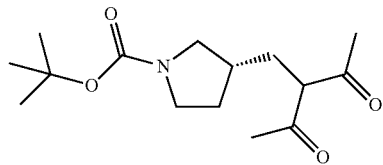 [SMILES: CC(=O)C(C[C@@H]1CCN(C(=O)OC(C)(C)C)C1)C(C)=O]

K₂CO₃ (48.3 g, 349.8 mmol) was added to (R)-tert-butyl 3-(bromomethyl)pyrrolidine-1-carboxylate (61.6 g, 233.2 mmol) and pentane-2,4-dione (23.35 g, 233.2 mmol) in DMF (600 mL) at rt. The reaction mixture was stirred at 80° C. for 16 h, then was allowed to cool to rt, diluted with EtOAc (500 mL), filtered and concentrated in vacuo. The resulting crude product was purified by fcc, eluting with 0-30% EtOAc in petroleum ether, to afford the title compound (43.9 g, 66%) as a pale yellow oil; m/z MH⁺ 284.

Intermediate 3: (R)-tert-butyl 3-((2,5,7-trimethyl-[1,2,4]triazolo[1,5-a]pyrimidin-6-yl)methyl)pyrrolidine-1-carboxylate

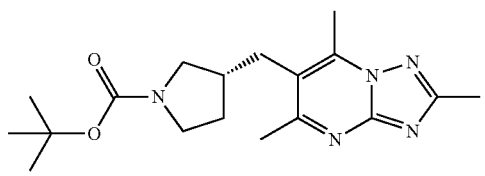 [SMILES: Cc1nc2nc(C)c(C[C@@H]3CCN(C(=O)OC(C)(C)C)C3)c(C)n2n1]

3-Methyl-1H-1,2,4-triazol-5-amine (15.20 g, 154.9 mmol) was added in one portion to (R)-tert-butyl 3-(2-acetyl-3-oxobutyl)pyrrolidine-1-carboxylate (43.9 g, 154.9 mmol) in AcOH (500 mL) at rt. The reaction mixture was heated at 80° C. for 16 h, then was allowed to cool to rt and concentrated in vacuo. The resulting crude product was purified by flash C18 chromatography, eluting with 5-80% MeOH in water, to afford the title compound (18.00 g, 34%) as a pale yellow gum; ¹H NMR (300 MHz, CDCl₃) 1.45 (9H, s), 1.70 (1H, dt), 1.91-2.07 (1H, m), 2.32-2.44 (1H, m), 2.60 (3H, s), 2.67 (3H, s), 2.78 (5H, s), 3.06 (1H, dt), 3.23-3.54 (3H, dt); m/z MH⁺ 346.

Intermediate 4: (R)-2,5,7-trimethyl-6-(pyrrolidin-3-ylmethyl)-[1,2,4]triazolo[1,5-a]pyrimidine (dihydrochloride salt)

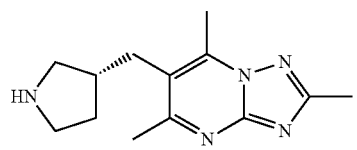 [SMILES: Cc1nc2nc(C)c(C[C@@H]3CCNC3)c(C)n2n1]

4 M HCl in 1,4-dioxane (200 ml, 800 mmol) was added to (R)-tert-butyl 3-((2,5,7-trimethyl-[1,2,4]triazolo[1,5-a]pyrimidin-6-yl)methyl)pyrrolidine-1-carboxylate (18 g, 52.11 mmol) in 1,4-dioxane (50 mL). The reaction mixture was stirred at rt for 16 h. The resulting precipitate was collected by filtration, washed with 1,4-dioxane (100 mL) and dried in vacuo to afford the title compound (13.80 g, 83%) as a white solid, which was used without further purification; ¹H NMR (300 MHz, DMSO) 1.63 (1H, dq), 1.90-2.05 (1H, m), 2.51 (4H, s), 2.65 (3H, s), 2.75-3.13 (7H, m), 3.26 (2H, ddt), 7.30 (1H, br s) 9.28 (1H, s), 9.52 (1H, s); m/z MH⁺ 246.

Intermediate 4B (free base of intermediate 4): (R)-2,5,7-trimethyl-6-(pyrrolidin-3-ylmethyl)-[1,2,4]triazolo[1,5-a]pyrimidine

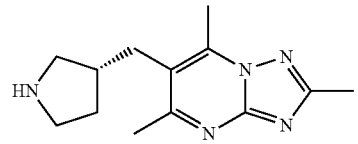 [SMILES: Cc1nc2nc(C)c(C[C@@H]3CCNC3)c(C)n2n1]

1.25 M HCl in EtOH (36.4 mL, 45.51 mmol) was added in one portion to (R)-tert-butyl 3-((2,5,7-trimethyl-[1,2,4]triazolo[1,5-a]pyrimidin-6-yl)methyl)pyrrolidine-1-carboxylate (2.62 g, 7.58 mmol) in EtOH (15 mL) at rt. The resulting solution was stirred at rt for 5 days. The solvent was evaporated in vacuo to afford crude HCl salt as an orange gum. The crude product was converted to the free base using ion exchange chromatography, using an SCX column. The desired product was eluted from the column using 1 M NH₃/MeOH and pure fractions were evaporated to dryness to afford the title compound (1.77 g, 95%) as an orange gum; ¹H NMR (500 MHz, CDCl₃) 1.51 (1H, dq), 1.92 (1H, ddd), 2.32 (1H, p), 2.60 (3H, s), 2.64 (1H, dd), 2.69 (3H, s), 2.80 (3H, s), 2.82 (2H, dd), 2.98 (1H, dt), 3.03-3.13 (2H, m) NH not observed; m/z MH⁺ 246.

Intermediate 5: (R)-6-((1-(5-bromopyridin-2-yl)pyrrolidin-3-yl)methyl)-2,5,7-trimethyl-[1,2,4]triazolo[1,5-a]pyrimidine

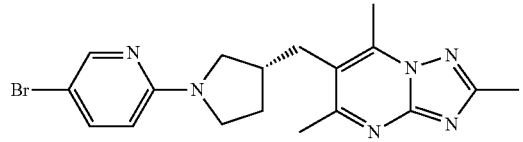 [SMILES: Cc1nc2nc(C)c(C[C@@H]3CCN(c4ccc(Br)cn4)C3)c(C)n2n1]

DIPEA (4.39 mL, 25.14 mmol), (R)-2,5,7-trimethyl-6-(pyrrolidin-3-ylmethyl)-[1,2,4]triazolo[1,5-a]pyrimidine dihydrochloride (2 g, 6.28 mmol) and 5-bromo-2-fluoropyridine (1.66 g, 9.43 mmol) were dissolved in n-propanol (10 mL) and sealed into a microwave tube. The reaction mixture was heated at 150° C. for 2.5 h in the microwave reactor and cooled to rt. The solvent was removed under reduced pressure. The reaction mixture was poured into water (100 mL), extracted with EtOAc (3×100 mL), the organic layer was dried over Na₂SO₄, filtered and evaporated to afford a yellow solid. The crude product was purified by crystallisation from EtOAc/petroleum ether to afford the title compound (1.30 g, 52%) as a pale yellow solid; ¹H NMR (300 MHz, CDCl₃) 1.90 (1H, dq), 2.19 (1H, dq), 2.63 (4H, s), 2.71 (3H, s), 2.80 (3H, s), 2.93 (2H, qd), 3.24 (1H, dd), 3.45 (1H, q), 3.63 (2H, q), 6.28 (1H, d), 7.54 (1H, dd), 8.19 (1H, d); m/z MH⁺ 401.

Intermediate 7: 1-((6-bromopyridin-3-yl)methyl)-4-methylpiperazine

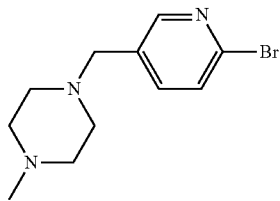

6-Bromonicotinaldehyde (3 g, 16.13 mmol) and 1-methylpiperazine (4.85 g, 48.39 mmol) were stirred in DCM (200 mL) at rt for 2 h. AcOH (0.097 g, 1.61 mmol) and sodium triacetoxyborohydride (6.84 g, 32.26 mmol) were added and the mixture was stirred at rt for 16 h. The reaction mixture was quenched with sat. aq. NaHCO$_3$ and the organic layer was separated. The aqeuous layer was extracted with EtOAc and the combined organic layers were dried (Na$_2$SO$_4$), filtered and concentrated in vacuo. The resulting crude product was purified by flash C18 chromatography, eluting with 0-80% MeOH in water, to afford the title compound (2.00 g, 46%) as a yellow oil; $^1$H NMR (300 MHz, DMSO) 2.55 (3H, s), 2.65 (4H, d), 2.91 (4H, s), 3.49 (2H, s), 7.37-7.54 (2H, m), 8.27 (1H, d); m/z MH$^+$ 270.

Intermediate 8: 1-((5-bromopyridin-2-yl)methyl)-4-methylpiperazine

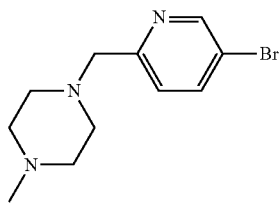

5-Bromopicolinaldehyde (3.5 g, 18.82 mmol) and 1-methylpiperazine (5.65 g, 56.45 mmol) in DCM (20 mL) was stirred at rt for 2 h. AcOH (0.113 g, 1.88 mmol) and sodium triacetoxyborohydride (7.98 g, 37.63 mmol) were added and the reaction mixture was stirred at rt for 16 h. The reaction mixture was concentrated in vacuo and the resulting crude product was purified by flash C18 chromatography, eluting with 0-100% MeOH in water, to afford the title compound (2.40 g, 47%) as a yellow oil; $^1$H NMR (300 MHz, DMSO) 2.26 (3H, s), 2.47 (8H, s), 3.58 (2H, s), 7.42 (1H, m), 8.03 (1H, dd), 8.62 (1H, dd); m/z MH$^+$ 270.

Intermediate 9: (6-((4-methylpiperazin-1-yl)methyl)pyridin-3-yl)boronic acid

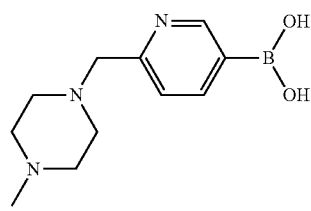 [SMILES: CN1CCN(Cc2ccc(B(O)O)cn2)CC1]

PdCl$_2$(dppf) (21.67 mg, 0.03 mmol) was added to 1-((5-bromopyridin-2-yl)methyl)-4-methylpiperazine (160 mg, 0.59 mmol), 4,4,4',4',5,5,5',5'-octamethyl-2,2'-bi(1,3,2-dioxaborolane) (165 mg, 0.65 mmol) and potassium acetate (116 mg, 1.18 mmol) in 1,4-dioxane (4 mL) at rt under nitrogen. The resulting mixture was stirred at 90° C. for 16 h.

The mixture was purified by flash C18-flash chromatography, elution gradient 5 to 100% MeCN in water to afford impure title compound (80 mg, 58%) as a yellow gum; m/z MH$^+$ 236 (compound assumed to be boronic acid based on LCMS data).

Intermediate 10: rac-6-((1-(5-bromopyrimidin-2-yl)pyrrolidin-3-yl)methyl)-2,5,7-trimethyl-[1,2,4]triazolo[1,5-a]pyrimidine

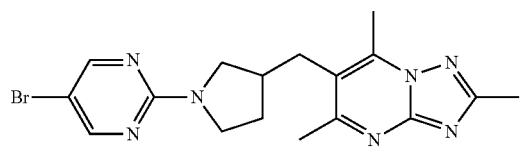 [SMILES: Cc1nc2nc(C)c(CC3CCN(c4ncc(Br)cn4)C3)c(C)n2n1]

DIPEA (0.878 mL, 5.03 mmol) was added to 5-bromo-2-chloropyrimidine (486 mg, 2.51 mmol) and rac-2,5,7-trimethyl-6-(pyrrolidin-3-ylmethyl)-[1,2,4]triazolo[1,5-a]pyrimidine dihydrochloride (800 mg, 2.51 mmol) (made in 4 steps in a similar fashion to Intermediate 4 starting from rac-tert-butyl 3-(hydroxymethyl)pyrrolidine-1-carboxylate), in EtOH (10 mL) at rt. The reaction mixture was heated at 70° C. for 16 h, then was allowed to cool to rt and was concentrated in vacuo. The resulting crude product was purified by fcc, eluting with 5-10% MeOH in DCM, to afford the title compound (350 mg, 35%) as a yellow solid; $^1$H NMR (300 MHz, CDCl$_3$) 1.79-1.93 (1H, m), 2.09-2.27 (1H, m), 2.49-2.62 (1H, m), 2.65 (3H, s), 2.72 (3H, s), 2.80 (3H, s), 2.92 (2H, dd), 3.30 (1H, dd), 3.46-3.61 (1H, m), 3.64-3.81 (2H, m), 8.31 (2H, s); m/z MH$^+$ 402.

Intermediate 11: (R)-2,5,7-trimethyl-6-((1-(pyridin-3-yl)pyrrolidin-3-yl)methyl)-[1,2,4]triazolo[1,5-a]pyrimidine

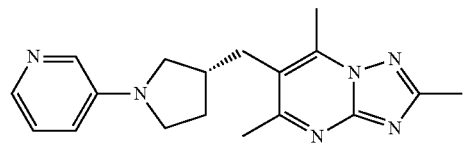

Cs$_2$CO$_3$ (1.97 g, 6.03 mmol) was added to (R)-2,5,7-trimethyl-6-(pyrrolidin-3-ylmethyl)-[1,2,4]triazolo[1,5-a]pyrimidine (0.74 g, 3.02 mmol) and 3-iodopyridine (0.68 g, 3.32 mmol) in 1,4-dioxane (10 mL). The reaction mixture was degassed and RuPhos 3rd generation precatalyst (0.25 g, 0.30 mmol) was added. The reaction mixture was heated at 90° C. for 5 h, then was allowed to cool to rt and diluted with DCM and filtered. The filtrate was concentrated in vacuo and purified by fcc eluting with 0-5% 1 M NH$_3$/MeOH in DCM, to afford the title compound (0.413 g, 43%) as a yellow solid; $^1$H NMR (500 MHz, CDCl$_3$) 1.88 (1H, dq), 2.18 (1H, dtd), 2.58-2.67 (4H, m), 2.70 (3H, s), 2.78

(3H, s), 2.89 (1H, dd), 2.93-3 (1H, m), 3.09 (1H, dd), 3.31-3.43 (2H, m), 3.49-3.56 (1H, m), 6.78 (1H, ddd), 7.11 (1H, ddd), 7.92-8 (2H, m); m/z MH+ 323.

Intermediate 12: (R)-6-((1-(6-bromopyridin-3-yl)pyrrolidin-3-yl)methyl)-2,5,7-trimethyl-[1,2,4]triazolo[1,5-a]pyrimidine

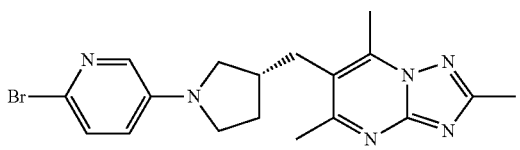 [SMILES: Cc1nc2nc(C)c(C[C@@H]3CCN(c4ccc(Br)nc4)C3)c(C)n2n1]

NBS (229 mg, 1.28 mmol) was added in one portion to (R)-2,5,7-trimethyl-6-((1-(pyridin-3-yl)pyrrolidin-3-yl)methyl)-[1,2,4]triazolo[1,5-a]pyrimidine (414 mg, 1.28 mmol) in MeCN (5 mL) at 0° C. under air. The reaction mixture was stirred at 0° C. and allowed to warm up slowly to rt over 3 h. The resulting precipitate was isolated by filtration and washed with MeCN (5 mL) to afford the title compound (298 mg, 58%) as a white solid; $^1$H NMR (500 MHz, CDCl$_3$) 1.88 (1H, dq), 2.11-2.24 (1H, m), 2.61 (3H, s), 2.62-2.67 (1H, m), 2.69 (3H, s), 2.78 (3H, s), 2.88 (1H, dd), 2.95 (1H, dd), 3.06 (1H, dd), 3.28-3.41 (2H, m), 3.48 (1H, td), 6.69 (1H, dd), 7.25 (1H, dd), 7.69 (1H, d); m/z MH+401.

Intermediate 13: 3-chloro-6-(chloromethyl)pyridazine

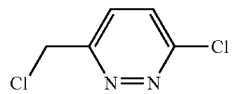

1,3,5-Trichloro-1,3,5-triazinane-2,4,6-trione (1.808 g, 7.78 mmol) was added in one portion to 3-chloro-6-methylpyridazine (2.00 g, 15.56 mmol) in DCE (100 mL) at rt. The reaction mixture was stirred at 60° C. for 2 h, then was allowed to cool to rt and filtered. The filtrate was concentrated in vacuo, and was purified by fcc, eluting with 10-50% EtOAc in heptane, to afford the title compound (1.60 g, 63%) as a pale yellow oil; $^1$H NMR (500 MHz, CDCl$_3$) 4.88 (2H, s), 7.58 (1H, d), 7.70 (1H, d); m/z MH+ 163.

Intermediate 14: 4-((6-chloropyridazin-3-yl)methyl)morpholine

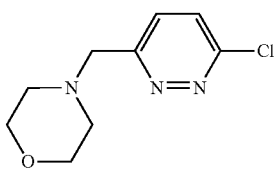 [SMILES: Clc1ccc(CN2CCOCC2)nn1]

Morpholine (0.86 mL, 9.82 mmol) was added in one portion to 3-chloro-6-(chloromethyl)pyridazine (1.6 g, 9.82 mmol) and DIPEA (2.05 mL, 11.8 mmol) in THF (16 mL) at rt. The reaction mixture was stirred at rt for 3 days, then was filtered and washed with THF. The combined filtrate was concentrated in vacuo and the resulting crude product was purified by fcc, eluting with 0-5% MeOH in DCM, to afford the title compound (1.380 g, 66%) as a white solid; $^1$H NMR (500 MHz, CDCl$_3$) 2.47-2.56 (4H, m), 3.68-3.76 (4H, m), 3.85 (2H, s), 7.50 (1H, d), 7.68 (1H, d); m/z MH+ 214.

Intermediate 15: (R)-2,5,7-trimethyl-6-((1-(pyrimidin-5-yl)pyrrolidin-3-yl)methyl)-[1,2,4]triazolo[1,5-a]pyrimidine

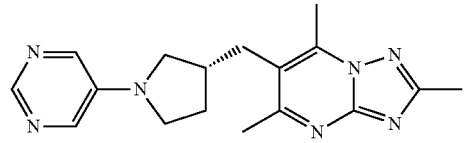

Cs$_2$CO$_3$ (6.16 g, 18.91 mmol) was added to (R)-2,5,7-trimethyl-6-(pyrrolidin-3-ylmethyl)-[1,2,4]triazolo[1,5-a]pyrimidine (2.32 g, 9.46 mmol) and 5-bromopyrimidine (1.503 g, 9.46 mmol) in 1,4-dioxane (64 mL). The reaction was degassed and RuPhos 3rd generation precatalyst (0.395 g, 0.47 mmol) and RuPhos (0.221 g, 0.47 mmol) were added. The reaction mixture was stirred at 90° C. for 18 h, then was allowed to cool to rt, diluted with DCM and filtered. The filtrate was concentrated in vacuo and purified by fcc eluting with 0-5% 1 M NH$_3$/MeOH in DCM, to afford the title compound (1.160 g, 38%) as a yellow solid; $^1$H NMR (500 MHz, CDCl$_3$) 1.88-1.95 (1H, m), 2.20 (1H, dtd), 2.61 (3H, s), 2.63-2.68 (1H, m), 2.70 (3H, s), 2.80 (3H, s), 2.91 (1H, dd), 2.98 (1H, dd), 3.12 (1H, dd), 3.37 (1H, dt), 3.47 (1H, s), 3.54 (1H, td), 8.05 (2H, s), 8.60 (1H, s); m/z MH+ 324.

Intermediate 16: (R)-6-((1-(2-bromopyrimidin-5-yl)pyrrolidin-3-yl)methyl)-2,5,7-trimethyl-[1,2,4]triazolo[1,5-a]pyrimidine

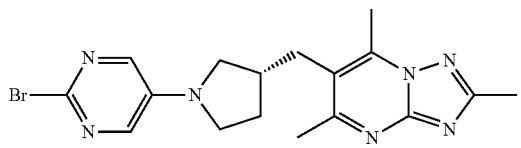

(R)-2,5,7-trimethyl-6-((1-(pyrimidin-5-yl)pyrrolidin-3-yl)methyl)-[1,2,4]triazolo[1,5-a]pyrimidine (1.59 g, 4.92 mmol) was added to MeCN (80 mL) and the reaction mixture was cooled to 0° C. NBS (1.050 g, 5.90 mmol) was then added in one portion. The reaction mixture was allowed to warm to rt and stirred for 2 h. The resulting suspension was filtered and the impure solid was collected and suspended in MeCN (10 mL) and heated at reflux. The suspension was allowed to cool to rt and the solid was collected by filtration to afford the title compound (0.652 g, 33%) as a yellow solid; NMR (500 MHz, CDCl$_3$) 1.90 (1H, dq), 2.16-2.25 (1H, m), 2.58-2.67 (4H, m), 2.70 (3H, s), 2.80 (3H, s), 2.88-2.94 (1H, m), 2.98 (1H, dd), 3.10 (1H, dd), 3.34 (1H, dt), 3.44 (1H, dd), 3.51 (1H, td), 7.87 (2H, s); m/z MH+ 402.

Intermediate 17: (S)-2,4-dimethyl-1-(4-(4,4,5,5-tetramethyl-1,3,2-dioxaborolan-2-yl)benzyl)piperazine

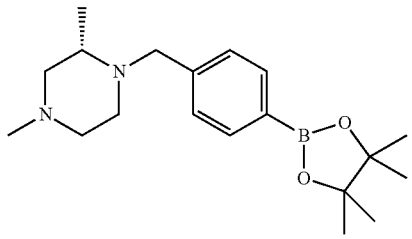

Potassium carbonate (2.43 g, 17.64 mmol) was added in one portion to 2-(4-(bromomethyl)phenyl)-4,4,5,5-tetramethyl-1,3,2-dioxaborolane (1.31 g, 4.41 mmol) and (S)-1,3-dimethylpiperazine dihydrochloride (0.83 g, 4.41 mmol) in MeCN (40 mL) at rt. The reaction mixture was stirred at 80° C. for 18 h, then allowed to cool to rt and filtered. The filtrate was concentrated in vacuo and the resulting crude product was purified by fcc, eluting with 0-10% 1 M NH$_3$/MeOH in DCM, to afford the title compound (506 mg, 35%) as a colourless oil; m/z MH$^+$ 331.

Intermediate 18: 3-methyl-4-(4,4,5,5-tetramethyl-1,3,2-dioxaborolan-2-yl)benzaldehyde

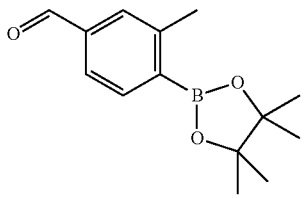 [SMILES: Cc1cc(C=O)ccc1B1OC(C)(C)C(C)(C)O1]

PdCl$_2$(dppf)-CH$_2$Cl$_2$ adduct (92 mg, 0.13 mmol) was added to 4-bromo-3-methylbenzaldehyde (500 mg, 2.51 mmol), 4,4,4',4',5,5,5',5'-octamethyl-2,2'-bi(1,3,2-dioxaborolane) (638 mg, 2.51 mmol) and potassium acetate (493 mg, 5.02 mmol) in 1,4-dioxane (10 mL) at rt. The reaction mixture was stirred at 90° C. for 16 h, then was allowed to cool to rt and was concentrate in vacuo. The resulting crude product was purified by fcc, eluting with 10% EtOAc in petroleum ether, to afford the title compound (580 mg, 94%) as a yellow solid; $^1$H NMR (400 MHz, CDCl$_3$) 1.39 (12H, s), 2.63 (3H, s), 7.64-7.70 (2H, m), 7.92 (1H, d), 10.03 (1H, s); m/z MH$^+$ 247.

Intermediate 19: (R)-4-(5-(3-((2,5,7-trimethyl-[1,2,4]triazolo[1,5-a]pyrimidin-6-yl)methyl)pyrrolidin-1-yl)pyrimidin-2-yl)benzaldehyde

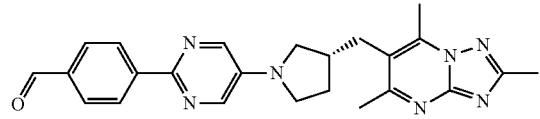

Pd(Ph$_3$P)$_4$ (0.287 g, 0.25 mmol) was added to (R)-6-((1-(2-bromopyrimidin-5-yl)pyrrolidin-3-yl)methyl)-2,5,7-trimethyl-[1,2,4]triazolo[1,5-a]pyrimidine (1.00 g, 2.49 mmol), 4-(4,4,5,5-tetramethyl-1,3,2-dioxaborolan-2-yl)benzaldehyde (0.692 g, 2.98 mmol) and 2 M sodium carbonate aq. solution (2.49 mL, 4.97 mmol) in degassed 1,4-dioxane (40 mL) and water (7.5 mL) at rt. The reaction mixture was stirred at 80° C. for 16 h, then allowed to cool to rt and concentrated in vacuo. The resulting residue was taken up in DCM and passed through a phase separating filter paper, then concentrated in vacuo and purified by fcc, eluting with 0-10% MeOH in DCM, to afford the title compound (0.510 g, 48%) as a yellow solid; $^1$H NMR (500 MHz, CDCl$_3$) 1.88-1.96 (1H, m), 2.23 (1H, ddd), 2.62 (3H, s), 2.72 (4H, s), 2.81 (3H, s), 2.88-3.04 (2H, m), 3.20 (1H, dd), 3.45 (1H, dt), 3.54 (1H, dd), 3.63 (1H, td), 7.9-7.99 (2H, m), 8.16 (2H, s), 8.42-8.53 (2H, m), 10.06 (1H, s); m/z MH$^+$ 428.

Intermediate 20: tert-butyl 4-(2-(dimethylamino)-2-oxoethyl)piperazine-1-carboxylate

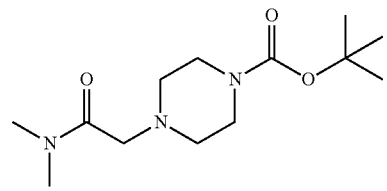 [SMILES: CN(C)C(=O)CN1CCN(C(=O)OC(C)(C)C)CC1]

HATU (3.74 g, 9.82 mmol) was added to 2-(4-(tert-butoxycarbonyl)piperazin-1-yl)acetic acid (2 g, 8.19 mmol) in DMF (25 mL) at rt under air and the reaction mixture was stirred at rt for 30 min. Dimethylamine (12.28 mL, 24.56 mmol) and DIPEA (4.29 mL, 24.56 mmol) were added to the mixture at rt under air. The reaction mixture was stirred at rt for 2 h and then poured into sat. aq. NaHCO$_3$ (200 mL) and extracted with EtOAc (3×100 mL). The combined organic layers were dried over Na$_2$SO$_4$, filtered and concentrated in vacuo. The resulting crude product was purified by flash C18 chromatography, eluting with 0-100% MeOH in water, to afford the title compound (1.65 g, 74%) as a pale yellow solid; $^1$H NMR (400 MHz, MeOD) 1.47 (9H, s), 2.49 (4H, t), 2.95 (3H, s), 3.11 (3H, s), 3.27 (2H, s), 3.43-3.50 (4H, m); m/z MH$^+$ 272.

Intermediate 21: N,N-dimethyl-2-(piperazin-1-yl)acetamide dihydrochloride

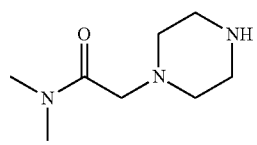

4 M HCl in EtOH (25 mL, 100 mmol) was added to tert-butyl 4-(2-(dimethylamino)-2-oxoethyl)piperazine-1-carboxylate (1.6 g, 5.9 mmol) in EtOH (25 mL) at rt under air. The reaction mixture was stirred at rt for 2 h, then was concentrated in vacuo to afford the title compound (1.4 g, 100%) as a white solid; m/z MH$^+$ 172.

Intermediate 22: 2-(4-(4-bromobenzyl)piperazin-1-yl)-N,N-dimethylacetamide

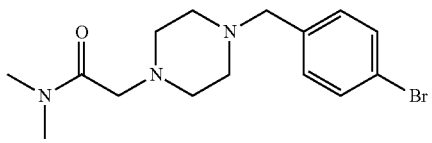 [SMILES: CN(C)C(=O)CN1CCN(Cc2ccc(Br)cc2)CC1]

N,N-dimethyl-2-(piperazin-1-yl)acetamide dihydrochloride (800 mg, 3.28 mmol) was added to 4-bromobenzaldehyde (606 mg, 3.28 mmol) in THF (25 mL) at rt under air and the reaction mixture was stirred at rt for 3 h. Sodium triacetoxyborohydride (1389 mg, 6.55 mmol) and AcOH (2 drops) were added to the mixture and the reaction mixture was stirred at rt for 16 h. The reaction mixture was diluted with water and concentrated in vacuo to almost dryness. The crude product was purified by flash C18 chromatography, eluting with 0-100% MeOH in water, to afford the title compound (704 mg, 63%) as a brown oil; $^1$H NMR (400 MHz, CDCl$_3$) 2.49 (4H, m), 2.56 (4H, m), 2.95 (3H, s), 3.08 (3H, s), 3.18 (2H, s), 3.46 (2H, s), 7.17-7.25 (2H, m), 7.40-7.49 (2H, m); m/z MH$^+$ 340

Intermediate 23: 2-(4-(4-bromobenzyl)piperazin-1-yl)ethanol

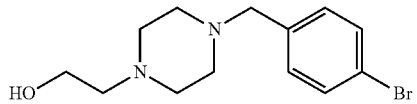 [SMILES: OCCN1CCN(Cc2ccc(Br)cc2)CC1]

2-(Piperazin-1-yl)ethanol (1.407 g, 10.81 mmol) was added to 4-bromobenzaldehyde (1 g, 5.40 mmol) in THF (25 mL) at rt and the reaction mixture was stirred at rt for 1 h. Sodium triacetoxyborohydride (2.291 g, 10.81 mmol) and AcOH (2 drops) were added to the mixture at rt under air and the reaction mixture was stirred at rt for 16 h, then was poured into water (20 mL) and concentrated in vacuo to almost dryness. The resulting crude product was purified by flash C18 chromatography, eluting with 0-100% MeOH in water, to afford the title compound (1.20 g, 74%) as a brown oil; $^1$H NMR (400 MHz, CDCl$_3$) 2.23-2.57 (11H, m), 3.48 (2H, s), 3.63 (2H, t), 7.22 (2H, d), 7.46 (2H, d); m/z MH$^+$299.

Intermediate 24: 4-(4-(5-bromopyrimidin-2-yl)benzyl)morpholine

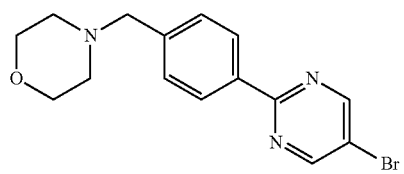 [SMILES: Brc1cnc(-c2ccc(CN3CCOCC3)cc2)nc1]

Pd(Ph$_3$P)$_4$ (578 mg, 0.50 mmol) was added to 4-(4-(4,4,5,5-tetramethyl-1,3,2-dioxaborolan-2-yl)benzyl)morpholine (1516 mg, 5.00 mmol), 5-bromo-2-iodopyrimidine (1424 mg, 5 mmol) and Na$_2$CO$_3$ (1060 mg, 10.00 mmol) in toluene (20 mL) and water (4 mL), and the reaction mixture was stirred at 120° C. for 3 days, then allowed to cool to rt and concentrated in vacuo. The residue was taken up in EtOAc (100 mL) and washed sequentially with water (2×20 mL). The organic layer was isolated and dried over Na$_2$SO$_4$, filtered and concentrated in vacuo. The resulting crude product was purified by flash C18 chromatography, eluting with 5-50% MeOH in water, to afford the title compound (510 mg, 31%) as a pale yellow solid; m/z MH$^+$ 334.

Intermediate 25: (R)-2,5,7-trimethyl-6-((1-phenylpyrrolidin-3-yl)methyl)-[1,2,4]triazolo[1,5-a]pyrimidine

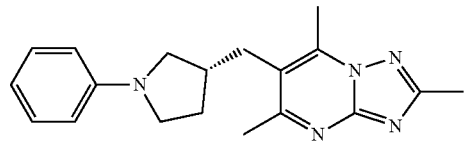

Degassed t-butanol (5 mL) was added to bromobenzene (74 µL, 0.7 mmol), (R)-2,5,7-trimethyl-6-(pyrrolidin-3-ylmethyl)-[1,2,4]triazolo[1,5-a]pyrimidine dihydrochloride (267 mg, 0.84 mmol), Cs$_2$CO$_3$ (1368 mg, 4.20 mmol), RuPhos (65 mg, 0.14 mmol) and RuPhos 3rd generation precatalyst (59 mg, 0.07 mmol). The reaction mixture was heated at 90° C. overnight, then was allowed to cool to rt and was concentrated in vacuo. The residue was dissolved in DCM (30 mL) and washed with water (30 mL). The aqueous layer was re-extracted with DCM (30 mL) and the combined organic layers were passed through a hydrophobic (phase separation) frit and concentrated in vacuo. The resulting crude product was purified by preparative HPLC to afford the title compound (72 mg, 32%) as a white solid; $^1$H NMR (500 MHz, CDCl$_3$) 1.78-1.9 (1H, m), 2.1-2.21 (1H, m), 2.55-2.64 (4H, m), 2.69 (3H, s), 2.78 (3H, s), 2.83-2.98 (2H, m), 3.08 (1H, dd), 3.28-3.39 (2H, m), 3.45-3.55 (1H, m), 6.54 (2H, dd), 6.70 (1H, tt), 7.23 (2H, dd); m/z MH$^+$ 322.

Intermediate 26: (R)-6-(1-(4-bromophenyl)pyrrolidin-3-yl)methyl)-2,5,7-trimethyl-[1,2,4]triazolo[1,5-a]pyrimidine

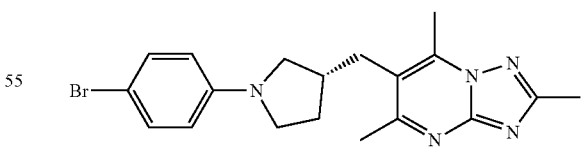

NBS (0.460 g, 2.58 mmol) was added to (R)-2,5,7-trimethyl-6-((1-phenylpyrrolidin-3-yl)methyl)-[1,2,4]triazolo[1,5-a]pyrimidine (0.83 g, 2.58 mmol) in THF (50 mL). The reaction mixture was stirred at rt for 2 h, then was concentrated in vacuo. The resulting crude product was purified by flash C18 chromatography, eluting with 0-90% MeOH in water, to afford the title compound (0.750 g, 73%) as a yellow solid; m/z MH$^+$ 400.

Intermediate 27: (R)-2,5,7-trimethyl-6-((1-(4-(4,4,5,5-tetramethyl-1,3,2-dioxaborolan-2-yl)phenyl)pyrrolidin-3-yl)methyl)-[1,2,4]triazolo[1,5-a]pyrimidine

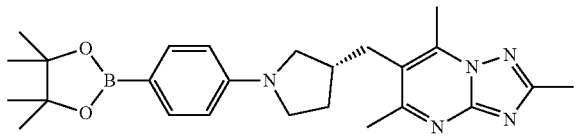

PdCl$_2$(dppf)-CH$_2$Cl$_2$ adduct (94 mg, 0.11 mmol) was added to (R)-6-((1-(4-bromophenyl)pyrrolidin-3-yl)methyl)-2,5,7-trimethyl-[1,2,4]triazolo[1,5-a]pyrimidine (460 mg, 1.15 mmol), 4,4,4',4',5,5,5',5'-octamethyl-2,2'-bi(1,3,2-dioxaborolane) (292 mg, 1.15 mmol) and potassium acetate (226 mg, 2.30 mmol) in 1,4-dioxane (5 mL) at rt. The reaction mixture was stirred at 90° C. for 16 h, then was allowed to cool to rt and concentrated in vacuo. The resulting crude product was purified by fcc, eluting with EtOAc, to afford the title compound (350 mg, 68%) as a pale yellow solid; m/z MH$^+$ 448.

Intermediate 28: 2-bromo-5-((4-methylpiperazin-1-yl)methyl)pyrazine

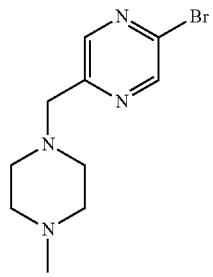

Potassium iodide (0.659 g, 3.97 mmol) was added to 1-methylpiperazine (0.398 g, 3.97 mmol), 2-bromo-5-(bromomethyl)pyrazine (1 g, 3.97 mmol) and K$_2$CO$_3$ (0.549 g, 3.97 mmol) in DMF (30 mL) under air. The reaction mixture was stirred at rt for 4 h, then was concentrated in vacuo. The resulting crude product was purified by flash C18 chromatography, eluting with 0-100% MeOH in water, to afford the title compound (0.520 g, 48%) as a yellow oil; m/z MH$^+$ 271.

Intermediate 29: 5-bromo-2-((4-methylpiperazin-1-yl)methyl)pyrimidine

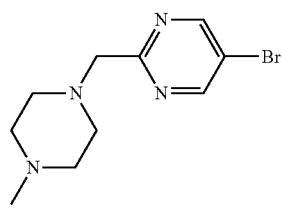

Potassium iodide (758 mg, 4.57 mmol) was added to 5-bromo-2-(bromomethyl)pyrimidine (767 mg, 3.04 mmol), 1-methylpiperazine (457 mg, 4.57 mmol) and K$_2$CO$_3$ (631 mg, 4.57 mmol) in DMF (15 mL). The reaction mixture was stirred at rt for 2 h, then was concentrated in vacuo. The resulting crude product was purified by flash C18 chromatography, eluting with 0-100% MeOH in water, to afford the title compound (340 mg, 41%) as a white solid; m/z MH$^+$ 271.

Intermediate 30: 4-((6-bromopyridin-3-yl)methyl)morpholine

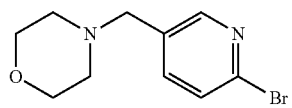

Potassium iodide (1.985 g, 11.96 mmol) was added to 2-bromo-5-(bromomethyl)pyridine (3 g, 11.96 mmol), morpholine (1.042 g, 11.96 mmol) and K$_2$CO$_3$ (1.652 g, 11.96 mmol) in DMF (25 mL), and the reaction mixture was stirred at rt for 16 h, then was poured into water (150 mL) and extracted with EtOAc (3×50 mL). The combined organic layers were dried over Na$_2$SO$_4$, filtered and concentrated in vacuo. The resulting crude product was purified by fcc, eluting with 0-75% EtOAc in petroleum ether, to afford the title compound (2.60 g, 85%) as a white solid; $^1$H NMR (400 MHz, CDCl$_3$) 2.41-2.48 (4H, m), 3.48 (2H, s), 3.68-3.75 (4H, m), 7.46 (1H, d), 7.58 (1H, dd), 8.31 (1H, d); m/z MH$^+$257.

Intermediate 31: 4-((6-(4-bromophenyl)pyridin-3-yl)methyl)morpholine

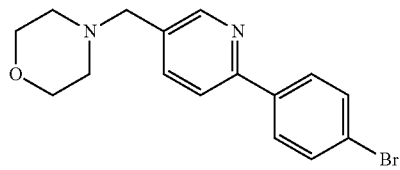

Pd(Ph$_3$P)$_4$ (0.674 g, 0.58 mmol) was added to 4-((6-bromopyridin-3-yl)methyl)morpholine (1.5 g, 5.83 mmol), (4-bromophenyl)boronic acid (1.289 g, 6.42 mmol) and Na$_2$CO$_3$ (1.237 g, 11.67 mmol) in 1,4-dioxane (14 mL) and water (7.00 mL) at rt. The reaction mixture was stirred at 80° C. for 5 h, then was allowed to cool to rt and concentrated in vacuo. The resulting crude product was purified by fcc, eluting with 50% EtOAc in petroleum ether, to afford the title compound (1.28 g, 66%) as a white solid; $^1$H NMR (400 MHz, DMSO) 2.39 (4H, dd), 3.49-3.64 (6H, m), 7.58-7.76 (2H, m), 7.82 (1H, dd), 7.93-8.01 (1H, m), 8.01-8.09 (2H, m), 8.59 (1H, d); m/z MH$^+$ 333.

Intermediate 32: 3-chloro-6-((4-methylpiperazin-1-yl)methyl)pyridazine

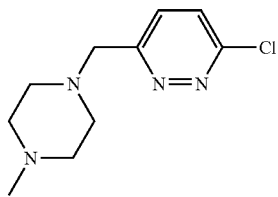

Potassium iodide (1.200 g, 7.23 mmol) was added to 3-(bromomethyl)-6-chloropyridazine (1 g, 4.82 mmol), 1-methylpiperazine (0.724 g, 7.23 mmol) and K$_2$CO$_3$ (0.999 g, 7.23 mmol) in DMF (15 mL). The reaction mixture was stirred at rt for 2 h, then was diluted with water and the resulting solution was purified by flash C18 chromatography, eluting with 0-100% MeOH in water, to afford the title compound (300 mg, 28%) as a white solid; $^1$H NMR (300 MHz, DMSO) 2.19 (3H, s), 2.40 (8H, m), 3.77 (2H, s), 7.76 (1H, d), 7.88 (1H, d); m/z MH$^+$ 227.

Intermediate 33: 2-(4-bromophenyl)-5-methylpyrimidine

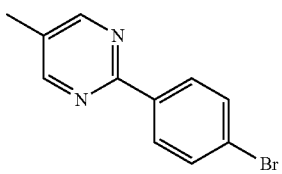

Pd(Ph$_3$P)$_4$ (1.002 g, 0.87 mmol) was added to 2-bromo-5-methylpyrimidine (1.5 g, 8.67 mmol), (4-bromophenyl)boronic acid (1.74 g, 8.7 mmol) and Na$_2$CO$_3$ (1.84 g, 17.3 mmol) in 1,4-dioxane (35 mL) and water (7 mL) under air. The reaction mixture was stirred at 80° C. for 16 h, then was allowed to cool to rt and concentrated in vacuo. The resulting crude product was purified by fcc, eluting with 2-5% EtOAc in petroleum ether, to afford the title compound (1.00 g, 46%) as a yellow solid; $^1$H NMR (300 MHz, CDCl$_3$) 2.37 (3H, s), 7.55 (2H, d), 8.30 (2H, d), 8.64 (2H, s); m/z MH$^+$ 249.

Intermediate 34: 5-(bromomethyl)-2-(4-bromophenyl)pyrimidine

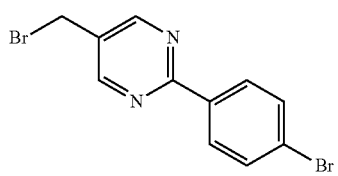 [SMILES: BrCc1cnc(-c2ccc(Br)cc2)nc1]

Benzoyl peroxide (58.3 mg, 0.24 mmol) was added to 2-(4-bromophenyl)-5-methylpyrimidine (600 mg, 2.41 mmol) and NBS (429 mg, 2.41 mmol) in CCl$_4$ (12 mL) under air. The reaction mixture was stirred at 80° C. for 4 h, then was allowed to cool to rt and concentrated in vacuo. The resulting crude product was purified by flash C18 chromatography, eluting with 5-100% MeOH in water, to afford the title compound (310 mg, 39%) as a yellow oil; m/z MH$^+$ 327.

Intermediate 35: 2-(4-bromophenyl)-5-((4-methylpiperazin-1-yl)methyl)pyrimidine

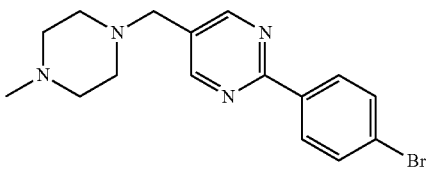 [SMILES: CN1CCN(Cc2cnc(-c3ccc(Br)cc3)nc2)CC1]

Potassium iodide (152 mg, 0.91 mmol) was added to 5-(bromomethyl)-2-(4-bromophenyl)pyrimidine (300 mg, 0.91 mmol), 1-methylpiperazine (82 mg, 0.82 mmol) and K$_2$CO$_3$ (126 mg, 0.91 mmol) in DMF (10 mL) under air. The resulting mixture was stirred at rt for 2 h. The solvent was removed in vacuo. The crude product was purified by flash C18 chromatography, eluting with 0-100% MeOH in water, to afford the title compound (195 mg, 61%) as a yellow oil; $^1$H NMR (300 MHz, CDCl$_3$) 2.61 (3H, s), 2.76-3.20 (8H, m), 3.61 (2H, s), 7.54 (2H, d), 8.33 (2H, d), 8.73 (2H, s); m/z MH$^+$ 347.

Intermediate 36: tert-butyl 4-((6-bromopyridin-3-yl)methyl)piperazine-1-carboxylate

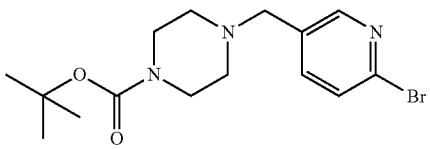 [SMILES: CC(C)(C)OC(=O)N1CCN(Cc2ccc(Br)nc2)CC1]

Sodium triacetoxyborohydride (4.56 g, 21.50 mmol) was added to 6-bromonicotinaldehyde (2.00 g, 10.75 mmol), tert-butyl piperazine-1-carboxylate (4.01 g, 21.50 mmol) and AcOH (0.062 mL, 1.08 mmol) in DCM (100 mL) at 20° C. The resulting solution was stirred at rt for 2 h. The reaction mixture was washed with sat. NaHCO$_3$, passed through a phase separating filter paper and the solvent was removed in vacuo. The crude product was purified by fcc, eluting with 0 to 70% EtOAc in heptane, to afford the title compound (2.80 g, 73.1%) as a colourless oil which crystallised on standing; $^1$H NMR (500 MHz, CDCl$_3$) 1.45 (9H, s), 2.31-2.43 (4H, m), 3.39-3.44 (4H, m), 3.47 (2H, s), 7.45 (1H, dd), 7.55 (1H, dd), 8.29 (1H, dd); m/z MH$^+$ 356

Intermediate 37: tert-butyl 4-((6-(4-bromophenyl)pyridin-3-yl)methyl)piperazine-1-carboxylate

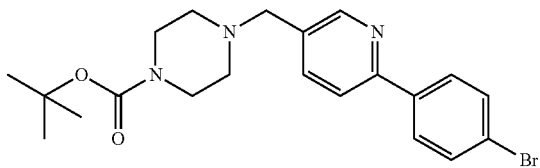 [SMILES: CC(C)(C)OC(=O)N1CCN(Cc2ccc(-c3ccc(Br)cc3)nc2)CC1]

Pd(Ph₃P)₄ (0.389 g, 0.34 mmol) was added to tert-butyl 4-((6-bromopyridin-3-yl)methyl)piperazine-1-carboxylate (2.40 g, 6.74 mmol), (4-bromophenyl)boronic acid (1.35 g, 6.74 mmol) and potassium carbonate (2.79 g, 20.2 mmol) in degassed 1,4-dioxane (12 mL) and water (3 mL) at rt. The reaction mixture was heated at 85° C. in a microwave reactor for 3 h, then was allowed to cool to rt and diluted with EtOAc. The organic phase was passed through a phase separator and then concentrated in vacuo. The resulting crude product was purified by fcc, eluting with 0-5% MeOH in DCM, to afford the title compound (1.20 g, 41%) as a yellow oil which solidified on standing; $^1$H NMR (500 MHz, CDCl₃) 1.46 (9H, s), 2.36-2.47 (4H, m), 3.4-3.47 (4H, m), 3.55 (2H, s), 7.56-7.62 (2H, m), 7.67 (1H, dd), 7.74 (1H, dd), 7.84-7.91 (2H, m), 8.57-8.63 (1H, m); m/z MH⁺ 432

Intermediate 38:
4-((5-bromopyrimidin-2-yl)methyl)morpholine

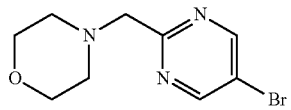

Potassium iodide (758 mg, 4.57 mmol) was added to 5-bromo-2-(bromomethyl)pyrimidine (767 mg, 3.04 mmol), morpholine (398 mg, 4.57 mmol) and K₂CO₃ (631 mg, 4.57 mmol) in DMF (15 mL). The reaction mixture was stirred at rt for 2 h, then was diluted with water and concentrated in vacuo. The resulting crude product was purified by flash C18 chromatography, eluting with 0-100% MeOH in water, to afford the title compound (720 mg, 92%) as a white solid; $^1$H NMR (400 MHz, CDCl₃) 2.55-2.63 (4H, m), 3.74-3.82 (6H, m), 8.79 (2H, s); m/z MH⁺ 258

Intermediate 39: 4-((5-(4-bromophenyl)pyrimidin-2-yl)methyl)morpholine

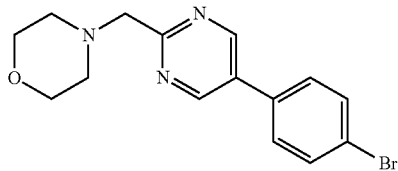 [SMILES: Brc1ccc(-c2cnc(CN3CCOCC3)nc2)cc1]

Pd(Ph₃P)₄ (179 mg, 0.15 mmol) was added to 4-((5-bromopyrimidin-2-yl)methyl)morpholine (400 mg, 1.55 mmol), (4-bromophenyl)boronic acid (311 mg, 1.55 mmol) and Na₂CO₃ (328 mg, 3.10 mmol) in 1,4-dioxane (5 mL) and water (2.5 mL) at rt. The reaction mixture was stirred at 80° C. for 16 h, then was allowed to cool to rt and concentrated in vacuo. The resulting crude product was purified by flash C18 chromatography, eluting with 0-100% MeOH in water, to afford the title compound (330 mg, 64%) as a white solid; NMR (400 MHz, CDCl₃) 2.62-2.69 (4H, m), 3.78-3.86 (4H, m), 3.90 (2H, s), 7.42-7.53 (2H, m), 7.63-7.74 (2H, m), 8.93 (2H, s); m/z MH⁺ 334.

Intermediate 40:
1-bromo-4-(bromomethyl)-2-methoxybenzene

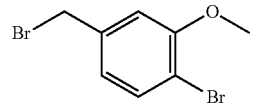

Triphenylphosphine (5.53 ml, 23.9 mmol) was added portionwise to (4-bromo-3-methoxyphenyl)methanol (4.32 g, 20.0 mmol) and carbon tetrabromide (7.26 g, 21.9 mmol) in DCM (100 ml) at 0° C. over a period of 2 min. The reaction mixture was allowed to warm to rt and was stirred at rt for 18 h, then was concentrated in vacuo. The resulting crude product was purified by fcc, eluting with 0-50% DCM in heptane, to afford the title compound (5.57 g, 100%) as a colourless gum; $^1$H NMR (400 MHz, CDCl₃) 3.91 (3H, s), 4.44 (2H, s), 6.86 (1H, dd), 6.92 (1H, d), 7.49 (1H, d).

Intermediate 41:
1-(4-bromo-3-methoxybenzyl)-4-methylpiperazine

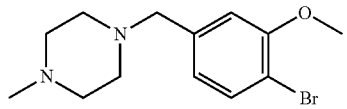

Potassium iodide (2.135 g, 12.86 mmol) was added to 1-bromo-4-(bromomethyl)-2-methoxybenzene (3 g, 10.7 mmol), 1-methylpiperazine (1.29 g, 12.9 mmol) and K₂CO₃ (1.78 g, 12.9 mmol) in DMF (50 mL). The reaction mixture was stirred at rt for 16 h, then was poured into water (200 mL) and extracted with EtOAc (3×100 mL). The combined organic layers were dried over Na₂SO₄, filtered and concentrated in vacuo. The resulting crude product was purified by fcc, eluting with 0-5% MeOH in DCM, to afford the title compound (1.70 g, 53%) as a pale yellow oil; $^1$H NMR (400 MHz, CDCl₃) 2.34 (3H, s), 2.50 (8H, br m), 3.48 (2H, s), 3.91 (3H, s), 6.82 (1H, dd), 6.91 (1H, d), 7.46 (1H, dd); m/z MH⁺ 299.

Intermediate 42: (2-methoxy-4-((4-methylpiperazin-1-yl)methyl)phenyl)boronic acid

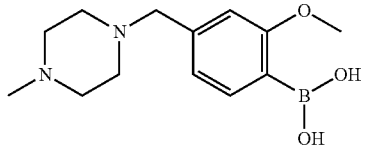 [SMILES: COc1cc(CN2CCN(C)CC2)ccc1B(O)O]

PdCl₂(dppf)-CH₂Cl₂ adduct (0.464 g, 0.57 mmol) was added to 1-(4-bromo-3-methoxybenzyl)-4-methylpiperazine (1.7 g, 5.68 mmol), 4,4,4',4',5,5,5',5'-octamethyl-2,2'-bi(1,3,2-dioxaborolane) (2.89 g, 11.4 mmol) and potassium acetate (1.67 g, 17.1 mmol) in 1,4-dioxane (25 mL) at rt. The reaction mixture was stirred at 90° C. for 48 h, then was allowed to cool to rt and concentrated in vacuo. The resulting crude product was purified by flash C18 chromatography, eluting with 0-100% MeOH in water (with 0.5% NH₄HCO₃), to afford the title compound (1.10 g, 73%) as a red solid; m/z MH⁺ 265.

Intermediate 43: (R)-6-((1-(6-chloropyrazin-2-yl)pyrrolidin-3-yl)methyl)-2,5,7-trimethyl-[1,2,4]triazolo[1,5-a]pyrimidine

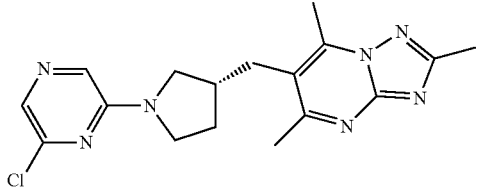 [SMILES: Cc1nc2nc(C)c(C[C@@H]3CCN(c4cncc(Cl)n4)C3)c(C)n2n1]

Triethylamine (2.10 mL, 15.1 mmol) was added to (R)-2,5,7-trimethyl-6-(pyrrolidin-3-ylmethyl)-[1,2,4]triazolo[1,5-a]pyrimidine dihydrochloride (1.2 g, 3.77 mmol) and 2,6-dichloropyrazine (0.562 g, 3.77 mmol) in n-propanol (20 mL). The reaction mixture was stirred at 90° C. for 16 h, then was allowed to cool to rt and concentrate in vacuo. Water (50 mL) was added to the residue and was extracted with EtOAc (3×50 mL). The combined organic layers were dried over Na₂SO₄, filtered and concentrated in vacuo. The resulting crude product was purified by fcc, eluting with 0-5% MeOH in DCM, to afford the title compound (1.10 g, 82%) as a pale yellow solid; ¹H NMR (300 MHz, DMSO) 1.81 (1H, dq), 2.07 (1H, m), 2.46 (3H, s), 2.62 (4H, s), 2.73 (3H, s), 2.91 (2H, d), 3.18 (1H, m), 3.35 (1H, q), 3.61 (2H, td), 7.75 (1H, m), 7.90 (1H, m); m/z MH⁺ 358.

Intermediate 44: (R)-2,5,7-trimethyl-6-((1-(6-methylpyrazin-2-yl)pyrrolidin-3-yl)methyl)-[1,2,4]triazolo[1,5-a]pyrimidine

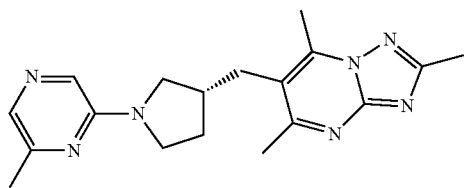 [SMILES: Cc1cncc(N2CC[C@@H](Cc3c(C)nc4nc(C)nn4c3C)C2)n1]

Pd(Ph₃P)₄ (0.355 g, 0.31 mmol) was added to (R)-6-((1-(6-chloropyrazin-2-yl)pyrrolidin-3-yl)methyl)-2,5,7-trimethyl-[1,2,4]triazolo[1,5-a]pyrimidine (1.1 g, 3.07 mmol), 2,4,6-trimethyl-1,3,5,2,4,6-trioxatriborinane in THF (50% wt) (1.54 g, 6.15 mmol) and Na₂CO₃ (1.30 g, 12.3 mmol) in 1,4-dioxane (6 mL) and water (3 mL). The reaction mixture was stirred at 80° C. for 16 h, then was allowed to cool to rt and concentrated in vacuo. The resulting crude product was purified by fcc, eluting with 1-5% MeOH in DCM, to afford the title compound (1.00 g, 96%) as a white solid; ¹H NMR (300 MHz, DMSO) 1.81 (1H, dq), 2.06 (1H, dq), 2.26 (3H, s), 2.54 (6H, d), 2.73 (3H, s), 2.92 (2H, m), 3.17 (1H, m), 3.36 (2H, m), 3.59 (2H, tt), 7.63 (1H, s), 7.73 (1H, s); m/z MH⁺ 338.

Intermediate 45: (R)-6-((1-(5-bromo-6-methylpyrazin-2-yl)pyrrolidin-3-yl)methyl)-2,5,7-trimethyl-[1,2,4]triazolo[1,5-a]pyrimidine

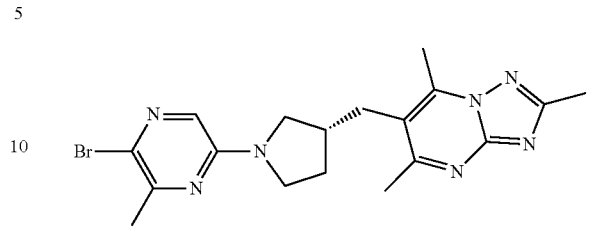

NBS (0.527 g, 2.96 mmol) was added to (R)-2,5,7-trimethyl-6-((1-(6-methylpyrazin-2-yl)pyrrolidin-3-yl)methyl)-[1,2,4]triazolo[1,5-a]pyrimidine (1 g, 2.96 mmol) in DCM (10 mL) at 0° C. under air. The reaction mixture was stirred at 0° C. for 1 h, then water was added (25 mL) and the mixture was extracted with DCM (3×25 mL). The combined organic layers were dried over Na₂SO₄, filtered and concentrated in vacuo. The resulting crude product was purified by fcc, eluting with 1-2% MeOH in DCM, to afford the title compound (0.90 g, 73%) as a pale yellow solid; ¹H NMR (300 MHz, DMSO) 1.81 (1H, dq), 2.06 (1H, dq), 2.39 (3H, s), 2.48 (3H, s), 2.55 (1H, m), 2.62 (3H, s), 2.73 (3H, s), 2.92 (2H, m), 3.15 (1H, m), 3.33 (1H, q), 3.58 (2H, ddd), 7.58 (1H, s); m/z MH⁺ 416.

Intermediate 46: (R)-6-((1-(5-bromopyrazin-2-yl)pyrrolidin-3-yl)methyl)-2,5,7-trimethyl-[1,2,4]triazolo[1,5-a]pyrimidine

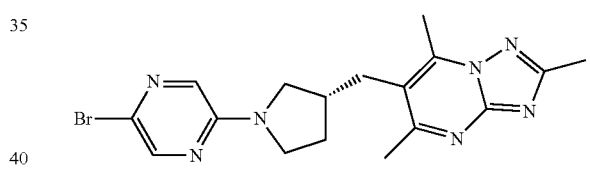

2,5-Dibromopyrazine (3.74 g, 15.7 mmol) was added to (R)-2,5,7-trimethyl-6-(pyrrolidin-3-ylmethyl)-[1,2,4]triazolo[1,5-a]pyrimidine dihydrochloride (5.00 g, 15.7 mmol) and DIPEA (13.7 mL, 78.6 mmol) in n-butanol (60 mL) at rt. The reaction mixture was heated at reflux for 2 h, then was allowed to cool to rt and concentrated in vacuo. The resulting crude product was triturated with water and filtered to afford the title compound (4.86 g, 77%) as a cream solid; ¹H NMR (500 MHz, CDCl₃) 1.89 (1H, dq), 2.16-2.24 (1H, m), 2.61 (4H, s), 2.70 (3H, s), 2.79 (3H, s), 2.93 (2H, tt), 3.23 (1H, dd), 3.45 (1H, dt), 3.6-3.68 (2H, m), 7.61 (1H, d), 8.10 (1H, d); m/z MH⁺ 402.

Intermediate 47: (R)-(4-(5-(3-((2,5,7-trimethyl-[1,2,4]triazolo[1,5-a]pyrimidin-6-yl)methyl)pyrrolidin-1-yl)pyrazin-2-yl)phenyl)methanol

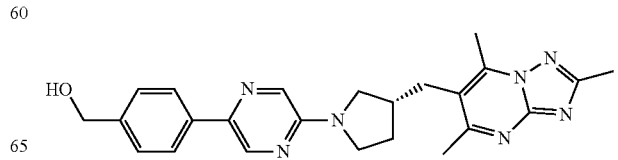

(4-(4,4,5,5-tetramethyl-1,3,2-dioxaborolan-2-yl)phenyl) methanol (165 mg, 0.71 mmol), (R)-6-((1-(5-bromopyrazin-2-yl)pyrrolidin-3-yl)methyl)-2,5,7-trimethyl-[1,2,4]triazolo [1,5-a]pyrimidine (237 mg, 0.59 mmol) and Cs$_2$CO$_3$ (384 mg, 1.18 mmol) were added to 1,4-dioxane (6.2 mL) and water (3.1 mL) and the reaction mixture was degassed for 10 minutes. XPhos 2$^{nd}$ generation precatalyst (23 mg, 0.03 mmol) was added and the reaction was stirred for 2 h at 90° C., then allowed to cool to rt. The reaction mixture was diluted with EtOAc (50 mL). The organic layer was isolated and washed with sat. brine and dried over MgSO$_4$, filtered and concentrated in vacuo. The resulting crude product was purified by fcc, eluting with 0-4% 1 M NH$_3$/MeOH in DCM, to afford the title compound (200 mg, 79%) as a white foam; $^1$H NMR (500 MHz, CDCl$_3$) 1.74 (1H, t), 1.92 (1H, dq), 2.18-2.27 (1H, m), 2.62 (4H, s), 2.71 (3H, s), 2.80 (3H, s), 2.87-3.02 (2H, m), 3.33 (1H, dd), 3.55 (1H, dt), 3.68-3.8 (2H, m), 4.74 (2H, d), 7.41-7.47 (2H, m), 7.84-7.91 (2H, m), 7.95 (1H, d), 8.51 (1H, d); m/z MH$^+$ 430.

Intermediate 48: (R)-6-((1-(5-(4-(chloromethyl)phenyl)pyrazin-2-yl)pyrrolidin-3-yl)methyl)-2,5,7-trimethyl-[1,2,4]triazolo[1,5-a]pyrimidine

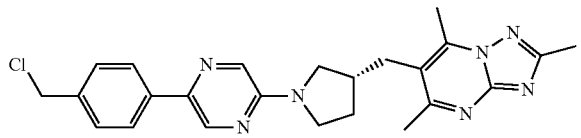 [SMILES: Cc1nc2nc(C)c(C[C@@H]3CCN(c4cnc(-c5ccc(CCl)cc5)cn4)C3)c(C)n2n1]

(R)-(4-(5-(3-((2,5,7-trimethyl-[1,2,4]triazolo[1,5-a]pyrimidin-6-yl)methyl)pyrrolidin-1-yl)pyrazin-2-yl)phenyl) methanol (200 mg, 0.47 mmol) was dissolved in DCM (7 mL) and DMF (0.34 mg, 4.66 μmop. The reaction mixture was cooled to 0° C. and thionyl chloride (0.037 mL, 0.51 mmol) was added dropwise. The reaction mixture was allowed to warm to rt and was stirred at rt for 3 h, then was diluted with DCM (50 mL) and adjusted to pH 8-9 with Na$_2$CO$_3$ (2 M aq solution). The organic layer was isolated and washed with sat. brine, passed through a phase separating cartridge and concentrated in vacuo to afford the title compound (181 mg, 87%) as a yellow solid which was used without further purification; m/z MH$^+$ 448.

Intermediate 49: (R)-4-(5-(3-((2,5,7-trimethyl-[1,2,4]triazolo[1,5-a]pyrimidin-6-yl)methyl)pyrrolidin-1-yl)pyrazin-2-yl)benzaldehyde

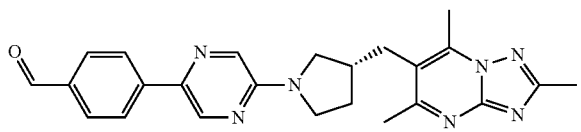 [SMILES: Cc1nc2nc(C)c(C[C@@H]3CCN(c4cnc(-c5ccc(C=O)cc5)cn4)C3)c(C)n2n1]

Pd(Ph$_3$P)$_4$ (0.373 g, 0.32 mmol) was added to (4-formylphenyl)boronic acid (0.485 g, 3.23 mmol), (R)-6-((1-(5-bromopyrazin-2-yl)pyrrolidin-3-yl)methyl)-2,5,7-trimethyl-[1,2,4]triazolo[1,5-a]pyrimidine (1.30 g, 3.23 mmol) and Na$_2$CO$_3$ (0.685 g, 6.46 mmol) in 1,4-dioxane (10 mL) and water (2 mL). The reaction mixture was stirred at 80° C. for 16 h, then allowed to cool to rt and concentrated in vacuo. The resulting crude product was purified by flash C18 chromatography, eluting with 5-80% MeOH in water, to afford the title compound (1.20 g, 87%) as a yellow solid; $^1$H NMR (300 MHz, CDCl$_3$) 1.94 (1H, dq), 2.25 (1H, dq), 2.57-3.07 (12H, m), 3.24-3.42 (1H, m), 3.45-3.87 (3H, m), 7.79-8.18 (5H, m), 8.60 (1H, d), 10.04 (1H, s); m/z MH$^+$ 428.

Intermediate 50: 1-(4-bromo-2-methylbenzyl)-4-methylpiperazine

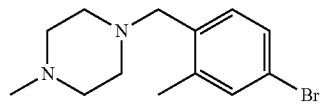 [SMILES: Cc1cc(Br)ccc1CN1CCN(C)CC1]

4-Bromo-2-methylbenzaldehyde (1 g, 5.02 mmol) and 1-methylpiperazine (0.503 g, 5.02 mmol) were combined with MeOH (20 mL) and the reaction mixture was stirred for 2 h at rt. NaCNBH$_4$ (0.631 g, 10.1 mmol) and AcOH (0.030 g, 0.50 mmol) were added and the reaction mixture was stirred at rt for 16 h, then concentrated in vacuo. The resulting crude product was purified by flash C18 chromatography, eluting with 1-70% MeOH in water, to afford the title compound (1.00 g, 70%) as a yellow solid; m/z MH$^+$ 283.

Intermediate 51: 1-methyl-4-(2-methyl-4-(4,4,5,5-tetramethyl-1,3,2-dioxaborolan-2-yl)benzyl)piperazine

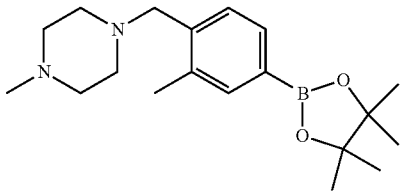

PdCl$_2$(dppf)-CH$_2$Cl$_2$ adduct (0.058 g, 0.07 mmol) was added to 1-(4-bromo-2-methylbenzyl)-4-methylpiperazine (0.2 g, 0.71 mmol), 4,4,4',4',5,5,5',5'-octamethyl-2,2'-bi(1,3,2-dioxaborolane) (0.215 g, 0.85 mmol) and potassium acetate (0.139 g, 1.41 mmol) in 1,4-dioxane (10 mL) at rt. The reaction mixture was stirred at 80° C. for 16 h, then was allowed to cool to rt and concentrated in vacuo. The resulting crude product was purified by fcc, eluting with 0-50% EtOAc in petroleum ether, to afford the title compound (70 mg, 30%) as a yellow solid; m/z MH$^+$ 331.

Intermediate 52: 1-(4-(4-(4,4,5,5-tetramethyl-1,3,2-dioxaborolan-2-yl)benzyl)piperazin-1-yl)ethanone

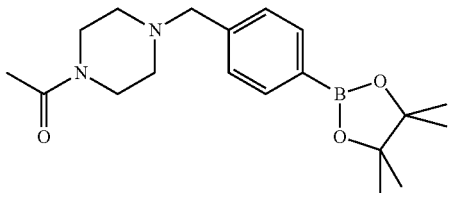 [SMILES: CC(=O)N1CCN(Cc2ccc(B3OC(C)(C)C(C)(C)O3)cc2)CC1]

Potassium carbonate (2.23 g, 16.2 mmol) was added in one portion to 2-(4-(bromomethyl)phenyl)-4,4,5,5-tetramethyl-1,3,2-dioxaborolane (2.4 g, 8.08 mmol) and 1-(piperazin-1-yl)ethanone (1.04 g, 8.08 mmol) in MeCN (70 mL) at rt. The reaction mixture was stirred at 80° C. for 18 h, then was allowed to cool to rt and filtered. The filtrate was concentrated in vacuo and the resulting crude product was purified by fcc, eluting with 0-5% 1 M NH$_3$/MeOH in DCM, to afford the title compound (2.73 g, 98%) as a colourless oil; $^1$H NMR (500 MHz, CDCl$_3$) 1.34 (12H, s), 2.07 (3H, s), 2.41 (4H, dq), 3.42-3.46 (2H, m), 3.53 (2H, s), 3.59-3.64 (2H, m), 7.33 (2H, d), 7.72-7.81 (2H, m); m/z MH$^+$ 345.

Intermediate 53: (R)-6-((1-(6-chloropyridazin-3-yl)pyrrolidin-3-yl)methyl)-2,5,7-trimethyl-[1,2,4]triazolo[1,5-a]pyrimidine

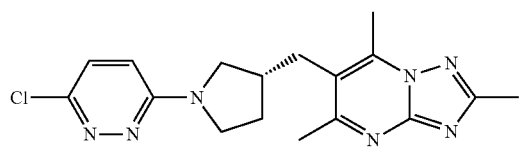 [SMILES: Cc1nc2nc(C)c(C[C@@H]3CCN(c4ccc(Cl)nn4)C3)c(C)n2n1]

Triethylamine (1.75 mL, 12.6 mmol) was added to (R)-2,5,7-trimethyl-6-(pyrrolidin-3-ylmethyl)-[1,2,4]triazolo[1,5-a]pyrimidine dihydrochloride (1 g, 3.14 mmol), 3,6-dichloropyridazine (0.468 g, 3.14 mmol) in n-propanol (10 mL) at rt under air. The reaction mixture was stirred at 90° C. for 16 h, then allowed to cool to rt and partially concentrated in vacuo. The precipitate was collected by filtration, washed with water (50 mL) and MeOH (10 mL) and dried in vacuo to afford the title compound (0.610 g, 54%) as a brown solid, which was used without further purification; $^1$H NMR (400 MHz, DMSO) 1.85 (1H, dq), 2.11 (1H, ddd), 2.48 (3H, s), 2.53-2.63 (1H, m), 2.64 (3H, s), 2.75 (3H, s), 2.94 (2H, d), 3.14-3.23 (1H, m), 3.40 (1H, dt), 3.49-3.93 (2H, m), 7.00 (1H, d), 7.47 (1H, d); m/z MH$^+$ 358.

Intermediate 54: 2,4-dioxopentan-3-yl benzoate

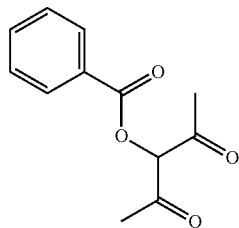 [SMILES: CC(=O)C(OC(=O)c1ccccc1)C(C)=O]

Potassium hydroxide (50.5 g, 901 mmol) was added to benzoic acid (100 g, 819 mmol) in DMF (1 L) at rt. The reaction mixture was stirred at 50° C. for 1 h, then 3-chloropentane-2,4-dione (110 g, 819 mmol) was added and reaction mixture was stirred at 50° C. overnight. The reaction mixture was allowed to cool to rt, diluted with EtOAc (3 L), and washed sequentially with water (1 L×2), sat. aq. NH$_4$Cl (500 mL) and sat. brine (500 mL). The organic layer was dried over Na$_2$SO$_4$, filtered and concentrated in vacuo. The resulting crude product was purified by fcc, eluting with 0-20% EtOAc in petroleum ether, to afford the title compound (130 g, 72%) as a yellow oil; m/z MH$^+$ 221.

Intermediate 55: 2,5,7-trimethyl-[1,2,4]triazolo[1,5-a]pyrimidin-6-yl benzoate

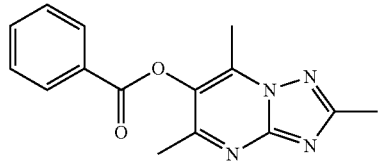 [SMILES: Cc1nc2nc(C)c(OC(=O)c3ccccc3)c(C)n2n1]

2,4-Dioxopentan-3-yl benzoate (58 g, 263 mmol) was added to 3-methyl-1H-1,2,4-triazol-5-amine (27.1 g, 277 mmol) in AcOH (300 mL) at rt. The reaction mixture was stirred at 90° C. for 10 h, then was allowed to cool to rt, concentrated in vacuo and adjusted to pH>7 with sat. aq. NaHCO$_3$. The mixture was extracted with EtOAc (3×500 mL). The combined organic layers were washed with sat. brine, passed through a phase separating filter paper and concentrated in vacuo to afford the title compound (52.0 g, 70%) as a beige solid; $^1$H NMR (400 MHz, CDCl$_3$) 2.57 (3H, s), 2.66 (3H, s), 2.70 (3H, s), 7.54-7.65 (2H, m), 7.71-7.80 (1H, m), 8.24-8.31 (2H, m); m/z MH$^+$ 283.

Intermediate 56: 2,5,7-trimethyl-[1,2,4]triazolo[1,5-a]pyrimidin-6-ol

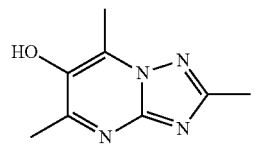

1 M aq. NaOH (177 mL, 177.11 mmol) was added to 2,5,7-trimethyl-[1,2,4]triazolo[1,5-a]pyrimidin-6-yl benzoate (50 g, 177 mmol) in EtOH (500 mL) at rt. The reaction mixture was stirred at rt for 3 h, then partially concentrated in vacuo and the solution was slowly acidified with 6 M aq. HCl until a precipitate formed (pH7). The precipitate was isolated by filtration, washed with water and dried in vacuo to afford the title compound (24 g, 76%) as a cream solid; m/z MH$^+$ 179.

Intermediate 57: tert-butyl (R)-3-((2,5,7-trimethyl-[1,2,4]triazolo[1,5-a]pyrimidin-6-yl)oxy)pyrrolidine-1-carboxylate

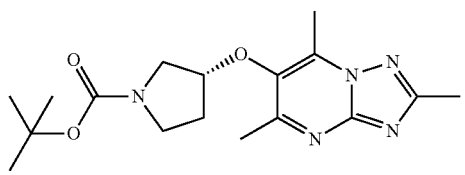 [SMILES: Cc1nc2nc(C)c(O[C@@H]3CCN(C(=O)OC(C)(C)C)C3)c(C)n2n1]

Diisopropyl azodicarboxylate (52.4 mL, 269 mmol) was added dropwise to 2,5,7-trimethyl-[1,2,4]triazolo[1,5-a]pyrimidin-6-ol (40 g, 224 mmol), tert-butyl (S)-3-hydroxypyrrolidine-1-carboxylate (46.2 g, 247 mmol) and triphenylphosphine (70.7 g, 269 mmol) in THF (800 mL) at rt over a period of 2 h, and the reaction mixture was stirred at rt for 10 min and concentrated in vacuo. The resulting crude product was purified by fcc, eluting with 0-100% EtOAc in petroleum ether, to afford the title compound (62.0 g, 80%) as a light yellow oil; $^1$H NMR (400 MHz, DMSO) 1.42 (9H, d), 2.07-2.14 (1H, m), 2.20-2.23 (1H, m), 2.47 (3H, s), 2.51-2.54 (3H, m), 2.63 (3H, d), 3.34 (2H, s), 3.43-3.56 (2H, m), 4.74 (1H, s); m/z MH$^+$ 348.

Intermediate 58: (R)-2,5,7-trimethyl-6-(pyrrolidin-3-yloxy)-[1,2,4]triazolo[1,5-a]pyrimidine dihydrochloride

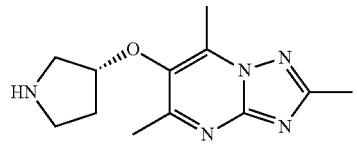

4 M HCl in 1,4-dioxane (150 mL, 600 mmol) was added to tert-butyl (R)-3-((2,5,7-trimethyl-[1,2,4]triazolo[1,5-a]pyrimidin-6-yl)oxy)pyrrolidine-1-carboxylate (52 g, 149.7 mmol) in MeOH (200 mL) and the reaction mixture was stirred at rt for 2 h and then concentrated in vacuo. Acetone was added to the residue and was stirred for 30 minutes. The precipitate was collected by filtration to afford the title compound (26 g, 55%) as a white solid; $^1$H NMR (400 MHz, DMSO) 2.03-2.13 (1H, m), 2.22-2.28 (1H, m), 2.51-2.54 (3H, m), 2.62 (3H, d), 2.74 (3H, s), 3.32-3.45 (3H, m), 3.46-3.56 (1H, m), 4.90 (1H, s), 9.91 (2H, s); m/z MH$^+$ 248.

Intermediate 58B (free base of Intermediate 58): (R)-2,5,7-trimethyl-6-(pyrrolidin-3-yloxy)-[1,2,4]triazolo[1,5-a]pyrimidine

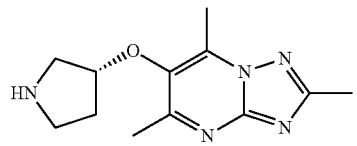 [SMILES: Cc1nc2nc(C)c(O[C@@H]3CCNC3)c(C)n2n1]

(R)-2,5,7-trimethyl-6-(pyrrolidin-3-yloxy)-[1,2,4]triazolo[1,5-a]pyrimidine dihydrochloride (4.12 g, 16.7 mmol) was dissolved in MeOH and loaded onto a 50 g SCX column. The column was washed with MeOH then eluted with 1 M NH$_3$ in MeOH. The solvent was removed in vacuo to afford the title compound (2.73 g, 66%) as an orange gum which was used in the next step without purification; $^1$H NMR (400 MHz, CDCl$_3$) 1.97-2.16 (2H, m), 2.60 (3H, s), 2.65 (3H, s), 2.76 (3H, s), 3.08 (2H, ddd), 3.19 (1H, s), 3.24-3.37 (2H, m), 4.62 (1H, ddt); m/z MH$^+$ 248.

Intermediate 59: (R)-6-((1-(5-bromopyridin-2-yl)pyrrolidin-3-yl)oxy)-2,5,7-trimethyl-[1,2,4]triazolo[1,5-a]pyrimidine

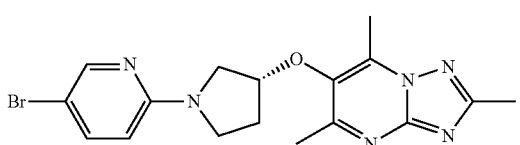

DIPEA (0.282 mL, 1.62 mmol) was added in one portion to 5-bromo-2-fluoropyridine (0.166 mL, 1.62 mmol) and (R)-2,5,7-trimethyl-6-(pyrrolidin-3-yloxy)-[1,2,4]triazolo[1,5-a]pyrimidine (400 mg, 1.62 mmol) in n-butanol (4 mL) at rt. The reaction mixture was heated at 150° C. in a microwave reactor for 2 h, then was allowed to cool to rt, diluted with EtOAc (50 mL), and washed sequentially with water (20 mL) and sat. brine (20 mL). The organic layer was dried with MgSO$_4$, filtered and concentrated in vacuo. The resulting crude product was purified by fcc, eluting with 0-5% MeOH in DCM, to afford the title compound (346 mg, 53%) as a yellow solid; m/z MH$^+$ 403.

Intermediate 60: (R)-2,5,7-trimethyl-6-((1-(pyrimidin-5-yl)pyrrolidin-3-yl)oxy)-[1,2,4]triazolo[1,5-a]pyrimidine

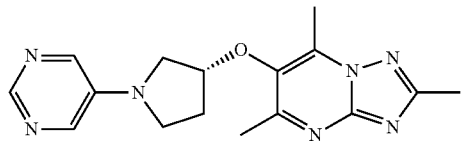

Cs$_2$CO$_3$ (1.98 g, 6.07 mmol) was added to (R)-2,5,7-trimethyl-6-(pyrrolidin-3-yloxy)-[1,2,4]triazolo[1,5-a]pyrimidine (500 mg, 2.02 mmol) and 5-bromopyrimidine (321 mg, 2.02 mmol) in 1,4-dioxane (20 mL). The reaction mixture was degassed and RuPhos 3rd generation precatalyst (169 mg, 0.20 mmol) and RuPhos (189 mg, 0.40 mmol) were added. The resulting suspension was stirred at 90° C. for 18 h, then allowed to cool to rt. The reaction mixture was diluted with EtOAc (50 mL) and was washed with water (30 mL) and sat. brine (25 mL). The organic layer was dried over MgSO$_4$, filtered and concentrated in vacuo. The resulting crude product was purified by fcc, eluting with 0-5% 1 M NH$_3$/MeOH in DCM, to afford the title compound (291 mg, 44%) as an orange gum; $^1$H NMR (500 MHz, CDCl$_3$) 2.32 (1H, dtd), 2.46-2.55 (1H, m), 2.60 (3H, s), 2.62 (3H, s), 2.67 (3H, s), 3.5-3.62 (3H, m), 3.7-3.81 (1H, m), 4.86 (1H, s), 8.12 (2H, s), 8.66 (1H, s); m/z MH$^+$ 326

Intermediate 61: (R)-6-((1-(2-bromopyrimidin-5-yl)pyrrolidin-3-yl)oxy)-2,5,7-trimethyl-[1,2,4]triazolo[1,5-a]pyrimidine

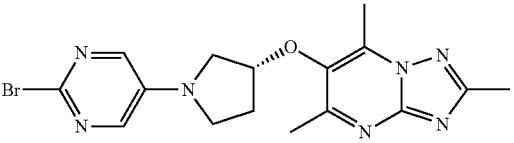

NBS (159 mg, 0.89 mmol) was added portionwise to (R)-2,5,7-trimethyl-6-((1-(pyrimidin-5-yl)pyrrolidin-3-yl)oxy)-[1,2,4]triazolo[1,5-a]pyrimidine (291 mg, 0.89 mmol) in MeCN (10 mL) at 0° C. over a period of 10 min under air. The reaction mixture was stirred at 0° C. for 3 h, then was diluted with DCM (50 mL), and washed sequentially with water (20 mL) and sat. brine (20 mL). The organic layer was isolated and dried over MgSO$_4$, filtered and concentrated in vacuo. The resulting crude product was purified by fcc, eluting with 0-4% 1 M NH₃/MeOH in DCM, to afford the title compound (140 mg, 39%) as a colourless gum; m/z MH⁺ 404.

Intermediate 62: (R)-6-((1-(5-bromopyrazin-2-yl)pyrrolidin-3-yl)oxy)-2,5,7-trimethyl-[1,2,4]triazolo[1,5-a]pyrimidine

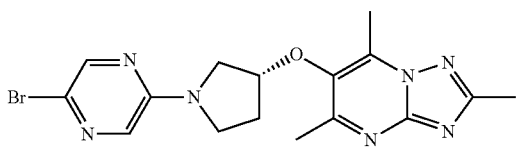 [SMILES: Cc1nc2nc(C)c(O[C@@H]3CCN(c4cnc(Br)cn4)C3)c(C)n2n1]

DIPEA (1.55 mL, 8.92 mmol) was added in one portion to 2,5-dibromopyrazine (1.06 g, 4.46 mmol) and (R)-2,5,7-trimethyl-6-(pyrrolidin-3-yloxy)-[1,2,4]triazolo[1,5-a]pyrimidine (735 mg, 2.97 mmol) in n-butanol (7 mL) at rt. The reaction mixture was stirred at 120° C. for 16 h then allowed to cool to rt and concentrated in vacuo. The resulting crude product was purified by fcc, eluting with 0-4% MeOH in DCM, to afford the title compound (740 mg, 62%) as a yellow foam; ¹H NMR (500 MHz, CDCl₃) 2.33 (1H, dtd), 2.52 (1H, ddq), 2.60 (3H, s), 2.61 (3H, s), 2.65 (3H, s), 3.55 (1H, dd), 3.72 (1H, td), 3.75-3.88 (2H, m), 4.81 (1H, tt), 7.70 (1H, d), 8.14 (1H, d); m/z MH⁺ 404.

Intermediate 63:
1-(4-Bromophenyl)-1,4-pentanedione

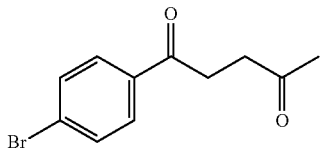

The title compound was synthesised according to reference Ryzhkov, I. O. et al
Chemistry of Heterocyclic Compounds, 47(2), 182-193; 2011.

Intermediate 64:
3-(4-bromophenyl)-6-methylpyridazine

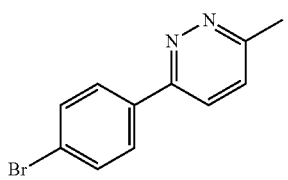

1-(4-Bromophenyl)-1,4-pentanedione (183 g, 0.717 mol) was dissolved in AcOH (1.8 L) and cooled to 0° C. Hydrazine monohydrate (35 mL, 0.717 mol) was then added and the mixture was stirred for 30 min. 2,3-Dichloro-5,6-dicyanobenzoquinone (244 g, 1.08 mol) was added portionwise over 30 min and the reaction was stirred at rt for 40 min, then was concentrated in vacuo. The residue was partitioned between EtOAc (4 L) and sat. aq. NaHCO₃ (4 L). The organic layer was isolated, and the aqueous layer was extracted with EtOAc (2 L). The combined organic layers were washed with sat. aq. NaHCO₃ (10×2 L) and dried over MgSO₄, then concentrated in vacuo. The resulting crude product was purified by suction column (4 L sinter, ~half full of silica, 1 L fractions, product loaded onto column by dissolving in DCM), eluting with 40-60% EtOAc/petroleum ether. The resulting impure product was stirred in diethyl ether (340 mL) for 30 min, then filtered and washed with Et₂O (2×75 mL), then petroleum ether (2×75 mL) and air dried to afford the title compound (91.2 g, 51%) as a beige solid; ¹H NMR (400 MHz, CDCl₃) 2.75 (3H, s), 7.38 (1H, d), 7.65-7.60 (2H, m), 7.71 (1H, d), 7.96-7.91 (2H, m); ¹³C NMR (400 MHz, CDCl₃) 22.1, 123.5, 124.4, 127.3, 128.4, 132.2, 135.4, 156.2, 158.6.

Intermediate 65: 4-((6-(4-bromophenyl)pyridazin-3-yl)methyl)morpholine

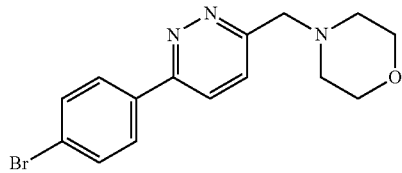 [SMILES: Brc1ccc(-c2ccc(CN3CCOCC3)nn2)cc1]

1,3,5-Trichloro-1,3,5-triazinane-2,4,6-trione (20.4 g, 87.8 mmol) was added portionwise to 3-(4-bromophenyl)-6-methylpyridazine (Intermediate 64) (50 g, 200.7 mmol) in DCM (600 mL) at rt. The reaction mixture was stirred at rt for 1 h then a further portion of 1,3,5-trichloro-1,3,5-triazinane-2,4,6-trione (0.7 g) was added and the reaction mixture was stirred for 30 min, then morpholine (87 mL, 1003.6 mmol) was added and the reaction mixture was stirred for 18 h. The reaction mixture was diluted with 300 mL of water. The organic layer was isolated and washed with water (300 mL) and concentrated in vacuo. The resulting residue was slurried in refluxing EtOAc (150 mL), cooled to rt and filtered. The filtered solid was washed with 200 mL of MTBE and dried in vacuo to afford the title compound (53.4 g, 80%) as a white solid; ¹H NMR (400 MHz, CDCl₃) 2.56 (4H, m), 3.73 (4H, m), 3.91 (2H, s), 7.64 (2H, m), 7.73 (1H, d), 7.81 (1H, d), 7.96 (2H, m); m/z MH⁺ 334.

Intermediate 66: 8-((6-(4-bromophenyl)pyridazin-3-yl)methyl)-3-methyl-3,8-diazabicyclo[3.2.1]octane

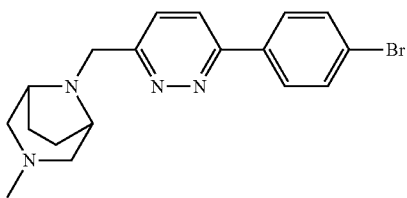 [SMILES: CN1CC2CCC(C1)N2Cc1ccc(-c2ccc(Br)cc2)nn1]

Trichloroisocyanuric acid (65.3 mg, 0.28 mmol) was added in one portion to a solution of 3-(4-bromophenyl)-6-methylpyridazine (Intermediate 64) (200 mg, 0.80 mmol) in DCE (5.9 mL) at rt under air, and the reaction mixture was stirred at rt for 30 min. LCMS confirmed chloro intermediate had been formed. 3-Methyl-3,8-diazabicyclo[3.2.1]octane (101 mg, 0.80 mmol) was added and the reaction mixture was stirred at rt for 18 h. The reaction mixture was diluted with DCM (50 mL), filtered and concentrated in vacuo. The resulting crude product was purified by fcc, eluting with 0-10% 1 M NH$_3$/MeOH in DCM, to afford the title compound (193 mg, 64%) as a yellow solid; NMR (400 MHz, DMSO) 1.93 (2H, q), 2.12 (2H, dd), 2.32 (3H, s), 2.37 (2H, d), 3.29 (2H, s), 4.01 (2H, s), 7.92-7.97 (2H, m), 8.08 (1H, d), 8.29 (2H, d), 8.41 (1H, d), 2H missing assumed to be under DMSO peak; m/z MH$^+$ 372

Intermediate 67: (R)-2-((6-(4-bromophenyl)pyridazin-3-yl)methyl)octahydropyrrolo[1,2-a]pyrazine

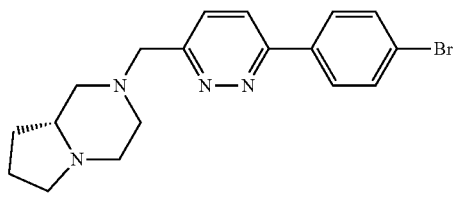 [SMILES: Brc1ccc(-c2ccc(CN3CCN4CCC[C@@H]4C3)nn2)cc1]

Trichloroisocyanuric acid (65.3 mg, 0.28 mmol) was added in one portion to a solution of 3-(4-bromophenyl)-6-methylpyridazine (Intermediate 64) (200 mg, 0.80 mmol) in DCE (5.2 mL) at rt under air. The reaction mixture was stirred at rt for 30 min. LCMS confirmed chloro intermediate had been formed. DIPEA (0.7 mL, 4.01 mmol) and (R)-octahydropyrrolo[1,2-a]pyrazine dihydrochloride (240 mg, 1.20 mmol) were added and the reaction mixture was stirred at rt for 18 h, then was diluted with DCM (50 mL), filtered and concentrated in vacuo. The resulting crude product was purified by fcc, eluting with 0-10% 1 M NH$_3$/MeOH in DCM to afford the title compound (189 mg, 63%) as a yellow solid; $^1$H NMR (400 MHz, DMSO) 1.19-1.31 (1H, m), 1.66 (3H, ddt), 1.89-2.09 (3H, m), 2.14 (1H, td), 2.27 (1H, td), 2.73 (1H, d), 2.86-2.98 (3H, m), 3.83-3.94 (2H, m), 7.74-7.8 (3H, m), 8.09-8.14 (2H, m), 8.23 (1H, d); m/z MH$^+$ 373.

Intermediate 68: (S)-2-((6-(4-bromophenyl)pyridazin-3-yl)methyl)octahydropyrrolo[1,2-a]pyrazine

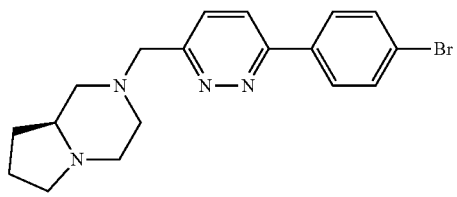 [SMILES: Brc1ccc(-c2ccc(CN3CCN4CCC[C@H]4C3)nn2)cc1]

Trichloroisocyanuric acid (65.3 mg, 0.28 mmol) was added in one portion to a solution of 3-(4-bromophenyl)-6-methylpyridazine (Intermediate 64) (200 mg, 0.80 mmol) in DCE (5.3 mL) at rt under air. The reaction mixture was stirred at rt for 30 min. LCMS confirmed chloro had been formed. DIPEA (0.6 mL, 3.21 mmol) and (S)-octahydropyrrolo[1,2-a]pyrazine hydrobromide (166 mg, 0.80 mmol) were added and the reaction mixture was stirred at rt for 3 days, then diluted with DCM (50 mL), filtered and concentrated in vacuo. The resulting crude product was purified by fcc, eluting with 0-10% 1 M NH$_3$/MeOH in DCM, to afford the title compound (299 mg, 100%) as a yellow solid; m/z MH$^+$ 373.

Intermediate 69: 1-(4-((6-(4-bromophenyl)pyridazin-3-yl)methyl)piperazin-1-yl)ethan-1-one

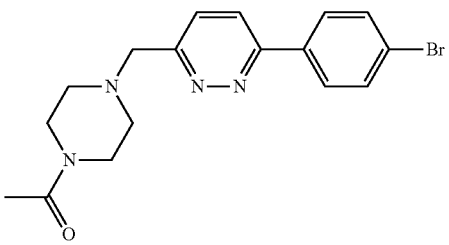 [SMILES: CC(=O)N1CCN(Cc2ccc(-c3ccc(Br)cc3)nn2)CC1]

Trichloroisocyanuric acid (65.3 mg, 0.28 mmol) was added in one portion to a solution of 3-(4-bromophenyl)-6-methylpyridazine (Intermediate 64) (200 mg, 0.80 mmol) in DCE (5.9 mL) at rt under air. The reaction mixture was stirred at rt for 30 min. A further 0.15 eq of trichloroisocyanuric acid was added and the reaction mixture was stirred for 30 min. 1-(Piperazin-1-yl)ethan-1-one (515 mg, 4.01 mmol) was added and the reaction mixture was stirred at rt for 18 h, then diluted with DCM (20 mL), filtered and concentrated in vacuo. The resulting crude product was purified by fcc, eluting with 0-4% 1 M NH$_3$/MeOH in DCM to afford the title compound (246 mg, 82%) as a white solid; $^1$H NMR (400 MHz, CDCl$_3$) 2.09 (3H, s), 2.56 (4H, dt), 3.45-3.51 (2H, m), 3.62-3.68 (2H, m), 3.94 (2H, s), 7.63-7.69 (2H, m), 7.71 (1H, d), 7.83 (1H, d), 7.94-8.02 (2H, m); m/z 375.

Intermediate 70: 3-(4-bromophenyl)-6-(piperidin-1-ylmethyl)pyridazine

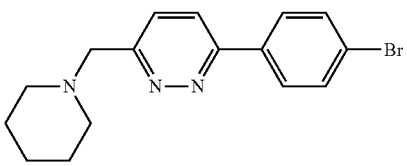 [SMILES: Brc1ccc(-c2ccc(CN3CCCCC3)nn2)cc1]

Trichloroisocyanuric acid (65.3 mg, 0.28 mmol) was added in one portion to a solution of 3-(4-bromophenyl)-6-methylpyridazine (Intermediate 64) (200 mg, 0.80 mmol) in DCE (5.5 mL) at rt under air. The reaction mixture was stirred at rt for 30 min. A further 0.15 eq of trichloroisocyanuric acid was added and the reaction mixture was stirred for 30 min. Piperidine (397 µl, 4.01 mmol) was added and the reaction mixture was stirred at rt for 18 h., then diluted with DCM (20 mL), filtered and concentrated in vacuo. The resulting crude product was purified by fcc, eluting with 0-4% 1 M NH$_3$/MeOH in DCM, to afford the title compound (246 mg, 92%) as a white solid; $^1$H NMR (400 MHz, DMSO) 1.43 (2H, q), 1.54 (4H, p), 2.38-2.48 (4H, m), 3.81 (2H, s), 7.76-7.81 (3H, m), 8.09-8.16 (2H, m), 8.23 (1H, d); m/z MH$^+$ 332.

Intermediate 71: 3-(4-bromophenyl)-6-((4-methylpiperazin-1-yl)methyl)pyridazine

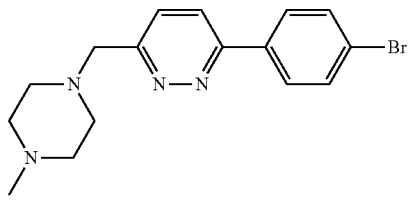 [SMILES: CN1CCN(Cc2ccc(-c3ccc(Br)cc3)nn2)CC1]

Trichloroisocyanuric acid (65.3 mg, 0.28 mmol) was added in one portion to a solution of 3-(4-bromophenyl)-6-methylpyridazine (Intermediate 64) (200 mg, 0.80 mmol) in DCE (5.5 mL) at rt under air. The reaction mixture was stirred at rt for 30 min. A further 0.15 eq of trichloroisocyanuric acid was added and the reaction mixture was stirred for 30 min. 1-Methylpiperazine (445 µl, 4.01 mmol) was added and the reaction mixture was stirred at rt for 18 h, then was diluted with DCM (50 mL), filtered and concentrated in vacuo. The resulting crude product was purified by fcc, eluting with 0-10% 1 M NH$_3$/MeOH in DCM, to afford the title compound (237 mg, 85%) as a yellow solid; $^1$H NMR (400 MHz, DMSO) 2.16 (3H, s), 2.28-2.4 (4H, m), 2.47 (4H, s), 3.83 (2H, s), 7.74-7.8 (3H, m), 8.09-8.14 (2H, m), 8.23 (1H, d); m/z MH$^+$ 347.

Intermediate 72: 3-(4-bromophenyl)-6-((4-ethylpiperazin-1-yl)methyl)pyridazine

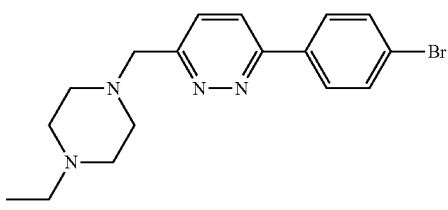 [SMILES: CCN1CCN(Cc2ccc(-c3ccc(Br)cc3)nn2)CC1]

Trichloroisocyanuric acid (0.327 g, 1.40 mmol) was added in one portion to a solution of 3-(4-bromophenyl)-6-methylpyridazine (Intermediate 64) (1 g, 4.01 mmol) in DCE (27.0 mL) at rt under air. The reaction mixture was stirred at rt for 30 min. 1-Ethylpiperazine (2.55 mL, 20.1 mmol) was added and the reaction mixture was stirred at rt for 18 h, then was diluted with DCM (20 mL), filtered and concentrated in vacuo. The resulting crude product was purified by fcc, eluting with 0-10% 1 M NH$_3$/MeOH, to afford the title compound (125 mg, 9%) as a white solid; $^1$H NMR (400 MHz, CDCl$_3$) 1.08 (3H, t), 2.42 (2H, q), 2.50 (4H, s), 2.62 (4H, s), 3.93 (2H, s), 7.63-7.68 (2H, m), 7.71 (1H, d), 7.80 (1H, d), 7.94-8.00 (2H, m); m/z MH$^+$ 361.

Intermediate 73: 3-(4-bromophenyl)-6-((4-(2-methoxyethyl)piperazin-1-yl)methyl)pyridazine

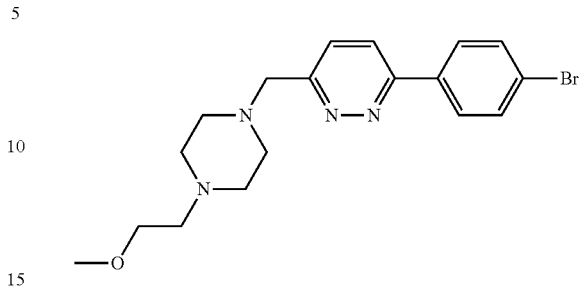

Trichloroisocyanuric acid (0.327 g, 1.40 mmol) was added in one portion to a solution of 3-(4-bromophenyl)-6-methylpyridazine (Intermediate 64) (1 g, 4.01 mmol) in DCE (26.5 mL) at rt under air. The reaction mixture was stirred at rt for 30 min. 1-(2-Methoxyethyl)piperazine (2.98 mL, 20.1 mmol) was added and the reaction mixture was stirred at rt for 18 h, then was diluted with DCM (20 mL), filtered and concentrated in vacuo. The resulting crude product was purified by fcc, eluting with 0-10% 1 M NH$_3$/MeOH in DCM, to afford the title compound (525 mg, 33%) as a white solid; $^1$H NMR (400 MHz, CDCl$_3$) 2.61 (10H, dt), 3.35 (3H, s), 3.5-3.55 (2H, m), 3.93 (2H, s), 7.62-7.67 (2H, m), 7.70 (1H, d), 7.80 (1H, d), 7.94-8 (2H, m); m/z MH$^+$ 391.

Intermediate 74: 4-((6-(4-bromophenyl)pyridazin-3-yl)methyl)-1,4-oxazepane

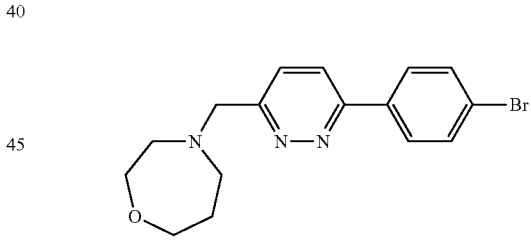

Trichloroisocyanuric acid (65.3 mg, 0.28 mmol) was added in one portion to a solution of 3-(4-bromophenyl)-6-methylpyridazine (Intermediate 64) (200 mg, 0.80 mmol) in DCE (5.9 mL) at rt under air. The reaction mixture was stirred at rt for 30 min. A further 0.15 eq of trichloroisocyanuric acid was added and the reaction mixture was stirred for 30 min. 1,4-Oxazepane (406 mg, 4.01 mmol) was added and the reaction mixture was stirred at rt for 18 h, then was diluted with DCM (50 mL), filtered and concentrated in vacuo. The resulting crude product was purified by fcc, eluting with 0-4% 1 M NH$_3$/MeOH in DCM to afford the title compound (200 mg, 72%) as a yellow solid; $^1$H NMR (400 MHz, DMSO) 1.83 (2H, p), 2.72 (4H, q), 3.6-3.67 (2H, m), 3.72 (2H, t), 4.01 (2H, s), 7.73-7.81 (2H, m), 7.83 (1H, d), 8.07-8.16 (2H, m), 8.24 (1H, d); m/z MH$^+$ 348.

Intermediate 75: 1-((6-(4-bromophenyl)pyridazin-3-yl)methyl)azepane

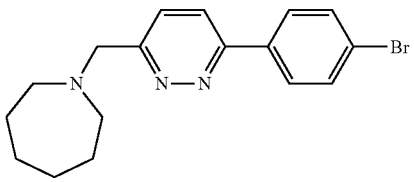 [SMILES: Brc1ccc(-c2ccc(CN3CCCCCC3)nn2)cc1]

Trichloroisocyanuric acid (65.3 mg, 0.28 mmol) was added in one portion to a solution of 3-(4-bromophenyl)-6-methylpyridazine (Intermediate 64) (200 mg, 0.80 mmol) in DCE (5.5 mL) at rt under air. The reaction mixture was stirred at rt for 30 min. A further 0.15 eq of trichloroisocyanuric acid was added and the reaction mixture was stirred for 30 min. Azepane (452 µl, 4.01 mmol) was added and the reaction mixture was stirred at rt for 3 days, then was diluted with DCM (50 mL), filtered and concentrated in vacuo. The resulting crude product was purified by fcc, eluting with 0-4% 1 M NH$_3$/MeOH in DCM to afford the title compound (88 mg, 32%) as a yellow solid; $^1$H NMR (400 MHz, DMSO) 1.59 (8H, s), 2.64-2.7 (4H, m), 3.98 (2H, s), 7.74-7.79 (2H, m), 7.82 (1H, d), 8.09-8.14 (2H, m), 8.23 (1H, d); m/z MH$^+$ 346.

Intermediate 76: 4-((5-chloropyrazin-2-yl)methyl)morpholine

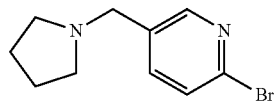

Sodium triacetoxyborohydride (4.46 g, 21.1 mmol) was added to 5-chloropyrazine-2-carbaldehyde (1 g, 7.02 mmol) and morpholine (0.614 mL, 7.02 mmol) in DCM (10 mL) at rt and the reaction mixture was stirred at rt for 4 h. The reaction mixture was diluted with sat. aq. NaHCO$_3$ and was stirred for 10 min, then passed through a phase separating filter paper and concentrated in vacuo to afford the title compound (1.180 g, 79%) as a colourless oil; $^1$H NMR (400 MHz, CDCl$_3$) 2.49-2.55 (4H, m), 3.69 (2H, s), 3.71-3.77 (4H, m), 8.47 (1H, d), 8.55 (1H, d); m/z MH$^+$ 214.

Intermediate 77: 4-((5-(4-bromophenyl)pyrazin-2-yl)methyl)morpholine

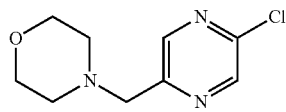 [SMILES: Clc1cnc(CN2CCOCC2)cn1]

Pd(Ph$_3$P)$_4$ (135 mg, 0.12 mmol) was added in one portion to a degassed mixture of (4-bromophenyl)boronic acid (470 mg, 2.34 mmol), 4-((5-chloropyrazin-2-yl)methyl)morpholine (500 mg, 2.34 mmol) and 2 M aq. Na$_2$CO$_3$ (2.34 mL, 4.68 mmol) in 1,4-dioxane (7.8 mL) and water (1.5 mL) at rt. The reaction mixture was stirred at 80° C. for 2 h, then was allowed to cool to rt, diluted with EtOAc (75 mL), and washed sequentially with water (20 mL) and sat. brine (20 mL). The organic layer was dried over MgSO$_4$, filtered and concentrated in vacuo. The resulting crude product was purified by fcc, eluting with 0-3% MeOH in DCM, to afford the title compound (730 mg, 93%) as a white solid; $^1$H NMR (400 MHz, CDCl$_3$) 2.57 (4H, q), 3.72-3.79 (6H, m), 7.62-7.66 (2H, m), 7.88-7.93 (2H, m), 8.71 (1H, d), 8.95 (1H, d); m/z MH$^+$ 334.

Intermediate 78: 2-bromo-5-(pyrrolidin-1-ylmethyl)pyridine

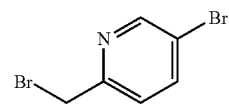

Potassium iodide (331 mg, 1.99 mmol) was added to 2-bromo-5-(bromomethyl)pyridine (500 mg, 1.99 mmol), pyrrolidine (142 mg, 1.99 mmol) and K$_2$CO$_3$ (275 mg, 1.99 mmol) in DMF (10 mL). The reaction mixture was stirred at rt for 16 h, then was diluted with water (50 mL), extracted with EtOAc (3×50 mL), and the combined organic layers were washed with sat. brine (3×50 mL) and dried over Na$_2$SO$_4$, filtered and concentrated in vacuo to afford the title compound (470 mg, 98%) as a yellow oil; m/z MH$^+$ 241.

Intermediate 79: 5-bromo-2-(bromomethyl)pyridine

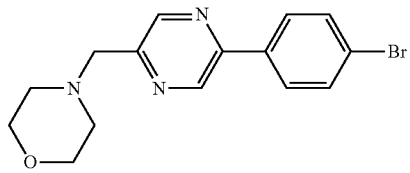 [SMILES: Brc1ccc(-c2cnc(CN3CCOCC3)cn2)cc1]

Benzoyl peroxide (0.063 g, 0.26 mmol) was added to 5-bromo-2-methylpyridine (0.9 g, 5.23 mmol), and NBS (0.978 g, 5.49 mmol) in CCl$_4$ (10 mL) at 15° C. The reaction mixture was heated at reflux for 15 h, then was allowed to cool to rt. The reaction mixture was diluted with DCM (100 mL), and washed sequentially with water (50 mL), and sat. brine (50 mL). The organic layer was dried over Na$_2$SO$_4$, filtered and concentrated in vacuo. The resulting crude product was purified by fcc, eluting with 5% EtOAc in petroleum ether, to afford the title compound (0.440 g, 34% if pure) as an impure purple oil; m/z MH⁺ 250.

Intermediate 80:
5-bromo-2-(pyrrolidin-1-ylmethyl)pyridine

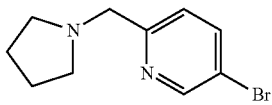 [SMILES: Brc1ccc(CN2CCCC2)nc1]

Potassium iodide (437 mg, 2.63 mmol) was added to 5-bromo-2-(bromomethyl)pyridine (660 mg, 2.63 mmol), pyrrolidine (187 mg, 2.63 mmol) and $K_2CO_3$ (364 mg, 2.63 mmol) in DMF (10 mL). The reaction mixture was stirred at rt for 16 h, then was quenched with water (50 mL) and extracted with EtOAc (3×50 mL). The combined organic layers were washed with sat. brine (3×50 mL) and dried over $Na_2SO_4$, filtered and concentrated in vacuo to afford the title compound (570 mg, 90%) as a black oil; m/z MH⁺ 241.

Intermediate 81: (R)-3-methyl-4-(5-(3-((2,5,7-trimethyl-[1,2,4]triazolo[1,5-a]pyrimidin-6-yl)methyl)pyrrolidin-1-yl)pyrimidin-2-yl)benzaldehyde

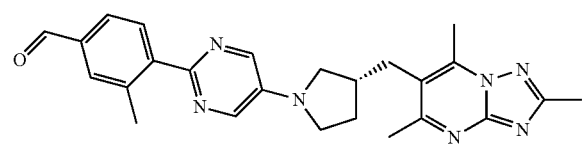 [SMILES: Cc1nc2nc(C)c(C[C@@H]3CCN(c4cnc(-c5ccc(C=O)cc5C)nc4)C3)c(C)n2n1]

XPhos palladium(II) biphenyl-2-amine chloride (20 mg, 0.02 mmol) was added to (R)-6-((1-(2-bromopyrimidin-5-yl)pyrrolidin-3-yl)methyl)-2,5,7-trimethyl-[1,2,4]triazolo[1,5-a]pyrimidine (Intermediate 16) (200 mg, 0.50 mmol), 3-methyl-4-(4,4,5,5-tetramethyl-1,3,2-dioxaborolan-2-yl)benzaldehyde (Intermediate 18) (122 mg, 0.50 mmol) and $Cs_2CO_3$ (324 mg, 0.99 mmol) in 1,4-dioxane (3 mL) and water (1.5 mL) at rt. The reaction mixture was stirred at 90° C. for 16 h, then allowed to cool to rt and concentrated in vacuo. The resulting crude product was purified by flash C18 chromatography, eluting with 5-100% MeCN in water, to afford the title compound (75 mg, 34%) as a yellow solid; ¹H NMR (400 MHz, CDCl₃) 1.90 (1H, s), 2.27 (1H, s), 2.66 (7H, d), 2.77 (3H, s), 2.86 (3H, s), 2.92-3.11 (2H, m), 3.24 (1H, s), 3.45-3.54 (1H, m), 3.59 (1H, s), 3.67 (1H, s), 7.82 (2H, dt), 7.98 (1H, d), 8.24 (2H, s), 10.06 (1H, s); m/z MH⁺ 442.

Intermediate 82: (R)-tert-butyl 4-((6-(4-(3-((2,5,7-trimethyl-[1,2,4]triazolo[1,5-a]pyrimidin-6-yl)methyl)pyrrolidin-1-yl)phenyl)pyridin-3-yl)methyl)piperazine-1-carboxylate

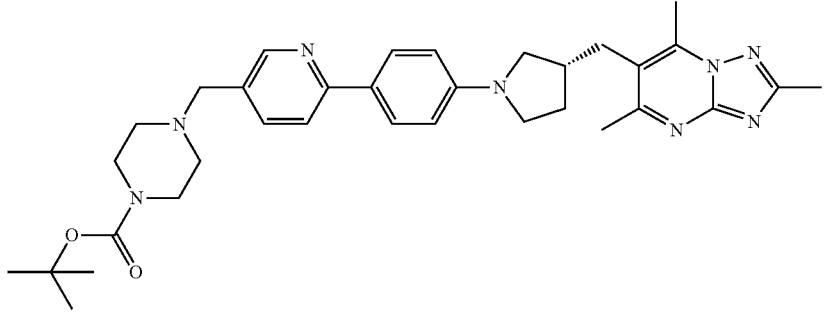 [SMILES: Cc1nc2nc(C)c(C[C@@H]3CCN(c4ccc(-c5ccc(CN6CCN(C(=O)OC(C)(C)C)CC6)cn5)cc4)C3)c(C)n2n1]

Degassed 1,4-dioxane (15 mL) was added to (R)-2,5,7-trimethyl-6-(pyrrolidin-3-ylmethyl)-[1,2,4]triazolo[1,5-a]pyrimidine dihydrochloride (Intermediate 4) (500 mg, 2.04 mmol) and tert-butyl 4-((6-(4-bromophenyl)pyridin-3-yl)methyl)piperazine-1-carboxylate (Intermediate 37) (881 mg, 2.04 mmol). $Cs_2CO_3$ (1.99 g, 6.11 mmol) was then added followed by RuPhos (190 mg, 0.41 mmol) and RuPhos 3rd generation precatalyst (341 mg, 0.41 mmol). The reaction mixture was heated at 90° C. for 24 h, allowed to cool to rt and concentrated in vacuo. The residue was taken up in DCM, filtered through Celite, concentrated in vacuo and purified by fcc, eluting with 0-10% MeOH in DCM, to afford the title compound (290 mg, 24%) as a beige solid; ¹H NMR (500 MHz, CDCl₃) 1.45 (9H, s), 1.82-1.94 (1H, m), 2.13-2.23 (1H, m), 2.41 (4H, s), 2.62 (4H, s), 2.70 (3H, s), 2.78 (3H, s), 2.86-2.99 (2H, m), 3.14 (1H, dd), 3.37-3.47 (6H, m), 3.52 (2H, s), 3.57 (1H, td), 6.58-6.64 (2H, m), 7.60 (1H, dd), 7.64 (1H, dd), 7.86-7.96 (2H, m), 8.51 (1H, d); m/z MH⁺ 597.

Example 1: (R)-4-((6'-(3-((2,5,7-trimethyl-[1,2,4]triazolo[1,5-a]pyrimidin-6-yl)methyl)pyrrolidin-1-yl)-[3,3'-bipyridin]-6-yl)methyl)morpholine

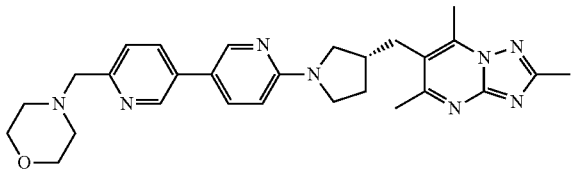 [SMILES: Cc1nc2nc(C)c(C[C@@H]3CCN(c4ccc(-c5ccc(CN6CCOCC6)nc5)cn4)C3)c(C)n2n1]

XPhos 2$^{nd}$ generation precatalyst (29.4 mg, 0.04 mmol) was added to (R)-6-((1-(5-bromopyridin-2-yl)pyrrolidin-3-yl)methyl)-2,5,7-trimethyl-[1,2,4]triazolo[1,5-a]pyrimidine (Intermediate 5) (150 mg, 0.37 mmol), (6-(morpholinomethyl)pyridin-3-yl)boronic acid (sourced commercially) (83 mg, 0.37 mmol) and Cs$_2$CO$_3$ (244 mg, 0.75 mmol) in 1,4-dioxane (2 mL) and water (1 mL). The reaction mixture was stirred at 80° C. for 3 h, then was allowed to cool to rt and concentrated in vacuo. The resulting crude product was purified by preparative HPLC to afford the formic acid salt of the title compound (80 mg, 36%) as a yellow solid; $^1$H NMR (300 MHz, MeOD) 1.89-2.08 (1H, m), 2.19-2.33 (1H, m), 2.56 (3H, s), 2.71-2.73 (4H, m), 2.77-2.89 (7H, m), 3.04 (2H, d), 3.24-3.33 (1H, m), 3.44-3.57 (1H, m), 3.57-3.75 (1H, m), 3.71-3.85 (5H, m), 3.98 (2H, d), 6.67 (1H, d), 7.58 (1H, d), 7.89 (1H, dd), 8.04 (1H, dd), 8.18 (2H, s, equates to 2 equivalents of formate salt), 8.33 (1H, d), 8.76 (1H, d) m/z MH$^+$ 499.

Example 4: (R)-2,5,7-trimethyl-6-(0-(6'-((4-methylpiperazin-1-yl)methyl)-[3,3'-bipyridin]-6-yl)pyrrolidin-3-yl)methyl)-[1,2,4]triazolo[1,5-a]pyrimidine

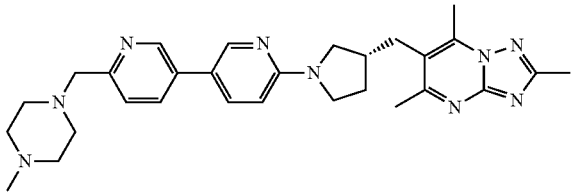 [SMILES: Cc1nc2nc(C)c(C[C@@H]3CCN(c4ccc(-c5ccc(CN6CCN(C)CC6)nc5)cn4)C3)c(C)n2n1]

Pd(Ph$_3$P)$_4$ (72.9 mg, 0.06 mmol) was added to (R)-6-((1-(5-bromopyridin-2-yl)pyrrolidin-3-yl)methyl)-2,5,7-trimethyl-[1,2,4]triazolo[1,5-a]pyrimidine (Intermediate 5) (253 mg, 0.63 mmol), (6-((4-methylpiperazin-1-yl)methyl)pyridin-3-yl)boronic acid (Intermediate 9) (200 mg, 0.85 mmol) and Na$_2$CO$_3$ (134 mg, 1.26 mmol) in toluene (10 mL) and water (2 mL). The reaction mixture was stirred at 80° C. for 16 h, allowed to cool to rt and concentrated in vacuo. The resulting crude product was purified by preparative HPLC to afford the formic acid salt of the title compound (60 mg, 17%) as a yellow solid; $^1$H NMR (300 MHz, DMSO) 1.84 (1H, m), 2.10 (1H, m), 2.20 (3H, s), 2.30-2.50 (12H, m), 2.63 (3H, s), 2.74 (3H, s), 2.92 (2H, d), 3.18 (1H, dd), 3.38 (1H, dt), 3.57 (4H, m), 6.55 (1H, d), 7.42 (1H, d), 7.84 (1H, dd), 7.96 (1H, dd), 8.20 (1H, s), 8.43 (1H, d), 8.72 (1H, dd); m/z MH$^+$ 512.

Example 5: (R)-2,5,7-trimethyl-6-(0-(5-(4-((4-methylpiperazin-1-yl)methyl)phenyl)pyridin-2-yl)pyrrolidin-3-yl)methyl)-[1,2,4]triazol[1,5-a]pyrimidine

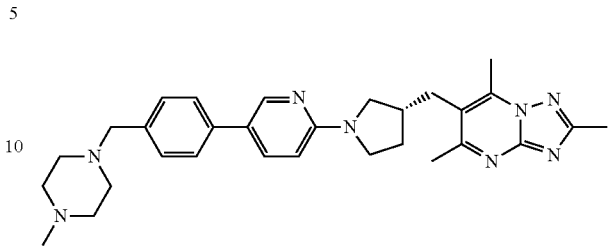

Pd(Ph$_3$P)$_4$ (17 mg, 0.01 mmol) was added to 1-methyl-4-(4-(4,4,5,5-tetramethyl-1,3,2-dioxaborolan-2-yl)benzyl)piperazine (sourced commercially) (95 mg, 0.30 mmol), (R)-6-((1-(5-bromopyridin-2-yl)pyrrolidin-3-yl)methyl)-2,5,7-trimethyl-[1,2,4]triazolo[1,5-a]pyrimidine (Intermediate 5) (120 mg, 0.30 mmol) and Na$_2$CO$_3$ (63.4 mg, 0.60 mmol) in 1,4-dioxane (3 mL) and water (1.5 mL) at rt. The reaction mixture was stirred at 80° C. for 16 h, allowed to cool to rt and then concentrated in vacuo. The resulting crude product was purified by flash C18 chromatography, eluting with 5-100% MeCN in water (+0.1% FA), to afford the formic acid salt of the title compound (55 mg, 33%) as a white solid; $^1$H NMR (400 MHz, MeOD) 1.99 (1H, dq), 2.26 (1H, dq), 2.57 (3H, s), 2.70 (11H, m), 2.85 (3H, s), 3.05 (6H, m), 3.25-3.34 (2H, m), 3.50 (1H, m), 3.60 (1H, m), 3.70 (3H, m), 6.63 (1H, d), 7.42 (2H, d), 7.55 (2H, d), 7.84 (1H, dd), 8.28 (1H, d), 8.47 (1H, s); m/z MH$^+$ 511.

Example 6: (R)-4-(4-(2-(3-((2,5,7-trimethyl-[1,2,4]-triazolo[1,5-a]pyrimidin-6-yl)methyl)pyrrolidin-1-yl)pyrimidin-5-yl)benzyl)morpholine

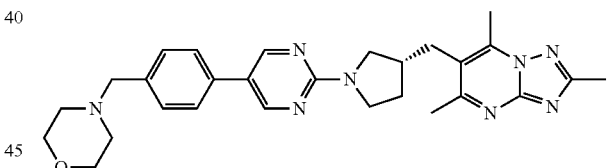

XPhos 2$^{nd}$ generation precatalyst (34 mg, 0.04 mmol) was added to rac-6-((1-(5-bromopyrimidin-2-yl)pyrrolidin-3-yl)methyl)-2,5,7-trimethyl-[1,2,4]triazolo[1,5-a]pyrimidine (Intermediate 10) (350 mg, 0.87 mmol), 4-(4-(4,4,5,5-tetramethyl-1,3,2-dioxaborolan-2-yl)benzyl)morpholine (sourced commercially) (264 mg, 0.87 mmol) and Cs$_2$CO$_3$ (567 mg, 1.74 mmol) in 1,4-dioxane (3 mL) and water (1.5 mL) at rt. The reaction mixture was stirred at 80° C. for 16 h, then was allowed to cool to rt and was concentrated in vacuo. The resulting crude product was purified by flash C18 chromatography, eluting with 5-100% MeCN in water (+0.08% NH$_4$CO$_3$). The resulting racemic product (390 mg) was separated by preparative chiral-HPLC on a Chiralpak IA column, eluting with 50% EtOH in TBME (modified with DEA) as eluent, to afford the title compound (120 mg, 31%) as a white solid; $^1$H NMR (400 MHz, MeOD) 1.90-2.04 (1H, m), 2.23 (1H, dt), 2.50 (4H, t), 2.57 (3H, s), 2.74 (4H, s), 2.86 (3H, s), 3.05 (2H, d), 3.39 (1H, dd), 3.60 (3H, d), 3.68-3.79 (5H, m), 3.86 (1H, ddd), 7.45 (2H, d), 7.55 (2H, d), 8.61 (2H, s); m/z MH$^+$499.

Example 7: (R)-4-((5-(5-(3-((2,5,7-trimethyl-[1,2,4]triazolo[1,5-a]pyrimidin-6-yl)methyl)pyrrolidin-1-yl)pyridin-2-yl)pyrazin-2-yl)methyl)morpholine

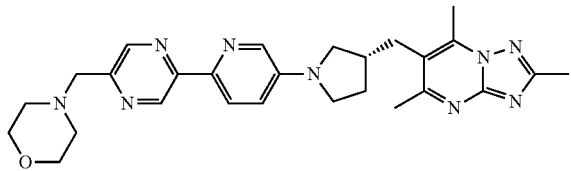

Pd(Ph₃P)₄ (46.1 mg, 0.04 mmol) was added to 4-((5-chloropyrazin-2-yl)methyl)morpholine (Intermediate 76) (85 mg, 0.40 mmol), (R)-6-((1-(6-bromopyridin-3-yl)pyrrolidin-3-yl)methyl)-2,5,7-trimethyl-[1,2,4]triazolo[1,5-a]pyrimidine (Intermediate 12) (160 mg, 0.40 mmol) and 1,1,1,2,2,2-hexamethyldistannane (131 mg, 0.40 mmol) in 1,4-dioxane (5 mL) at rt. The reaction mixture was stirred at 110° C. for 16 h, then allowed to cool to rt and concentrated in vacuo. The resulting crude product was purified by flash C18 chromatography, eluting with 5-100% MeCN in water (+0.1% FA), to afford the title compound (87 mg, 43%) as a yellow solid; ¹H NMR (300 MHz, MeOD) 1.89-2.08 (1H, m), 2.18-2.31 (1H, m), 2.56 (3H, s), 2.60-2.87 (10H, m), 3.05 (2H, dd), 3.23 (1H, dd), 3.37-3.85 (10H, m), 7.10 (1H, dd), 8.03 (1H, d), 8.20 (1H, d), 8.66 (1H, d), 9.31 (1H, d); m/z MH⁺ 500.

Example 8: (R)-2,5,7-trimethyl-6-(0-(6-(4-((4-methylpiperazin-1-yl)methyl)phenyl)pyridin-3-yl)pyrrolidin-3-yl)methyl)-[1,2,4]triazolo[1,5-a]pyrimidine

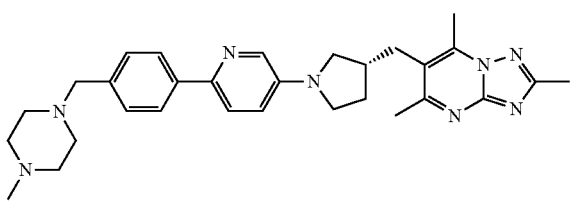 [SMILES: Cc1nc2nc(C)c(C[C@@H]3CCN(c4ccc(-c5ccc(CN6CCN(C)CC6)cc5)nc4)C3)c(C)n2n1]

Pd(Ph₃P)₄ (202 mg, 0.17 mmol) was added to (R)-6-((1-(6-bromopyridin-3-yl)pyrrolidin-3-yl)methyl)-2,5,7-trimethyl-[1,2,4]triazolo[1,5-a]pyrimidine (Intermediate 12) (700 mg, 1.74 mmol), 1-methyl-4-(4-(4,4,5,5-tetramethyl-1,3,2-dioxaborolan-2-yl)benzyl)piperazine (sourced commercially) (607 mg, 1.92 mmol) and 1 M aq. Na₂CO₃ (3.49 mL, 3.49 mmol) in degassed 1,4-dioxane (7 mL) at rt. The reaction mixture was stirred at 80° C. for 18 h, then allowed to cool to rt and concentrated in vacuo. The residue was taken up in DCM, filtered and the resulting crude product was purified by fcc, eluting with 0-10% 1 M NH₃/MeOH in DCM, then further purified by recrystallization from EtOAc (with a small amount of MeOH), to afford the title compound (240 mg, 27%) as a pale yellow crystalline solid; ¹H NMR (500 MHz, CDCl₃) 1.86-1.94 (1H, m), 2.14-2.23 (1H, m), 2.28 (3H, s), 2.49 (8H, s), 2.62 (4H, s), 2.71 (3H, s), 2.79 (3H, s), 2.86-3.01 (2H, m), 3.14 (1H, dd), 3.37-3.48 (2H, m), 3.54 (2H, s), 3.55-3.61 (1H, m), 6.86 (1H, dd), 7.37 (2H, d), 7.59 (1H, dd), 7.82-7.88 (2H, m), 8.06 (1H, d); m/z MH⁺ 511.

Example 9: (R)-4-((6-(5-(3-((2,5,7-trimethyl-[1,2,4]triazolo[1,5-a]pyrimidin-6-yl)methyl)pyrrolidin-1-yl)pyridin-2-yl)pyridazin-3-yl)methyl)morpholine

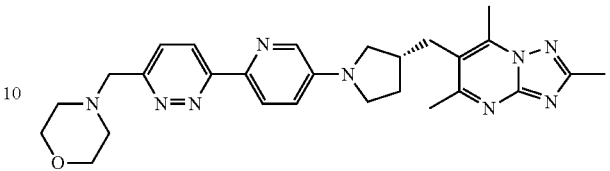

Pd(Ph₃P)₄ (343 mg, 0.30 mmol) was added in one portion to 4-((6-chloropyridazin-3-yl)methyl)morpholine (Intermediate 14) (634 mg, 2.97 mmol), (R)-6-((1-(6-bromopyridin-3-yl)pyrrolidin-3-yl)methyl)-2,5,7-trimethyl-[1,2,4]triazolo[1,5-a]pyrimidine (Intermediate 12) (1.19 g, 2.97 mmol) and 1,1,1,2,2,2-hexamethyldistannane (0.615 mL, 2.97 mmol) in 1,4-dioxane (30 mL) at rt. The reaction mixture was stirred at 100° C. for 20 h, then allowed to cool to rt, filtered and washed with DCM (20 mL). The filtrate was concentrated in vacuo and the resulting crude product was purified by fcc, eluting with 0-10% 1 M NH₃/MeOH in DCM, then further purified by preparative HPLC, then dissolved in MeOH and loaded onto a 50 g SCX column. The column was washed with MeOH (2×column volumes) then eluted with 1 M NH₃/MeOH. The resulting gum was triturated with Et₂O to give a solid which was filtered and dried in vacuo to afford the title compound (608 mg, 41%) as a pale yellow solid; ¹H NMR (500 MHz, DMSO) 1.87 (1H, dq), 2.06-2.22 (1H, m), 2.45 (7H, d), 2.64 (4H, s), 2.74 (3H, s), 2.93 (2H, d), 3.12 (1H, dd), 3.33-3.38 (1H, m), 3.48 (1H, dd), 3.51-3.64 (5H, m), 3.79 (2H, s), 7.06 (1H, dd), 7.71 (1H, d), 8.05 (1H, d), 8.33 (2H, dd); m/z MH⁺500.

Example 10: 6-(((R)-1-(2-(4-(((S)-2,4-dimethylpiperazin-1-yl)methyl)phenyl)pyrimidin-5-yl)pyrrolidin-3-yl)methyl)-2,5,7-trimethyl-[1,2,4]triazolo[1,5-a]pyrimidine

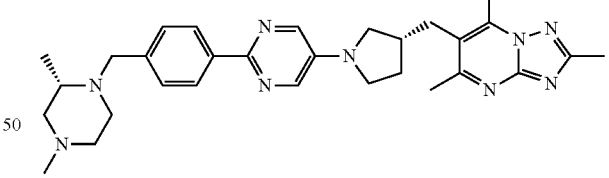

(R)-6-((1-(2-bromopyrimidin-5-yl)pyrrolidin-3-yl)methyl)-2,5,7-trimethyl-[1,2,4]triazolo[1,5-a]pyrimidine (Intermediate 16) (300 mg, 0.75 mmol), (S)-2,4-dimethyl-1-(4-(4,4,5,5-tetramethyl-1,3,2-dioxaborolan-2-yl)benzyl)piperazine (Intermediate 17) (296 mg, 0.89 mmol), Pd(Ph₃P)₄ (86 mg, 0.07 mmol) and potassium carbonate (206 mg, 1.49 mmol) were dissolved in 1,4-dioxane (12 mL) and water (4 mL) and heated at 80° C. for 18 h. The reaction mixture allowed to cool to rt, then poured into DCM (50 mL). The aqueous layer was separated then extracted with 20% MeOH/DCM. The combined organic layers were dried over MgSO₄, filtered and concentrated in vacuo. The resulting crude product was purified by fcc, eluting with 0-5% 1 M NH₃/MeOH in DCM. The resulting gum was triturated with EtOAc and the resulting solid was filtered and dried in vacuo to afford the title compound (52 mg, 13%) as a white solid; ¹H NMR (500 MHz, DMSO) 1.06 (3H, d), 1.78-1.9 (2H, m), 1.98 (1H, d), 2.10 (5H, s), 2.41 (1H, s), 2.47 (4H, s), 2.55 (2H, d), 2.64 (4H, s), 2.74 (3H, s), 2.92 (2H, d), 3.04-3.18 (2H, m), 3.34 (1H, d), 3.46 (1H, dd), 3.5-3.58 (1H, m), 3.97 (1H, d), 7.33 (2H, d), 8.16 (2H, d), 8.20 (2H, s); m/z MH⁺ 526.

Example 11: (R)-4-((5-(5-(3-((2,5,7-trimethyl-[1,2,4]triazolo[1,5-a]pyrimidin-6-yl)methyl)pyrrolidin-1-yl)pyrimidin-2-yl)pyridin-2-yl)methyl)morpholine

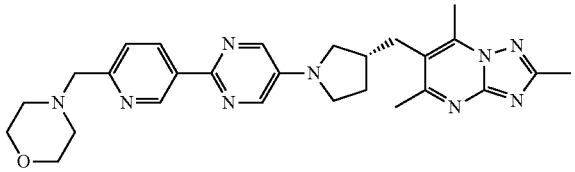 [SMILES: Cc1nc2nc(C)c(C[C@@H]3CCN(c4ccc(-c5ccc(CN6CCOCC6)nn5)nc4)C3)c(C)n2n1]

XPhos 2$^{nd}$ generation precatalyst (9 mg, 0.01 mmol) was added to (R)-6-((1-(2-bromopyrimidin-5-yl)pyrrolidin-3-yl)methyl)-2,5,7-trimethyl-[1,2,4]triazolo[1,5-a]pyrimidine (Intermediate 16) (90 mg, 0.22 mmol), (6-(morpholinomethyl)pyridin-3-yl)boronic acid (sourced commercially) (50 mg, 0.22 mmol) and Cs₂CO₃ (146 mg, 0.45 mmol) in 1,4-dioxane (3 mL) and water (1.5 mL) at rt. The reaction mixture was stirred at 90° C. for 16 h, then allowed to cool to rt and concentrated in vacuo. The resulting crude product was purified by flash C18 chromatography, eluting with 5-100% MeCN in water, to afford the title compound (22 mg, 20%) as a white solid; ¹H NMR (400 MHz, MeOD) 2.00 (1H, dq), 2.26 (1H, dq), 2.57 (3H, s), 2.64 (4H, s), 2.75 (4H, s), 2.86 (3H, s), 3.08 (2H, h), 3.25 (1H, dd), 3.46 (1H, dt), 3.54-3.72 (2H, m), 3.72-3.83 (6H, m), 7.63 (1H, d), 8.24 (2H, s), 8.61 (1H, dd), 9.34 (1H, d); m/z MH⁺ 500.

Example 12: (R)-6-((1-(2-(2-methoxy-4-((4-methylpiperazin-1-yl)methyl)phenyl)pyrimidin-5-yl)pyrrolidin-3-yl)methyl)-2,5,7-trimethyl-[1,2,4]triazolo[1,5-a]pyrimidine

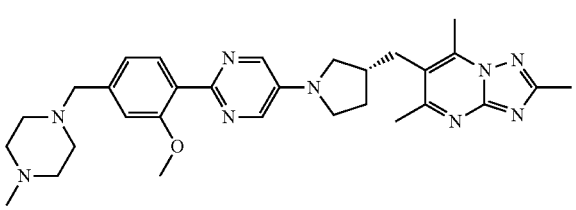 [SMILES: COc1cc(CN2CCN(C)CC2)ccc1-c1ncc(N2CC[C@@H](Cc3c(C)nc4nc(C)nn4c3C)C2)cn1]

XPhos 2$^{nd}$ generation precatalyst (20 mg, 0.02 mmol) was added to (R)-6-((1-(2-bromopyrimidin-5-yl)pyrrolidin-3-yl)methyl)-2,5,7-trimethyl-[1,2,4]triazolo[1,5-a]pyrimidine (Intermediate 16) (200 mg, 0.50 mmol), (2-methoxy-4-((4-methylpiperazin-1-yl)methyl)phenyl)boronic acid (Intermediate 42) (131 mg, 0.50 mmol) and Cs₂CO₃ (324 mg, 0.99 mmol) in 1,4-dioxane (3 mL) and water (1.5 mL) at rt. The reaction mixture was stirred at 90° C. for 16 h, allowed to cool to rt and concentrated in vacuo. The resulting crude product was purified by flash C18 chromatography, eluting with 5-100% MeCN in water, to afford the formic acid salt of the title compound (56 mg, 19%) as a pale yellow solid; ¹H NMR (400 MHz, MeOD) 2.00 (1H, dq), 2.25 (1H, ddd), 2.57 (3H, s), 2.72 (10H, m), 2.87 (3H, s), 2.99-3.15 (7H, m), 3.22 (1H, dd), 3.44 (1H, dt), 3.51-3.72 (4H, m), 3.83 (3H, s), 7.04 (1H, dd), 7.14 (1H, d), 7.49 (1H, d), 8.19 (2H, s), 8.49 (1H, s); m/z MH⁺ 542.

Example 13: (R)-2,5,7-trimethyl-6-((1-(2-(2-methyl-4-((4-methylpiperazin-1-yl)methyl)phenyl)pyrimidin-5-yl)pyrrolidin-3-yl)methyl)-[1,2,4]triazolo[1,5-a]pyrimidine

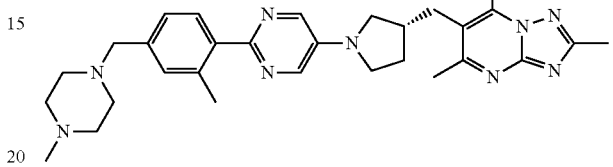

1-Methylpiperazine (34 mg, 0.34 mmol) was added to (R)-3-methyl-4-(5-(3-((2,5,7-trimethyl-[1,2,4]triazolo[1,5-a]pyrimidin-6-yl)methyl)pyrrolidin-1-yl)pyrimidin-2-yl)benzaldehyde (75 mg, 0.17 mmol) in DCM (0.5 mL) at rt under air and the reaction mixture was stirred for 2 h. Sodium triacetoxyborohydride (180 mg, 0.85 mmol) was added and the reaction mixture was stirred at rt for 50 h, then was concentrated in vacuo. The resulting crude product was purified by flash C18 chromatography, eluting with 5-100% MeCN in water, to afford the title compound (60 mg, 67%) as a yellow solid; ¹H NMR (400 MHz, MeOD) 2.00 (1H, dq), 2.26 (1H, ddd), 2.42 (3H, s), 2.57 (3H, s), 2.72 (10H, m), 2.87 (3H, s), 3.06 (7H, m), 3.23 (1H, dd), 3.44 (1H, dt), 3.52-3.70 (4H, m), 7.24-7.32 (2H, m), 7.54 (1H, d), 8.23 (2H, s); m/z MH⁺ 526.

Example 14: 6-(((R)-1-(2-(4-(((3R,5S)-3,5-dimethylpiperazin-1-yl)methyl)phenyl)pyrimidin-5-yl)pyrrolidin-3-yl)methyl)-2,5,7-trimethyl-[1,2,4]triazolo[1,5-a]pyrimidine

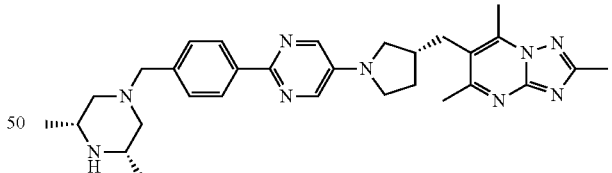

(R)-4-(5-(3-((2,5,7-trimethyl-[1,2,4]triazolo[1,5-a]pyrimidin-6-yl)methyl)pyrrolidin-1-yl)pyrimidin-2-yl)benzaldehyde (Intermediate 19) (120 mg, 0.28 mmol) was added to (2R,6S)-2,6-dimethylpiperazine (sourced commercially) (32 mg, 0.28 mmol) in DCM (3 mL), and the reaction mixture was stirred at rt for 2 h. AcOH (1.607 μl, 0.03 mmol) and sodium triacetoxyborohydride (178 mg, 0.84 mmol) were added and the reaction mixture was stirred for 2 h, then was concentrated in vacuo. The resulting crude product was purified by preparative HPLC to afford the title compound (16 mg, 11%) as a white solid; ¹H NMR (300 MHz, MeOD) 1.18 (6H, s), 1.94 (3H, ddd), 2.21 (1H, m), 2.56 (3H, s), 2.73 (4H, m), 2.84 (3H, s), 3.08 (4H, m), 3.18 (3H, m), 3.58 (2H, m), 3.62 (4H, m), 7.41 (2H, dd), 8.17 (4H, dt); m/z MH⁺ 526.

Example 15: (R)-N,N-dimethyl-2-(4-(4-(5-(3-((2,5,7-trimethyl-[1,2,4]triazolo[1,5-a]pyrimidin-6-yl)methyl)pyrrolidin-1-yl)pyrimidin-2-yl)benzyl)piperazin-1-yl)acetamide

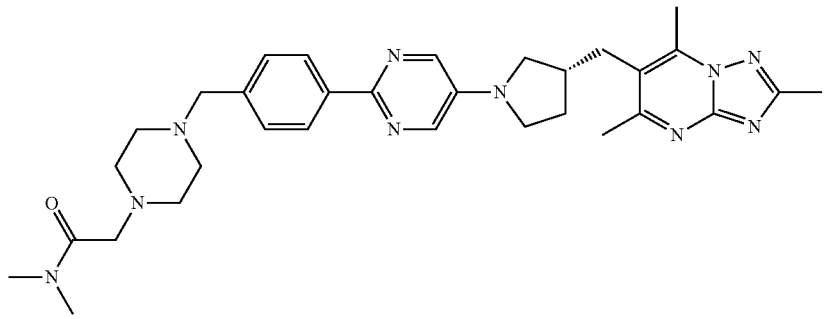

PdCl$_2$(dppf)-CH$_2$Cl$_2$ adduct (168 mg, 0.21 mmol) was added to 2-(4-(4-bromobenzyl)piperazin-1-yl)-N,N-dimethylacetamide (Intermediate 22) (700 mg, 2.06 mmol), 4,4,4',4',5,5,5',5'-octamethyl-2,2'-bi(1,3,2-dioxaborolane) (627 mg, 2.47 mmol) and potassium acetate (404 mg, 4.11 mmol) in 1,4-dioxane (10 mL) at rt. The reaction mixture was stirred at 80° C. for 16 h, then allowed to cool to rt and concentrated in vacuo. The resulting crude product was purified by flash C18 chromatography, eluting with 0-100% MeOH in water, to afford (4-((4-(2-(dimethylamino)-2-oxoethyl)piperazin-1-yl)methyl)phenyl) boronic acid (186 mg, 30%) that was used directly without characterisation. Pd(Ph$_3$P)$_4$ (31.6 mg, 0.03 mmol) was added to (4-((4-(2-(dimethylamino)-2-oxoethyl)piperazin-1-yl)methyl)phenyl) boronic acid (92 mg, 0.30 mmol), (R)-6-((1-(2-bromopyrimidin-5-yl)pyrrolidin-3-yl)methyl)-2,5,7-trimethyl-[1,2,4]triazolo[1,5-a]pyrimidine (Intermediate 16) (110 mg, 0.27 mmol) and Na$_2$CO$_3$ (58.0 mg, 0.55 mmol) in 1,4-dioxane (2 mL) and water (1 mL) at rt. The reaction mixture was stirred at 80° C. for 16 h, then was allowed to cool to rt and concentrated in vacuo. The resulting crude product was purified by flash C18 chromatography, eluting with 0-100% MeCN in water (+0.1% FA), then further purified by preparative HPLC to afford the title compound (50 mg, 31%) as a white solid; $^1$H NMR (300 MHz, MeOD) 1.98 (1H, dt), 2.16-2.34 (1H, m), 2.43-2.64 (10H, m), 2.73 (4H, s), 2.84 (3H, s), 2.93 (3H, s), 2.97-3.15 (5H, m), 3.22 (3H, d), 3.33-3.49 (2H, m), 3.48-3.70 (4H, m), 7.41 (2H, d), 8.11-8.21 (4H, m); m/z MH$^+$ 583.

Example 16: (R)-2-(4-(4-(5-(3-((2,5,7-trimethyl-[1,2,4]triazolo[1,5-a]pyrimidin-6-yl)methyl)pyrrolidin-1-yl)pyrimidin-2-yl)benzyl)piperazin-1-yl)ethanol

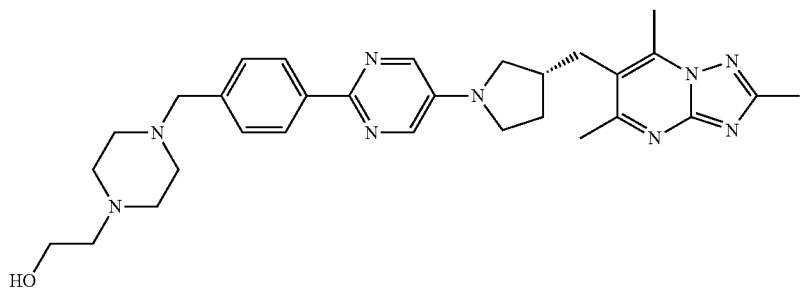 [SMILES: Cc1nc2nc(C)c(C[C@@H]3CCN(c4cnc(-c5ccc(CN6CCN(CCO)CC6)cc5)nc4)C3)c(C)n2n1]

PdCl₂(dppf)-CH₂Cl₂ adduct (164 mg, 0.20 mmol) was added to 2-(4-(4-bromobenzyl)piperazin-1-yl)ethanol (Intermediate 23) (600 mg, 2.01 mmol), 4,4,4',4',5,5,5',5'-octamethyl-2,2'-bi(1,3,2-dioxaborolane) (611 mg, 2.41 mmol) and potassium acetate (394 mg, 4.01 mmol) in 1,4-dioxane (10 mL) at rt. The reaction mixture was stirred at 80° C. for 16 h, then was allowed to cool to rt and concentrated in vacuo. The resulting crude product was purified by flash C18 chromatography, eluting with 0-100% MeOH in water, to afford (4-((4-(2-hydroxyethyl)piperazin-1-yl)methyl)phenyl)boronic acid (143 mg, 27%) as a brown solid that was used directly without characterisation. Pd(Ph₃P)₄ (31.6 mg, 0.03 mmol) was added to (4-((4-(2-hydroxyethyl)piperazin-1-yl)methyl)phenyl)boronic acid (87 mg, 0.33 mmol), (R)-6-((1-(2-bromopyrimidin-5-yl)pyrrolidin-3-yl)methyl)-2,5,7-trimethyl-[1,2,4]triazolo[1,5-a]pyrimidine (Intermediate 16) (110 mg, 0.27 mmol) and Na₂CO₃ (58.0 mg, 0.55 mmol) in 1,4-dioxane (2 mL) and water (1 mL) at rt. The reaction mixture was stirred at 80° C. for 16 h, then was allowed to cool to rt and concentrated in vacuo. The resulting crude product was purified by flash C18 chromatography, eluting with 0-100% MeCN in water (+0.1% FA), then further purified by preparative HPLC to afford the title compound (50 mg, 34%) as a white solid; ¹H NMR (300 MHz, CDCl₃) 1.88-2.02 (1H, m), 2.15-2.26 (1H, m), 2.68 (18H, m), 2.82 (3H, s), 2.87-3.05 (2H, m), 3.18 (1H, dd), 3.36-3.58 (2H, m), 3.58-3.71 (5H, m), 7.41 (2H, d), 8.14 (2H, s), 8.21-8.30 (2H, m); m/z MH⁺ 542.

Example 17: (R)-1-(4-(4-(5-(3-((2,5,7-trimethyl-[1,2,4]triazolo[1,5-a]pyrimidin-6-yl)methyl)pyrrolidin-1-yl)pyrimidin-2-yl)benzyl)piperazin-1-yl)ethanone

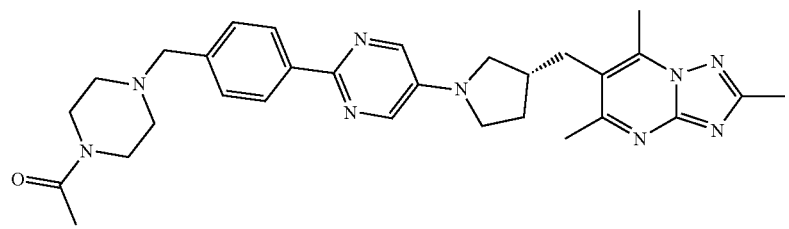 [SMILES: CC(=O)N1CCN(Cc2ccc(-c3ncc(N4CC[C@@H](Cc5c(C)nc6nc(C)nn6c5C)C4)cn3)cc2)CC1]

Pd(Ph₃P)₄ (28.7 mg, 0.02 mmol) was added to 1-(4-(4-(4,4,5,5-tetramethyl-1,3,2-dioxaborolan-2-yl)benzyl)piperazin-1-yl)ethanone (Intermediate 52) (86 mg, 0.25 mmol), (R)-6-((1-(2-bromopyrimidin-5-yl)pyrrolidin-3-yl)methyl)-2,5,7-trimethyl-[1,2,4]triazolo[1,5-a]pyrimidine (Intermediate 16) (100 mg, 0.25 mmol) and Na₂CO₃ (53 mg, 0.50 mmol) in 1,4-dioxane (5 mL) and water (1 mL). The reaction mixture was stirred at 80° C. for 16 h, then allowed to cool to rt and concentrated in vacuo. The resulting crude product was purified by preparative HPLC to afford the title compound (50 mg, 37%) as a yellow solid; ¹H NMR (300 MHz, MeOD) 1.96 (1H, dq), 2.10 (3H, s), 2.22 (1H, m), 2.64 (11H, m), 2.84 (3H, s), 3.03 (2H, dd), 3.20 (1H, dd), 3.60 (9H, m), 7.43 (2H, m), 8.19 (4H, d); m/z MH⁺ 540.

Example 18: (R)-6-((1-(2-(4-((4-(2-methoxyethyl)
piperazin-1-yl)methyl)phenyl)pyrimidin-5-yl)pyrro-
lidin-3-yl)methyl)-2,5,7-trimethyl-[1,2,4]triazolo[1,
5-a]pyrimidine

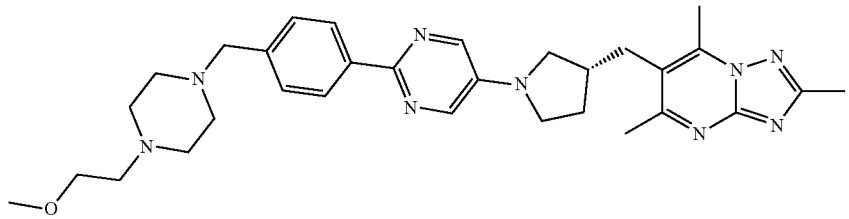

Sodium triacetoxyborohydride (283 mg, 1.33 mmol) was added to (R)-4-(5-(3-((2,5,7-trimethyl-[1,2,4]triazolo[1,5-a]pyrimidin-6-yl)methyl)pyrrolidin-1-yl)pyrimidin-2-yl)benzaldehyde (Intermediate 19) (190 mg, 0.44 mmol) and 1-(2-methoxyethyl)piperazine (77 mg, 0.53 mmol) and AcOH (0.013 mL, 0.22 mmol) in DCM (20 mL) at rt. The reaction mixture was stirred at rt for 4 h, then was concentrated in vacuo, neutralised with 1 M $NH_3$/MeOH and concentrated in vacuo. The resulting residue was taken up in DCM, filtered and purified by fcc, eluting with 0-5% 1 M $NH_3$/MeOH in DCM, to afford the title compound (175 mg, 71%) as a pale yellow solid; $^1$H NMR (500 MHz, $CDCl_3$) 1.86-1.96 (1H, m), 2.14-2.25 (1H, m), 2.39-2.6 (10H, m), 2.62 (3H, s), 2.64-2.69 (1H, m), 2.71 (3H, s), 2.80 (3H, s), 2.87-3.02 (2H, m), 3.17 (1H, dd), 3.34 (3H, s), 3.39-3.46 (1H, m), 3.47-3.53 (3H, m), 3.56 (2H, s), 3.59 (1H, td), 7.39 (2H, d), 8.13 (2H, s), 8.23 (2H, d); m/z $MH^+$ 556.

Example 19: (R)-4-(4-(5-(3-((2,5,7-trimethyl-[1,2,4]
triazolo[1,5-a]pyrimidin-6-yl)methyl)pyrrolidin-1-
yl)pyrimidin-2-yl)benzyl)morpholine

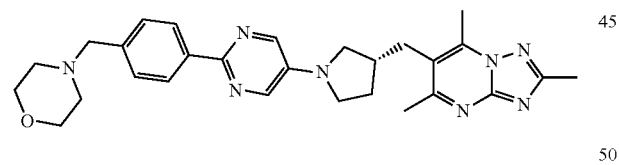

RuPhos 3rd generation precatalyst (50 mg, 0.06 mmol) was added to 4-(4-(5-bromopyrimidin-2-yl)benzyl)morpholine (Intermediate 24) (200 mg, 0.60 mmol), (R)-2,5,7-trimethyl-6-(pyrrolidin-3-ylmethyl)-[1,2,4]triazolo[1,5-a]pyrimidine.2HCl (Intermediate 4) (190 mg, 0.60 mmol), $Cs_2CO_3$ (780 mg, 2.39 mmol) and RuPhos (55.8 mg, 0.12 mmol) in 1,4-dioxane (8 mL) at rt. The reaction mixture was stirred at 90° C. for 6 h, allowed to cool to rt and concentrated in vacuo. The resulting crude product was purified by flash C18 chromatography, eluting with 0-100% MeOH in water (+0.1% FA), to afford the title compound (180 mg, 60%) as a yellow solid; $^1$H NMR (300 MHz, MeOD) 1.87-2.06 (1H, m), 2.16-2.27 (1H, m), 2.53-2.62 (7H, m), 2.73 (4H, s), 2.84 (3H, s), 3.04 (2H, dd), 3.20 (1H, dd), 3.41 (1H, dt), 3.49-3.71 (4H, m), 3.71-3.77 (4H, m), 7.43 (2H, d), 8.13-8.22 (4H, m); m/z $MH^+$ 499.

Example 20: (R)-2,5,7-trimethyl-6-((1-(2-(4-((4-methylpiperazin-1-yl)methyl)phenyl)pyrimidin-5-yl)pyrrolidin-3-yl)methyl)-[1,2,4]triazolo[1,5-a]pyrimidine

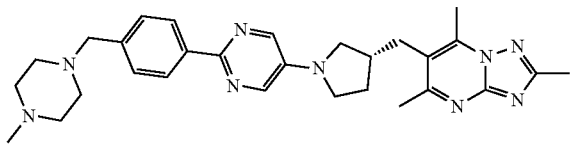

Pd(Ph₃P)₄ (43.1 mg, 0.04 mmol) was added to (R)-6-((1-(2-bromopyrimidin-5-yl)pyrrolidin-3-yl)methyl)-2,5,7-trimethyl-[1,2,4]triazolo[1,5-a]pyrimidine (Intermediate 16) (300 mg, 0.75 mmol), 1-methyl-4-(4-(4,4,5,5-tetramethyl-1,3,2-dioxaborolan-2-yl)benzyl)piperazine (sourced commercially) (236 mg, 0.75 mmol) and Na₂CO₃ (158 mg, 1.49 mmol) in 1,4-dioxane (10 mL) and water (5 mL) at rt. The reaction mixture was stirred at 80° C. for 16 h, allowed to cool to rt and concentrated in vacuo. The crude product was purified by flash C18 chromatography, eluting with 5-100% MeCN in water (+0.1 mmol/L NH₄HCO₃), to afford the title compound (285 mg, 75%) as a white solid; $^1$H NMR (400 MHz, MeOD) 1.94-2.05 (1H, m), 2.31 (4H, s), 2.57 (11H, s), 2.75 (4H, s), 2.86 (3H, s), 3.06 (2H, p), 3.22 (1H, dd), 3.38-3.49 (1H, m), 3.51-3.69 (4H, m), 7.42 (2H, d), 8.14-8.22 (4H, m); m/z MH⁺ 512.

Example 21: (R)-2,5,7-trimethyl-6-((1-(4-(5-((4-methylpiperazin-1-yl)methyl)pyrazin-2-yl)phenyl)pyrrolidin-3-yl)methyl)-[1,2,4]triazolo[1,5-a]pyrimidine

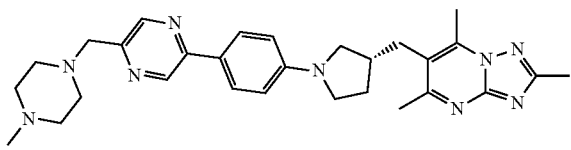

Pd(Ph₃P)₄ (51.7 mg, 0.04 mmol) was added to 2-bromo-5-((4-methylpiperazin-1-yl)methyl)pyrazine (Intermediate 28) (121 mg, 0.45 mmol), (R)-2,5,7-trimethyl-6-((1-(4-(4,4,5,5-tetramethyl-1,3,2-dioxaborolan-2-yl)phenyl)pyrrolidin-3-yl)methyl)-[1,2,4]triazolo[1,5-a]pyrimidine (Intermediate 27) (200 mg, 0.45 mmol) and Na₂CO₃ (95 mg, 0.89 mmol) in toluene (0.2 mL) and water (1 mL). The reaction mixture was stirred at 80° C. for 16 h, allowed to cool to rt and concentrated in vacuo. The resulting crude product was purified by flash C18 chromatography, eluting with 0-100% MeCN in water, to afford the title compound (11 mg, 5%) as a yellow solid; $^1$H NMR (300 MHz, CDCl₃) 1.91 (1H, dq), 2.21 (1H, dq), 2.40 (3H, s), 2.67 (14H, d), 2.80 (3H, s), 2.95 (3H, s), 3.16 (1H, dd), 3.35-3.67 (3H, m), 3.73 (2H, s), 6.59-6.68 (2H, m), 7.87-7.99 (2H, m), 8.56 (1H, d), 8.90 (1H, d); m/z MH⁺ 512.

Example 22: (R)-2,5,7-trimethyl-6-(0-(4-(2-((4-methylpiperazin-1-yl)methyl)pyrimidin-5-yl)phenyl)pyrrolidin-3-yl)methyl)-[1,2,4]triazolo[1,5-a]pyrimidine

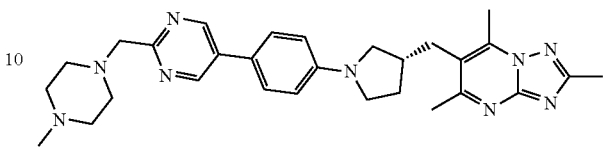

Pd(Ph₃P)₄ (63.9 mg, 0.06 mmol) was added to (R)-2,5,7-trimethyl-6-((1-(4-(4,4,5,5-tetramethyl-1,3,2-dioxaborolan-2-yl)phenyl)pyrrolidin-3-yl)methyl)-[1,2,4]triazolo[1,5-a]pyrimidine (Intermediate 27) (247 mg, 0.55 mmol), 5-bromo-2-((4-methylpiperazin-1-yl)methyl)pyrimidine (Intermediate 29) (150 mg, 0.55 mmol) and Na₂CO₃ (117 mg, 1.11 mmol) in 1,4-dioxane (2 mL) and water (1 mL). The reaction mixture was stirred at 80° C. for 16 h, allowed to cool to rt and concentrated in vacuo. The resulting crude product was purified by preparative HPLC to afford the title compound (40 mg, 14%) as a yellow solid; $^1$H NMR (300 MHz, DMSO) 1.85 (1H, dq), 2.10 (1H, dq), 2.26 (3H, s), 2.49 (4H, m), 2.63 (8H, m), 2.74 (3H, s), 2.92 (2H, d), 3.06 (1H, dd), 3.26 (6H, m), 3.70 (2H, s), 6.64 (2H, d), 7.62 (2H, d), 8.99 (2H, s); m/z MH⁺ 512.

Example 23: (R)-4-((6-(4-(3-((2,5,7-trimethyl-[1,2,4]triazolo[1,5-a]pyrimidin-6-yl)methyl)pyrrolidin-1-yl)phenyl)pyridin-3-yl)methyl)morpholine

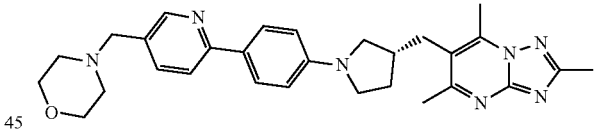

RuPhos 3rd generation precatalyst (39 mg, 0.05 mmol) was added to (R)-2,5,7-trimethyl-6-(pyrrolidin-3-ylmethyl)-[1,2,4]triazolo[1,5-a]pyrimidine dihydrochloride (Intermediate 4) (150 mg, 0.47 mmol), 4-((6-(4-bromophenyl)pyridin-3-yl)methyl)morpholine (Intermediate 31) (157 mg, 0.47 mmol), Cs₂CO₃ (768 mg, 2.36 mmol) and RuPhos (44 mg, 0.09 mmol) in 1,4-dioxane (3 mL) at rt. The reaction mixture was stirred at 90° C. for 16 h, allowed to cool to rt and concentrated in vacuo. The resulting crude product was purified by preparative HPLC to afford the title compound (54 mg, 23%) as a white solid; $^1$H NMR (300 MHz, MeOD) 1.87-2.05 (1H, m), 2.22 (1H, dq), 2.50 (4H, dd), 2.55 (3H, s), 2.71 (4H, s), 2.82 (3H, s), 2.94-3.09 (2H, m), 3.16 (1H, dd), 3.32-3.51 (2H, m), 3.54-3.63 (3H, m), 3.63-3.76 (4H, m), 6.61-6.73 (2H, m), 7.67-7.87 (4H, m), 8.44 (1H, d); m/z MH⁺ 498.

Example 24: (R)-2,5,7-trimethyl-6-(0-(4-(6-((4-methylpiperazin-1-yl)methyl)pyridazin-3-yl)phenyl)pyrrolidin-3-yl)methyl)-[1,2,4]triazolo[1,5-a]pyrimidine

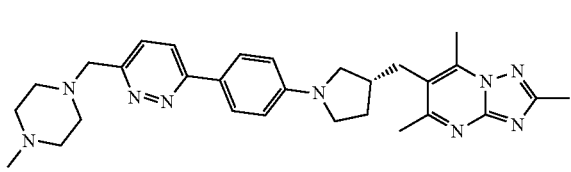

Pd(Ph₃P)₄ (26 mg, 0.02 mmol) was added to (R)-2,5,7-trimethyl-6-((1-(4-(4,4,5,5-tetramethyl-1,3,2-dioxaborolan-2-yl)phenyl)pyrrolidin-3-yl)methyl)-[1,2,4]triazolo[1,5-a]pyrimidine (Intermediate 27) (100 mg, 0.22 mmol), 3-chloro-6-((4-methylpiperazin-1-yl)methyl)pyridazine (Intermediate 32) (51 mg, 0.22 mmol) and Na₂CO₃ (47 mg, 0.45 mmol) in 1,4-dioxane (5 mL) and water (1 mL). The reaction mixture was stirred at 80° C. for 16 h, allowed to cool to rt and concentrated in vacuo. The resulting crude product was purified by preparative HPLC to afford the title compound (35 mg, 31%) as a white solid; ¹H NMR (300 MHz, DMSO) 1.87 (1H, m), 2.15 (4H, m), 2.20-2.50 (11H, m), 2.64 (4H, m), 2.75 (3H, s), 2.93 (2H, d), 3.09 (1H, dd), 3.30-3.60 (3H, m), 3.74 (2H, s), 6.65 (2H, m), 7.59 (1H, d), 8.00 (3H, m); m/z MH⁺ 512.

Example 25: (R)-2,5,7-trimethyl-6-(0-(4-(5-((4-methylpiperazin-1-yl)methyl)pyrimidin-2-yl)phenyl)pyrrolidin-3-yl)methyl)-[1,2,4]triazolo[1,5-a]pyrimidine

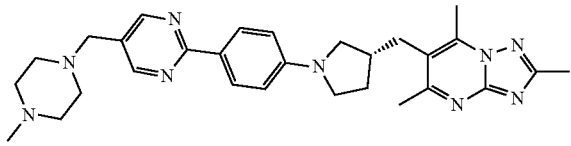

RuPhos 3rd generation precatalyst (36 mg, 0.04 mmol) and RuPhos (20 mg, 0.04 mmol) was added to 2-(4-bromophenyl)-5-((4-methylpiperazin-1-yl)methyl)pyrimidine (Intermediate 35) (150 mg, 0.43 mmol), (R)-2,5,7-trimethyl-6-(pyrrolidin-3-ylmethyl)-[1,2,4]triazolo[1,5-a]pyrimidine dihydrochloride (Intermediate 4) (137 mg, 0.43 mmol) and Cs₂CO₃ (563 mg, 1.73 mmol) in 1,4-dioxane (5 mL). The reaction mixture was stirred at 80° C. for 16 h, allowed to cool to rt and concentrated in vacuo. The resulting crude product was purified by flash C18 chromatography, eluting with 0-100% MeCN in water, to afford the title compound (58 mg, 26%) as a white solid; ¹H NMR (300 MHz, CDCl₃) 1.81-1.99 (2H, m), 2.19 (1H, dt), 2.35 (3H, s), 2.67 (14H, m), 2.76-3.04 (5H, m), 3.18 (1H, dd), 3.36-3.68 (5H, m), 6.55-6.66 (2H, m), 8.26-8.38 (2H, m), 8.64 (2H, s); m/z MH⁺512.

Example 26: (R)-4-((5-(4-(3-((2,5,7-trimethyl-[1,2,4]triazolo[1,5-a]pyrimidin-6-yl)methyl)pyrrolidin-1-yl)phenyl)pyrazin-2-yl)methyl)morpholine

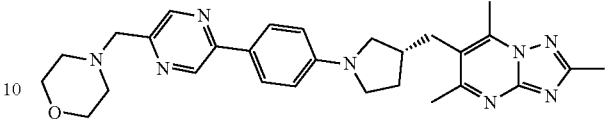

Pd(Ph₃P)₄ (34 mg, 0.03 mmol) was added to (R)-2,5,7-trimethyl-6-((1-(4-(4,4,5,5-tetramethyl-1,3,2-dioxaborolan-2-yl)phenyl)pyrrolidin-3-yl)methyl)-[1,2,4]triazolo[1,5-a]pyrimidine (Intermediate 27) (130 mg, 0.29 mmol), 4-((5-chloropyrazin-2-yl)methyl)morpholine (Intermediate 76) (62 mg, 0.29 mmol) and Na₂CO₃ (62 mg, 0.58 mmol) in 1,4-dioxane (3 mL) and water (1.5 mL). The reaction mixture was stirred at 90° C. for 16 h, allowed to cool to rt and concentrated in vacuo. The resulting crude product was purified by flash C18 chromatography, eluting with 0-100% MeCN in water (+0.1% FA), to afford the title compound (70 mg, 48%) as a pale yellow solid; ¹H NMR (300 MHz, CDCl₃) 1.91 (1H, dq), 2.21 (1H, dq), 2.67 (11H, m), 2.80 (3H, s), 2.95 (2H, m), 3.16 (1H, dd), 3.35-3.54 (2H, m), 3.60 (1H, td), 3.71 (2H, s), 3.77 (4H, t), 6.58-6.69 (2H, m), 7.88-8.00 (2H, m), 8.60 (1H, s), 8.91 (1H, d); m/z MH⁺ 499.

Example 27: (R)-2,5,7-trimethyl-6-(0-(4-(5-((4-methylpiperazin-1-yl)methyl)pyridin-2-yl)phenyl)pyrrolidin-3-yl)methyl)-[1,2,4]triazolo[1,5-a]pyrimidine

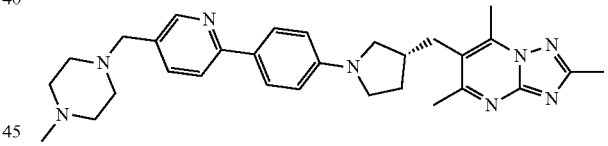

Formaldehyde (37% in water) (5 mL, 67.2 mmol) was added in one portion to (R)-tert-butyl 4-((6-(4-(3-((2,5,7-trimethyl-[1,2,4]triazolo[1,5-a]pyrimidin-6-yl)methyl)pyrrolidin-1-yl)phenyl)pyridin-3-yl)methyl)piperazine-1-carboxylate (Intermediate 82) (290 mg, 0.49 mmol) in formic acid (10 mL) at rt. The reaction mixture was stirred at 55° C. for 4 h, allowed to cool to rt and concentrated in vacuo. The residue was redissolved in 2 M NH₃/MeOH and was purified by preparative HPLC to afford the title compound (58 mg, 26%) as a white solid; ¹H NMR (500 MHz, CDCl₃) 1.83-1.93 (1H, m), 2.12-2.22 (1H, m), 2.29 (3H, s), 2.53 (8H, d), 2.62 (4H, s), 2.70 (3H, s), 2.79 (3H, s), 2.85-2.99 (2H, m), 3.14 (1H, dd), 3.37-3.47 (2H, m), 3.52 (2H, s), 3.57 (1H, td), 6.55-6.65 (2H, m), 7.59 (1H, dd), 7.65 (1H, dd), 7.87-7.95 (2H, m), 8.51 (1H, d); m/z MH⁺ 511.

Example 28: (R)-4-((5-(4-(3-((2,5,7-trimethyl-[1,2,4]triazolo[1,5-a]pyrimidin-6-yl)methyl)pyrrolidin-1-yl)phenyl)pyrimidin-2-yl)methyl)morpholine

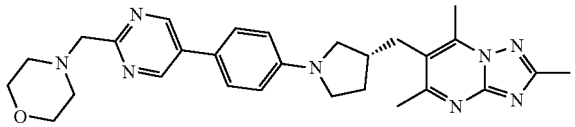

RuPhos 3rd generation precatalyst (53 mg, 0.06 mmol) was added to (R)-2,5,7-trimethyl-6-(pyrrolidin-3-ylmethyl)-[1,2,4]triazolo[1,5-a]pyrimidine dihydrochloride (Intermediate 4) (200 mg, 0.63 mmol), 4-((5-(4-bromophenyl)pyrimidin-2-yl)methyl)morpholine (Intermediate 39) (231 mg, 0.69 mmol), Cs$_2$CO$_3$ (819 mg, 2.51 mmol) and Ruphos (59 mg, 0.13 mmol) in 1,4-dioxane (8 mL). The reaction mixture was stirred at 90° C. for 16 h, allowed to cool to rt and concentrated in vacuo. The resulting crude product was purified by flash C18 chromatography, eluting with 0-100% MeCN in water (+0.1% FA), to afford the title compound (180 mg, 57%) as a white solid; $^1$H NMR (300 MHz, MeOD) 1.88-2.06 (1H, m), 2.22 (1H, dq), 2.55 (3H, s), 2.60-2.69 (4H, m), 2.71 (4H, m), 2.82 (3H, s), 3.02 (2H, dd), 3.15 (1H, dd), 3.31-3.50 (2H, m), 3.52-3.66 (1H, m), 3.69-3.79 (4H, m), 3.83 (2H, s), 6.67-6.77 (2H, m), 7.52-7.63 (2H, m), 8.97 (2H, s); m/z MH$^+$ 499.

Example 29: (R)-4-((6-(4-(3-((2,5,7-trimethyl-[1,2,4]triazolo[1,5-a]pyrimidin-6-yl)methyl)pyrrolidin-1-yl)phenyl)pyridazin-3-yl)methyl)morpholine

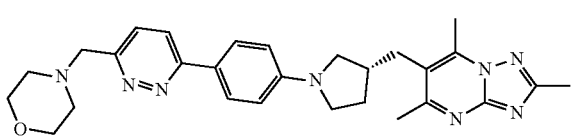 [SMILES: Cc1nc2nc(C)c(C[C@@H]3CCN(c4ccc(-c5cnc(CN6CCOCC6)cn5)cc4)C3)c(C)n2n1]

Degassed 1,4-dioxane (10 mL) was added to (R)-2,5,7-trimethyl-6-(pyrrolidin-3-ylmethyl)-[1,2,4]triazolo[1,5-a]pyrimidine (Intermediate 4) (257 mg, 1.05 mmol) and 4-((6-(4-bromophenyl)pyridazin-3-yl)methyl)morpholine (Intermediate 65) (350 mg, 1.05 mmol). Cs$_2$CO$_3$ (1.02 g, 3.14 mmol) was then added followed by RuPhos (24 mg, 0.05 mmol) and RuPhos 3rd generation precatalyst (44 mg, 0.05 mmol). The reaction mixture was heated at 90° C. for 6 h, allowed to cool to rt, diluted with DCM (50 mL) and filtered. The filtrate was concentrated in vacuo. The resulting crude product was purified by fcc, eluting with 0-5% 1 M NH$_3$/MeOH in DCM. The resulting oil was triturated with EtOAc:heptane (4:1, 10 mL) and the precipitate was isolated by filtration and dried in vacuo to afford the title compound (270 mg, 52%) as a yellow solid; $^1$H NMR (500 MHz, CDCl$_3$) 1.90 (1H, dq), 2.20 (1H, td), 2.56 (4H, q), 2.62 (4H, s), 2.70 (3H, s), 2.79 (3H, s), 2.93 (2H, qd), 3.15 (1H, dd), 3.37-3.49 (2H, m), 3.55-3.63 (1H, m), 3.69-3.77 (4H, m), 3.87 (2H, s), 6.59-6.68 (2H, m), 7.59 (1H, d), 7.75 (1H, d), 7.98-8.06 (2H, m); m/z MH$^+$ 499.

Example 30: (S)-4-((6-(4-(3-((2,5,7-trimethyl-[1,2,4]triazolo[1,5-a]pyrimidin-6-yl)methyl)pyrrolidin-1-yl)phenyl)pyridazin-3-yl)methyl)morpholine

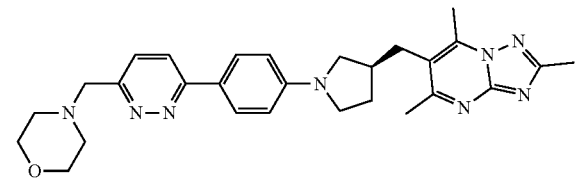 [SMILES: Cc1nc2nc(C)c(C[C@H]3CCN(c4ccc(-c5ccc(CN6CCOCC6)nn5)cc4)C3)c(C)n2n1]

Example 30 was prepared in a similar way to Example 29 in 5 steps from commercially available (S)-tert-butyl 3-(hydroxymethyl)pyrrolidine-1-carboxylate to afford the title compound (122 mg, 30% final step) as a white solid; $^1$H NMR (500 MHz, DMSO) 1.86 (1H, dq), 2.07-2.16 (1H, m), 2.38-2.45 (4H, m), 2.47 (3H, s), 2.59 (1H, d), 2.64 (3H, s), 2.74 (3H, s), 2.93 (2H, d), 3.09 (1H, dd), 3.32 (1H, d), 3.43 (1H, dd), 3.46-3.53 (1H, m), 3.54-3.63 (4H, m), 3.75 (2H, s), 6.65 (2H, d), 7.62 (1H, d), 7.98 (2H, d), 8.02 (1H, d); m/z MH$^+$ 499.

Example 31: (R)-6-((1-(5-(2-methoxy-4-((4-methylpiperazin-1-yl)methyl)phenyl)-6-methylpyrazin-2-yl)pyrrolidin-3-yl)methyl)-2,5,7-trimethyl-[1,2,4]triazolo[1,5-a]pyrimidine

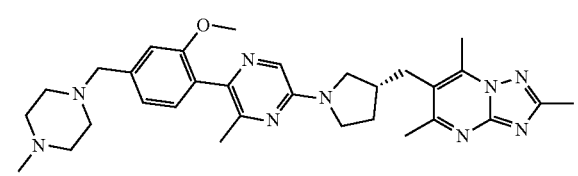

XPhos 2$^{nd}$ generation precatalyst (30 mg, 0.04 mmol) was added to (2-methoxy-4-((4-methylpiperazin-1-yl)methyl)phenyl)boronic acid (Intermediate 42) (112 mg, 0.42 mmol), (R)-6-((1-(5-bromo-6-methylpyrazin-2-yl)pyrrolidin-3-yl)methyl)-2,5,7-trimethyl-[1,2,4]triazolo[1,5-a]pyrimidine (Intermediate 45) (160 mg, 0.38 mmol) and Cs$_2$CO$_3$ (250 mg, 0.77 mmol) in 1,4-dioxane (2 mL) and water (1 mL) at rt. The reaction mixture was stirred at 80° C. for 16 h, allowed to cool to rt and concentrated in vacuo. The resulting crude product was purified by preparative HPLC to afford the title compound (90 mg, 42%) as a white solid; $^1$H NMR (300 MHz, CDCl$_3$) 1.78-2.24 (3H, m), 2.27 (3H, s), 2.31-2.77 (17H, m), 2.82 (3H, s), 2.87-3.06 (2H, m), 3.34 (1H, dd), 3.45-3.61 (3H, m), 3.66-3.83 (5H, m), 6.93-7.04 (2H, m), 7.22 (1H, d), 7.77 (1H, s); m/z MH$^+$ 556.

Example 32: 2,5,7-trimethyl-6-(((R)-1-(5-(4-(((3R,5S)-3,4,5-trimethylpiperazin-1-yl)methyl)phenyl)pyrazin-2-yl)pyrrolidin-3-yl)methyl)-[1,2,4]triazolo[1,5-a]pyrimidine

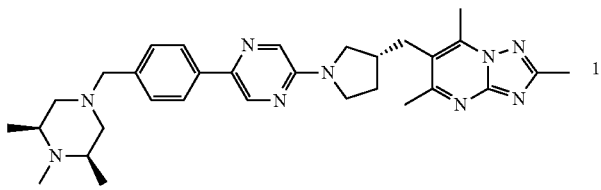

(2S,6R)-1,2,6-trimethylpiperazine (sourced commercially) (104 mg, 0.81 mmol) was added in one portion to (R)-6-((1-(5-(4-(chloromethyl)phenyl)pyrazin-2-yl)pyrrolidin-3-yl)methyl)-2,5,7-trimethyl-[1,2,4]triazolo[1,5-a]pyrimidine (Intermediate 48) (181 mg, 0.40 mmol) and triethylamine (0.28 mL, 2.02 mmol) in THF (5 mL) at rt under air. The reaction mixture was stirred at 60° C. for 24 h, allowed to cool to rt, and diluted with EtOAc (50 mL) and water (15 mL). The organic layer was isolated and washed with sat. brine (15 mL), dried over MgSO$_4$, filtered and concentrated in vacuo. The resulting crude product was purified by fcc, eluting with 0-4% 1 M NH$_3$/MeOH in DCM, to afford the title compound (115 mg, 53%) as a pale yellow solid; $^1$H NMR (500 MHz, DMSO) 0.92 (6H, d), 1.75 (2H, t), 1.8-1.91 (1H, m), 2.06-2.16 (5H, m), 2.46 (3H, s), 2.5-2.52 (1H, m), 2.63 (6H, d), 2.74 (3H, s), 2.93 (2H, d), 3.2-3.26 (1H, m), 3.37-3.47 (3H, m), 3.63 (1H, dd), 3.66-3.73 (1H, m), 7.32 (2H, d), 7.87 (2H, d), 8.02 (1H, d), 8.61 (1H, d); m/z MH$^+$ 540.

Example 33: 6-(((R)-1-(5-(4-(((R)-3,4-dimethylpiperazin-1-yl)methyl)phenyl)pyrazin-2-yl)pyrrolidin-3-yl)methyl)-2,5,7-trimethyl-[1,2,4]triazolo[1,5-a]pyrimidine

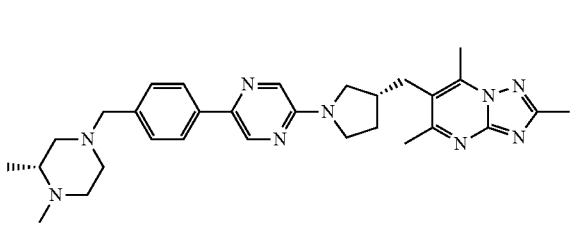

(R)-4-(5-(3-((2,5,7-trimethyl-[1,2,4]triazolo[1,5-a]pyrimidin-6-yl)methyl)pyrrolidin-1-yl)pyrazin-2-yl)benzaldehyde (Intermediate 49) (200 mg, 0.47 mmol) and (R)-1,2-dimethylpiperazine (sourced commercially) (267 mg, 2.34 mmol) in MeOH (10 mL) was stirred at rt for 1 h, then sodium triacetoxyborohydride (397 mg, 1.87 mmol) and AcOH (2.81 mg, 0.05 mmol) were added and the reaction mixture was stirred at rt for 16 h, then concentrated in vacuo. The resulting crude product was purified by preparative HPLC to afford the title compound (126 mg, 51%) as a white solid; $^1$H NMR (300 MHz, CDCl$_3$) 1.06 (3H, d), 1.93 (2H, dq), 2.22 (3H, dt), 2.33 (4H, s), 2.56-3.06 (15H, m), 3.34 (1H, dd), 3.56 (3H, d), 3.67-3.84 (2H, m), 7.40 (2H, d), 7.78-7.88 (2H, m), 7.95 (1H, d), 8.51 (1H, d); m/z MH$^+$ 526.

Example 34: 6-(((R)-1-(5-(4-(((R)-2,4-dimethylpiperazin-1-yl)methyl)phenyl)pyrazin-2-yl)pyrrolidin-3-yl)methyl)-2,5,7-trimethyl-[1,2,4]triazolo[1,5-a]pyrimidine

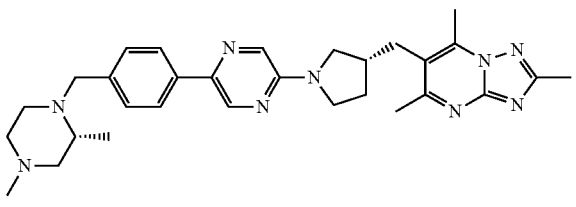 [SMILES: Cc1nc2nc(C)c(C[C@@H]3CCN(c4cnc(-c5ccc(CN6CCN(C)C[C@H]6C)cc5)cn4)C3)c(C)n2n1]

(R)-1,3-dimethylpiperazine dihydrochloride (sourced commercially) (167 mg, 0.89 mmol) was added in one portion to (R)-6-((1-(5-(4-(chloromethyl)phenyl)pyrazin-2-yl)pyrrolidin-3-yl)methyl)-2,5,7-trimethyl-[1,2,4]triazolo[1,5-a]pyrimidine (Intermediate 48) (200 mg, 0.45 mmol) and triethylamine (0.31 mL, 2.23 mmol) in 1,4-dioxane (5 mL) at rt under air. The reaction mixture was stirred at 80° C. for 24 h, allowed to cool to rt and diluted with EtOAc (50 mL) and water (15 mL). The organic layer was isolated and washed with sat. brine (15 mL), dried over MgSO$_4$, filtered and concentrated in vacuo. The resulting crude product was purified by fcc, eluting with 0-4% 1 M NH$_3$/MeOH in DCM, then further purified by preparative HPLC to afford the title compound (32 mg, 14%) as a yellow foam; $^1$H NMR (500 MHz, DMSO) 1.06 (3H, d), 1.79-1.91 (2H, m), 1.99 (1H, s), 2.10 (5H, s), 2.41 (1H, s), 2.46 (4H, s), 2.52-2.62 (3H, m), 2.63 (3H, s), 2.74 (3H, s), 2.93 (2H, d), 3.12 (1H, d), 3.23 (1H, dd), 3.4-3.49 (1H, m), 3.63 (1H, dd), 3.65-3.74 (1H, m), 3.95 (1H, d), 7.32 (2H, d), 7.82-7.90 (2H, m), 8.02 (1H, d), 8.60 (1H, d); m/z MH$^+$ 526.

Example 35: 2,5,7-trimethyl-6-(((R)-1-(5-(4-(((2R,5R)-2,4,5-trimethylpiperazin-1-yl)methyl)phenyl)pyrazin-2-yl)pyrrolidin-3-yl)methyl)-[1,2,4]triazolo[1,5-a]pyrimidine

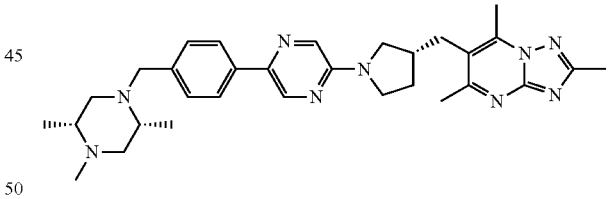

(2R,5R)-1,2,5-trimethylpiperazine hydrochloride (sourced commercially) (147 mg, 0.89 mmol) was added in one portion to (R)-6-((1-(5-(4-(chloromethyl)phenyl)pyrazin-2-yl)pyrrolidin-3-yl)methyl)-2,5,7-trimethyl-[1,2,4]triazolo[1,5-a]pyrimidine (Intermediate 48) (200 mg, 0.45 mmol) and triethylamine (0.31 mL, 2.23 mmol) in 1,4-dioxane (5 mL) at rt under air. The reaction mixture was stirred at 80° C. for 24 h, allowed to cool to rt and diluted with EtOAc (50 mL) and water (15 mL). The organic layer was isolated and washed with sat. brine solution (15 ml), dried over MgSO$_4$, filtered and dried in vacuo. The resulting crude product was purified by fcc, eluting with 0-4% 1 M NH$_3$/MeOH in DCM, then further purified by trituration with MeOH to afford the title compound (78 mg, 32%) as a pale yellow solid; $^1$H NMR (500 MHz, DMSO) 0.90 (3H, d), 1.03 (3H, d), 1.8-1.91 (1H, m), 2.10 (5H, s), 2.22-2.32 (3H, m), 2.46 (4H, s), 2.57-2.61 (1H, m), 2.63 (3H, s), 2.74 (4H, s), 2.93 (2H, d), 3.23 (1H, dd), 3.41-3.48 (2H, m), 3.55-3.66 (2H, m), 3.66-3.73 (1H, m), 7.35 (2H, d), 7.86 (2H, d), 8.02 (1H, d), 8.60 (1H, d); m/z MH+ 540.

Example 36: 2,5,7-trimethyl-6-(((R)-1-(5-(4-(((2S, 5R)-2,4,5-trimethylpiperazin-1-yl)methyl)phenyl) pyrazin-2-yl)pyrrolidin-3-yl)methyl)-[1,2,4]triazolo [1,5-a]pyrimidine

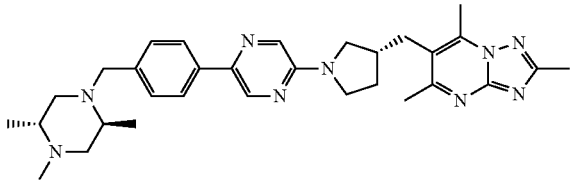

(2R,5S)-1,2,5-trimethylpiperazine dihydrochloride (sourced commercially) (180 mg, 0.89 mmol) was added in one portion to (R)-6-((1-(5-(4-(chloromethyl)phenyl) pyrazin-2-yl)pyrrolidin-3-yl)methyl)-2,5,7-trimethyl-[1,2,4] triazolo[1,5-a]pyrimidine (Intermediate 48) (200 mg, 0.45 mmol) and triethylamine (0.31 mL, 2.23 mmol) in 1,4-dioxane (5 mL) at rt under air. The reaction mixture was stirred at 80° C. for 24 h, allowed to cool to rt and diluted with EtOAc (50 mL) and water (15 mL). The organic layer was isolate and washed with sat. brine solution (15 mL), dried over MgSO4, filtered and concentrated in vacuo. The resulting crude product was purified by fcc, eluting with 0-4% 1 M NH3/MeOH in DCM, then further purified by preparative HPLC to afford the title compound (81 mg, 34%) as a pale yellow solid; ¹H NMR (500 MHz, DMSO) 0.83 (3H, d), 1.07 (3H, d), 1.73 (1H, t), 1.80-1.93 (3H, m), 2.09 (4H, s), 2.35 (1H, s), 2.46 (3H, s), 2.63 (5H, s), 2.74 (3H, s), 2.93 (2H, d), 3.01 (1H, d), 3.20-3.26 (1H, m), 3.43 (1H, d), 3.59-3.74 (2H, m), 4.02 (1H, d), 7.32 (2H, d), 7.86 (2H, d), 8.02 (1H, s), 8.61 (1H, s), 1H missing assumed to be under DMSO peak; m/z MH+ 540.

Example 37: 2,5,7-trimethyl-6-[[(3R)-1-[5-[4-(1-piperidylmethyl)phenyl]pyrazin-2-yl]pyrrolidin-3-yl] methyl]-[1,2,4]triazolo[1,5-a]pyrimidine

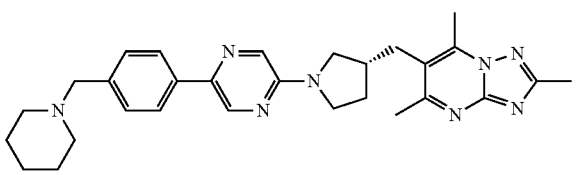 [SMILES: Cc1nc2nc(C)c(C[C@@H]3CCN(c4cnc(-c5ccc(CN6CCCCC6)cc5)cn4)C3)c(C)n2n1]

(R)-4-(5-(3-((2,5,7-trimethyl-[1,2,4]triazolo[1,5-a]py-rimidin-6-yl)methyl)pyrrolidin-1-yl)pyrazin-2-yl)benzaldehyde (Intermediate 49) (30 mg, 0.07 mmol), piperidine (12 mg, 0.14 mmol), DCM (2 mL) and AcOH (2 drop) were combined and the reaction mixture was stirred at rt for 5 h. Sodium triacetoxyborohydride (45 mg, 0.21 mmol) was added and the reaction mixture was stirred at rt for 16 h. The resulting crude product was purified by preparative HPLC to afford the title compound (15 mg, 44%); 1H NMR (400 MHz, DMSO) 1.47 (6H, d), 1.82-1.92 (1H, m), 2.12 (1H, dd), 2.36 (4H, s), 2.48 (3H, s), 2.65 (4H, s), 2.76 (3H, s), 2.95 (2H, d), 3.25 (2H, dd), 3.41-3.51 (2H, m), 3.62-3.75 (2H, m), 7.37 (2H, s), 7.90 (2H, s), 8.04 (1H, d), 8.64 (1H, s); m/z MH+ 497.

Example 38: (R)-6-(0-(5-(4-((4-ethylpiperazin-1-yl) methyl)phenyl)pyrazin-2-yl)pyrrolidin-3-yl)methyl)-2,5,7-trimethyl-[1,2,4]triazolo[1,5-a]pyrimidine

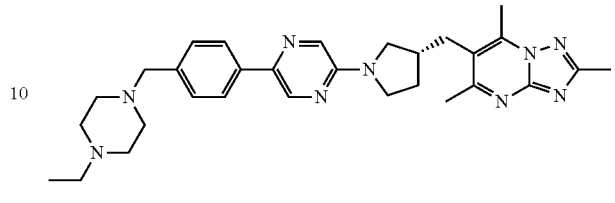

1-Ethylpiperazine (136 mg, 1.19 mmol) was added to (R)-4-(5-(3-((2,5,7-trimethyl-[1,2,4]triazolo[1,5-a]pyrimi-din-6-yl)methyl)pyrrolidin-1-yl)pyrazin-2-yl)benzaldehyde (Intermediate 49) (170 mg, 0.40 mmol) in MeOH (5 mL) at rt, and the reaction mixture was stirred for 1 h. Sodium triacetoxyborohydride (421 mg, 1.99 mmol) was added. The reaction mixture was stirred at rt for 60 h, then was concentrated in vacuo. The resulting crude product was purified by flash C18 chromatography, eluting with 5-100% MeCN in water (+0.1% FA), to afford the formic acid salt of the title compound (114 mg, 51%) as a pale yellow solid; ¹H NMR (300 MHz, CDCl₃) 1.25 (3H, t), 1.93 (1H, dq), 2.15-2.32 (1H, m), 2.56-3.06 (22H, m), 3.34 (1H, dd), 3.48-3.65 (3H, m), 3.76 (2H, ddt), 7.34-7.44 (2H, m), 7.78-7.89 (2H, m), 7.95 (1H, d), 8.47-8.55 (2H, m); m/z MH+ 526.

Example 39: (R)-2,5,7-trimethyl-6-((1-(5-(5-((4-methylpiperazin-1-yl)methyl)pyridin-2-yl)pyrazin-2-yl)pyrrolidin-3-yl)methyl)-[1,2,4]triazolo[1,5-a]py-rimidine

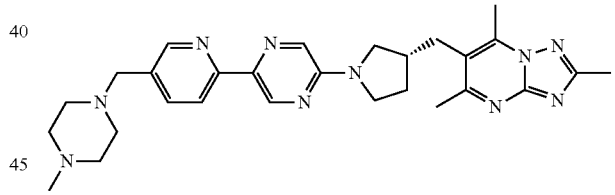

Bis(triphenylphosphoranyl)palladium(IV) chloride (35 mg, 0.05 mmol) was added to 1-((6-bromopyridin-3-yl) methyl)-4-methylpiperazine (Intermediate 7) (135 mg, 0.50 mmol), 1,1,1,2,2,2-hexamethyldistannane (180 mg, 0.55 mmol) in THF (3 mL) at rt. The reaction mixture was stirred at 85° C. for 16 h. (R)-6-((1-(5-bromopyrazin-2-yl)pyrroli-din-3-yl)methyl)-2,5,7-trimethyl-[1,2,4]triazolo[1,5-a]py-rimidine (Intermediate 46) (200 mg, 0.50 mmol) and Pd(Ph₃P)₄ (57.4 mg, 0.05 mmol) and THF (5 mL) were added. The reaction mixture was transferred to a microwave vial and was heated at 100° C. for 10 h in a microwave reactor and then allowed to cool to rt and concentrated in vacuo. The resulting crude product was purified by flash C18 chromatography, eluting with 5-100% MeCN in water (+0.1% FA), to afford the title compound (59 mg, 23%) as a yellow solid; ¹H NMR (400 MHz, CDCl₃) 1.95 (1H, dq), 2.25 (1H, tt), 2.47 (3H, s), 2.60-2.75 (15H, m), 2.82 (3H, s), 2.97 (2H, qd), 3.38 (1H, dd), 3.54-3.65 (3H, m), 3.80 (2H, td), 7.73 (1H, dd), 7.92 (1H, d), 8.11 (1H, d), 8.53-8.59 (1H, m), 9.09 (1H, d); m/z MH+ 513.

Example 40: 6-(((R)-1-(5-(4-(((3R,5S)-3,5-dimethylpiperazin-1-yl)methyl)phenyl)pyrazin-2-yl)pyrrolidin-3-yl)methyl)-2,5,7-trimethyl-[1,2,4]triazolo[1,5-a]pyrimidine

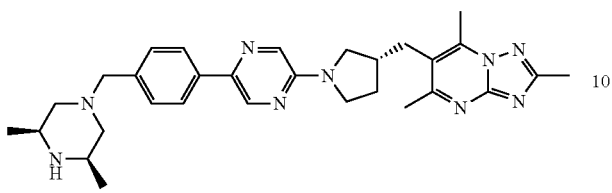

(R)-4-(5-(3-((2,5,7-trimethyl-[1,2,4]triazolo[1,5-a]pyrimidin-6-yl)methyl)pyrrolidin-1-yl)pyrazin-2-yl)benzaldehyde (Intermediate 49) (200 mg, 0.47 mmol) was added to (2R,6S)-1,2,6-trimethylpiperazine (sourced commercially) (120 mg, 0.94 mmol) in DCM (10 mL). The reaction mixture was stirred at rt for 2 h. AcOH (2.7 μl, 0.05 mmol) and sodium cyanoborohydride (118 mg, 1.87 mmol) were added and the reaction mixture was stirred for 16 h, then was concentrated in vacuo. The resulting crude product was purified by preparative HPLC to afford the title compound (75 mg, 31%) as a white solid; $^1$H NMR (300 MHz, CDCl$_3$) 1.06 (6H, d), 1.73 (2H, t), 1.93 (1H, dq), 2.23 (1H, dq), 2.82 (17H, m), 3.34 (1H, dd), 3.55 (3H, d), 3.75 (2H, m), 7.40 (2H, m), 7.83 (2H, m), 7.95 (1H, d), 8.51 (1H, d); m/z MH$^+$ 526.

Example 41: 2-{4-[4-(5-{(3R)-3-[(2,5,7-trimethyl[1,2,4]triazolo[1,5-a]pyrimidin-6-yl)methyl]pyrrolidin-1-yl}pyrazin-2-yl)benzyl]piperazin-1-yl}ethanol

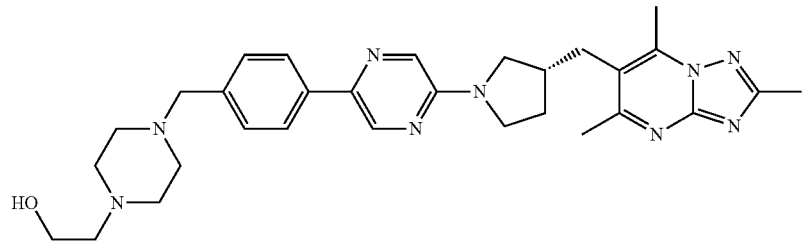 [SMILES: Cc1nc2nc(C)c(C[C@@H]3CCN(c4cnc(-c5ccc(CN6CCN(CCO)CC6)cc5)cn4)C3)c(C)n2n1]

(R)-4-(5-(3-((2,5,7-trimethyl-[1,2,4]triazolo[1,5-a]pyrimidin-6-yl)methyl)pyrrolidin-1-yl)pyrazin-2-yl)benzaldehyde (Intermediate 49) (30 mg, 0.07 mmol), 2-piperazin-1-ylethanol (18.23 mg, 0.14 mmol), DCM (2 mL) and AcOH (2 drop) were combined and the reaction mixture was stirred at rt for 5 h. Sodium triacetoxyborohydride (45 mg, 0.21 mmol) was then added and the reaction mixture was stirred at rt for 16 h. The resulting crude product was purified by preparative HPLC to afford the title compound (8 mg, 20%); $^1$H NMR (400 MHz, DMSO) 1.81-1.93 (1H, m), 2.12 (1H, d), 2.31-2.44 (10H, m), 2.48 (3H, s), 2.65 (4H, s), 2.76 (3H, s), 2.95 (2H, d), 3.22-3.27 (2H, m), 3.47 (4H, s), 3.62-3.76 (2H, m), 4.32 (1H, s), 7.34 (2H, d), 7.88 (2H, d), 8.04 (1H, d), 8.62 (1H, d); m/z MH$^+$ 542.

Example 42: (R)-6-((1-(5-(4-((4-(2-methoxyethyl)piperazin-1-yl)methyl)phenyl)pyrazin-2-yl)pyrrolidin-3-yl)methyl)-2,5,7-trimethyl-[1,2,4]triazolo[1,5-a]pyrimidine

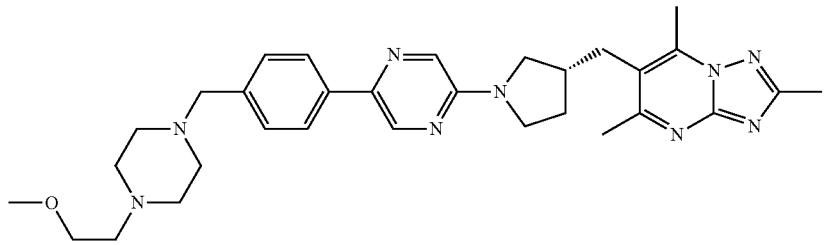

1-(2-Methoxyethyl)piperazine (202 mg, 1.40 mmol) was added to (R)-4-(5-(3-((2,5,7-trimethyl-[1,2,4]triazolo[1,5-a]pyrimidin-6-yl)methyl)pyrrolidin-1-yl)pyrazin-2-yl)benzaldehyde (Intermediate 49) (200 mg, 0.47 mmol) in DCM (5 mL) at rt under air and the reaction mixture was stirred for 1 h. Sodium triacetoxyborohydride (496 mg, 2.34 mmol) was added and the reaction mixture was stirred at rt for 16 h, then concentrated in vacuo. The resulting crude product was purified by flash C18 chromatography, eluting with 5-100% MeCN in water (+0.1% FA), to afford the formic acid salt of the title compound (194 mg, 70%) as a yellow solid; $^1$H NMR (400 MHz, CDCl$_3$) 1.89-2.01 (1H, m), 2.18-2.31 (1H, m), 2.59-3.05 (22H, m), 3.35 (4H, s), 3.52-3.67 (3H, m), 3.67-3.83 (4H, m), 7.38-7.46 (2H, m), 7.82-7.90 (2H, m), 7.97 (1H, s), 8.45 (1H, s), 8.54 (1H, d); m/z MH$^+$ 556.

Example 43: (R)-6-(0-(5-(2-methoxy-4-((4-methylpiperazin-1-yl)methyl)phenyl)pyrazin-2-yl)pyrrolidin-3-yl)methyl)-2,5,7-trimethyl-[1,2,4]triazolo[1,5-a]pyrimidine

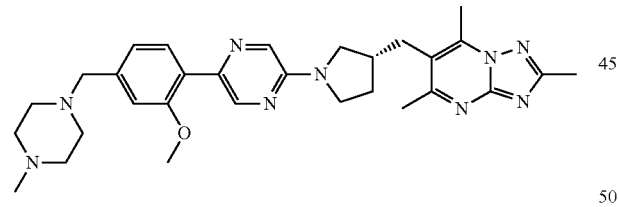

XPhos 2$^{nd}$ generation precatalyst (14.7 mg, 0.02 mmol) was added to (R)-6-((1-(5-bromopyrazin-2-yl)pyrrolidin-3-yl)methyl)-2,5,7-trimethyl-[1,2,4]triazolo[1,5-a]pyrimidine (Intermediate 46) (150 mg, 0.37 mmol), (2-methoxy-4-((4-methylpiperazin-1-yl)methyl)phenyl)boronic acid (Intermediate 42) (108 mg, 0.41 mmol) and Cs$_2$CO$_3$ (243 mg, 0.75 mmol) in 1,4-dioxane (3 mL) and water (1.5 mL) at rt. The reaction mixture was stirred at 90° C. for 4 h, allowed to cool to rt and concentrated in vacuo. The resulting crude product was purified by flash C18 chromatography, eluting with 5-100% MeCN in water (+0.1% FA), to afford the formic acid salt of the title compound (168 mg, 79%) as a pale yellow solid; $^1$H NMR (400 MHz, CDCl$_3$) 1.93 (1H, dq), 2.23 (1H, dq), 2.54-3.05 (24H, m), 3.34 (1H, dd), 3.51-3.65 (3H, m), 3.76 (2H, ddd), 3.89 (3H, s), 6.96-7.06 (2H, m), 7.73 (1H, d), 7.98 (1H, d), 8.69 (1H, d); m/z MH$^+$ 542.

Example 44: {1-[4-(5-{(3R)-3-[(2,5,7-trimethyl[1,2,4]triazolo[1,5-a]pyrimidin-6-yl)methyl]pyrrolidin-1-yl}pyrazin-2-yl)benzyl]piperidin-4-yl}methanol

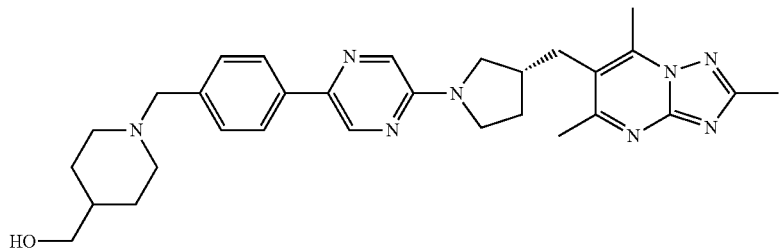 [SMILES: Cc1nc2nc(C)c(C[C@@H]3CCN(c4cnc(-c5ccc(CN6CCC(CO)CC6)cc5)cn4)C3)c(C)n2n1]

(R)-4-(5-(3-((2,5,7-trimethyl-[1,2,4]triazolo[1,5-a]pyrimidin-6-yl)methyl)pyrrolidin-1-yl)pyrazin-2-yl)benzaldehyde (Intermediate 49) (30 mg, 0.07 mmol), 4-piperidylmethanol (16.12 mg, 0.14 mmol), DCM (2 mL) and AcOH (2 drop) were combined, and the reaction mixture was stirred at rt for 5 h. Sodium triacetoxyborohydride (45 mg, 0.21 mmol) was then added and the reaction mixture was stirred at rt for 16 h. The mixture was purified by preparative HPLC to afford the title compound (17.4 mg, 47%); $^1$H NMR (400 MHz, DMSO) 1.07-1.2 (2H, m), 1.34 (1H, s), 1.62 (2H, d), 1.85-1.95 (3H, m), 2.12 (1H, dd), 2.48 (3H, s), 2.65 (4H, s), 2.76 (3H, s), 2.82 (2H, d), 2.95 (2H, d), 3.21-3.28 (4H, m), 3.45 (2H, s), 3.62-3.75 (2H, m), 4.37 (1H, s), 7.34 (2H, d), 7.88 (2H, d), 8.04 (1H, d), 8.62 (1H, d); m/z MH$^+$ 527.

Example 45: 6-{[(3R)-1-(5-{4-[(1,1-dioxidothiomorpholin-4-yl)methyl]phenyl}pyrazin-2-yl)pyrrolidin-3-yl]methyl}-2,5,7-trimethyl[1,2,4]triazolo[1,5-a]pyrimidine

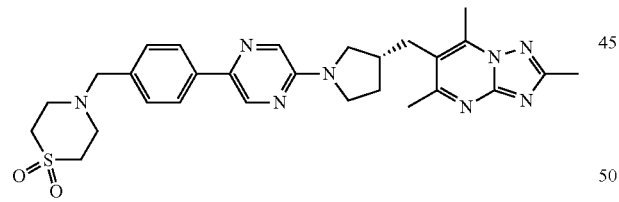

(R)-4-(5-(3-((2,5,7-trimethyl-[1,2,4]triazolo[1,5-a]pyrimidin-6-yl)methyl)pyrrolidin-1-yl)pyrazin-2-yl)benzaldehyde (Intermediate 49) (30 mg, 0.07 mmol), 1,4-thiazinane 1,1-dioxide hydrochloride salt (24.03 mg, 0.14 mmol), DCM (2 mL) and AcOH (2 drop) were combined and the mixture was stirred at rt for 5 h. Sodium triacetoxyborohydride (45 mg, 0.21 mmol) was then added and the reaction mixture was stirred at rt for 16 h. The mixture was purified by preparative HPLC to afford the title compound (12 mg, 30%); $^1$H NMR (400 MHz, DMSO) 1.87 (1H, dd), 2.12 (1H, dd), 2.48 (3H, s), 2.65 (4H, s), 2.76 (3H, s), 2.86-2.93 (4H, m), 2.95 (2H, d), 3.09-3.14 (4H, m), 3.25 (1H, dd), 3.45 (1H, dt), 3.62-3.76 (4H, m), 7.39 (2H, d), 7.91 (2H, d), 8.04 (1H, d), 8.64 (1H, d); m/z MH$^+$ 547.

Example 46: 2,5,7-trimethyl-6-({(3R)-1-[5-(4-{[4-(methylsulfonyl)piperidin-1-yl]methyl}phenyl)pyrazin-2-yl]pyrrolidin-3-yl}methyl)[1,2,4]triazolo[1,5-a]pyrimidine

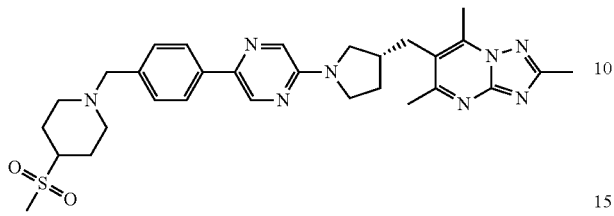

(R)-4-(5-(3-((2,5,7-trimethyl-[1,2,4]triazolo[1,5-a]pyrimidin-6-yl)methyl)pyrrolidin-1-yl)pyrazin-2-yl)benzaldehyde (Intermediate 49) (30 mg, 0.07 mmol), 4-methylsulfonylpiperidine (22.9 mg, 0.14 mmol), DCM (2 mL) and AcOH (2 drop) were combined and the mixture was stirred at rt for 5 h. Sodium triacetoxyborohydride (45 mg, 0.21 mmol) was then added and the reaction mixture was stirred at rt for 16 h. The mixture was purified by preparative HPLC and lyophilized to afford the title compound (15 mg, 38%); $^1$H NMR (500 MHz, DMSO) 1.56 (2H, tt), 1.76-1.85 (1H, m), 1.92 (4H, t), 2.05 (1H, dd), 2.41 (3H, s), 2.58 (4H, s), 2.69 (3H, s), 2.84 (3H, s), 2.88 (4H, d), 2.98 (1H, ddt), 3.18 (1H, dd), 3.38 (1H, dt), 3.44 (2H, s), 3.55-3.68 (2H, m), 7.28 (2H, d), 7.82 (2H, d), 7.97 (1H, d), 8.55 (1H, d); m/z MH$^+$ 575.

Example 47: (R)-4-((6-(3-methyl-5-(3-((2,5,7-trimethyl-[1,2,4]triazolo[1,5-a]pyrimidin-6-yl)methyl)pyrrolidin-1-yl)pyrazin-2-yl)pyridin-3-yl)methyl)morpholine

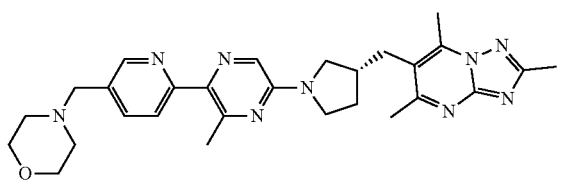 [SMILES: Cc1nc2nc(C)c(C[C@@H]3CCN(c4cnc(-c5ccc(CN6CCOCC6)cn5)c(C)n4)C3)c(C)n2n1]

Bis(triphenylphosphoranyl)palladium(IV) chloride (164 mg, 0.23 mmol) was added to 4-((6-bromopyridin-3-yl)methyl)morpholine (Intermediate 30) (600 mg, 2.33 mmol), 1,1,1,2,2,2-hexamethyldistannane (841 mg, 2.57 mmol) in THF (8 mL) at rt. The reaction mixture was stirred at 85° C. for 16 h. (R)-6-((1-(5-bromo-6-methylpyrazin-2-yl)pyrrolidin-3-yl)methyl)-2,5,7-trimethyl-[1,2,4]triazolo[1,5-a]pyrimidine (Intermediate 45) (300 mg, 0.72 mmol) and Pd(Ph$_3$P)$_4$ (83 mg, 0.07 mmol) were added and the mixture was transferred to a microwave tube with THF (10 mL). The reaction mixture was heated at 100° C. for 5 h in the microwave reactor and allowed to cool to rt, then concentrated in vacuo. The resulting crude product was purified by flash C18 chromatography, eluting with 5-100% MeCN in water (+0.1% FA), then further purified by preparative HPLC to afford the title compound (160 mg, 43%) as a white solid; $^1$H NMR (300 MHz, MeOD) 1.97 (1H, dq), 2.24 (1H, dq), 2.47-2.59 (10H, m), 2.73 (4H, s), 2.84 (3H, s), 3.04 (2H, dd), 3.32-3.42 (1H, m), 3.47-3.66 (3H, m), 3.66-3.87 (6H, m), 7.72 (1H, dd), 7.81 (1H, s), 7.91 (1H, dd), 8.53-8.60 (1H, m); m/z MH$^+$514.

Example 48: 6-(((R)-1-(5-(4-(((S)-3,4-dimethylpiperazin-1-yl)methyl)phenyl)pyrazin-2-yl)pyrrolidin-3-yl)methyl)-2,5,7-trimethyl-[1,2,4]triazolo[1,5-a]pyrimidine

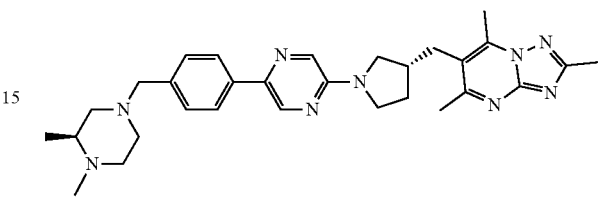

(R)-4-(5-(3-((2,5,7-trimethyl-[1,2,4]triazolo[1,5-a]pyrimidin-6-yl)methyl)pyrrolidin-1-yl)pyrazin-2-yl)benzaldehyde (Intermediate 49) (200 mg, 0.47 mmol) was added to (S)-1,2-dimethylpiperazine dihydrochloride (350 mg, 1.87 mmol) in MeOH (10 mL). The reaction mixture was stirred at rt for 2 h. AcOH (2.81 mg, 0.05 mmol) and sodium triacetoxyborohydride (397 mg, 1.87 mmol) were added and the reaction mixture was stirred for 16 h. The reaction mixture was quenched with water and the resulting solution was purified by preparative HPLC to afford the title compound (132 mg, 54%) as a white solid; $^1$H NMR (400 MHz, CDCl$_3$) 1.07 (3H, d), 1.94 (2H, dq), 2.18-2.35 (6H, m), 2.39 (1H, s), 2.59-2.85 (13H, m), 2.97 (2H, qd), 3.35 (1H, dd), 3.56 (3H, d), 3.76 (2H, ddt), 7.38-7.45 (2H, m), 7.80-7.88 (2H, m), 7.96 (1H, d), 8.52 (1H, d); m/z MH$^+$ 526.

Example 49: (R)-4-((5-(5-(3-((2,5,7-trimethyl-[1,2,4]triazolo[1,5-a]pyrimidin-6-yl)methyl)pyrrolidin-1-yl)pyrazin-2-yl)pyridin-2-yl)methyl)morpholine

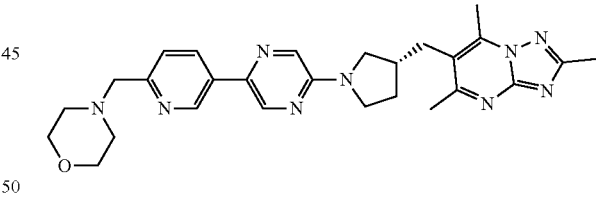

XPhos 2$^{nd}$ generation precatalyst (19.6 mg, 0.02 mmol) was added to (R)-6-((1-(5-bromopyrazin-2-yl)pyrrolidin-3-yl)methyl)-2,5,7-trimethyl-[1,2,4]triazolo[1,5-a]pyrimidine (Intermediate 46) (200 mg, 0.50 mmol), (6-(morpholinomethyl)pyridin-3-yl)boronic acid (sourced commercially) (110 mg, 0.50 mmol) and Cs$_2$CO$_3$ (324 mg, 0.99 mmol) in 1,4-dioxane (4 mL) and water (2 mL) at rt. The reaction mixture was stirred at 80° C. for 16 h, allowed to cool to rt and concentrated in vacuo. The resulting crude product was purified by preparative HPLC to afford the title compound (172 mg, 69%) as a yellow solid; $^1$H NMR (400 MHz, MeOD) 1.91-2.06 (1H, m), 2.23-2.29 (1H, m), 2.53-2.57 (7H, m), 2.66-2.74 (4H, m), 2.85 (3H, d), 2.97-3.11 (2H, m), 3.35-3.38 (1H, m), 3.53-3.59 (1H, m), 3.67-3.85 (8H, m), 7.61 (1H, d), 8.05 (1H, s), 8.30 (1H, dd), 8.56 (1H, s), 9.01-9.02 (1H, m); m/z MH$^+$ 500.

Example 50: 6-(((R)-1-(5-(4-(((S)-2,4-dimethylpiperazin-1-yl)methyl)phenyl)pyrazin-2-yl)pyrrolidin-3-yl)methyl)-2,5,7-trimethyl-[1,2,4]triazolo[1,5-a]pyrimidine

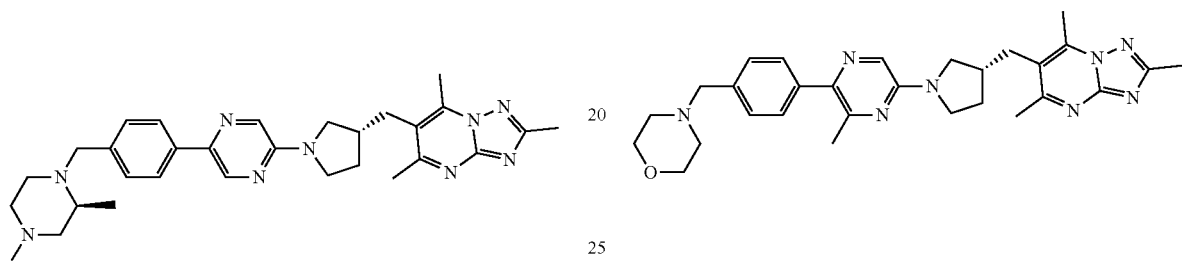

(S)-1,3-Dimethylpiperazine dihydrochloride (167 mg, 0.89 mmol) was added in one portion to (R)-6-((1-(5-(4-(chloromethyl)phenyl)pyrazin-2-yl)pyrrolidin-3-yl)methyl)-2,5,7-trimethyl-[1,2,4]triazolo[1,5-a]pyrimidine (Intermediate 48) (200 mg, 0.45 mmol) and triethylamine (0.31 mL, 2.23 mmol) in 1,4-dioxane (5 mL) at rt under air. The reaction mixture was stirred at 80° C. for 24 h, allowed to cool to rt and diluted with EtOAc (50 mL) and water (15 mL). The organic layer was isolated and washed with sat. brine (15 mL), dried over MgSO$_4$, filtered and concentrated in vacuo. The resulting crude product was purified by fcc, eluting with 0-4% 1 M NH$_3$/MeOH in DCM to afford the title compound (54 mg, 23%) as a pale yellow solid; $^1$H NMR (500 MHz, DMSO) 1.06 (3H, d), 1.80-1.91 (2H, m), 1.94-2.04 (1H, m), 2.05-2.14 (5H, m), 2.37-2.43 (1H, m), 2.46 (4H, s), 2.52-2.61 (3H, m), 2.63 (3H, s), 2.74 (3H, s), 2.93 (2H, d), 3.12 (1H, d), 3.23 (1H, dd), 3.43 (1H, dt), 3.63 (1H, dd), 3.66-3.73 (1H, m), 3.95 (1H, d), 7.33 (2H, d), 7.82-7.91 (2H, m), 8.02 (1H, d), 8.60 (1H, d); m/z MH$^+$ 526.

Example 51: (R)-4-(4-(3-methyl-5-(3-((2,5,7-trimethyl-[1,2,4]-triazolo[1,5-a]pyrimidin-6-yl)methyl)pyrrolidin-1-yl)pyrazin-2-yl)benzyl)morpholine XPhos 2$^{nd}$ generation precatalyst (11.3 mg, 0.01 mmol) was added to 4-(4-(4,4,5,5-tetramethyl-1,3,2-dioxaborolan-2-yl)benzyl)morpholine (sourced commercially) (87 mg, 0.29 mmol), (R)-6-((1-(5-bromo-6-methylpyrazin-2-yl)pyrrolidin-3-yl)methyl)-2,5,7-trimethyl-[1,2,4]triazolo[1,5-a]pyrimidine (Intermediate 45) (120 mg, 0.29 mmol) and Cs$_2$CO$_3$ (188 mg, 0.58 mmol) in 1,4-dioxane (4 mL) and water (1.5 mL). The reaction mixture was stirred at 90° C. for 16 h, allowed to cool to rt and filtered through celite. The filtrate was concentrated in vacuo and the resulting crude product was purified by preparative HPLC to afford the title compound (49 mg, 31%) as a pale yellow solid; $^1$H NMR (300 MHz, MeOD) 1.92-1.99 (1H, m), 2.17-2.27 (1H, m), 2.41 (3H, s), 2.55 (3H, s), 2.61-2.83 (11H, m), 2.96-3.03 (2H, m), 3.29-3.35 (1H, m), 3.47-3.55 (1H, m), 3.65-3.79 (6H, m), 3.86 (2H, s), 7.47-7.53 (4H, m), 7.75 (1H, s); m/z MH$^+$ 513.

Example 52: 2,5,7-trimethyl-6-({(3R)-1-[5-(4-{[4-(methylsulfonyl)piperazin-1-yl]methyl}phenyl)pyrazin-2-yl]pyrrolidin-3-yl}methyl)[1,2,4]triazolo[1,5-a]pyrimidine

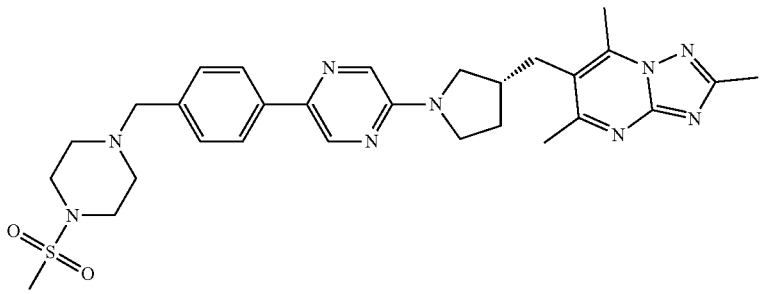 [SMILES: Cc1nc2nc(C)c(C[C@@H]3CCN(c4cnc(-c5ccc(CN6CCN(S(C)(=O)=O)CC6)cc5)cn4)C3)c(C)n2n1]

(R)-4-(5-(3-((2,5,7-trimethyl-[1,2,4]triazolo[1,5-a]pyrimidin-6-yl)methyl)pyrrolidin-1-yl)pyrazin-2-yl)benzaldehyde (Intermediate 49) (30 mg, 0.07 mmol), 1-methylsulfonylpiperazine (22.99 mg, 0.14 mmol), DCM (2 mL) and AcOH (2 drop) were combined and the mixture was stirred at rt for 5 h. Sodium triacetoxyborohydride (45 mg, 0.21 mmol) was then added and the reaction mixture was stirred at rt for 16 h. The mixture was purified by preparative HPLC to afford the title compound (11.9 mg, 30%); $^1$H NMR (400 MHz, DMSO) 1.87 (1H, dd), 2.12 (1H, dd), 2.48 (7H, s), 2.65 (4H, s), 2.76 (3H, s), 2.87 (3H, s), 2.95 (2H, d), 3.09-3.16 (4H, m), 3.25 (1H, dd), 3.41-3.50 (1H, m), 3.55 (2H, s), 3.62-3.75 (2H, m), 7.37 (2H, d), 7.90 (2H, d), 8.04 (1H, d), 8.63 (1H, d); m/z MH$^+$ 576.

Example 53: (R)-N,N-dimethyl-2-(4-(4-(5-(3-((2,5,7-trimethyl-[1,2,4]triazolo[1,5-a]pyrimidin-6-yl)methyl)pyrrolidin-1-yl)pyrazin-2-yl)benzyl)piperazin-1-yl)acetamide

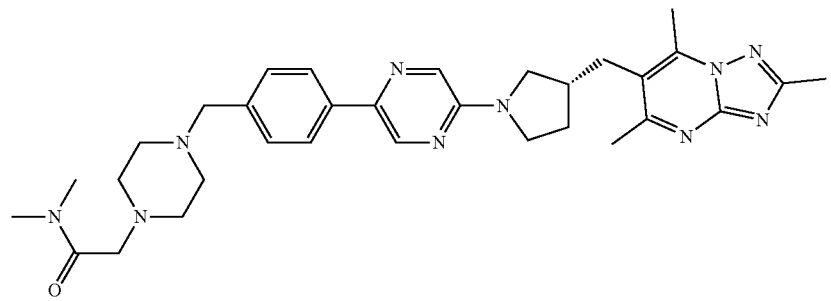

N,N-dimethyl-2-(piperazin-1-yl)acetamide (Intermediate 21) (240 mg, 1.40 mmol) was added to (R)-4-(5-(3-((2,5,7-trimethyl-[1,2,4]triazolo[1,5-a]pyrimidin-6-yl)methyl)pyrrolidin-1-yl)pyrazin-2-yl)benzaldehyde (Intermediate 49) (200 mg, 0.47 mmol) in DCM (5 mL) at rt, and the reaction mixture was stirred for 1 h. Sodium triacetoxyborohydride (496 mg, 2.34 mmol) was added and the reaction mixture was stirred at rt for 16 h, then concentrated in vacuo. The resulting crude product was purified by flash C18 chromatography, eluting with 5-100% MeCN in water (+0.1% FA) to afford a partial (0.6 equivalents) formic acid salt of the title compound (172 mg, 60%) as a yellow solid; $^1$H NMR (400 MHz, CDCl$_3$) 1.87-2.01 (1H, m), 2.18-2.30 (1H, m), 2.64 (3H, s), 2.60-2.71 (1H, m), 2.72-2.78 (11H, m), 2.83 (3H, s), 2.96 (3H, s), 2.88-3.05 (2H, m), 3.05 (3H, s), 3.24 (2H, s), 3.35 (1H, dd), 3.52-3.63 (1H, m), 3.72-3.81 (1H, m), 3.78 (3H, s), 7.45 (2H, d), 7.87 (2H, d), 7.97 (1H, d), 8.42 (0.6H, s, equates to 0.6 eq. formate salt), 8.52 (1H, d); m/z MH$^+$ 583.

Example 54: (R)-2,5,7-trimethyl-6-((1-(6-methyl-5-(4-((4-methylpiperazin-1-yl)methyl)phenyl)pyrazin-2-yl)pyrrolidin-3-yl)methyl)-[1,2,4]triazolo[1,5-a]pyrimidine

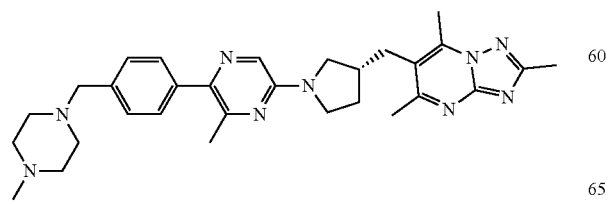

XPhos 2nd generation precatalyst (28 mg, 0.04 mmol) was added to 1-methyl-4-(4-(4,4,5,5-tetramethyl-1,3,2-dioxaborolan-2-yl)benzyl)piperazine (125 mg, 0.40 mmol), (R)-6-((1-(5-bromo-6-methylpyrazin-2-yl)pyrrolidin-3-yl)methyl)-2,5,7-trimethyl-[1,2,4]triazolo[1,5-a]pyrimidine (Intermediate 45) (150 mg, 0.36 mmol) and $Cs_2CO_3$ (235 mg, 0.72 mmol) in 1,4-dioxane (3 mL) and water (1.5 mL) at rt. The reaction mixture was stirred at 90° C. for 16 h, allowed to cool to rt and concentrated in vacuo. The resulting crude product was purified by preparative HPLC to afford the title compound (110 mg, 58%) as a white solid; $^1$H NMR (300 MHz, $CDCl_3$) 1.81-2.00 (1H, m), 2.20 (1H, dq), 2.31-2.76 (21H, m), 2.82 (3H, s), 2.94 (2H, qd), 3.34 (1H, dd), 3.46-3.61 (3H, m), 3.74 (2H, ddd), 7.38 (2H, d), 7.43-7.53 (2H, m), 7.79 (1H, s); m/z $MH^+$ 526.

Example 55: N,N-dimethyl-4-[4-(5-{(3R)-3-[(2,5,7-trimethyl[1,2,4]triazolo[1,5-a]pyrimidin-6-yl)methyl]pyrrolidin-1-yl}pyrazin-2-yl)benzyl]piperazine-1-carboxamide

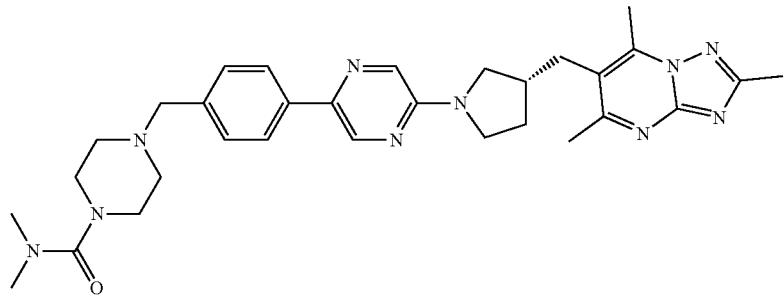

(R)-4-(5-(3-((2,5,7-trimethyl-[1,2,4]triazolo[1,5-a]pyrimidin-6-yl)methyl)pyrrolidin-1-yl)pyrazin-2-yl)benzaldehyde (Intermediate 49) (30 mg, 0.07 mmol), N,N-dimethylpiperazine-1-carboxamide (23 mg, 0.14 mmol), DCM (2 mL) and AcOH (2 drop) were combined and the mixture was stirred at rt for 5 h. Sodium triacetoxyborohydride (45 mg, 0.21 mmol) was then added and the reaction mixture was stirred at rt for 16 h. The mixture was purified by preparative HPLC to afford the title compound (13 mg, 33%); $^1$H NMR (400 MHz, DMSO) 1.82-1.92 (1H, m), 2.07-2.17 (1H, m), 2.35-2.41 (4H, m), 2.48 (3H, s), 2.65 (4H, s), 2.72 (6H, s), 2.76 (3H, s), 2.95 (2H, d), 3.07-3.15 (4H, m), 3.22-3.27 (1H, m), 3.41-3.54 (3H, m), 3.68 (2H, ddd), 7.36 (2H, d), 7.89 (2H, d), 8.04 (1H, d), 8.63 (1H, d); m/z $MH^+$ 569.

Example 56: (R)-2,5,7-trimethyl-6-((1-(5-(3-methyl-4-((4-methylpiperazin-1-yl)methyl)phenyl)pyrazin-2-yl)pyrrolidin-3-yl)methyl)-[1,2,4]triazolo[1,5-a]pyrimidine

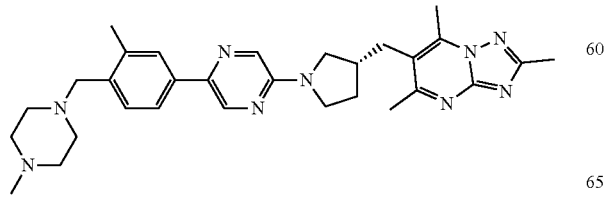

Pd(Ph₃P)₄ (35 mg, 0.03 mmol) was added to (R)-6-((1-(5-bromopyrazin-2-yl)pyrrolidin-3-yl)methyl)-2,5,7-trimethyl-[1,2,4]triazolo[1,5-a]pyrimidine (Intermediate 46) (122 mg, 0.30 mmol), 1-methyl-4-(2-methyl-4-(4,4,5,5-tetramethyl-1,3,2-dioxaborolan-2-yl)benzyl)piperazine (Intermediate 51) (100 mg, 0.30 mmol) and Na₂CO₃ (64.2 mg, 0.61 mmol) in toluene (4 mL) and water (1 mL). The reaction mixture was stirred at 80° C. for 16 h, allowed to cool to rt and concentrated in vacuo. The resulting crude product was purified by preparative HPLC to afford the title compound (15 mg, 9%) as a white solid; ¹H NMR (300 MHz, CDCl₃) 1.94 (1H, m), 2.22 (1H, dt), 2.30-2.75 (21H, m), 2.81 (3H, s), 2.95 (2H, t), 3.34 (1H, dd), 3.54 (3H, m), 3.75 (2H, m), 7.34 (1H, m), 7.65 (2H, m), 7.94 (1H, d), 8.50 (1H, s); m/z MH⁺ 526.

Example 57: (R)-2,5,7-trimethyl-6-((1-(5-(6-((4-methylpiperazin-1-yl)methyl)pyridin-3-yl)pyrazin-2-yl)pyrrolidin-3-yl)methyl)-[1,2,4]triazolo[1,5-a]pyrimidine

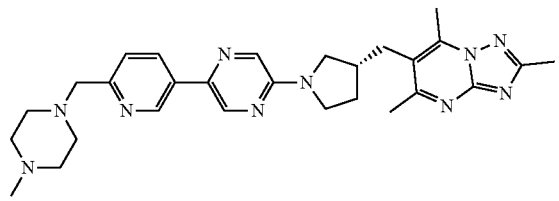

XPhos 2ⁿᵈ generation precatalyst (10.76 mg, 0.01 mmol) was added to (R)-6-((1-(5-bromopyrazin-2-yl)pyrrolidin-3-yl)methyl)-2,5,7-trimethyl-[1,2,4]triazolo[1,5-a]pyrimidine (Intermediate 46) (110 mg, 0.27 mmol), (6-((4-methylpiperazin-1-yl)methyl)pyridin-3-yl)boronic acid (Intermediate 9) (71 mg, 0.30 mmol) and Cs₂CO₃ (178 mg, 0.55 mmol) in 1,4-dioxane (3 mL) and water (1.5 mL) at rt. The reaction mixture was stirred at 80° C. for 4 h, allowed to cool to rt and concentrated in vacuo. The resulting crude product was purified by flash C18 chromatography, eluting with 5-100% MeCN in water (+0.1% FA) to afford the partial (0.5 eq.) formic acid salt of the title compound (141 mg, 96%) as a white solid; ¹H NMR (400 MHz, CDCl₃) 1.96 (1H, dq), 2.25 (1H, dt), 2.62-2.76 (10H, m), 2.83 (3H, s), 2.89-3.06 (10H, m), 3.36 (1H, dd), 3.59 (1H, dt), 3.71-3.84 (4H, m), 7.41 (1H, d), 7.99 (1H, d), 8.18 (1H, dd), 8.40 (0.5H, s, from 0.5 eq. formate salt), 8.53 (1H, d), 9.11 (1H, d); m/z MH⁺ 513.

Example 58: (R)-1-(4-(4-(5-(3-((2,5,7-trimethyl-[1,2,4]triazolo[1,5-a]pyrimidin-6-yl)methyl)pyrrolidin-1-yl)pyrazin-2-yl)benzyl)piperazin-1-yl)ethanone

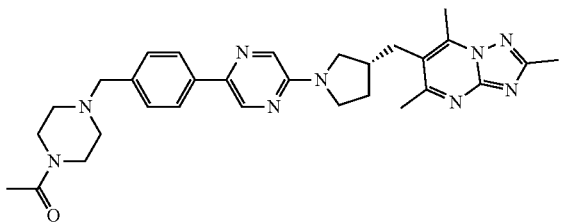 [SMILES: CC(=O)N1CCN(Cc2ccc(-c3cnc(N4CC[C@@H](Cc5c(C)nc6nc(C)nn6c5C)C4)cn3)cc2)CC1]

1-(4-(4-(4,4,5,5-tetramethyl-1,3,2-dioxaborolan-2-yl)benzyl)piperazin-1-yl)ethanone (Intermediate 52) (667 mg, 1.94 mmol), (R)-6-((1-(5-bromopyrazin-2-yl)pyrrolidin-3-yl)methyl)-2,5,7-trimethyl-[1,2,4]triazolo[1,5-a]pyrimidine (Intermediate 46) (600 mg, 1.49 mmol) and Cs₂CO₃ (972 mg, 2.98 mmol) were added to 1,4-dioxane (30 mL) and water (15 mL) and the mixture was degassed for 10 min. XPhos 2ⁿᵈ generation precatalyst (59 mg, 0.07 mmol) was added and the reaction mixture was stirred for 18 h at 90° C., then allowed to cool to rt and diluted with EtOAc (50 mL). The organic layer was isolated and washed with sat. brine solution and dried over MgSO₄, filtered and concentrated in vacuo. The resulting crude product was purified by fcc, eluting with 0-4% 1 M NH₃/MeOH in DCM. The product was dissolved in EtOAc (2 mL) and stirred for 2 h, and the resulting precipitate was isolated by filtration and dried in vacuo to afford the title compound (209 mg, 26%) as a white solid; ¹H NMR (500 MHz, DMSO) 1.78-1.91 (1H, m), 1.96 (3H, s), 2.03-2.16 (1H, m), 2.26-2.33 (2H, m), 2.34-2.4 (2H, m), 2.46 (3H, s), 2.55-2.67 (4H, m), 2.74 (3H, s), 2.93 (2H, d), 3.2-3.26 (1H, m), 3.35-3.47 (5H, m), 3.50 (2H, s), 3.59-3.75 (2H, m), 7.34 (2H, d), 7.88 (2H, d), 8.02 (1H, s), 8.62 (1H, s); m/z MH⁺ 540.

Example 59: (R)-2,5,7-trimethyl-6-(0-(5-(4-((4-methylpiperazin-1-yl)methyl)phenyl)pyrazin-2-yl)pyrrolidin-3-yl)methyl)-[1,2,4]triazolo[1,5-a]pyrimidine

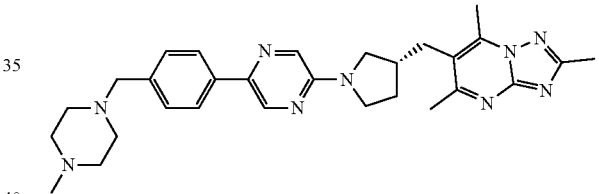

XPhos 2ⁿᵈ generation precatalyst (0.780 g, 0.99 mmol) was added to a mixture of (R)-6-((1-(5-bromopyrazin-2-yl)pyrrolidin-3-yl)methyl)-2,5,7-trimethyl-[1,2,4]triazolo[1,5-a]pyrimidine (Intermediate 46) (7.98 g, 19.84 mmol), 1-methyl-4-(4-(4,4,5,5-tetramethyl-1,3,2-dioxaborolan-2-yl)benzyl)piperazine (sourced commercially) (7.53 g, 23.8 mmol) and Cs₂CO₃ (12.93 g, 39.7 mmol) in 1,4-dioxane (187 mL) and water (75 mL). The reaction mixture was heated at 90° C. for 3 h, allowed to cool to rt and concentrated in vacuo. The residue was taken up in water (1 L) and extracted with DCM (3×800 mL). The combined organic layers were washed with water, sat. brine, dried over MgSO₄, filtered and concentrated in vacuo. The resulting crude product was purified by fcc, eluting with 0-15% MeOH in DCM. The product was taken up in MeCN (150 ml) and stirred for 2 h after sonication. The resulting precipitate was isolated by filtration, washed with diethyl ether and then n-heptane, and dried in vacuo to afford the title compound (6.30 g, 62%) as a pale cream solid; ¹H NMR (500 MHz, DMSO) 1.82-1.88 (1H, m), 2.10-2.14 (1H, m), 2.15 (3H, s), 2.30-2.34 (4H, m), 2.37-2.41 (4H, m), 2.47 (3H, s), 2.58-2.64 (1H, m), 2.64 (3H, s), 2.75 (3H, s), 2.91-2.95 (2H, m), 3.23-3.26 (1H, m), 3.43-3.46 (1H, m), 3.47 (2H, s), 3.64-3.67 (1H, m), 3.68-3.72 (1H, m), 7.32 (2H, d), 7.85 (2H, d), 8.00 (1H, s), 8.56 (1H, s); m/z MH⁺ 512.

Example 60: (R)-4-(4-(5-(3-((2,5,7-trimethyl-[1,2,4]triazolo[1,5-a]pyrimidin-6-yl)methyl)pyrrolidin-1-yl)pyrazin-2-yl)benzyl)morpholine

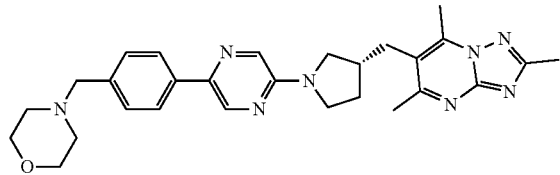 [SMILES: Cc1nc2nc(C)c(C[C@@H]3CCN(c4cnc(-c5ccc(CN6CCOCC6)cc5)cn4)C3)c(C)n2n1]

XPhos 2$^{nd}$ generation precatalyst (24.45 mg, 0.03 mmol) was added to (R)-6-((1-(5-bromopyrazin-2-yl)pyrrolidin-3-yl)methyl)-2,5,7-trimethyl-[1,2,4]triazolo[1,5-a]pyrimidine (Intermediate 46) (250 mg, 0.62 mmol), 4-(4-(4,4,5,5-tetramethyl-1,3,2-dioxaborolan-2-yl)benzyl)morpholine (sourced commercially) (188 mg, 0.62 mmol) and Cs$_2$CO$_3$ (405 mg, 1.24 mmol) in 1,4-dioxane (5 mL) and water (2.5 mL) at rt. The reaction mixture was stirred at 80° C. for 16 h, allowed to cool to rt, filtered through Celite and concentrated in vacuo. The resulting crude product was purified by preparative HPLC to afford the title compound (191 mg, 56%) as a pale yellow solid; $^1$H NMR (300 MHz, MeOD) 1.93-2.02 (1H, m), 2.18-2.28 (1H, m), 2.55 (3H, s), 2.65-2.74 (4H, m), 2.78-2.83 (7H, m), 3.02-3.04 (2H, m), 3.29-3.35 (1H, m), 3.49-3.58 (1H, m), 3.66-3.81 (6H, m), 3.86 (2H, s), 7.47 (2H, d), 7.90 (2H, d), 7.99 (1H, s), 8.49 (1H, s); m/z MH$^+$ 499.

Example 61: (R)-4-(4-(6-(3-((2,5,7-trimethyl-[1,2,4]triazolo[1,5-a]pyrimidin-6-yl)methyl)pyrrolidin-1-yl)pyridazin-3-yl)benzyl)morpholine

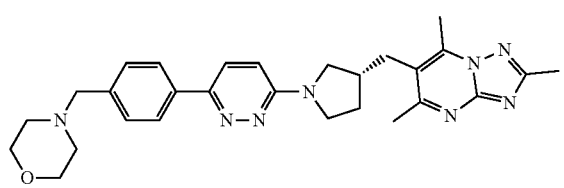

XPhos 2$^{nd}$ generation precatalyst (11 mg, 0.01 mmol) was added to (R)-6-((1-(6-chloropyridazin-3-yl)pyrrolidin-3-yl)methyl)-2,5,7-trimethyl-[1,2,4]triazolo[1,5-a]pyrimidine (Intermediate 53) (100 mg, 0.28 mmol), 4-(4-(4,4,5,5-tetramethyl-1,3,2-dioxaborolan-2-yl)benzyl)morpholine (sourced commercially) (85 mg, 0.28 mmol) and Cs$_2$CO$_3$ (182 mg, 0.56 mmol) in 1,4-dioxane (2 mL) and water (1 mL) at rt. The reaction mixture was stirred at 90° C. for 2 h, allowed to cool to rt and concentrated in vacuo. The resulting crude product was purified by flash C18 chromatography, eluting with 5-100% MeCN in water (+0.08% NH$_4$HCO$_3$), to afford the title compound (101 mg, 73%) as a white solid; $^1$H NMR (400 MHz, MeOD) 2.01 (1H, dq), 2.26 (1H, dt), 2.54 (7H, d), 2.75 (4H, s), 2.86 (3H, s), 3.07 (2H, dd), 3.38 (1H, dd), 3.52-3.63 (3H, m), 3.68-3.86 (6H, m), 7.04 (1H, d), 7.44-7.51 (2H, m), 7.82-7.95 (3H, m); m/z MH$^+$ 499.

Example 62: (R)-4-((6-(4-(3-((2,5,7-trimethyl-[1,2,4]triazolo[1,5-a]pyrimidin-6-yl)oxy)pyrrolidin-1-yl)phenyl)pyridazin-3-yl)methyl)morpholine

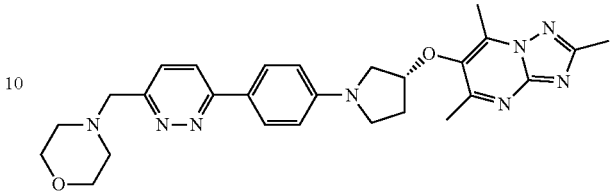

Cs$_2$CO$_3$ (50 g, 153 mmol), 4-((6-(4-bromophenyl)pyridazin-3-yl)methyl)morpholine (10 g, 29.80 mmol) (Intermediate 65) and (R)-2,5,7-trimethyl-6-(pyrrolidin-3-yloxy)-[1,2,4]triazolo[1,5-a]pyrimidine dihydrochloride (Intermediate 58) (10 g, 29.80 mmol), RuPhos 3rd generation precatalyst (1.87 g, 2.24 mmol) and RuPhos (1.04 g, 2.24 mmol) were combined. A degassed mixture of 2-methyltetrahydrofuran (80 mL) and water (40 mL) was added and the reaction mixture was heated at reflux for 17 h, then allowed to cool to rt and diluted with DCM (250 mL) and water (250 mL). The organic layer was isolated and washed with 1:1 sat. brine:water (100 mL), then filtered through a pad of silica, then concentrated in vacuo to afford crude product. The reaction was then repeated using the following; Cs$_2$CO$_3$ (75 g, 230 mmol), 4-((6-(4-bromophenyl)pyridazin-3-yl)methyl)morpholine (15 g, 44.70 mmol), (R)-2,5,7-trimethyl-6-(pyrrolidin-3-yloxy)-[1,2,4]triazolo[1,5-a]pyrimidine dihydrochloride (15 g, 44.7 mmol), RuPhos 3rd generation precatalyst (2.80 g, 3.35 mmol) and RuPhos (1.56 g, 3.35 mmol) in a degassed mixture of 2-methyltetrahydrofuran (120 mL) and water (60 mL). The second reaction was worked up in an identical way to that described to the first. The two batches of crude product were combined and purified by SFC (Kromasil SIL column 250×50 mm, 10 μm at a flow rate of 450 ml/min using 33% MeOH in scCO$_2$ at 130 bar and oven temperature of 30° C.) to afford the title compound (29 g, 80% yield based on combining both batches) as a white solid; $^1$H NMR (600 MHz, DMSO) 2.31 (1H, dtd), 2.42 (5H, d), 2.46 (3H, s), 2.52 (3H, s), 2.58 (3H, s), 3.45 (1H, dd), 3.54 (1H, td), 3.58 (5H, q), 3.62-3.68 (1H, m), 3.77 (2H, s), 4.96 (1H, s), 6.74 (2H, d), 7.65 (1H, d), 8.03 (2H, d), 8.07 (1H, d); m/z MH$^+$ 501.

Form A

The final product, (R)-4-((6-(4-(3-((2,5,7-trimethyl-[1,2,4]triazolo[1,5-a]pyrimidin-6-yl)oxy)pyrrolidin-1-yl)phenyl)pyridazin-3-yl)methyl)morpholine, was analysed by XRPD and DSC and found to be crystalline. XRPD of a sample of the material gave rise to a diffraction pattern as shown in FIG. 1. (R)-4-((6-(4-(3-((2,5,7-trimethyl-[1,2,4]triazolo[1,5-a]pyrimidin-6-yl)oxy)pyrrolidin-1-yl)phenyl)pyridazin-3-yl)methyl)morpholine, Form A is characterised by at least one peak at a 2θ value of 7.8° or 19.0°, measured using CuKα radiation. The ten most prominent peaks of the XRPD are shown in Table A.

TABLE A

Ten most prominent XRPD peaks for Form A, (R)-4-((6-(4-(3-((2,5,7-trimethyl-[1,2,4]triazolo[1,5-a]pyrimidin-6-yl)oxy)pyrrolidin-1-yl)phenyl)pyridazin-3-yl)methyl)morpholine

| Angle 2-Theta (2θ) | Intensity % |
| --- | --- |
| 7.8 | 100 |
| 19.0 | 59 |
| 18.3 | 54.7 |
| 9.2 | 49.3 |
| 15.8 | 38.8 |
| 11.6 | 32.6 |
| 9.5 | 31.4 |
| 10.4 | 31.4 |
| 25.3 | 29.2 |
| 22.3 | 29 |

Example 62.1: Scale up of (R)-4-((6-(4-(3-((2,5,7-trimethyl-[1,2,4]triazolo[1,5-a]pyrimidin-6-yl)oxy)pyrrolidin-1-yl)phenyl)pyridazin-3-yl)methyl)morpholine 1$^{st}$ Arm of Convergence Route

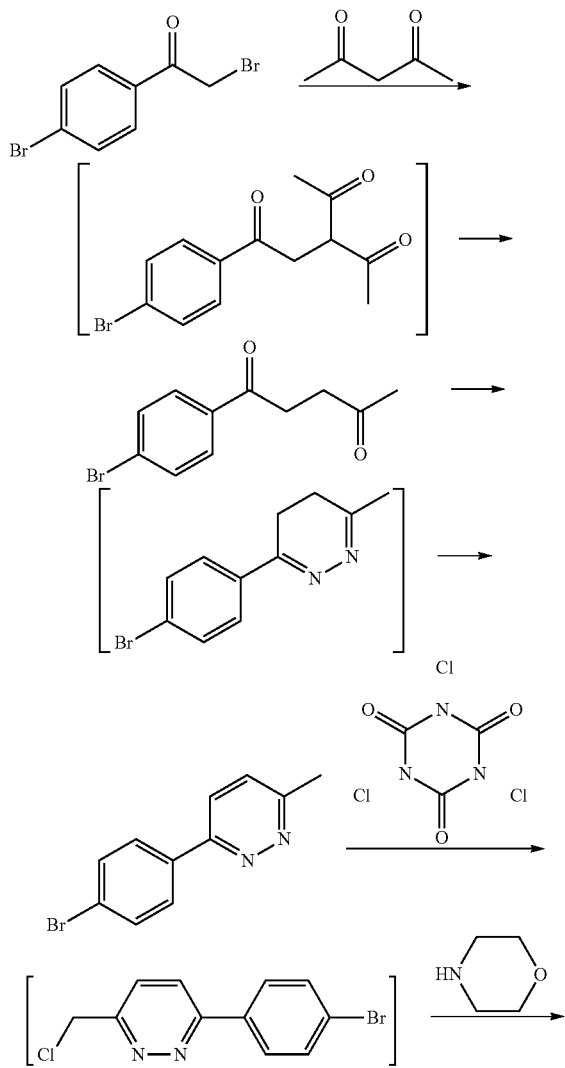

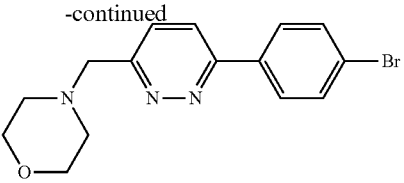

Stage 1: 1-(4-bromophenyl)-1,4-pentanedione (Intermediate 63)

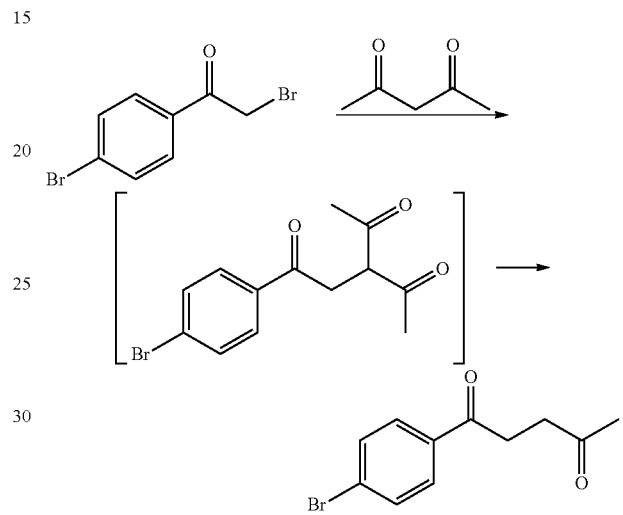

2-bromo-1-(4-bromophenyl)ethenone (12.2 Kg, 43.89 mol), 2,4-pentanedione (9.2 Kg, 91.89 mol), and potassium carbonate (12.2 Kg, 88.27 mol) were slurried in ethanol (72.25 L) for approximately 24 h at room temperature. Ethyl acetate (84.26 L) and water (74 L) were added to give a phase separation, where the lower phase was discarded. Solvent swapping the organic phase into n-heptane (2×84.8 L and 1×73.1 L) resulted in a solid, which was isolated by filtration, and washed with n-heptane (17.54 L) to afford the title compound (7.26 Kg, 59.4% yield based on assay value of 91.6% w/w). $^1$H NMR (400 MHz, CDCl$_3$) 2.15 (3H, s), 2.56 (2H, t), 3.07 (2H, t), 7.44 (2H, d), 7.89 (2H, d).

Stage 2: 3-(4-bromophenyl)-6-methylpyridazine (Intermediate 64)

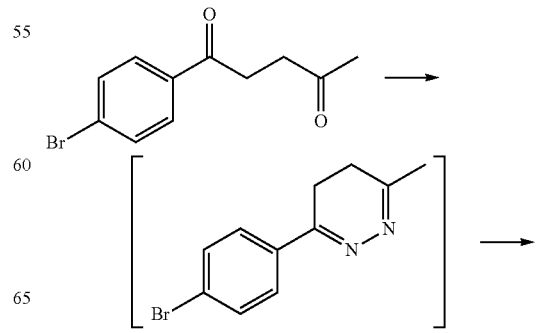

-continued

-continued

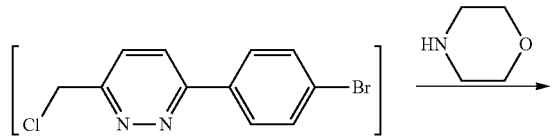

1-(4-bromophenyl)-1,4-pentadione (13.2 Kg, 51.74 mol) and hydrazine hydrate (10.9 Kg, 217.74 mol) were mixed in ethanol (54.5 L) for approximately 6 h at room temperature. Addition of water gave a solid which was isolated by filtration and washed with water (3×66 L) and n-heptane (2×36.5 L). The solid was mixed with tetrachloro-1,4-benzoquinone (14.5 Kg, 58.97 mol) and acetonitrile (137.4 L) for approximately 6 h at room temperature. The reaction was quenched with 12.5% w/w sodium sulfite solution (85 L), and the acetonitrile removed by distillation. Addition of water (66 L) and 2M sodium hydroxide solution (66 L) gave a solid which was isolated by filtration and washed with 2M sodium hydroxide (2×40 L) and water (2×145 L). The solid was mixed with dichloromethane (140 L) and again filtered before washing with water (3×145 L). The organic phase was then treated with activated carbon followed by a solvent swap into methyl tert-butyl ether (100 L) and finally washed with methyl tert-butyl ether (2×55 L). This afforded the title compound (8.25 Kg, 61% yield based on assay value of 95.2% w/w). $^1$H NMR (400 MHz, CDCl$_3$) 2.75 (3H, s), 7.38 (1H, d), 7.65-7.60 (2H, m), 7.71 (1H, d), 7.96-7.91 (2H, m); $^{13}$C NMR (400 MHz, CDCl$_3$) 22.1, 123.5, 124.4, 127.3, 128.4, 132.2, 135.4, 156.2, 158.6.

Stage 3: 4-((6-(4-bromophenyl)pyridazin-3-yl)methyl)morpholine (Intermediate 65)

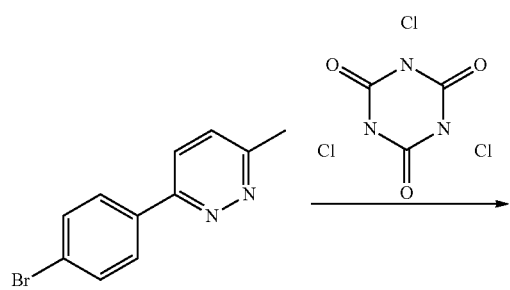

1,3,5-trichloro-1,3,5-triazinane-2,4,6-trione (2.8 Kg, 12.05 mol) was added portionwise to 3-(4-bromophenyl)-6-methylpyridazine (Intermediate 64) (7.15 Kg, 27.32 mol) in DCM (338.35 L) at rt. The reaction mixture was stirred at rt for 3 h then a further portion of 1,3,5-trichloro-1,3,5-triazinane-2,4,6-trione (0.31 Kg, 1.33 mol) was added and the reaction mixture was stirred for 3 h at rt. The reaction mixture was filtered, and the organic filtrate was washed with water (68 L) before a solvent swap into acetonitrile (55 L). Morpholine (4.75 Kg, 54.52 mol) was added and the mixture heated for 4 h before concentration and filtration to give a solid which was washed with acetonitrile (6 L) and water (6 L). The solid was dissolved using 4N hydrochloric acid (7.5 Kg) and water (45 L). The acidic solution was washed with ethyl acetate (2×2.5 L) before pH adjustment with 15% w/w sodium hydroxide (11 Kg) to give a solid which was isolated by filtration. This afforded the title compound (6.2 Kg, 67% yield based on assay value of 98.7% w/w). $^1$H NMR (400 MHz, CDCl$_3$) 2.56 (4H, m), 3.73 (4H, m), 3.91 (2H, s), 7.64 (2H, m), 7.73 (1H, d), 7.81 (1H, d), 7.96 (2H, m); m/z MH$^+$ 334.

2$^{nd}$ Arm of Convergence Route

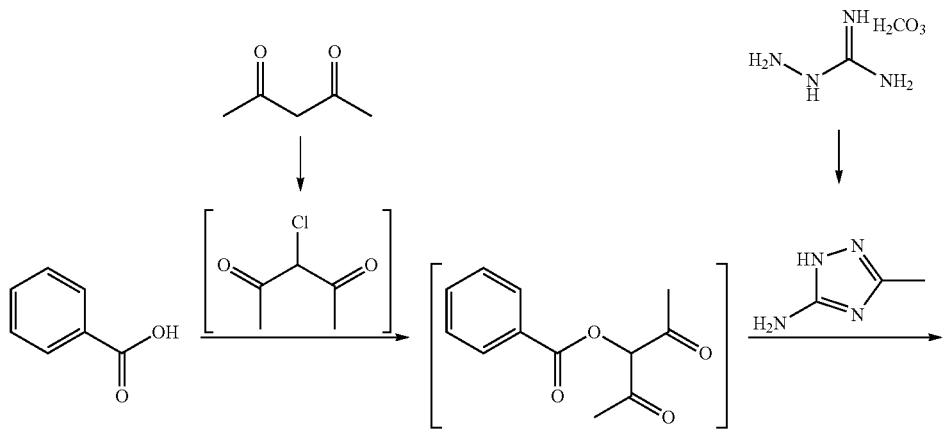

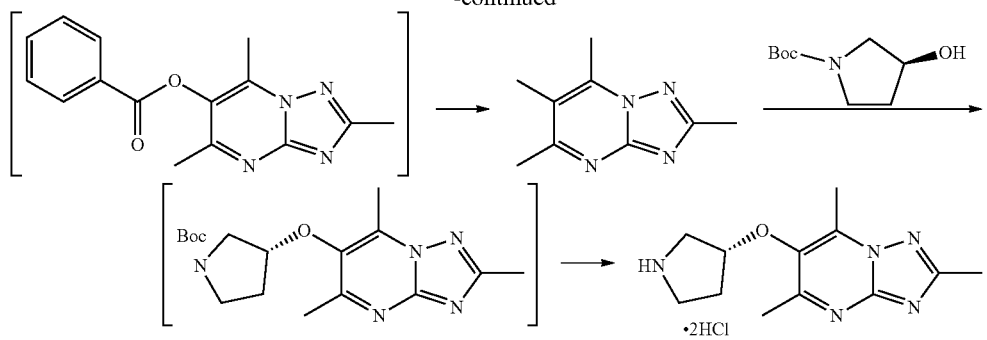

Stage 4: 3-methyl-1H-1,2,4-triazol-5-amine

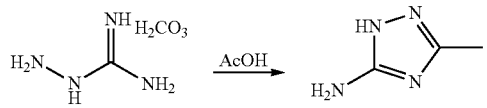

Aminoguananidine bicarbonate (17.7 Kg, 130.04 mol) was mixed with nitric acid (165 g, 2.62 mol) in acetic acid (29.8 L, 521.21 mol) for 64 h at 90° C. The mixture was cooled and diluted with isopropyl acetate (30 L) and filtered to afford the title compound. The crude material (13.9 Kg, 36.7% yield based on 33.7% w/w assay) was used directly in stage 5.

Stage 5: 2,5,7-trimethyl-[1,2,4]triazolo[1,5-a]pyrimidin-6-ol (Intermediate 56)

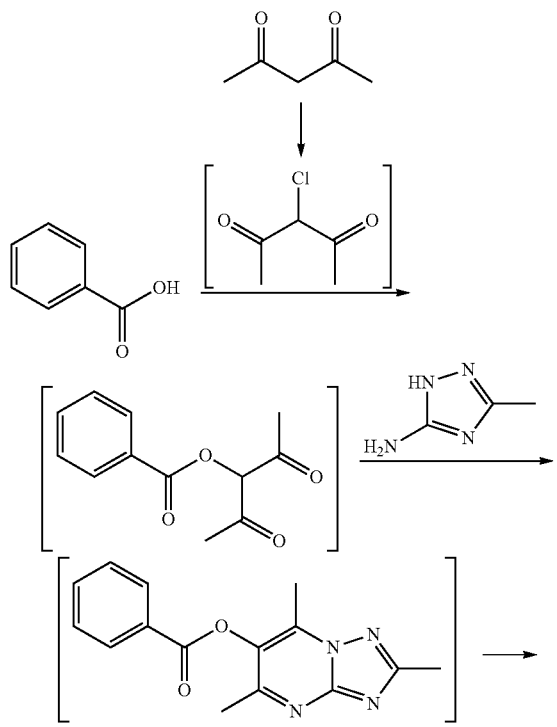

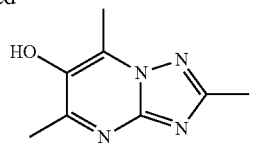

2,4-pentanedione (5.6 Kg, 55.93 mol) and tetra-n-butylammonium bromide (0.9 Kg, 2.79 mol) were cooled in acetonitrile (39.44 L). Slow addition of trimethylsilyl chloride (7.3 Kg, 67.19 mol) and dimethylsulfoxide (4.4 Kg, 56.32 mol) gave the intermediate 3-chloro-2,4-pentanedione as an acetonitrile solution. To this solution is charged benzoic acid (4.9 Kg, 40.12 mol) and diisopropylethylamine (8.6 Kg, 66.54 mol) to give 2,4-dioxopentan-3-yl benzoate (Intermediate 54). Solvent swapping with 2-methyl tetrahydrofuran (28.1 L) followed by washing with 5% sodium sulfate was followed by addition of 3-methyl-1H-1,2,4-triazole-5-amine (12.8 Kg, 43.97 mol). Addition of acetic acid (32.19 L) and heating at 90° C. for 20 hours gave 2,5,7-trimethyl-[1,2,4]triazolo[1,5-a]pyrimidin-6-yl benzoate (Intermediate 55). Solvent swapping with toluene (25 L) and stirring at room temperature with 5M Sodium Hydroxide (63 L) for 20 hours at room temperature afforded the title compound. Addition of 6M hydrochloric acid resulted in a solid which was isolated by filtration and washed with water (16 L). The solid was slurried in water (40 L) and toluene (15 L) and filtered then washed with water (16 L) and dried to give 5.8 Kg (94.6% w/w assay, 30.79 mol, 76.7% yield from benzoic acid).

Stage 6: Intermediate 58: (R)-2,5,7-trimethyl-6-(pyrrolidin-3-yloxy)-[1,2,4]triazolo[1,5-a]pyrimidine dihydrochloride (Intermediate 58)

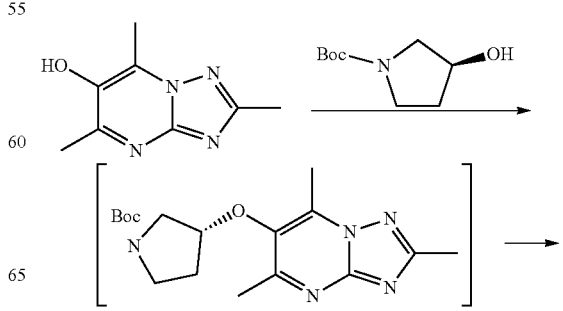

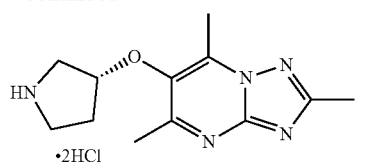

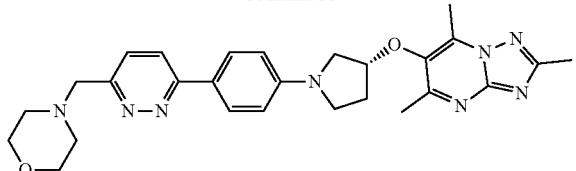

Example 62

Diisopropyl azodicarboxylate (6.9 Kg, 34.12 mol) in THF (14.62) was added dropwise to 2,5,7-trimethyl-[1,2,4]triazolo[1,5-a]pyrimidin-6-ol (4.55 Kg, 24.16 mol), tert-butyl (S)-3-hydroxypyrrolidine-1-carboxylate (5.3 Kg, 28.31 mol) and triphenylphosphine (7.3 Kg, 27.83 mol) in THF (85.49 L) at 0° C. and then stirred at room temperature for 20 h. This was followed by a solvent swap into 2-methyl THF (46.84 L) and washing with 25% w/w sodium chloride (2×22 Kg). The 2-methyl THF was removed by solvent swapping into isopropyl alcohol (45 L) and the Boc group removed by addition of 15% hydrochloric acid in isopropyl alcohol (73.8 Kg) and stirring for 15 hours at room temperature. Cooling and addition of seed (R)-2,5,7-trimethyl-6-(pyrrolidine-3-yloxy)-[1,2,4]trazolo[1.5-a]pyrimidine dihydrochloride (120 g, 370 mmol) gives a solid which was isolated by filtration, and washed with isopropyl alcohol. The solid was finally slurried in ethyl acetate (45 L) before a final filtration and wash with ethyl acetate (45 L) to give 5.35 Kg (74% w/w assay*, 16.01 mol, 66% yield). $^1$H NMR (400 MHz, DMSO) 2.03-2.13 (1H, m), 2.22-2.28 (1H, m), 2.51-2.54 (3H, m), 2.62 (3H, d), 2.74 (3H, s), 3.32-3.45 (3H, m), 3.46-3.56 (1H, m), 4.90 (1H, s), 9.91 (2H, s); m/z MH$^+$ 248. * Assay is based on the free base equivalent.

Convergence

Stage 7: (R)-4-((6-(4-(3-((2,5,7-trimethyl-[1,2,4]triazolo[1,5-a]pyrimidin-6-yl)oxy)pyrrolidin-1-yl)phenyl)pyridazin-3-yl)methyl)morpholine (Example 62)

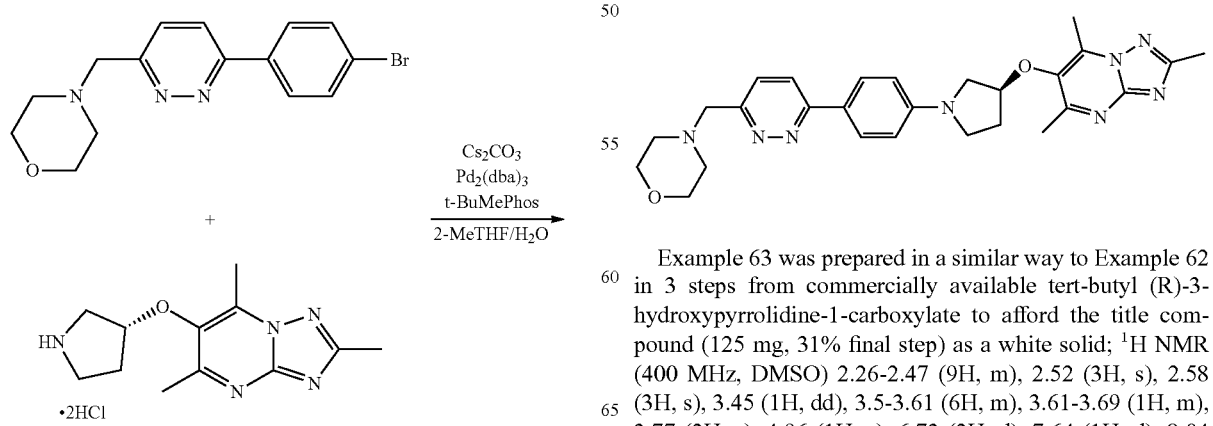

Cs$_2$CO$_3$ (23.8 Kg g, 73.0 mol), 4-((6-(4-bromophenyl)pyridazin-3-yl)methyl)morpholine (4.89 Kg, 14.63 mol) (Intermediate 65) and (R)-2,5,7-trimethyl-6-(pyrrolidin-3-yloxy)-[1,2,4]triazolo[1,5-a]pyrimidine dihydrochloride (Intermediate 58) (4.33 Kg, 17.51 mol*), 2-ditert-butylphosphino-2'-methylbiphenyl (0.23 Kg, 736 mmol) and tris(dibenzylidenacetone)dipalladium(O) (0.33 Kg, 360 mmol) were combined. A degassed mixture of 2-methyltetrahydrofuran (80 L) and water (40 L) was added and the reaction mixture was heated at reflux for 24 h, then allowed to cool to rt and diluted with DCM (100 L) and water (50 L). The reaction mixture was filtered and the organic phase was solvent swapped into ethyl acetate to give 8.4 Kg of crude material. This was dissolved in DCM (200 L) and washed sequentially with 2M hydrochloric acid (2×90 L), 2M sodium hydroxide (140 L), and 5% sodium thiosulphate (2×50 L). The resulting DCM solution is passed through a silica thiol resin (0.5 Kg) before solvent swapping into ethyl acetate to give 5 Kg of crude material. This was dissolved in DCM (25 L) and the correct Form A was generated by addition of n-heptane (25 L) with seed ((R)-4-((6-(4-(3-((2,5,7-trimethyl-[1,2,4]triazolo[1,5-a]pyrimidin-6-yl)oxy)pyrrolidin-1-yl)phenyl)pyridazin-3-yl)methyl)morpholine Form A) used to control the nucleation point. Filtration, and drying (30° C.) afforded the title compound (4.06 Kg, 8.11 mol, 55% yield) as a white solid; NMR (600 MHz, DMSO) 2.31 (1H, dtd), 2.42 (5H, d), 2.46 (3H, s), 2.52 (3H, s), 2.58 (3H, s), 3.45 (1H, dd), 3.54 (1H, td), 3.58 (5H, q), 3.62-3.68 (1H, m), 3.77 (2H, s), 4.96 (1H, s), 6.74 (2H, d), 7.65 (1H, d), 8.03 (2H, d), 8.07 (1H, d); m/z MH$^+$ 501. * Charge is strength adjusted to the free base of Intermediate 58 bulk charge=5.85 Kg of dihydrochloride salt.

Example 63: (S)-4-((6-(4-(3-((2,5,7-trimethyl-[1,2,4]triazolo[1,5-a]pyrimidin-6-yl)oxy)pyrrolidin-1-yl)phenyl)pyridazin-3-yl)methyl)morpholine Example 63 was prepared in a similar way to Example 62 in 3 steps from commercially available tert-butyl (R)-3-hydroxypyrrolidine-1-carboxylate to afford the title compound (125 mg, 31% final step) as a white solid; $^1$H NMR (400 MHz, DMSO) 2.26-2.47 (9H, m), 2.52 (3H, s), 2.58 (3H, s), 3.45 (1H, dd), 3.5-3.61 (6H, m), 3.61-3.69 (1H, m), 3.77 (2H, s), 4.96 (1H, s), 6.73 (2H, d), 7.64 (1H, d), 8.04 (3H, dd); m/z MH$^+$ 501.

Example 64: (R)-2,5,7-trimethyl-6-(0-(4-(6-(piperidin-1-ylmethyl)pyridazin-3-yl)phenyl)pyrrolidin-3-yl)oxy)-[1,2,4]triazolo[1,5-a]pyrimidine

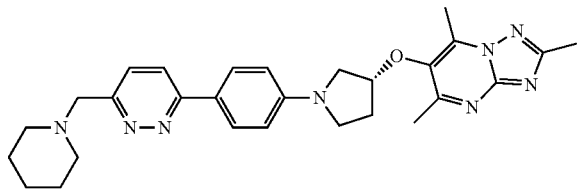 [SMILES: Cc1nc2nc(C)c(O[C@@H]3CCN(c4ccc(-c5ccc(CN6CCCCC6)nn5)cc4)C3)c(C)n2n1]

Cs$_2$CO$_3$ (593 mg, 1.82 mmol) was added to (R)-2,5,7-trimethyl-6-(pyrrolidin-3-yloxy)-[1,2,4]triazolo[1,5-a]pyrimidine (Intermediate 58B) (150 mg, 0.61 mmol) and 3-(4-bromophenyl)-6-(piperidin-1-ylmethyl)pyridazine (Intermediate 70) (202 mg, 0.61 mmol) in 2-methyltetrahydrofuran (1.6 mL) and water (0.8 mL). The reaction was degassed and RuPhos 3rd generation precatalyst (38 mg, 0.05 mmol) and RuPhos (21 mg, 0.05 mmol) were added. The reaction mixture was heated at reflux for 18 h, allowed to cool to rt and then diluted with DCM (10 mL) and water (5 mL) and passed through a phase separating cartridge. The resulting DCM layer was concentrated in vacuo. The resulting crude product was purified by preparative HPLC to afford the title compound (83 mg, 27%) as a white solid; $^1$H NMR (400 MHz, DMSO) 1.37-1.45 (2H, m), 1.52 (4H, p), 2.32 (1H, dt), 2.40 (5H, s), 2.47 (3H, s), 2.53 (3H, s), 2.59 (3H, s), 3.46 (1H, dd), 3.51-3.61 (2H, m), 3.66 (1H, q), 3.74 (2H, s), 4.98 (1H, s), 6.75 (2H, d), 7.63 (1H, d), 8-8.07 (3H, m); m/z MH$^+$ 499.

Example 65: (R)-2,5,7-trimethyl-6-(0-(4-(6-((4-methylpiperazin-1-yl)methyl)pyridazin-3-yl)phenyl)pyrrolidin-3-yl)oxy)-[1,2,4]triazolo[1,5-a]pyrimidine

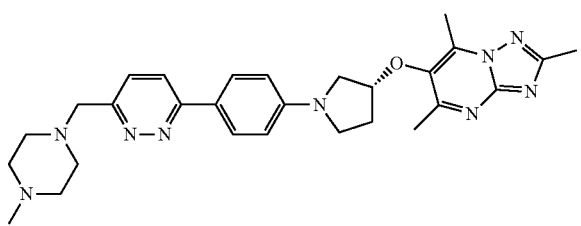 [SMILES: Cc1nc2nc(C)c(O[C@@H]3CCN(c4ccc(-c5ccc(CN6CCN(C)CC6)nn5)cc4)C3)c(C)n2n1]

Cs$_2$CO$_3$ (593 mg, 1.82 mmol) was added to (R)-2,5,7-trimethyl-6-(pyrrolidin-3-yloxy)-[1,2,4]triazolo[1,5-a]pyrimidine (Intermediate 58B) (150 mg, 0.61 mmol) and 3-(4-bromophenyl)-6-((4-methylpiperazin-1-yl)methyl)pyridazine (Intermediate 71) (211 mg, 0.61 mmol) in 2-methyltetrahydrofuran (1.6 mL) and water (0.8 mL). The reaction was degassed and RuPhos 3rd generation precatalyst (38 mg, 0.05 mmol) and RuPhos (21 mg, 0.05 mmol) were added. The reaction mixture was heated at reflux for 18 h, allowed to cool to rt and then diluted with DCM (10 mL) and water (5 mL) and passed through a phase separating cartridge. The resulting DCM layer was concentrated in vacuo. The resulting crude product was purified by preparative HPLC to afford the title compound (154 mg, 49%) as a cream solid; $^1$H NMR (400 MHz, DMSO) 2.16 (3H, s), 2.27-2.38 (5H, m), 2.38-2.48 (8H, m), 2.53 (3H, s), 2.59 (3H, s), 3.46 (1H, dd), 3.51-3.61 (2H, m), 3.66 (1H, q), 3.77 (2H, s), 4.97 (1H, s), 6.74 (2H, d), 7.62 (1H, d), 8.01-8.09 (3H, m); m/z MH$^+$ 514.

Example 66: 2,5,7-trimethyl-6-(((3R)-1-(4-(6-((3-methyl-3,8-diazabicyclo[3.2.1]octan-8-yl)methyl)pyridazin-3-yl)phenyl)pyrrolidin-3-yl)oxy)-[1,2,4]triazolo[1,5-a]pyrimidine

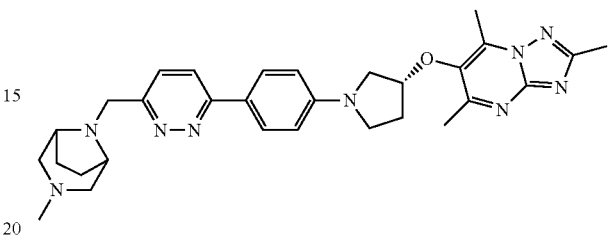

Cs$_2$CO$_3$ (494 mg, 1.52 mmol) was added to (R)-2,5,7-trimethyl-6-(pyrrolidin-3-yloxy)-[1,2,4]triazolo[1,5-a]pyrimidine (Intermediate 58B) (125 mg, 0.51 mmol) and 8-((6-(4-bromophenyl)pyridazin-3-yl)methyl)-3-methyl-3,8-diazabicyclo[3.2.1]octane (Intermediate 66) (189 mg, 0.51 mmol) in 2-methyltetrahydrofuran (1.6 mL) and water (0.8 mL). The reaction was degassed and RuPhos 3rd generation precatalyst (31.7 mg, 0.04 mmol) and RuPhos (17.69 mg, 0.04 mmol) were added. The reaction mixture was heated at reflux for 18 h, allowed to cool to rt then diluted with DCM (10 mL) and water (5 mL) and passed through a phase separating cartridge. The resulting DCM layer was concentrated in vacuo. The resulting crude product was purified by preparative HPLC to afford the title compound (121 mg, 44%) as a cream solid; $^1$H NMR (400 MHz, CDCl$_3$) 1.86 (2H, q), 2.05 (2H, dd), 2.23 (3H, s), 2.27-2.39 (3H, m), 2.46-2.54 (1H, m), 2.57-2.63 (8H, m), 2.65 (3H, s), 3.13 (2H, s), 3.48-3.65 (3H, m), 3.73-3.82 (1H, m), 3.87 (2H, s), 4.85 (1H, s), 6.68 (2H, d), 7.74-7.82 (2H, m), 8.04 (2H, d); m/z MH$^+$ 540.

Example 67: 6-(((R)-1-(4-(6-(((R)-hexahydropyrrolo[1,2-a]pyrazin-2(1H)-yl)methyl)pyridazin-3-yl)phenyl)pyrrolidin-3-yl)oxy)-2,5,7-trimethyl-[1,2,4]triazolo[1,5-a]pyrimidine

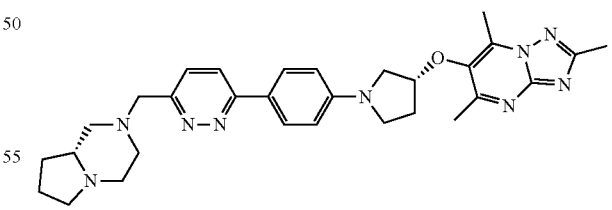

Cs$_2$CO$_3$ (494 mg, 1.52 mmol) was added to (R)-2,5,7-trimethyl-6-(pyrrolidin-3-yloxy)-[1,2,4]triazolo[1,5-a]pyrimidine (Intermediate 58B) (125 mg, 0.51 mmol) and (R)-2-((6-(4-bromophenyl)pyridazin-3-yl)methyl)octahydropyrrolo[1,2-a]pyrazine (Intermediate 67) (189 mg, 0.51 mmol) in 2-methyltetrahydrofuran (1.6 mL) and water (0.8 mL). The reaction was degassed and RuPhos 3rd generation precatalyst (31.7 mg, 0.04 mmol) and RuPhos (17.7 mg, 0.04 mmol) were added. The reaction mixture was heated at reflux for 18 h, allowed to cool to rt and then diluted with DCM (10 mL) and water (5 mL) and passed through a phase separating cartridge. The resulting DCM layer was concentrated in vacuo. The resulting crude product was purified by preparative HPLC to afford the title compound (33 mg, 12%) as a cream solid; $^1$H NMR (400 MHz, DMSO) 1.20-1.31 (1H, m), 1.66 (3H, ttd), 1.87-2.06 (3H, m), 2.14 (1H, td), 2.25 (1H, td), 2.33 (1H, dtd), 2.42 (1H, dd), 2.47 (3H, s), 2.53 (3H, s), 2.59 (3H, s), 2.73 (1H, d), 2.86-2.98 (3H, m), 3.46 (1H, dd), 3.51-3.62 (2H, m), 3.62-3.71 (1H, m), 3.77-3.87 (2H, m), 4.97 (1H, s), 6.75 (2H, d), 7.62 (1H, d), 8.05 (3H, t); m/z MH$^+$ 540.

Example 68: 6-(((R)-1-(4-(6-(((S)-hexahydropyrrolo[1,2-a]pyrazin-2(1H)-yl)methyl)pyridazin-3-yl)phenyl)pyrrolidin-3-yl)oxy)-2,5,7-trimethyl-[1,2,4]triazolo[1,5-a]pyrimidine

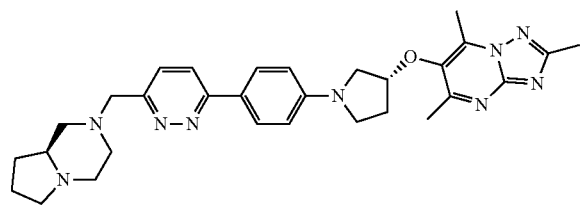 [SMILES: Cc1nc2nc(C)c(O[C@@H]3CCN(c4ccc(-c5ccc(CN6CCN7CCC[C@H]7C6)nn5)cc4)C3)c(C)n2n1]

Cs$_2$CO$_3$ (494 mg, 1.52 mmol) was added to (R)-2,5,7-trimethyl-6-(pyrrolidin-3-yloxy)-[1,2,4]triazolo[1,5-a]pyrimidine (Intermediate 58B) (125 mg, 0.51 mmol) and (S)-2-((6-(4-bromophenyl)pyridazin-3-yl)methyl)octahydropyrrolo[1,2-a]pyrazine (Intermediate 68) (189 mg, 0.51 mmol) in 2-methyltetrahydrofuran (1.6 mL) and water (0.8 mL). The reaction was degassed and RuPhos 3rd generation precatalyst (31.7 mg, 0.04 mmol) and RuPhos (17.7 mg, 0.04 mmol) were added. The reaction mixture was heated at reflux for 18 h, allowed to cool to rt, then diluted with DCM (10 mL) and water (5 mL) and passed through a phase separating cartridge. The resulting DCM layer was concentrated in vacuo. The resulting crude product was purified by preparative HPLC to afford the title compound (76 mg, 28%) as a cream solid; $^1$H NMR (400 MHz, DMSO) 1.20-1.32 (1H, m), 1.66 (3H, dqd), 1.88-2.06 (3H, m), 2.14 (1H, td), 2.25 (1H, td), 2.3-2.37 (1H, m), 2.42 (1H, d), 2.47 (3H, s), 2.53 (3H, d), 2.60 (3H, s), 2.73 (1H, d), 2.85-2.98 (3H, m), 3.47 (1H, dd), 3.51-3.62 (2H, m), 3.66 (1H, q), 3.77-3.87 (2H, m), 4.98 (1H, s), 6.75 (2H, d), 7.62 (1H, d), 8.01-8.09 (3H, m); m/z MH$^+$ 540.

Example 69: (R)-4-((5-(4-(3-((2,5,7-trimethyl-[1,2,4]triazolo[1,5-a]pyrimidin-6-yl)oxy)pyrrolidin-1-yl)phenyl)pyrimidin-2-yl)methyl)morpholine

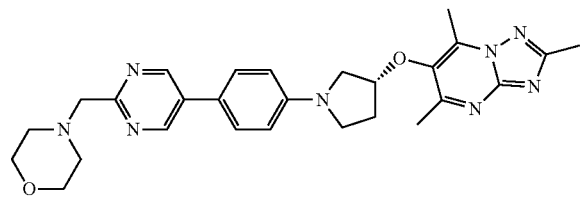 [SMILES: Cc1nc2nc(C)c(O[C@@H]3CCN(c4ccc(-c5cnc(CN6CCOCC6)nc5)cc4)C3)c(C)n2n1]

Cs$_2$CO$_3$ (401 mg, 1.23 mmol) was added to (R)-2,5,7-trimethyl-6-(pyrrolidin-3-yloxy)-[1,2,4]triazolo[1,5-a]pyrimidine (Intermediate 58B) (101 mg, 0.41 mmol) and 4-((5-(4-bromophenyl)pyrimidin-2-yl)methyl)morpholine (Intermediate 39) (137 mg, 0.41 mmol) in 2-methyltetrahydrofuran (1.4 mL) and water (0.7 mL). The reaction was degassed and RuPhos 3rd generation precatalyst (25.7 mg, 0.03 mmol) and RuPhos (14.4 mg, 0.03 mmol) were added. The reaction mixture was heated at reflux for 18 h, allowed to cool to rt, then diluted with DCM (10 mL) and water (5 mL) and passed through a phase separating cartridge. The resulting DCM layer was concentrated in vacuo. The resulting crude product was purified by preparative HPLC to afford the title compound (82 mg, 40%) as a white solid; $^1$H NMR (400 MHz, CDCl$_3$) 2.34 (1H, dp), 2.47-2.55 (1H, m), 2.60 (3H, s), 2.61-2.65 (7H, m), 2.65 (3H, s), 3.45-3.54 (2H, m), 3.58 (1H, td), 3.72-3.78 (1H, m), 3.78-3.83 (4H, m), 3.85 (2H, s), 4.83-4.89 (1H, m), 6.65-6.72 (2H, m), 7.46-7.53 (2H, m), 8.89 (2H, s); m/z MH$^+$ 501.

Example 70: (R)-4-((5-(4-(3-((2,5,7-trimethyl-[1,2,4]triazolo[1,5-a]pyrimidin-6-yl)oxy)pyrrolidin-1-yl)phenyl)pyrazin-2-yl)methyl)morpholine

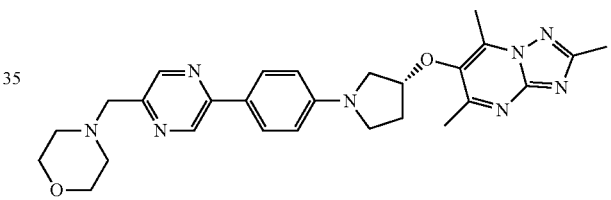

Cs$_2$CO$_3$ (668 mg, 2.05 mmol) was added to (R)-2,5,7-trimethyl-6-(pyrrolidin-3-yloxy)-[1,2,4]triazolo[1,5-a]pyrimidine (Intermediate 58B) (169 mg, 0.68 mmol) and 4-((5-(4-bromophenyl)pyrazin-2-yl)methyl)morpholine (Intermediate 77) (228 mg, 0.68 mmol) in 2-methyltetrahydrofuran (2.3 mL) and water (1.1 mL). The reaction was degassed and RuPhos 3rd generation precatalyst (42.9 mg, 0.05 mmol) and RuPhos (23.9 mg, 0.05 mmol) were added. The reaction mixture was heated at reflux for 18 h, allowed to cool to rt, then diluted with DCM (10 mL) and water (5 mL) and passed through a phase separating cartridge. The resulting DCM layer was concentrated in vacuo. The resulting crude product was purified by preparative HPLC to afford the title compound (104 mg, 30%) as a cream solid; $^1$H NMR (400 MHz, CDCl$_3$) 2.33 (1H, dtd), 2.50 (1H, dd), 2.53-2.57 (4H, m), 2.60 (3H, s), 2.61 (3H, s), 2.64 (3H, s), 3.46-3.6 (2H, m), 3.61 (1H, td), 3.70 (2H, s), 3.72-3.83 (5H, m), 4.85 (1H, dt), 6.63-6.71 (2H, m), 7.91-8.00 (2H, m), 8.60 (1H, d), 8.91 (1H, d); m/z MH$^+$ 501.

Example 71: (R)-1-(4-((6-(4-(3-((2,5,7-trimethyl-[1,2,4]-triazolo[1,5-a]pyrimidin-6-yl)oxy)pyrrolidin-1-yl)phenyl)pyridazin-3-yl)methyl)piperazin-1-yl)ethan-1-one

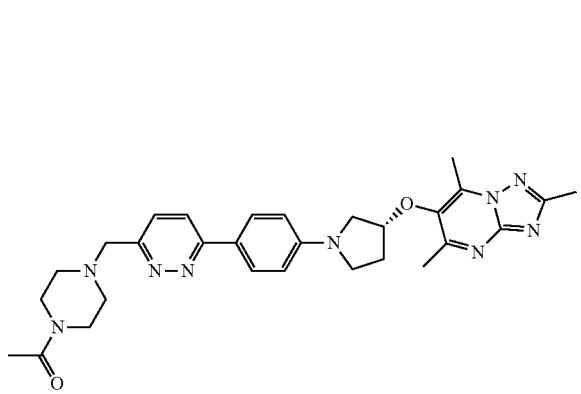 [SMILES: CC(=O)N1CCN(Cc2ccc(-c3ccc(N4CC[C@@H](Oc5c(C)nc6nc(C)nn6c5C)C4)cc3)nn2)CC1]

Example 72: (R)-6-(0-(4-(6-((4-ethylpiperazin-1-yl)methyl)pyridazin-3-yl)phenyl)pyrrolidin-3-yl)oxy)-2,5,7-trimethyl-[1,2,4]triazolo[1,5-a]pyrimidine

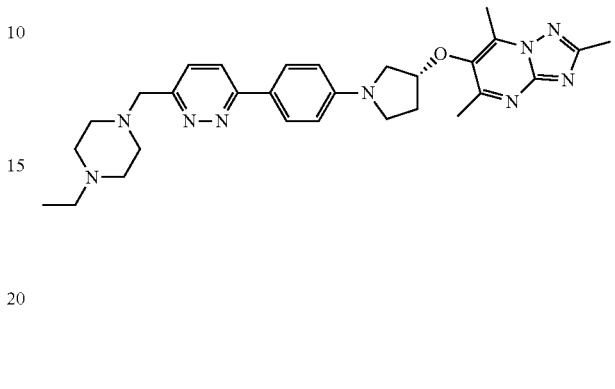

Cs$_2$CO$_3$ (632 mg, 1.94 mmol) was added to (R)-2,5,7-trimethyl-6-(pyrrolidin-3-yloxy)-[1,2,4]triazolo[1,5-a]pyrimidine (Intermediate 58B) (160 mg, 0.65 mmol) and 1-(4-((6-(4-bromophenyl)pyridazin-3-yl)methyl)piperazin-1-yl)ethan-1-one (Intermediate 69) (243 mg, 0.65 mmol) in 2-methyltetrahydrofuran (1.7 mL) and water (0.9 mL). The reaction was degassed and RuPhos 3rd generation precatalyst (40.6 mg, 0.05 mmol) and RuPhos (22.6 mg, 0.05 mmol) were added. The resulting suspension was heated at reflux for 18 h, allowed to cool to rt, diluted with DCM (10 mL) and water (5 mL) and passed through a phase separating cartridge. The resulting DCM layer was concentrated in vacuo. The resulting crude product was purified by preparative HPLC to afford the title compound (154 mg, 44%) as a pale yellow solid; $^1$H NMR (400 MHz, DMSO) 1.99 (3H, s), 2.33 (1H, d), 2.37-2.43 (3H, m), 2.47 (5H, s), 2.53 (3H, s), 2.59 (3H, s), 3.46 (5H, dd), 3.56 (2H, q), 3.66 (1H, q), 3.82 (2H, s), 4.98 (1H, s), 6.75 (2H, d), 7.66 (1H, d), 8.06 (3H, dd); m/z MH$^+$ 542.

Cs$_2$CO$_3$ (336 mg, 1.03 mmol) was added to (R)-2,5,7-trimethyl-6-(pyrrolidin-3-yloxy)-[1,2,4]triazolo[1,5-a]pyrimidine (Intermediate 58B) (85 mg, 0.34 mmol) and 3-(4-bromophenyl)-6-((4-ethylpiperazin-1-yl)methyl)pyridazine (Intermediate 72) (124 mg, 0.34 mmol) in 2-methyltetrahydrofuran (0.9 mL) and water (0.5 mL). The reaction was degassed and RuPhos 3rd generation precatalyst (21.6 mg, 0.03 mmol) and RuPhos (12.0 mg, 0.03 mmol) were added. The reaction mixture was heated at reflux for 18 h, allowed to cool to rt, diluted with DCM (10 mL) and water (5 mL) and passed through a phase separating cartridge. The resulting DCM layer was concentrated in vacuo. The resulting crude product was purified by preparative HPLC to afford the title compound (65 mg, 36%) as a pale yellow solid; $^1$H NMR (400 MHz, CDCl$_3$) 1.08 (3H, t), 2.33 (1H, dtd), 2.42 (3H, q), 2.45-2.54 (4H, m), 2.57-2.64 (10H, m), 2.65 (3H, s), 3.52 (2H, dd), 3.57-3.65 (1H, m), 3.78 (1H, td), 3.89 (2H, s), 4.85 (1H, dt), 6.68 (2H, d), 7.60 (1H, d), 7.74 (1H, d), 8-8.08 (2H, m); m/z MH$^+$ 528.

Example 73: (R)-6-(0-(4-(6-((4-(2-methoxyethyl)piperazin-1-yl)methyl)pyridazin-3-yl)phenyl)pyrrolidin-3-yl)oxy)-2,5,7-trimethyl-[1,2,4]triazolo[1,5-a]pyrimidine

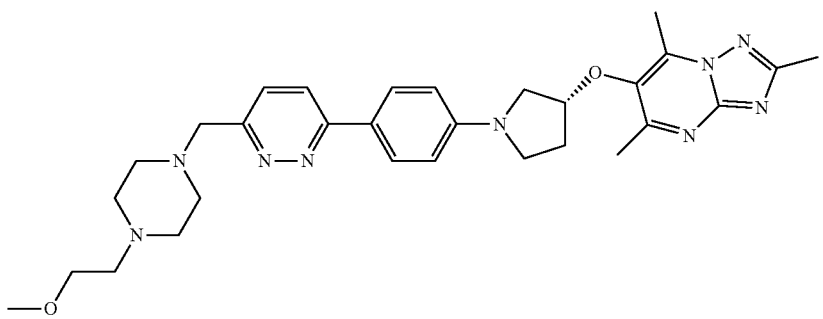

Cs$_2$CO$_3$ (870 mg, 2.67 mmol) was added to (R)-2,5,7-trimethyl-6-(pyrrolidin-3-yloxy)-[1,2,4]triazolo[1,5-a]pyrimidine (Intermediate 58B) (220 mg, 0.89 mmol) and 3-(4-bromophenyl)-6-((4-(2-methoxyethyl)piperazin-1-yl)methyl)pyridazine (Intermediate 73) (348 mg, 0.89 mmol) in 2-methyltetrahydrofuran (2.4 mL) and water (1.1 mL). The reaction was degassed and RuPhos 3rd generation precatalyst (55.8 mg, 0.07 mmol) and RuPhos (31.1 mg, 0.07 mmol) were added. The reaction mixture was heated at reflux for 18 h, allowed to cool to rt, diluted with DCM (10 mL) and water (5 mL) and passed through a phase separating cartridge. The resulting DCM layer was concentrated in vacuo. The resulting crude product was purified by preparative HPLC to afford the title compound (211 mg, 43%) as a pale yellow foamy solid; $^1$H NMR (400 MHz, CDCl$_3$) 2.33 (1H, dtd), 2.49 (1H, dd), 2.51-2.64 (16H, m), 2.65 (3H, s), 3.35 (3H, s), 3.46-3.56 (4H, m), 3.57-3.64 (1H, m), 3.78 (1H, td), 3.89 (2H, s), 4.84 (1H, dd), 6.68 (2H, d), 7.59 (1H, d), 7.74 (1H, d), 8.00-8.07 (2H, m); m/z MH$^+$ 558.

Example 74: (R)-4-((6'-(3-((2,5,7-trimethyl-[1,2,4]-triazolo[1,5-a]pyrimidin-6-yl)oxy)pyrrolidin-1-yl)-[2,3'-bipyridin]-5-yl)methyl)morpholine

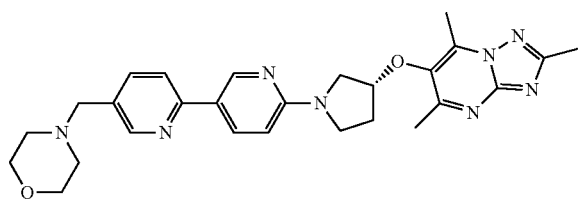 [SMILES: Cc1nc2nc(C)c(O[C@@H]3CCN(c4ccc(-c5ccc(CN6CCOCC6)cn5)cn4)C3)c(C)n2n1]

To (R)-6-((1-(5-bromopyridin-2-yl)pyrrolidin-3-yl)oxy)-2,5,7-trimethyl-[1,2,4]triazolo[1,5-a]pyrimidine (Intermediate 59) (190 mg, 0.47 mmol), 4,4,4',4',5,5,5',5'-octamethyl-2,2'-bi(1,3,2-dioxaborolane) (144 mg, 0.57 mmol) and potassium acetate (92 mg, 0.94 mmol) in 1,4-dioxane (5 mL) in a microwave vial was added PdCl$_2$(dppf)-CH$_2$Cl$_2$ adduct (19 mg, 0.02 mmol) and the reaction was heated at 90° C. overnight, then allowed to cool to rt. 4-((6-bromopyridin-3-yl)methyl)morpholine (Intermediate 30) (121 mg, 0.47 mmol) was added followed by Cs$_2$CO$_3$ (307 mg, 0.94 mmol), XPhos 2$^{nd}$ generation precatalyst (74 mg, 0.05 mmol) and water (3 mL). The reaction mixture was heated at 90° C. for 18 h, then allowed to cool to rt and diluted with EtOAc (50 mL) and water (10 mL) and the layers separated. The aqueous layer was further extracted with DCM (50 mL) and the combined organic layers were dried over MgSO$_4$, filtered and concentrated in vacuo. The resulting crude product was purified by preparative HPLC to afford the title compound (44 mg, 19%) as a pale brown foam; $^1$H NMR (400 MHz, CDCl$_3$) 2.34 (1H, dtd), 2.42-2.56 (5H, m), 2.60 (3H, s), 2.61 (3H, s), 2.64 (3H, s), 3.53 (2H, s), 3.61 (1H, dd), 3.68-3.73 (4H, m), 3.74-3.92 (3H, m), 4.82 (1H, s), 6.51 (1H, d), 7.60 (1H, d), 7.70 (1H, dd), 8.21 (1H, dd), 8.55 (1H, d), 8.76 (1H, d); m/z MH$^+$ 501.

Example 75: (R)-4-((6'-(3-((2,5,7-trimethyl-[1,2,4]-triazolo[1,5-a]pyrimidin-6-yl)oxy)pyrrolidin-1-yl)-[3,3'-bipyridin]-6-yl)methyl)morpholine

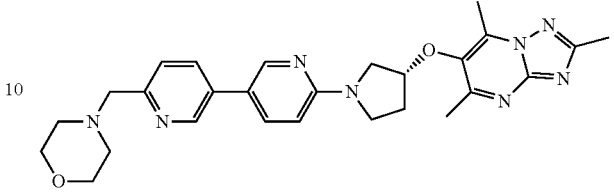

Cs$_2$CO$_3$ (242 mg, 0.74 mmol) was added to (6-(morpholinomethyl)pyridin-3-yl)boronic acid (83 mg, 0.37 mmol) and (R)-6-((1-(5-bromopyridin-2-yl)pyrrolidin-3-yl)oxy)-2,5,7-trimethyl-[1,2,4]triazolo[1,5-a]pyrimidine (Intermediate 59) (150 mg, 0.37 mmol) in 1,4-dioxane (2.5 mL) and water (1.2 mL). The reaction was degassed and XPhos 2$^{nd}$ generation precatalyst (59 mg, 0.04 mmol) was added. The reaction mixture was stirred at 80° C. for 18 h, allowed to cool to rt, diluted with DCM (10 mL) and water (5 mL) and passed through a phase separating cartridge. The resulting DCM layer was concentrated in vacuo. The resulting crude product was dissolved in DMSO (2 mL) and purified by preparative HPLC, then further purified by fcc, eluting with 0-3% 1 M NH$_3$/MeOH in DCM to afford the title compound (18 mg, 10%) as a colourless gum; $^1$H NMR (400 MHz, CDCl$_3$) 2.34 (1H, dtd), 2.48-2.53 (1H, m), 2.52-2.57 (4H, m), 2.60 (3H, s), 2.62 (3H, s), 2.65 (3H, s), 3.60 (1H, dd), 3.69 (2H, s), 3.76 (5H, h), 3.8-3.89 (2H, m), 4.83 (1H, dt), 6.48-6.54 (1H, m), 7.46 (1H, d), 7.72 (1H, dd), 7.78 (1H, dd), 8.41 (1H, dd), 8.74 (1H, dd); m/z MH$^+$ 501.

Example 76: (R)-2,5,7-trimethyl-6-(0-(2-(4-((4-methylpiperazin-1-yl)methyl)phenyl)pyrimidin-5-yl)pyrrolidin-3-yl)oxy)-[1,2,4]triazolo[1,5-a]pyrimidine

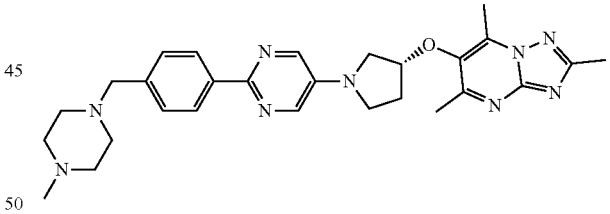

1-Methyl-4-(4-(4,4,5,5-tetramethyl-1,3,2-dioxaborolan-2-yl)benzyl)piperazine (131 mg, 0.42 mmol), (R)-6-((1-(2-bromopyrimidin-5-yl)pyrrolidin-3-yl)oxy)-2,5,7-trimethyl-[1,2,4]triazolo[1,5-a]pyrimidine (Intermediate 61) (140 mg, 0.35 mmol) and Cs$_2$CO$_3$ (226 mg, 0.69 mmol) were added to 1,4-dioxane (3.7 mL) and water (1.8 mL) and the mixture was degassed for 10 minutes. XPhos 2$^{nd}$ generation precatalyst (13.62 mg, 0.02 mmol) was added and the reaction mixture was stirred for 2 h at 85° C., allowed to cool to rt and poured into water (25 mL), and extracted with EtOAc (2×50 mL). The combined organic layers were dried over MgSO$_4$, filtered and concentrated in vacuo. The resulting crude product was purified by preparative HPLC, then further purified by fcc, eluting with 0-5% 1 M NH$_3$/MeOH in DCM to afford the title compound (54 mg, 30%) as a white foam; $^1$H NMR (500 MHz, DMSO) 2.16 (3H, s), 2.24-2.46 (9H, m), 2.48 (3H, s), 2.52-2.54 (1H, m), 2.55 (3H, s), 2.60 (3H, s), 3.44-3.52 (3H, m), 3.57-3.64 (1H, m), 3.69 (2H, dd), 5.00 (1H, s), 7.37 (2H, d), 8.18-8.24 (2H, m), 8.31 (2H, s); m/z MH+ 514.

Example 77: (R)-2,5,7-trimethyl-6-(0-(5-(4-((4-methylpiperazin-1-yl)methyl)phenyl)pyrazin-2-yl) pyrrolidin-3-yl)oxy)-[1,2,4]triazolo[1,5-a]pyrimidine

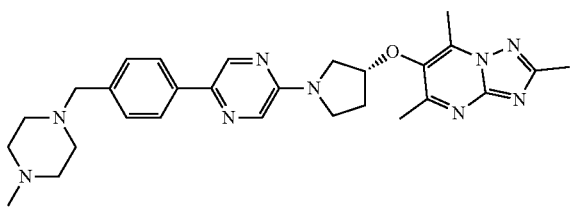 [SMILES: Cc1nc2nc(C)c(O[C@@H]3CCN(c4cnc(-c5ccc(CN6CCN(C)CC6)cc5)cn4)C3)c(C)n2n1]

Palladium (II) acetate (3.2 mg, 0.01 mmol) was added to (R)-6-((1-(5-bromopyrazin-2-yl)pyrrolidin-3-yl)oxy)-2,5,7-trimethyl-[1,2,4]triazolo[1,5-a]pyrimidine (Intermediate 62) (115 mg, 0.28 mmol), 1-methyl-4-(4-(4,4,5,5-tetramethyl-1,3,2-dioxaborolan-2-yl)benzyl)piperazine (117 mg, 0.37 mmol), potassium phosphate (151 mg, 0.71 mmol) and dicyclohexyl(2',4',6'-triisopropyl-[1,1'-biphenyl]-2-yl)phosphine (13.6 mg, 0.03 mmol) in degassed water (1.6 mL) and THF (5 mL) at rt. The reaction mixture was heated at reflux for 1 h, allowed to cool to r, diluted with EtOAc (50 mL) and washed with water (50 mL). The organic layer was isolated and dried over MgSO4, filtered and concentrated in vacuo. The resulting crude product was dissolved in DCM (1 mL) and purified by fcc, eluting with 0-5% 1 M NH3/MeOH in DCM to afford the title compound (83 mg, 57%) as a yellow foam; 1H NMR (500 MHz, CDCl3) 2.29 (3H, s), 2.3-2.59 (10H, m), 2.60 (3H, s), 2.63 (3H, s), 2.66 (3H, s), 3.55 (2H, s), 3.63 (1H, dd), 3.78-3.93 (3H, m), 4.84 (1H, s), 7.41 (2H, d), 7.79-7.88 (2H, m), 8.02 (1H, d), 8.53 (1H, d); m/z MH+ 514.

Example 78: (R)-4-(4-(5-(3-((2,5,7-trimethyl-[1,2,4]triazolo[1,5-a]pyrimidin-6-yl)oxy)pyrrolidin-1-yl)pyrazin-2-yl)benzyl)morpholine

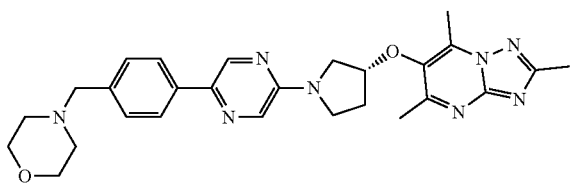 [SMILES: Cc1nc2nc(C)c(O[C@@H]3CCN(c4cnc(-c5ccc(CN6CCOCC6)cc5)cn4)C3)c(C)n2n1]

Palladium (II) acetate (6.9 mg, 0.03 mmol) was added to (R)-6-((1-(5-bromopyrazin-2-yl)pyrrolidin-3-yl)oxy)-2,5,7-trimethyl-[1,2,4]triazolo[1,5-a]pyrimidine (Intermediate 62) (250 mg, 0.62 mmol), 4-(4-(4,4,5,5-tetramethyl-1,3,2-dioxaborolan-2-yl)benzyl)morpholine (225 mg, 0.74 mmol), potassium phosphate (328 mg, 1.55 mmol) and dicyclohexyl (2',4',6'-triisopropyl-[1,1'-biphenyl]-2-yl)phosphine (29.5 mg, 0.06 mmol) in degassed water (3.33 mL) and THF (10 mL) at rt. The reaction mixture was heated at reflux for 1 h, allowed to cool to rt, diluted with EtOAc (50 mL) and washed with water (50 mL). The organic layer was isolated and dried over MgSO4, filtered and concentrated in vacuo. The resulting crude product was dissolved in DCM (1 mL) and purified by fcc, eluting with 0-5% 1 M NH3/MeOH in DCM to afford the title compound (58 mg, 19%) as a yellow foam; 1H NMR (500 MHz, CDCl3) 2.35 (1H, dtd), 2.44-2.5 (4H, m), 2.50-2.58 (1H, m), 2.60 (3H, s), 2.62 (3H, s), 2.66 (3H, s), 3.54 (2H, s), 3.63 (1H, dd), 3.70-3.75 (4H, m), 3.82 (1H, td), 3.85-3.93 (2H, m), 4.83 (1H, d), 7.42 (2H, d), 7.81-7.88 (2H, m), 8.02 (1H, d), 8.53 (1H, d); m/z MH+ 501.

Example 79: 1-[4-[[4-[5-[(3R)-3-[(2,5,7-trimethyl-[1,2,4]triazolo[1,5-a]pyrimidin-6-yl)methyl]pyrrolidin-1-yl]pyrazin-2-yl]phenyl]methyl]-1,4-diazepan-1-yl]ethanone

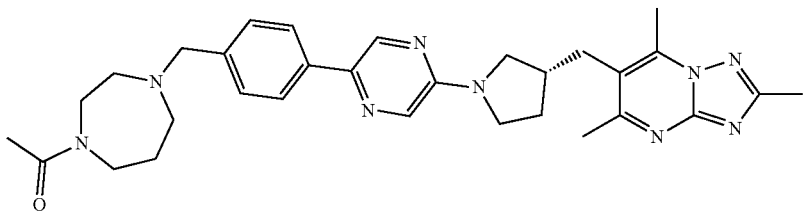 [SMILES: CC(=O)N1CCCN(Cc2ccc(-c3cnc(N4CC[C@@H](Cc5c(C)nc6nc(C)nn6c5C)C4)cn3)cc2)CC1]

(R)-4-(5-(3-((2,5,7-trimethyl-[1,2,4]triazolo[1,5-a]pyrimidin-6-yl)methyl)pyrrolidin-1-yl)pyrazin-2-yl)benzaldehyde (Intermediate 49) (30 mg, 0.07 mmol), 1-(1,4-diazepan-1-yl)ethanone (19.9 mg, 0.14 mmol), DCM (2 mL) and AcOH (2 drops) were combined and the reaction mixture was stirred at rt for 5 h. Sodium triacetoxyborohydride (45 mg, 0.21 mmol) was added and the reaction mixture was stirred at rt for 16 h. The resulting mixture was purified by preparative HPLC to afford the title compound (18 mg, 47%); 1H NMR (400 MHz, DMSO) 1.71 (1H, s), 1.81 (1H, d), 1.87 (1H, dd), 2.00 (3H, d), 2.14 (1H, dd), 2.48 (3H, s), 2.54-2.62 (4H, m), 2.65-2.69 (4H, m), 2.76 (3H, s), 2.95 (2H, d), 3.25 (1H, dd), 3.41-3.52 (5H, m), 3.61-3.75 (4H, m), 7.37 (2H, dd), 7.89 (2H, dd), 8.04 (1H, d), 8.63 (1H, d); m/z MH+ 554.

Example 80: (R)-2,5,7-trimethyl-6-((1-(5-(4-(pyrrolidin-1-ylmethyl)phenyl)pyrazin-2-yl)pyrrolidin-3-yl)methyl)-[1,2,4]triazolo[1,5-a]pyrimidine

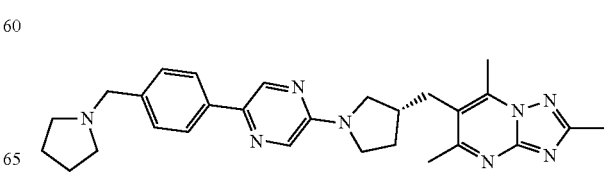

XPhos 2nd generation precatalyst (19.56 mg, 0.02 mmol) was added to (R)-6-((1-(5-bromopyrazin-2-yl)pyrrolidin-3-yl)methyl)-2,5,7-trimethyl-[1,2,4]triazolo[1,5-a]pyrimidine (200 mg, 0.50 mmol), 1-(4-(4,4,5,5-tetramethyl-1,3,2-dioxaborolan-2-yl)benzyl)pyrrolidine (143 mg, 0.50 mmol) and Cs$_2$CO$_3$ (324 mg, 0.99 mmol) in degassed 1,4-dioxane (4 mL) and water (2 mL) at rt. The reaction mixture was stirred at 90° C. for 16 h, allowed to cool to rt and purified by flash C18 chromatography, eluting with 5-100% MeCN in water (+0.08% NH$_4$HCO$_3$) to afford the title compound (63 mg, 26%) as a pale yellow solid; $^1$H NMR (400 MHz, MeOD) 1.85 (4H, p), 1.99 (1H, dq), 2.26 (1H, dq), 2.59 (7H, d), 2.75 (4H, s), 2.86 (3H, s), 3.05 (2H, dt), 3.33-3.42 (1H, m), 3.56 (1H, dt), 3.66-3.85 (4H, m), 7.41-7.48 (2H, m), 7.81-7.90 (2H, m), 8.01 (1H, d), 8.50 (1H, d); m/z MH$^+$ 483.

Example 81: (R)-2,5,7-trimethyl-6-((1-(5-(5-(pyrrolidin-1-ylmethyl)pyridin-2-yl)pyrazin-2-yl)pyrrolidin-3-yl)methyl)-[1,2,4]triazolo[1,5-a]pyrimidine

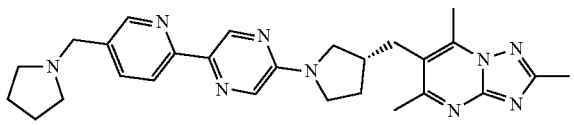

Bis(triphenylphosphine)palladium(II) chloride (137 mg, 0.19 mmol) was added to 2-bromo-5-(pyrrolidin-1-ylmethyl)pyridine (Intermediate 78) (470 mg, 1.95 mmol), 1,1,1,2,2,2-hexamethyldistannane (702 mg, 2.14 mmol) in THF (6 mL) at rt. The reaction mixture was stirred at 85° C. for 16 h. The reaction mixture was transferred to a microwave vial and (R)-6-((1-(5-bromopyrazin-2-yl)pyrrolidin-3-yl)methyl)-2,5,7-trimethyl-[1,2,4]triazolo[1,5-a]pyrimidine (300 mg, 0.75 mmol) and Pd(Ph$_3$P)$_4$ (86 mg, 0.07 mmol) were added. The reaction mixture was heated at 100° C. for 5 h in a microwave reactor then allowed to cool to rt. The resulting mixture was purified by flash C18 chromatography, eluting with 5-100% MeCN in water (+0.1% FA), then further purified by preparative HPLC, eluting with decreasingly polar mixtures of water (containing 10 mmol NH$_4$HCO$_3$) and MeCN to afford the title compound (115 mg, 32%) as a pale yellow solid; $^1$H NMR (400 MHz, MeOD) 1.86 (4H, p), 2.00 (1H, dq), 2.26 (1H, dq), 2.60 (7H, d), 2.75 (4H, s), 2.86 (3H, s), 3.07 (2H, dd), 3.38 (1H, dd), 3.58 (1H, dt), 3.71-3.88 (4H, m), 7.87 (1H, dd), 8.04 (1H, d), 8.14 (1H, d), 8.51-8.57 (1H, m), 8.92 (1H, d); m/z MH$^+$ 484.

Example 82: (R)-2,5,7-trimethyl-6-(0-(5-(6-(pyrrolidin-1-ylmethyl)pyridin-3-yl)pyrazin-2-yl)pyrrolidin-3-yl)methyl)-[1,2,4]triazolo[1,5-a]pyrimidine

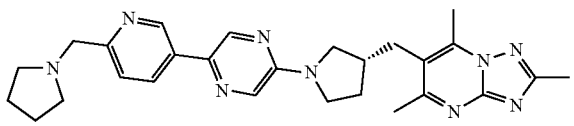 [SMILES: Cc1nc2nc(C)c(C[C@@H]3CCN(c4cnc(-c5ccc(CN6CCCC6)cc5)cn4)C3)c(C)n2n1]

PdCl$_2$(dppf)-CH$_2$Cl$_2$ adduct (85 mg, 0.12 mmol) was added to 5-bromo-2-(pyrrolidin-1-ylmethyl)pyridine (Intermediate 80) (560 mg, 2.32 mmol), 4,4,4',4',5,5,5',5'-octamethyl-2,2'-bi(1,3,2-dioxaborolane) (590 mg, 2.32 mmol) and potassium acetate (456 mg, 4.64 mmol) in 1,4-dioxane (10 mL) at rt. The reaction mixture was stirred at 90° C. for 16 h, and allowed to cool to rt. The reaction mixture was purified by flash C18 chromatography, eluting with 5-100% MeOH in water to afford impure 2-(pyrrolidin-1-ylmethyl)-5-(4,4,5,5-tetramethyl-1,3,2-dioxaborolan-2-yl)pyridine (280 mg, 42% if pure) as a yellow solid. XPhos 2$^{nd}$ generation precatalyst (29.3 mg, 0.04 mmol) was added to (R)-6-((1-(5-bromopyrazin-2-yl)pyrrolidin-3-yl)methyl)-2,5,7-trimethyl-[1,2,4]triazolo[1,5-a]pyrimidine (300 mg, 0.75 mmol), impure 2-(pyrrolidin-1-ylmethyl)-5-(4,4,5,5-tetramethyl-1,3,2-dioxaborolan-2-yl)pyridine from the first step (258 mg, 0.89 mmol if pure) and Cs$_2$CO$_3$ (486 mg, 1.49 mmol) in 1,4-dioxane (4 mL) and water (2 mL) at rt. The reaction mixture was stirred at 90° C. for 16 h. The crude product was purified by flash C18 chromatography, eluting with 5-100% MeCN in water (+0.1% FA), to afford the title compound (54 mg, 15%) as a pale yellow solid; $^1$H NMR (400 MHz, MeOD) 1.87-2.07 (5H, m), 2.27 (1H, dq), 2.57 (3H, s), 2.67-2.89 (11H, m), 3.07 (2H, dd), 3.34-3.42 (1H, m), 3.54-3.64 (1H, m), 3.69-3.88 (2H, m), 3.98 (2H, s), 7.58 (1H, d), 8.08 (1H, d), 8.33 (1H, dd), 8.54-8.61 (1H, m), 9.06 (1H, dd); m/z MH$^+$ 484.

Example 83: (R)-2,5,7-trimethyl-6-((1-(5-(4-((4-methyl-1,4-diazepan-1-yl)methyl)phenyl)pyrazin-2-yl)pyrrolidin-3-yl)methyl)-[1,2,4]triazolo[1,5-a]pyrimidine

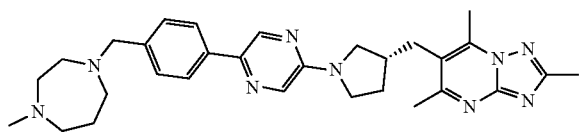

1-Methyl-1,4-diazepane (53 mg, 0.47 mmol) was added to (R)-4-(5-(3-((2,5,7-trimethyl-[1,2,4]triazolo[1,5-a]pyrimidin-6-yl)methyl)pyrrolidin-1-yl)pyrazin-2-yl)benzaldehyde (Intermediate 49) (200 mg, 0.47 mmol) in DCM (5 mL) at rt under air and the reaction mixture was stirred for 1 h. Sodium triacetoxyborohydride (496 mg, 2.34 mmol) was added and the reaction mixture was stirred at rt for 16 h, then concentrated in vacuo. The resulting crude product was purified by flash C18 chromatography, eluting with 5-100% MeCN in water (+0.1% FA), to afford the formic acid salt of the title compound (129 mg, 48%) as a white solid; $^1$H NMR (400 MHz, CDCl$_3$) 1.88-2.02 (1H, m), 2.08 (2H, dt), 2.25 (1H, dq), 2.60-2.76 (10H, m), 2.79-3.06 (11H, m), 3.14-3.22 (2H, m), 3.35 (1H, dd), 3.58 (1H, dt), 3.69-3.84 (4H, m), 7.38-7.45 (2H, m), 7.81-7.89 (2H, m), 7.97 (1H, d), 8.52 (1H, d), 8.60 (1H, s); m/z MH$^+$ 526.

Example 84: (R)-4-((6-(4-(3-((2,5,7-trimethyl-[1,2,4]triazolo[1,5-a]pyrimidin-6-yl)oxy)pyrrolidin-1-yl)phenyl)pyridazin-3-yl)methyl)-1,4-oxazepane

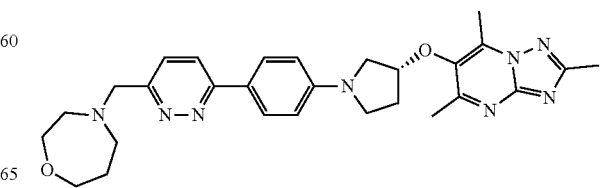

Cs₂CO₃ (553 mg, 1.70 mmol) was added to (R)-2,5,7-trimethyl-6-(pyrrolidin-3-yloxy)-[1,2,4]triazolo[1,5-a]pyrimidine (Intermediate 58B) (140 mg, 0.57 mmol) and 4-((6-(4-bromophenyl)pyridazin-3-yl)methyl)-1,4-oxazepane (Intermediate 74) (197 mg, 0.57 mmol) in 2-methyltetrahydrofuran (1.5 mL) and water (0.76 mL). The reaction was degassed and RuPhos 3rd generation precatalyst (35.5 mg, 0.04 mmol) and RuPhos (19.8 mg, 0.04 mmol) were added. The reaction mixture was stirred at 88° C. for 18 h, allowed to cool to rt, diluted with DCM (10 mL) and water (5 mL) and passed through a phase separating cartridge. The resulting DCM layer was concentrated in vacuo. The resulting crude product was dissolved in DMSO (2 mL) and purified by preparative HPLC to afford the title compound (136 mg, 47%) as a pale yellow solid; ¹H NMR (400 MHz, DMSO) 1.84 (2H, p), 2.35 (1H, tt), 2.43 (1H, dd), 2.48 (3H, s), 2.54 (3H, s), 2.60 (3H, s), 2.72 (4H, q), 3.47 (1H, dd), 3.56 (2H, dd), 3.60-3.69 (3H, m), 3.72 (2H, t), 3.95 (2H, s), 4.98 (1H, s), 6.75 (2H, d), 7.69 (1H, d), 8.02-8.11 (3H, m); m/z MH⁺ 515.

Example 85: (R)-6-((1-(4-(6-(azepan-1-ylmethyl)pyridazin-3-yl)phenyl)pyrrolidin-3-yl)oxy)-2,5,7-trimethyl-[1,2,4]triazolo[1,5-a]pyrimidine

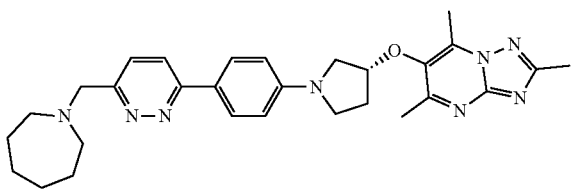 [SMILES: Cc1nc2nc(C)c(O[C@@H]3CCN(c4ccc(-c5ccc(CN6CCCCCC6)nn5)cc4)C3)c(C)n2n1]

Cs₂CO₃ (249 mg, 0.76 mmol) was added to (R)-2,5,7-trimethyl-6-(pyrrolidin-3-yloxy)-[1,2,4]triazolo[1,5-a]pyrimidine (Intermediate 58B) (63 mg, 0.25 mmol) and 1-((6-(4-bromophenyl)pyridazin-3-yl)methyl)azepane (Intermediate 75) (88 mg, 0.25 mmol) in 2-methyltetrahydrofuran (0.6 mL) and water (0.3 mL). The reaction was degassed and RuPhos 3rd generation precatalyst (16 mg, 0.02 mmol) and RuPhos (9 mg, 0.02 mmol) were added. The reaction mixture was stirred at 88° C. for 18 h, allowed to cool to rt, diluted with DCM (10 mL) and water (5 mL) and passed through a phase separating cartridge. The resulting DCM layer was concentrated in vacuo. The resulting crude product was dissolved in DMSO (2 mL) and purified by preparative HPLC. The resulting product was loaded onto a 5 g SCX column, washing with MeOH (2×column volumes) then eluting with 1 M NH₃ in MeOH (2×column volumes), and concentrated in vacuo to afford the title compound (35 mg, 27%) as a white solid; ¹H NMR (400 MHz, DMSO) 1.60 (8H, s), 2.3-2.37 (1H, m), 2.43 (1H, d), 2.48 (3H, s), 2.54 (3H, d), 2.61 (3H, s), 2.66 (4H, d), 3.48 (1H, dd), 3.52-3.63 (2H, m), 3.67 (1H, q), 3.92 (2H, s), 4.99 (1H, s), 6.76 (2H, d), 7.68 (1H, d), 8.01-8.11 (3H, m); m/z MH⁺ 513.

Examples 86 and 87: 4-[(1R)-1-[4-[5-[(3R)-3-[(2,5,7-trimethyl-[1,2,4]triazolo[1,5-a]pyrimidin-6-yl)oxy]pyrrolidin-1-yl]pyrazin-2-yl]phenyl]ethyl]morpholine and 4-[(1S)-1-[4-[5-[(3R)-3-[(2,5,7-trimethyl-[1,2,4]triazolo[1,5-a]pyrimidin-6-yl)oxy]pyrrolidin-1-yl]pyrazin-2-yl]phenyl]ethyl]morpholine

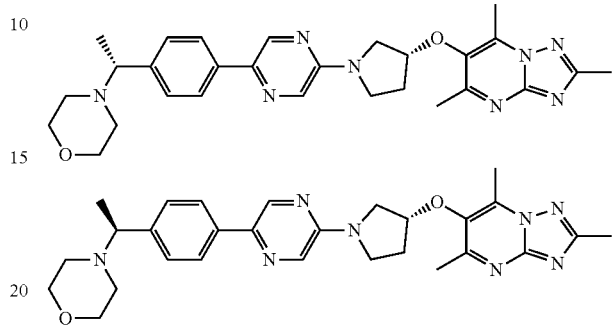

Tetrakis(triphenylphosphine)palladium(O) (157 mg, 0.14 mmol) was added to a degassed solution of 4-(1-(4-(4,4,5,5-tetramethyl-1,3,2-dioxaborolan-2-yl)phenyl)ethyl)morpholine (sourced commercially) (432 mg, 1.36 mmol), (R)-6-((1-(5-bromopyrazin-2-yl)pyrrolidin-3-yl)oxy)-2,5,7-trimethyl-[1,2,4]triazolo[1,5-a]pyrimidine (Intermediate 62) (550 mg, 1.36 mmol) and sodium carbonate (2.0 mL, 4.1 mmol) in 1,4-dioxane (7.7 mL) and water (3.9 mL) under nitrogen. The resulting solution was stirred at 80° C. for 2 hours then allowed to cool to rt. The reaction mixture was diluted with EtOAc (50 mL), and washed sequentially with water (25 mL) and sat. brine (25 mL). The organic layer was dried over MgSO₄, filtered and concentrated in vacuo. The resulting crude product was purified by fcc, elution gradient 0-5% MeOH in DCM, to afford the title compound as a mixture of two diastereomers (355 mg). The isomers were isolated by chiral SFC (Phenomonex C1, 30×250 mm, 5 micron column at a flow rate of 80 ml/min using 40% IPA+0.1% DEA/60% scCO₂ at 120 bar and column temperature of 40° C.) to afford a single diastereomer (unknown chirality alpha to morpholine) of 4-(1-(4-(5-((R)-3-((2,5,7-trimethyl-[1,2,4]triazolo[1,5-a]pyrimidin-6-yl)oxy)pyrrolidin-1-yl)pyrazin-2-yl)phenyl)ethyl)morpholine (62 mg, 18%); ¹H NMR (400 MHz, CDCl₃) 1.38 (3H, d), 2.28-2.47 (3H, m), 2.47-2.58 (3H, m), 2.60 (3H, s), 2.62 (3H, s), 2.66 (3H, s), 3.35 (1H, q), 3.59-3.75 (5H, m), 3.77-3.96 (3H, m), 4.84 (1H, s), 7.40 (2H, d), 7.84 (2H, d), 8.01 (1H, d), 8.52 (1H, d); m/z MH⁺ 515; followed by a second diastereomer (unknown chirality alpha to morpholine) of 4-(1-(4-(5-((R)-3-((2,5,7-trimethyl-[1,2,4]triazolo[1,5-a]pyrimidin-6-yl)oxy)pyrrolidin-1-yl)pyrazin-2-yl)phenyl)ethyl)morpholine (68 mg, 19%); ¹H NMR (400 MHz, CDCl₃) 1.38 (3H, d), 2.27-2.46 (3H, m), 2.46-2.58 (3H, m), 2.60 (3H, s), 2.62 (3H, s), 2.66 (3H, s), 3.35 (1H, q), 3.57-3.76 (5H, m), 3.77-3.96 (3H, m), 4.84 (1H, s), 7.40 (2H, d), 7.84 (2H, d), 8.01 (1H, d), 8.52 (1H, d); m/z MH⁺ 515.

The invention claimed is:

1. A compound of Formula (I):

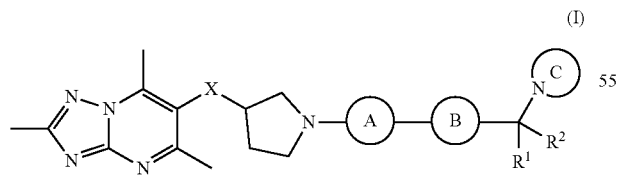

(I)

or a pharmaceutically acceptable salt thereof, wherein:
$R^1$ and $R^2$ each independently represent hydrogen or methyl;
X represents $CH_2$ or O;
Ring A and Ring B each independently represent a ring selected from phenyl, pyridinyl, pyrazinyl, pyrimidinyl and pyridazinyl, wherein each of Ring A and Ring B are independently optionally substituted with one or more substituents selected from $C_{1-3}$ alkyl and $C_{1-3}$ alkoxy;
Ring C represents a 5 to 9 membered monocyclic or bicyclic saturated heterocycloalkyl optionally containing one or more additional heteroatoms independently selected from O, N and S, wherein Ring C is optionally substituted with one or more substituents selected from $C_{1-3}$ alkyl, optionally substituted with methoxy or hydroxyl; dioxo, $C_{0-2}$ alkyl-C(O)N(Me)$_2$, C(O)$C_{1-2}$ alkyl and S(O)$_2C_{1-2}$ alkyl.

2. A compound of Formula (I), or a pharmaceutically acceptable salt thereof, as claimed in claim 1, wherein X represents $CH_2$.

3. A compound of Formula (I), or a pharmaceutically acceptable salt thereof, as claimed in claim 1, wherein X represents O.

4. A compound of Formula (I), or a pharmaceutically acceptable salt thereof, as claimed in claim 1, wherein $R^1$ and $R^2$ are both hydrogen.

5. A compound of Formula (I), or a pharmaceutically acceptable salt thereof, as claimed in claim 1, wherein Ring C is selected from morpholinyl, piperazinyl, piperidinyl, thiomorpholinyl, diazabicyclooctanyl, octahydropyrrolo[1,2-a]pyrazinyl, pyrrolidinyl, diazepanyl, oxazepanyl and azepanyl.

6. A compound of Formula (I), or a pharmaceutically acceptable salt thereof, as claimed in claim 1, wherein Ring A and Ring B are each independently optionally substituted with one or more substituents selected from methyl and methoxy.

7. A compound of Formula (I), or a pharmaceutically acceptable salt thereof, as claimed in claim 1, wherein Ring C is optionally substituted with one or more substituents selected from methyl optionally substituted with hydroxyl; ethyl optionally substituted with methoxy or hydroxyl; dioxo, $C(O)N(Me)_2$, $CH_2C(O)N(Me)_2$, C(O)Me and $S(O)_2Me$.

8. A compound of Formula (I), as claimed in claim 1, wherein the compound of Formula (I) is a compound of Formula (Ia):

(Ia)

or a pharmaceutically acceptable salt thereof, wherein X, $R^1$, $R^2$ and Ring C are as defined in claim 1 and wherein D, E, G, J, L, M, Q and R each independently represent N or $CR^3$, wherein no more than two of D, E, G and J represent N and wherein no more than two of L, M, Q and R represent N, and $R^3$ represents hydrogen, $C_{1-3}$ alkyl or $C_{1-3}$ alkoxy.

9. A compound of Formula (I), as claimed in claim 1, wherein the compound of Formula (I) is a compound of Formula (Ib):

(Ib)

or a pharmaceutically acceptable salt thereof, wherein $R^1$, $R^2$, X, Ring A, Ring B and Ring C are as defined in claim 1.

10. A compound of Formula (I), as claimed in claim 8, wherein the compound of Formula (I) is a compound of Formula (Ic):

(Ic)

or a pharmaceutically acceptable salt thereof, wherein $R^1$, $R^2$, X, D, E, G, J, L, M, Q, R, Ring A, Ring B and Ring C are as defined in claim 8.

11. A compound of Formula (I), or a pharmaceutically acceptable salt thereof, as claimed in claim 1, wherein the compound is selected from the group consisting of:

(R)-4-((6'-(3-((2,5,7-trimethyl-[1,2,4]triazolo[1,5-a]pyrimidin-6-yl)methyl)pyrrolidin-1-yl)-[3,3'-bipyridin]-6-yl)methyl)morpholine;

(R)-2,5,7-trimethyl-6-((1-(6'-((4-methylpiperazin-1-yl)methyl)-[3,3'-bipyridin]-6-yl)pyrrolidin-3-yl)methyl)-[1,2,4]triazolo[1,5-a]pyrimidine;

(R)-2,5,7-trimethyl-6-((1-(5-(4-((4-methylpiperazin-1-yl)methyl)phenyl)pyridin-2-yl)pyrrolidin-3-yl)methyl)-[1,2,4]triazolo[1,5-a]pyrimidine;

(R)-4-(4-(2-(3-((2,5,7-trimethyl-[1,2,4]triazolo[1,5-a]pyrimidin-6-yl)methyl)pyrrolidin-1-yl)pyrimidin-5-yl)benzyl)morpholine;

(R)-4-((5-(5-(3-((2,5,7-trimethyl-[1,2,4]triazolo[1,5-a]pyrimidin-6-yl)methyl)pyrrolidin-1-yl)pyridin-2-yl)pyrazin-2-yl)methyl)morpholine;

(R)-2,5,7-trimethyl-6-((1-(6-(4-((4-methylpiperazin-1-yl)methyl)phenyl)pyridin-3-yl)pyrrolidin-3-yl)methyl)-[1,2,4]triazolo[1,5-a]pyrimidine;

(R)-4-((6-(5-(3-((2,5,7-trimethyl-[1,2,4]triazolo[1,5-a]pyrimidin-6-yl)methyl)pyrrolidin-1-yl)pyridin-2-yl)pyridazin-3-yl)methyl)morpholine;

6-(((R)-1-(2-(4-(((S)-2,4-dimethylpiperazin-1-yl)methyl)phenyl)pyrimidin-5-yl)pyrrolidin-3-yl)methyl)-2,5,7-trimethyl-[1,2,4]triazolo[1,5-a]pyrimidine;

(R)-4-((5-(5-(3-((2,5,7-trimethyl-[1,2,4]triazolo[1,5-a]pyrimidin-6-yl)methyl)pyrrolidin-1-yl)pyrimidin-2-yl)pyridin-2-yl)methyl)morpholine;

(R)-6-((1-(2-(2-methoxy-4-((4-methylpiperazin-1-yl)methyl)phenyl)pyrimidin-5-yl)pyrrolidin-3-yl)methyl)-2,5,7-trimethyl-[1,2,4]triazolo[1,5-a]pyrimidine;

(R)-2,5,7-trimethyl-6-((1-(2-(2-methyl-4-((4-methylpiperazin-1-yl)methyl)phenyl)pyrimidin-5-yl)pyrrolidin-3-yl)methyl)-[1,2,4]triazolo[1,5-a]pyrimidine;

6-(((R)-1-(2-(4-(((3R,5S)-3,5-dimethylpiperazin-1-yl)methyl)phenyl)pyrimidin-5-yl)pyrrolidin-3-yl)methyl)-2,5,7-trimethyl-[1,2,4]triazolo[1,5-a]pyrimidine;

(R)-N,N-dimethyl-2-(4-(4-(5-(3-((2,5,7-trimethyl-[1,2,4]triazolo[1,5-a]pyrimidin-6-yl)methyl)pyrrolidin-1-yl)pyrimidin-2-yl)benzyl)piperazin-1-yl)acetamide;

(R)-2-(4-(4-(5-(3-((2,5,7-trimethyl-[1,2,4]triazolo[1,5-a]pyrimidin-6-yl)methyl)pyrrolidin-1-yl)pyrimidin-2-yl)benzyl)piperazin-1-yl)ethanol;

(R)-1-(4-(4-(5-(3-((2,5,7-trimethyl-[1,2,4]triazolo[1,5-a]pyrimidin-6-yl)methyl)pyrrolidin-1-yl)pyrimidin-2-yl)benzyl)piperazin-1-yl)ethenone;

(R)-6-((1-(2-(4-((4-(2-methoxyethyl)piperazin-1-yl)methyl)phenyl)pyrimidin-5-yl)pyrrolidin-3-yl)methyl)-2,5,7-trimethyl-[1,2,4]triazolo[1,5-a]pyrimidine;

(R)-4-(4-(5-(3-((2,5,7-trimethyl-[1,2,4]triazolo[1,5-a]pyrimidin-6-yl)methyl)pyrrolidin-1-yl)pyrimidin-2-yl)benzyl)morpholine;

(R)-2,5,7-trimethyl-6-((1-(2-(4-((4-methylpiperazin-1-yl)methyl)phenyl)pyrimidin-5-yl)pyrrolidin-3-yl)methyl)-[1,2,4]triazolo[1,5-a]pyrimidine;

(R)-2,5,7-trimethyl-6-((1-(4-(5-((4-methylpiperazin-1-yl)methyl)pyrazin-2-yl)phenyl)pyrrolidin-3-yl)methyl)-[1,2,4]triazolo[1,5-a]pyrimidine;

(R)-2,5,7-trimethyl-6-((1-(4-(2-((4-methylpiperazin-1-yl)methyl)pyrimidin-5-yl)phenyl)pyrrolidin-3-yl)methyl)-[1,2,4]triazolo[1,5-a]pyrimidine;

(R)-4-((6-(4-(3-((2,5,7-trimethyl-[1,2,4]triazolo[1,5-a]pyrimidin-6-yl)methyl)pyrrolidin-1-yl)phenyl)pyridin-3-yl)methyl)morpholine;

(R)-2,5,7-trimethyl-6-((1-(4-(6-((4-methylpiperazin-1-yl)methyl)pyridazin-3-yl)phenyl)pyrrolidin-3-yl)methyl)-[1,2,4]triazolo[1,5-a]pyrimidine;

(R)-2,5,7-trimethyl-6-((1-(4-(5-((4-methylpiperazin-1-yl)methyl)pyrimidin-2-yl)phenyl)pyrrolidin-3-yl)methyl)-[1,2,4]triazolo[1,5-a]pyrimidine;

(R)-4-((5-(4-(3-((2,5,7-trimethyl-[1,2,4]triazolo[1,5-a]pyrimidin-6-yl)methyl)pyrrolidin-1-yl)phenyl)pyrazin-2-yl)methyl)morpholine;

(R)-2,5,7-trimethyl-6-((1-(4-(5-((4-methylpiperazin-1-yl)methyl)pyridin-2-yl)phenyl)pyrrolidin-3-yl)methyl)-[1,2,4]triazolo[1,5-a]pyrimidine;

(R)-4-((5-(4-(3-((2,5,7-trimethyl-[1,2,4]triazolo[1,5-a]pyrimidin-6-yl)methyl)pyrrolidin-1-yl)phenyl)pyrimidin-2-yl)methyl)morpholine;

(R)-4-((6-(4-(3-((2,5,7-trimethyl-[1,2,4]triazolo[1,5-a]pyrimidin-6-yl)methyl)pyrrolidin-1-yl)phenyl)pyridazin-3-yl)methyl)morpholine;

(S)-4-((6-(4-(3-((2,5,7-trimethyl-[1,2,4]triazolo[1,5-a]pyrimidin-6-yl)methyl)pyrrolidin-1-yl)phenyl)pyridazin-3-yl)methyl)morpholine;

(R)-6-((1-(5-(2-methoxy-4-((4-methylpiperazin-1-yl)methyl)phenyl)-6-methylpyrazin-2-yl)pyrrolidin-3-yl)methyl)-2,5,7-trimethyl-[1,2,4]triazolo[1,5-a]pyrimidine;

2,5,7-trimethyl-6-(((R)-1-(5-(4-(((3R,5S)-3,4,5-trimethylpiperazin-1-yl)methyl)phenyl)pyrazin-2-yl)pyrrolidin-3-yl)methyl)-[1,2,4]triazolo[1,5-a]pyrimidine;

6-(((R)-1-(5-(4-(((R)-3,4-dimethylpiperazin-1-yl)methyl)phenyl)pyrazin-2-yl)pyrrolidin-3-yl)methyl)-2,5,7-trimethyl-[1,2,4]triazolo[1,5-a]pyrimidine;

6-(((R)-1-(5-(4-(((R)-2,4-dimethylpiperazin-1-yl)methyl)phenyl)pyrazin-2-yl)pyrrolidin-3-yl)methyl)-2,5,7-trimethyl-[1,2,4]triazolo[1,5-a]pyrimidine;

2,5,7-trimethyl-6-(((R)-1-(5-(4-(((2R,5R)-2,4,5-trimethylpiperazin-1-yl)methyl)phenyl)pyrazin-2-yl)pyrrolidin-3-yl)methyl)-[1,2,4]triazolo[1,5-a]pyrimidine;

2,5,7-trimethyl-6-(((R)-1-(5-(4-(((2S,5R)-2,4,5-trimethylpiperazin-1-yl)methyl)phenyl)pyrazin-2-yl)pyrrolidin-3-yl)methyl)-[1,2,4]triazolo[1,5-a]pyrimidine;

2,5,7-trimethyl-6-[[(3R)-1-[5-[4-(1-piperidylmethyl)phenyl]pyrazin-2-yl]pyrrolidin-3-yl]methyl]-[1,2,4]triazolo[1,5-a]pyrimidine;

(R)-6-((1-(5-(4-((4-ethylpiperazin-1-yl)methyl)phenyl)pyrazin-2-yl)pyrrolidin-3-yl)methyl)-2,5,7-trimethyl-[1,2,4]triazolo[1,5-a]pyrimidine;

(R)-2,5,7-trimethyl-6-((1-(5-(5-((4-methylpiperazin-1-yl)methyl)pyridin-2-yl)pyrazin-2-yl)pyrrolidin-3-yl)methyl)-[1,2,4]triazolo[1,5-a]pyrimidine;

6-(((R)-1-(5-(4-(((3R,5S)-3,5-dimethylpiperazin-1-yl)methyl)phenyl)pyrazin-2-yl)pyrrolidin-3-yl)methyl)-2,5,7-trimethyl-[1,2,4]triazolo[1,5-a]pyrimidine;

2-{4-[4-(5-{(3R)-3-[(2,5,7-trimethyl[1,2,4]triazolo[1,5-a]pyrimidin-6-yl)methyl]pyrrolidin-1-yl}pyrazin-2-yl)benzyl]piperazin-1-yl}ethanol;

(R)-6-((1-(5-(4-((4-(2-methoxyethyl)piperazin-1-yl)methyl)phenyl)pyrazin-2-yl)pyrrolidin-3-yl)methyl)-2,5,7-trimethyl-[1,2,4]triazolo[1,5-a]pyrimidine;

(R)-6-((1-(5-(2-methoxy-4-((4-methylpiperazin-1-yl)methyl)phenyl)pyrazin-2-yl)pyrrolidin-3-yl)methyl)-2,5,7-trimethyl-[1,2,4]triazolo[1,5-a]pyrimidine;

{1-[4-(5-{(3R)-3-[(2,5,7-trimethyl[1,2,4]triazolo[1,5-a]pyrimidin-6-yl)methyl]pyrrolidin-1-yl}pyrazin-2-yl)benzyl]piperidin-4-yl}methanol;

6-{[(3R)-1-(5-{4-[(1,1-dioxidothiomorpholin-4-yl)methyl]phenyl}pyrazin-2-yl)pyrrolidin-3-yl]methyl}-2,5,7-trimethyl[1,2,4]triazolo[1,5-a]pyrimidine;

2,5,7-trimethyl-6-({(3R)-1-[5-(4-{[4-(methylsulfonyl)piperidin-1-yl]methyl}phenyl)pyrazin-2-yl]pyrrolidin-3-yl}methyl)[1,2,4]triazolo[1,5-a]pyrimidine;

(R)-4-((6-(3-methyl-5-(3-((2,5,7-trimethyl-[1,2,4]triazolo[1,5-a]pyrimidin-6-yl)methyl)pyrrolidin-1-yl)pyrazin-2-yl)pyridin-3-yl)methyl)morpholine;

6-(((R)-1-(5-(4-(((S)-3,4-dimethylpiperazin-1-yl)methyl)phenyl)pyrazin-2-yl)pyrrolidin-3-yl)methyl)-2,5,7-trimethyl-[1,2,4]triazolo[1,5-a]pyrimidine;

(R)-4-((5-(5-(3-((2,5,7-trimethyl-[1,2,4]triazolo[1,5-a]pyrimidin-6-yl)methyl)pyrrolidin-1-yl)pyrazin-2-yl)pyridin-2-yl)methyl)morpholine;

6-(((R)-1-(5-(4-(((S)-2,4-dimethylpiperazin-1-yl)methyl)phenyl)pyrazin-2-yl)pyrrolidin-3-yl)methyl)-2,5,7-trimethyl-[1,2,4]triazolo[1,5-a]pyrimidine;

(R)-4-(4-(3-methyl-5-(3-((2,5,7-trimethyl-[1,2,4]triazolo[1,5-a]pyrimidin-6-yl)methyl)pyrrolidin-1-yl)pyrazin-2-yl)benzyl)morpholine;

2,5,7-trimethyl-6-({(3R)-1-[5-(4-{[4-(methylsulfonyl)piperazin-1-yl]methyl}phenyl)pyrazin-2-yl]pyrrolidin-3-yl}methyl)[1,2,4]triazolo[1,5-a]pyrimidine;

(R)-N,N-dimethyl-2-(4-(4-(5-(3-((2,5,7-trimethyl-[1,2,4]triazolo[1,5-a]pyrimidin-6-yl)methyl)pyrrolidin-1-yl)pyrazin-2-yl)benzyl)piperazin-1-yl)acetamide;

(R)-2,5,7-trimethyl-6-((1-(6-methyl-5-(4-((4-methylpiperazin-1-yl)methyl)phenyl)pyrazin-2-yl)pyrrolidin-3-yl)methyl)-[1,2,4]triazolo[1,5-a]pyrimidine;

N,N-dimethyl-4-[4-(5-{(3R)-3-[(2,5,7-trimethyl[1,2,4]triazolo[1,5-a]pyrimidin-6-yl)methyl]pyrrolidin-1-yl}pyrazin-2-yl)benzyl]piperazine-1-carboxamide;

(R)-2,5,7-trimethyl-6-((1-(5-(3-methyl-4-((4-methylpiperazin-1-yl)methyl)phenyl)pyrazin-2-yl)pyrrolidin-3-yl)methyl)-[1,2,4]triazolo[1,5-a]pyrimidine;

(R)-2,5,7-trimethyl-6-((1-(5-(6-((4-methylpiperazin-1-yl)methyl)pyridin-3-yl)pyrazin-2-yl)pyrrolidin-3-yl)methyl)-[1,2,4]triazolo[1,5-a]pyrimidine;

(R)-1-(4-(4-(5-(3-((2,5,7-trimethyl-[1,2,4]triazolo[1,5-a]pyrimidin-6-yl)methyl)pyrrolidin-1-yl)pyrazin-2-yl)benzyl)piperazin-1-yl)ethenone;

(R)-2,5,7-trimethyl-6-((1-(5-(4-((4-methylpiperazin-1-yl)methyl)phenyl)pyrazin-2-yl)pyrrolidin-3-yl)methyl)-[1,2,4]triazolo[1,5-a]pyrimidine;

(R)-4-(4-(5-(3-((2,5,7-trimethyl-[1,2,4]triazolo[1,5-a]pyrimidin-6-yl)methyl)pyrrolidin-1-yl)pyrazin-2-yl)benzyl)morpholine;

(R)-4-(4-(6-(3-((2,5,7-trimethyl-[1,2,4]triazolo[1,5-a]pyrimidin-6-yl)methyl)pyrrolidin-1-yl)pyridazin-3-yl)benzyl)morpholine;

(R)-4-((6-(4-3-((2,5,7-trimethyl-[1,2,4]triazolo[1,5-a]pyrimidin-6-yl)oxy)pyrrolidin-1-yl)phenyl)pyridazin-3-yl)methyl)morpholine;
(S)-4-((6-(4-(3-((2,5,7-trimethyl-[1,2,4]triazolo[1,5-a]pyrimidin-6-yl)oxy)pyrrolidin-1-yl)phenyl)pyridazin-3-yl)methyl)morpholine;
(R)-2,5,7-trimethyl-6-((1-(4-(6-(piperidin-1-ylmethyl)pyridazin-3-yl)phenyl)pyrrolidin-3-yl)oxy)-[1,2,4]triazolo[1,5-a]pyrimidine;
(R)-2,5,7-trimethyl-6-((1-(4-(6-((4-methylpiperazin-1-yl)methyl)pyridazin-3-yl)phenyl)pyrrolidin-3-yl)oxy)-[1,2,4]triazolo[1,5-a]pyrimidine;
2,5,7-trimethyl-6-(((3R)-1-(4-(6-((3-methyl-3,8-diazabicyclo[3.2.1]octan-8-yl)methyl)pyridazin-3-yl)phenyl)pyrrolidin-3-yl)oxy)-[1,2,4]triazolo[1,5-a]pyrimidine;
6-(((R)-1-(4-(6-(((R)-hexahydropyrrolo[1,2-a]pyrazin-2(1H)-yl)methyl)pyridazin-3-yl)phenyl)pyrrolidin-3-yl)oxy)-2,5,7-trimethyl-[1,2,4]triazolo[1,5-a]pyrimidine;
6-(((R)-1-(4-(6-(((S)-hexahydropyrrolo[1,2-a]pyrazin-2(1H)-yl)methyl)pyridazin-3-yl)phenyl)pyrrolidin-3-yl)oxy)-2,5,7-trimethyl-[1,2,4]triazolo[1,5-a]pyrimidine;
(R)-4-((5-(4-(3-((2,5,7-trimethyl-[1,2,4]triazolo[1,5-a]pyrimidin-6-yl)oxy)pyrrolidin-1-yl)phenyl)pyrimidin-2-yl)methyl)morpholine;
(R)-4-((5-(4-(3-((2,5,7-trimethyl-[1,2,4]triazolo[1,5-a]pyrimidin-6-yl)oxy)pyrrolidin-1-yl)phenyl)pyrazin-2-yl)methyl)morpholine;
(R)-1-(4-((6-(4-(3-((2,5,7-trimethyl-[1,2,4]triazolo[1,5-a]pyrimidin-6-yl)oxy)pyrrolidin-1-yl)phenyl)pyridazin-3-yl)methyl)piperazin-1-yl)ethan-1-one;
(R)-6-((1-(4-(6-((4-ethylpiperazin-1-yl)methyl)pyridazin-3-yl)phenyl)pyrrolidin-3-yl)oxy)-2,5,7-trimethyl-[1,2,4]triazolo[1,5-a]pyrimidine;
(R)-6-((1-(4-(6-((4-(2-methoxyethyl)piperazin-1-yl)methyl)pyridazin-3-yl)phenyl)pyrrolidin-3-yl)oxy)-2,5,7-trimethyl-[1,2,4]triazolo[1,5-a]pyrimidine;
(R)-4-((6'-(3-((2,5,7-trimethyl-[1,2,4]triazolo[1,5-a]pyrimidin-6-yl)oxy)pyrrolidin-1-yl)-[2,3'-bipyridin]-5-yl)methyl)morpholine;
(R)-4-((6'-(3-((2,5,7-trimethyl-[1,2,4]triazolo[1,5-a]pyrimidin-6-yl)oxy)pyrrolidin-1-yl)-[3,3'-bipyridin]-6-yl)methyl)morpholine;
(R)-2,5,7-trimethyl-6-((1-(2-(4-((4-methylpiperazin-1-yl)methyl)phenyl)pyrimidin-5-yl)pyrrolidin-3-yl)oxy)-[1,2,4]triazolo[1,5-a]pyrimidine;
(R)-2,5,7-trimethyl-6-((1-(5-(4-((4-methylpiperazin-1-yl)methyl)phenyl)pyrazin-2-yl)pyrrolidin-3-yl)oxy)-[1,2,4]triazolo[1,5-a]pyrimidine;
(R)-4-(4-(5-(3-((2,5,7-trimethyl-[1,2,4]triazolo[1,5-a]pyrimidin-6-yl)oxy)pyrrolidin-1-yl)pyrazin-2-yl)benzyl)morpholine;
1-[4-[[4-[5-[(3R)-3-[(2,5,7-trimethyl-[1,2,4]triazolo[1,5-a]pyrimidin-6-yl)methyl]pyrrolidin-1-yl]pyrazin-2-yl]phenyl]methyl]-1,4-diazepan-1-yl]ethenone;
(R)-2,5,7-trimethyl-6-((1-(5-(4-(pyrrolidin-1-ylmethyl)phenyl)pyrazin-2-yl)pyrrolidin-3-yl)methyl)-[1,2,4]triazolo[1,5-a]pyrimidine;
(R)-2,5,7-trimethyl-6-((1-(5-(5-(pyrrolidin-1-ylmethyl)pyridin-2-yl)pyrazin-2-yl)pyrrolidin-3-yl)methyl)-[1,2,4]triazolo[1,5-a]pyrimidine;
(R)-2,5,7-trimethyl-6-((1-(5-(6-(pyrrolidin-1-ylmethyl)pyridin-3-yl)pyrazin-2-yl)pyrrolidin-3-yl)methyl)-[1,2,4]triazolo[1,5-a]pyrimidine;
(R)-2,5,7-trimethyl-6-((1-(5-(4-((4-methyl-1,4-diazepan-1-yl)methyl)phenyl)pyrazin-2-yl)pyrrolidin-3-yl)methyl)-[1,2,4]triazolo[1,5-a]pyrimidine;
(R)-4-((6-(4-(3-((2,5,7-trimethyl-[1,2,4]triazolo[1,5-a]pyrimidin-6-yl)oxy)pyrrolidin-1-yl)phenyl)pyridazin-3-yl)methyl)-1,4-oxazepane;
(R)-6-((1-(4-(6-(azepan-1-ylmethyl)pyridazin-3-yl)phenyl)pyrrolidin-3-yl)oxy)-2,5,7-trimethyl-[1,2,4]triazolo[1,5-a]pyrimidine;
4-[(1R)-1-[4-[5-[(3R)-3-[(2,5,7-trimethyl-[1,2,4]triazolo[1,5-a]pyrimidin-6-yl)oxy]pyrrolidin-1-yl]pyrazin-2-yl]phenyl]ethyl]morpholine; and
4-[(1S)-1-[4-[5-[(3R)-3-[(2,5,7-trimethyl-[1,2,4]triazolo[1,5-a]pyrimidin-6-yl)oxy]pyrrolidin-1-yl]pyrazin-2-yl]phenyl]ethyl]morpholine.

12. A compound of Formula (I), or a pharmaceutically acceptable salt thereof, as claimed in claim 1, wherein the compound is selected from:
(R)-4-((6-(4-(3-((2,5,7-trimethyl-[1,2,4]triazolo[1,5-a]pyrimidin-6-yl)oxy)pyrrolidin-1-yl)phenyl)pyridazin-3-yl)methyl)morpholine;
(R)-1-(4-((6-(4-(3-((2,5,7-trimethyl-[1,2,4]triazolo[1,5-a]pyrimidin-6-yl)oxy)pyrrolidin-1-yl)phenyl)pyridazin-3-yl)methyl)piperazin-1-yl)ethan-1-one;
(R)-2,5,7-trimethyl-6-((1-(5-(4-((4-methylpiperazin-1-yl)methyl)phenyl)pyrazin-2-yl)pyrrolidin-3-yl)methyl)-[1,2,4]triazolo[1,5-a]pyrimidine;
(R)-4-((6-(4-(3-((2,5,7-trimethyl-[1,2,4]triazolo[1,5-a]pyrimidin-6-yl)methyl)pyrrolidin-1-yl)phenyl)pyridazin-3-yl)methyl)morpholine; and
(S)-4-((6-(4-(3-((2,5,7-trimethyl-[1,2,4]triazolo[1,5-a]pyrimidin-6-yl)oxy)pyrrolidin-1-yl)phenyl)pyridazin-3-yl)methyl)morpholine.

13. A compound of Formula (I), as claimed in claim 1, wherein the compound is (R)-4-((6-(4-(3-((2,5,7-trimethyl-[1,2,4]triazolo[1,5-a]pyrimidin-6-yl)oxy)pyrrolidin-1-yl)phenyl)pyridazin-3-yl)methyl)morpholine, or a pharmaceutically acceptable salt thereof.

14. A compound of Formula (I), as claimed in claim 1, wherein the compound is (S)-4-((6-(4-(3-((2,5,7-trimethyl-[1,2,4]triazolo[1,5-a]pyrimidin-6-yl)oxy)pyrrolidin-1-yl)phenyl)pyridazin-3-yl)methyl)morpholine, or a pharmaceutically acceptable salt thereof.

15. A compound of Formula (I), as claimed in claim 1, wherein the compound is (R)-4-((6-(4-(3-((2,5,7-trimethyl-[1,2,4]triazolo[1,5-a]pyrimidin-6-yl)oxy)pyrrolidin-1-yl)phenyl)pyridazin-3-yl)methyl)morpholine.

16. A compound of Formula (I), as claimed in claim 1, wherein the compound is (S)-4-((6-(4-(3-((2,5,7-trimethyl-[1,2,4]triazolo[1,5-a]pyrimidin-6-yl)oxy)pyrrolidin-1-yl)phenyl)pyridazin-3-yl)methyl)morpholine.

17. A compound of Formula (I), as claimed in claim 15, wherein the compound is in crystalline form with an XRPD substantially as shown in FIG. 1, measured using CuKα radiation.

18. A pharmaceutical composition which comprises a compound of Formula (I), or a pharmaceutically acceptable salt thereof, as claimed in claim 1, and at least one pharmaceutically acceptable excipient.

* * * * *

SEQUENCE LISTING

<160> NUMBER OF SEQ ID NOS: 1

<210> SEQ ID NO 1
<211> LENGTH: 1398

```
<212> TYPE: DNA
<213> ORGANISM: Artificial Sequence
<220> FEATURE:
<223> OTHER INFORMATION: DNA encoding human MCT4

<400> SEQUENCE: 1
atgggagggg ccgtggtgga cgagggcccc acaggcgtca aggcccctga cggcggctgg      60
ggctgggccg tgctcttcgg ctgtttcgtc atcactggct tctcctacgc cttccccaag     120
gccgtcagtg tcttcttcaa ggagctcata caggagtttg ggatcggcta cagcgacaca     180
gcctggatct cctccatcct gctggccatg ctctacggga caggtccgct ctgcagtgtg     240
tgcgtgaacc gctttggctg ccggcccgtc atgcttgtgg ggggtctctt tgcgtcgctg     300
ggcatggtgg ctgcgtcctt tgccggagc atcatccagg tctacctcac cactggggtc      360
atcacggggt tgggtttggc actcaacttc cagccctcgc tcatcatgct gaaccgctac     420
ttcagcaagc ggcgcccat ggccaacggg ctggcggcag caggtagccc tgtcttcctg      480
tgtgccctga gcccgctggg gcagctgctg caggaccgct acggctggcg gggcggcttc     540
ctcatcctgg gcggcctgct gctcaactgc tgcgtgtgtg ccgcactcat gaggcccctg     600
gtggtcacgg cccagccggg ctcggggccg ccgcgaccct ccggcgcct gctagacctg      660 agcgtcttcc gggaccgcgg ctttgtgctt tacgccgtgg ccgcctcggt catggtgctg     720
gggctcttcg tcccgcccgt gttcgtggtg agctacgcca aggacctggg cgtgcccgac     780
accaaggccg ccttcctgct caccatcctg ggcttcattg acatcttcgc gcggccggcc     840
gcgggcttcg tggcggggct tgggaaggtg cggccctact ccgtctacct cttcagcttc     900
tccatgttct tcaacggcct cgcggacctg gcgggctcta cggcgggcga ctacggcggc     960
ctcgtggtct tctgcatctt ctttggcatc tcctacggca tggtggggc cctgcagttc    1020 gaggtgctca tggccatcgt gggcacccac aagttctcca gtgccattgg cctggtgctg    1080
ctgatggagg cggtggccgt gctcgtcggg cccccttcgg gaggcaaact cctggatgcg    1140
acccacgtct acatgtacgt gttcatcctg gcggggccg aggtgctcac ctcctccctg     1200
attttgctgc tgggcaactt cttctgcatt aggaagaagc ccaaagagcc acagcctgag    1260
gtggcggccg cggaggagga gaagctccac aagcctcctg cagactcggg ggtggacttg    1320
cgggaggtgg agcatttcct gaaggctgag cctgagaaaa acggggaggt ggttcacacc    1380
ccggaaacaa gtgtctga                                                  1398
```